(12) United States Patent
Sokoloff et al.

(10) Patent No.: US 9,381,195 B2
(45) Date of Patent: Jul. 5, 2016

(54) DERIVATIVES OF AZAINDAZOLE OR DIAZAINDAZOLE TYPE FOR TREATING PAIN

(71) Applicant: PIERRE FABRE MEDICAMENT, Boulogne-Billancourt (FR)

(72) Inventors: Pierre Sokoloff, Belleserre (FR); Frédéric Cachoux, Caraman (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/417,507

(22) PCT Filed: Jul. 29, 2013

(86) PCT No.: PCT/EP2013/065907
§ 371 (c)(1),
(2) Date: Jan. 26, 2015

(87) PCT Pub. No.: WO2014/016433
PCT Pub. Date: Jan. 30, 2014

(65) Prior Publication Data
US 2015/0190394 A1 Jul. 9, 2015

(30) Foreign Application Priority Data

Jul. 27, 2012 (EP) .................... 12305922

(51) Int. Cl.
*A61K 31/20* (2006.01)
*A61K 31/4985* (2006.01)
*A61K 31/437* (2006.01)
*A61K 31/4545* (2006.01)
*A61K 31/496* (2006.01)

(52) U.S. Cl.
CPC .......... *A61K 31/4985* (2013.01); *A61K 31/437* (2013.01); *A61K 31/4545* (2013.01); *A61K 31/496* (2013.01)

(58) Field of Classification Search
CPC .................................................. A61K 31/437
USPC ........................................................ 514/560
See application file for complete search history.

(56) References Cited

U.S. PATENT DOCUMENTS 8,883,821 B2 * 11/2014 Kaloun ................ C07D 471/04
514/303

FOREIGN PATENT DOCUMENTS

| WO | WO 01/98284 A1 | 12/2001 | |
|---|---|---|---|
| WO | WO 2004/113303 A1 | 12/2004 | |
| WO | WO 2007/023110 | * 3/2007 | .......... C07D 487/04 |
| WO | WO 2007/023110 A2 | 3/2007 | |
| WO | WO 2008/010964 A1 | 1/2008 | |
| WO | WO 2008/074749 A1 | 6/2008 | |
| WO | WO 2008/089307 A2 | 7/2008 | |
| WO | WO 2008/112695 A2 | 9/2008 | |
| WO | WO 2009/013126 A1 | 1/2009 | |
| WO | WO 2010/069966 A1 | 6/2010 | |
| WO | WO 2012/101239 A1 | 8/2012 | |

OTHER PUBLICATIONS

West, Solid State Chemistry and Its Applications, John Wiley & Sons, 1984.*
Bardin et al., "Profound, Non-Opioid Analgesia Produced by the High-Efficacy 5-HT 1A Agonist F 13640 in the Formalin Model of Tonic Nociceptive Pain," Pharmacology, vol. 67, 2003, pp. 182-191, 193-194.
Cattaneo, "Tanezumab, A Recombinant Humanized mAb Against Nerve Growth Factor for the Treatment of Acute and Chronic Pain," Current Opinion in Molecular Therapeutics, vol. 12, No. 1, 2010, pp. 94-106.
Cheng et al., "Intracellular Signaling in Primary Sensory Neurons and Persistent Pain," Neurochem Res, vol. 33, No. 10, Oct. 2008, pp. 1-14.
Coull et al., "BDNF From Microglia Causes the Shift in Neuronal Anion Gradient Underlying Neuropathic Pain," Nature, vol. 438, Dec. 15, 2005, pp. 1017-1021.
Dale et al., "The Process Development of a Scaleable Route to the PDE5 Inhibitor UK-357,903", Organic Process Research & Development, vol. 6, No. 6, 2002 (Published on Web Sep. 17, 2002), pp. 767-772.
Dyachenko et al., "Heterocyclization of 1,3-Butadienethiolates," Chemistry of Heterocyclic Compounds, vol. 41, No. 4, 2005, pp. 503-510.
Enguehard-Gueiffier et al., "A general and efficient method for the copper-catalyzed cross-coupling of amides and thiophenols with 6-halogenoimidazo[1,2-a] pyridines", Tetrahedron, vol. 62, 2006 (Available online May 2, 2006), pp. 6042-6049.

(Continued)

*Primary Examiner* — Nizal Chandrakumar
(74) *Attorney, Agent, or Firm* — Birch, Stewart, Kolasch & Birch, LLP

(57) ABSTRACT

The present invention relates to a compound of following formula (I): or a pharmaceutically acceptable salt or solvate of same, a tautomer of same, or a stereoisomer or mixture of stereoisomers of same in any proportions, such as a mixture of enantiomers, notably a racemic mixture; for use in the treatment of pain.

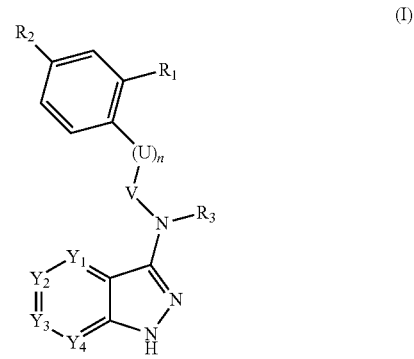

(I)

21 Claims, 3 Drawing Sheets

(56) References Cited

OTHER PUBLICATIONS

Fang et al., "trkA is Expressed in Nociceptive Neurons and Influences Electrophysiological Properties via Nav1.8 Expression in Rapidly Conducting Nociceptors," The Journal of Neuroscience, vol. 25, No. 19, May 11, 2005, pp. 4868-4878.

Ghilardi et al., "Administration of a Tropomyosin Receptor Kinase Inhibitor Attenuates Sarcoma-Induced Nerve Sprouting, Neuroma Formation and Bone Cancer Pain," Molecular Pain, vol. 6, No. 87, Dec. 7, 2010, pp. 1-12.

Guo et al., "Supraspinal Brain-Derived Neurotrophic Factor Signaling: A Novel Mechanism for Descending Pain Facilitation," The Journal of Neuroscience, vol. 26, No. 1, Jan. 4, 2006, pp. 126-137.

Hayashi et al., "Dichloro[1, 1'-bis (diphenylphosphino) ferrocene]palladium-(II): An Effective Catalyst for Cross-Coupling of Secondary and Primary Alkyl Grignard and Alkylzinc Reagents with Organic Halides," J. Am. Chem. Soc., vol. 106, No. 1, 1984, pp. 158-163.

Hefti et al., "Novel Class of Pain Drugs Based on Antagonism of NGF," TRENDS in Pharmacological Sciences, vol. 27, No. 2, Feb. 2006, pp. 85-91.

Indo et al., "Congenital Insensitivity to Pain with Anhidrosis (CIPA): Novel Mutations of the TRKA (NTRK1) Gene, a Putative Uniparental Disomy, and a Linkage of the Mutant TRKA and PKLR Genes in a Family with CIPA and Pyruvate Kinase Deficiency," Human Mutation, vol. 18, 2001, pp. 308-318.

Indo et al., "Mutations in the TRKA/NGF Receptor Gene in Patients with Congenital Insensitivity to Pain with Anhidrosis," Nature Genetics, vol. 13, Aug. 1996, pp. 485-488.

Laske et al., "Increased BDNF Serum Concentration in Fibromyalgia with or without Depression or Antidepressants," Journal of Psychiatric Research, vol. 41, 2007, pp. 600-605.

McNamee et al., "Treatment of Murine Osteoarthritis with TrkAd5 Reveals a Pivotal Role for Nerve Growth Factor in Non-Inflammatory Joint Pain," Pain, vol. 149, 2010, pp. 386-392.

Merighi et al., "BDNF as a Pain Modulator," Progress in Neurobiology, vol. 85, 2008, pp. 297-317.

Milhavet et al., "Synthesis, Reactivity and C-NMR of 1H-Pyrazolo[3,4-c]-Pyridine Derivatives", Heterocycles, vol. 51, No. 7, 1999, pp. 1661-1667.

Obata et al., "BDNF in Sensory Neurons and Chronic Pain," Neuroscience Research, vol. 55, 2006, Available online Mar. 3, 2006, pp. 1-10.

Pacharinsak et al., "Animal Models of Cancer Pain," Comparative Medicine, vol. 58, No. 3, Jun. 2008, pp. 220-233.

Pezet et al., "Neurotrophins: Mediators and Modulators of Pain," Annu. Rev. Neurosci, vol. 29, First published online as a Review in Advance on Mar. 21, 2006, pp. 507-538.

Ponticello et al., "Synthesis of 2-Chloro-5-hydroxynicotinonitrile: The Required Intermediate in the Total Synthesis of a Hydroxylated Metabolite of (S)-2-(3-t-Butylamino-2-hydroxypropoxy)-3-cyanopyridine," J. Heterocyclic Chem., vol. 17, May 1980, pp. 445-448.

Sah et al., "Neurotrophic Factors as Novel Therapeutics for Neuropathic Pain," Nature Reviews, vol. 2, Jun. 2003, pp. 460-472.

Schuligoi et al., "Differential Effects of Treatment with Nerve Growth Factor on Thermal Nociception and on Calcitonin Gene-Related Peptide Content of Primary Afferent Neurons in the Rat," Neuroscience Letters, vol. 252, 1998, pp. 147-149.

Seidel et al., "Nerve Growth Factor in Rheumatic Diseases," Semin Arthritis Rheum, vol. 40, 2010, pp. 109-126.

Sevcik et al., "Anti-NGF Therapy Profoundly Reduces Bone Cancer Pain and the Accompanying Increase in Markers of Peripheral and Central Sensitization," Pain, vol. 115, 2005, pp. 128-141.

Shi et al., "Design and synthesis of 1,4,5,6-tetrahydropyrrolo[3,4-c]pyrazoles and pyrazolo[3,4-b]pyridines for Aurora-A kinase inhibitors", Bioorganic & Medicinal Chemistry Letters, vol. 20, 2010 (Available online May 10, 2010), pp. 4273-4278.

Sonogashira et al., "A Convenient Synthesis of Acetylenes: Catalytic Substitutions of Acetylenic Hydrogen with Bromoalkenes, Iodoarenes, and Bromopyridines", Tetrahedron Letters, No. 50, 1975, pp. 4467-4470.

Su et al., "Chemical Synthesis and Biological Activities of 5-Deazaaminopterin Analogues Bearing Substituent(s) at the 5- and/or 7-Position(s)", J. Med. Chem. vol. 31, No. 6, 1988, pp. 1209-1215.

Tan et al., "Monitoring Interactions between Receptor Tyrosine Kinases and Their Downstream Effector Proteins in Living Cells Using Bioluminescence Resonance Energy Transfer," Molecular Pharmacology, vol. 72, No. 6, 2007, pp. 1440-1446.

Tapley et al., "K252a is a Selective Inhibitor of the Tyrosine Protein Kinase Activity of the trk Family of Oncogenes and Neurotrophin Receptors," Oncogene, vol. 7, 1992, pp. 371-381.

Wang et al., "Trk kinase inhibitors as new treatments for cancer and pain", Expert Opinion on Therapeutic Patents, vol. 19, No. 3, Mar. 1, 2009, XP-002557234, pp. 305-319.

Wheeler-Aceto et al., "The Rat Paw Formalin Test: Comparison of Noxious Agents," Pain, vol. 40, 1990, pp. 229-238.

Winkler et al., "Analgesic Effects of a Potent and Selective Kinase Inhibitor of Neurotrophin Receptors TrkA, TrkB and TrkC," 8th International Association for the Study of Pain Research Symposium, Poster #348, Array BioPharma Inc., 2009, 1 page, with abstract.

Witherington et al., "5-Aryl-pyrazolo[3,4-b]pyridines: Potent Inhibitors of Glycogen Synthase Kinase-3 (GSK-3)", Bioorganic & Medicinal Chemistry Letters, vol. 13, 2003, pp. 1577-1580.

Yakunin et al., "Synthesis of 3-cyano-5-ethoxycarbonyl-6-hydroxypyridine-2-thiol derivatives", Russian Chemical Bulletin, vol. 48, No. 1, Jan. 1999, pp. 195-196.

Zhu et al., "Design and synthesis of pyridine-pyrazolopyridine-based inhibitors of protein kinase B/Akt", Bioorganic & Medicinal Chemistry, vol. 15, 2007 (Available online Jan. 17, 2007), pp. 2441-2452.

* cited by examiner

***P <0.001 vs. NGF

*P <0.05 vs. NGF

DERIVATIVES OF AZAINDAZOLE OR DIAZAINDAZOLE TYPE FOR TREATING PAIN

The present invention relates to azaindazole and diazaindazole fused bicyclic derivatives for use in the treatment or prevention of pain, in particular pain associated with at least one Trk protein.

Pain is a term used to describe an abnormal sensation and painful received by a living being and perceived by the brain. This is an unpleasant sensory and emotional experience associated with tissue damage, or described present or potential in terms of such damage. Pain can be acute or chronic and is associated with various pathologies.

Several mechanisms at the origin of pain have been described:

Nociceptive pain: this is an alarm signal in response to an aggression against the body, for example, pain caused by burns, trauma, contusion, shingles, surgery or tooth extraction. A message is sent to the brain to alert him of the attack.

Inflammatory pain is associated with acute or chronic inflammation, as it can be found in infections, arthritis or Crohn's disease.

Neuropathic pain: it is a pain following nerve injury. This lesion causes a malfunction of the peripheral or central nervous system. It may be a neuropathic pain of central origin, such as following brain lesion or infract, or a peripheral neuropathic pain such as sciatica due to disc herniation.

Idiopathic pain: it is a pain syndrome whose causes are poorly explained. The tests are normal, but the pain is there. Such pain is present in patients presenting with, for example, functional syndromes such as fibromyalgia or irritable bowel syndrome.

Psychogenic pain: it is a pain of psychological origin (bereavement, depression, trauma, etc.). It is notably chronic pain found in depression.

Pain is sometimes of mixed origin: nociceptive and inflammatory, as for example in cancers.

Analgesics or painkillers are drugs used to relieve pain. They were classified into three levels by the World Health Organization (WHO):

Level 1 consists of non-opioid analgesics (paracetamol, anti-inflammatory drugs). They are used for mild to moderate pain;

Level 2 includes weak opioids (eg codeine). They are used for moderate to severe pain, or when level 1 painkillers were not effective for pain relief;

Level 3 consists of strong opioids (eg morphine). These drugs are used for acute pain, or when the level 2 analgesics were not effective for pain relief.

Other classes of drugs are also used to treat certain pain, such as neuroleptics or antidepressants for neuropathic pain, or triptans for migraine headaches.

The need to find new treatments for pain is unavoidable given the limited effectiveness or side effects of current treatments, whatever the level of the WHO analgesic, the type or origin of pain. For example, Level I analgesics according to WHO, which include among other paracetamol, aspirin, non-steroidal anti-inflammatory drugs (NSAIDs) and cyclo-oxygenase inhibitors are generally ineffective against intense pain, but are well tolerated, although adverse gastric effects may occur. Nevertheless, selective inhibitors of type 2 cyclo-oxygenase, as rofecoxib (Vioxx®) have shown serious cardiovascular risks. Opiates such as morphine and derivatives are effective on certain acute pains or severe chronic pain, but can cause drowsiness, nausea and vomiting at initiation of treatment, and then constipation, or respiratory depression in overdose. Repeated or chronic use of opioids can lead to tolerance to the analgesic effect, which requires higher doses, closer to toxic doses, dependence and withdrawal syndrome on discontinuation of treatment. Opiates and derivatives are not very effective on neuropathic pain and chronic pain in the low to moderate intensity.

Protein kinases are enzymes that play a key role in cell signal transduction. They are involved in physiological processes such as cell proliferation, mitosis, differentiation, cell invasion and mobility, and apoptosis, for example.

Deregulation of the physiological mechanisms controlled by protein kinases is central to the appearance and development of many pathologies, notably including cancers and pain.

Of particular interest in the context of the invention, tyrosine receptor kinases of the tropomyosine-related kinases (Trks) have been associated with acute or chronic pain. Trks are receptor tyrosine kinases involved in the development of nervous system. The Trk receptor family is composed of three members TrkA, TrkB and TrkC activated by specific ligands called neurotrophins Trk proteins and their associated ligands have been described to play a role in the development of pain (Sah et al. 2003 *Nat Rev Drug Discovery.* 2:460-472).

For instance, mutations in the TrkA receptor gene have been described in patients with congenital insensitivity to pain (Indo et al., 1996, *Nat Genet.* 13: 485-488; Indo et al., 2001, *Hum Mutations,* 18: 308-318). TrkA is expressed in nociceptive neurons, the neurons that convey pain messages, and influences electrophysiological properties of sodium channels involved in pain message transmission (Fang et al., *J. Neurosci.* 25: 4868-4878). Several review articles highlight the role of TrkA and its ligand Nerve growth Factor (NGF) in the initiation of pain at the level of nociceptive neurons, particularly in inflammatory pain states, for instance rheumatic diseases such as osteoarthritis, lower back pain, lumbar disc herniation and nerve root compression (Hefti et al., 2006; *Trends Pharmacol Sci.* 27:85-91; Pezet and McMahon, 2006, *Ann Rev Neurosci.* 29:507-538; Cheng and Ji, 2008, *Neurochem Res.* 33:1970-1978; Seidel et al. 2010, *Semin Arthritis Rheum.* 40:109-126).

TrkB and its ligand Brain-Derived Neurotrophic factor (BDNF) have also been implicated in chronic pain. BDNF is synthesized in primary sensory neurons and anterogradely transported to the central terminals of the primary afferents in the spinal chord (Obata et al., 2006, *Neurosci Res.* 55: 1-10). BDNF synthesised by microglia in the spinal chord causes the shift in neuronal anion gradient, leading to disinhibition of pain transmission after nerve injury (Coull et al., 2005, *Nature,* 438: 1017-1021). This result indicates that blocking BDNF/TrkB pathway will be useful to treat neuropathic pain. Supraspinal BDNF also plays a role in pain facilitation (Guo et al., 2006, *J Neurosci.* 26: 126-137). Increased BDNF serum concentration has also been reported in fibromyalgia (Laske et al., 2006, *J Psychiatric Res,* 41: 600-605). The role of the BDNF/TrkB signalling in pain modulation has been reviewed (Merighi et al., 2008 85: 297-317).

Blocking the TrkA or TrkB pathway can be achieved by soluble Trk receptors or neutralizing antibodies. Such strategies has been validated for the NGF/TrkA pathway in animals, where it reduced pain associated with bone cancer (Sevcik et al., 2005, *Pain* 115: 128-141) or non-inflammatory joint pain (McNamee et al., 2010 *Pain* 149:386-392). Tanezumab, a recombinant humanized monoclonal antibody against NGF is currently being tested as a treatment in humans for acute and chronic pain associated with several conditions (Cattaneo, 2010, *Curr Opin Mol Ther* 12: 94-106). However, such therapy must be administered via repeated intravenous infusions. Other forms of treatment, such as small Trk inhibitor molecules with oral bioavailability are highly desirable.

The number of Trk inhibitors reported in the literature is limited and until yet none is used as a drug against pain, although Trk inhibitors have already demonstrated analgesic efficacy in experimental preclinical models, notably models of bone cancer pain (Ghilardi et al. 2010, *Mol Pain* 6: 87) and chronic inflammatory pain (Winckler et al. 2009, 8th International Association for the Study of Pain Research Symposium, Poster #348).

There is thus a need for compounds capable of inhibiting Trk.

The article of Wang et al. (*Expert Opin. Ther. Patents* 2009, 19(3), 305-319) is a review of patent applications since 2002 relative to Trk inhibitors and their use in the treatment of cancer and pain. None of the compounds described corresponds to an azaindazole or diazaindazole compound.

WO 2008/112695 describes compounds of type 5-azaindazole or 5,7-diazaindazole substituted in position 6 as inhibitors of protein kinases such as Trk. However, no biological result is present in this application proving the inhibition of any protein kinases and in particular of the protein kinase Trk. Moreover, it is never specified in this application that the compounds can treat or prevent pain.

WO 2004/113303 describes notably compounds of type 5-azaindazole substituted in position 6 as inhibitors of the protein kinase JNK. It is never mentioned that such compounds could also inhibit the protein kinase Trk.

WO 2007/023110 describes notably compounds of type azaindazole or diazaindazole as inhibitors of the protein kinase p38. It is never mentioned that such compounds could also inhibit the protein kinase Trk.

WO 2008/089307 describes notably compounds of type azaindazole or diazaindazole as inhibitors of the Δ5-desaturase activity. It is never mentioned that such compounds could also inhibit the protein kinase Trk.

The compounds of the present invention have the property of inhibiting or modulating the enzymatic activity of Trk proteins. Consequently, said compounds can be used as drugs in the treatment or prevention of pain, in particular pain associated with at least one Trk protein.

Furthermore, the compounds according to the invention are particularly interesting insofar as the inventors were able to show that they inhibit or modulate the activity of more than one Trk protein. They thus allow treating at the same time pains of several origins (for example, the association of inflammatory and nociceptive pains as is observed in case of cancer).

More particularly, the present invention thus has as an object a compound of following general formula (I):

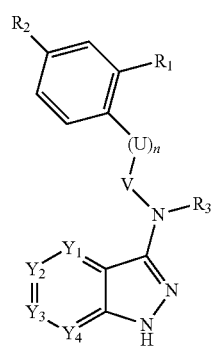

or a pharmaceutically acceptable salt or solvate of same, a tautomer of same, a stereoisomer or a mixture of stereoisomers of same in any proportions, such as a mixture of enantiomers, notably a racemic mixture, wherein:

$Y_1$ and $Y_4$ each represent, independently of each other, a CH group or a nitrogen atom, $Y_2$ represents a nitrogen atom or a CH or C—X—Ar group, $Y_3$ represents a nitrogen atom or a C—X—Ar or C—W group, on the condition that:

at least one and at most two $Y_1$, $Y_2$, $Y_3$, and $Y_4$ groups represent a nitrogen atom, $Y_2$ and $Y_4$ cannot represent a nitrogen atom at the same time, when $Y_2$=C—X—Ar, then $Y_3$ represents a nitrogen atom or a C—W group, and when $Y_2$=CH or N, then $Y_3$ represents a C—X—Ar group, Ar represents an aryl or heteroaryl group optionally substituted by one or more groups selected from a halogen atom, $(C_1-C_6)$alkyl, $(C_1-C_6)$haloalkyl, $(C_1-C_6)$haloalkoxy, $(C_1-C_6)$halothioalkoxy, CN, $NO_2$, $OR_{11}$, $SR_{12}$, $NR_{13}R_{14}$, $CO_2R_{15}$, $CONR_{16}R_{17}$, $SO_2R_{18}$, $SO_2NR_{19}R_{20}$, $COR_{21}$, $NR_{22}COR_{23}$, $NR_{24}SO_2R_{25}$, and $R_{26}NR_{27}R_{28}$ and/or optionally fused to a heterocycle, X represents a divalent group selected from O, S, S(O), $S(O)_2$, $NR_4$, $S(NR_4)$, $S(O)(NR_4)$, $S(O)_2(NR_4)$, $NR_4S$, $NR_4S(O)$, $NR_4S(O)_2$, $CH_2$, $CH_2S$, $CH_2S(O)$, $CH_2S(O)_2$, $SCH_2$, $S(O)CH_2$, $S(O)_2CH_2$, $CH_2CH_2$, CH=CH, C≡C, $CH_2O$, $OCH_2$, $NR_4CH_2$, and $CH_2NR_4$, W represents an $R_5$, $SR_5$, $OR_5$ or $NR_5R_6$ group, U represents a $CH_2$ or NH group, one or more hydrogen atoms which may be replaced by a $(C_1-C_6)$alkyl group, V represents C(O), C(S) or $CH_2$, n represents 0 or 1, $R_1$ represents a hydrogen atom, or an $OR_7$ or $NR_7R_8$ group, $R_2$ represents a hydrogen atom, an optionally substituted heterocycle, $NO_2$, $OR_9$ or $NR_9R_{10}$, $R_3$, $R_4$, $R_{11}$ to $R_{25}$ and $R_{27}$ to $R_{28}$ each represent, independently of each other, a hydrogen atom or a $(C_1-C_6)$alkyl group, $R_5$ and $R_6$ each represent, independently of each other, a hydrogen atom or a $(C_1-C_6)$alkyl, optionally substituted aryl or optionally substituted benzyl group, $R_7$, $R_8$, $R_9$ and $R_{10}$ each represent, independently of each other, a hydrogen atom or an optionally substituted $(C_1-C_6)$alkyl or $(C_3-C_{12})$cycloalkyl group or an optionally substituted heterocycle, and $R_{26}$ represents $(C_1-C_6)$alkyl, for use in the treatment or prevention of pain, in particular pain associated with at least on Trk protein.

In the preceding definitions, all the combinations of substituents or variables are possible insofar as they lead to stable compounds.

It should be noted moreover that at least one but only one of $Y_2$ and $Y_3$ represents a C—X—Ar group.

In a preferred embodiment the present invention has as an object a compound of following general formula (I):

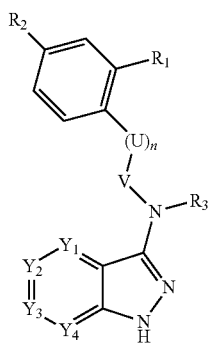
(I)

or a pharmaceutically acceptable salt or solvate of same, a tautomer of same, or a stereoisomer or mixture of stereoisomers of same in any proportions, such as a mixture of enantiomers, notably a racemic mixture,
wherein:
$Y_1$ and $Y_4$ each represent, independently of each other, a CH group or a nitrogen atom on the condition that at least one of $Y_1$ and $Y_4$ represent a nitrogen atom,
$Y_2$ represents a C—X—Ar group,
$Y_3$ represents a C—W group,
Ar represents an aryl or heteroaryl group optionally substituted by one or more groups selected from a halogen atom, $(C_1-C_6)$alkyl, $(C_1-C_6)$haloalkyl, $(C_1-C_6)$haloalkoxy, $(C_1-C_6)$halothioalkoxy, CN, $NO_2$, $OR_{11}$, $SR_{12}$, $NR_{13}R_{14}$, $CO_2R_{15}$, $CONR_{16}R_{17}$, $SO_2R_{18}$, $SO_2NR_{19}R_{20}$, $COR_{21}$, $NR_{22}COR_{23}$, $NR_{24}SO_2R_{25}$, and $R_{26}NR_{27}R_{28}$ and/or optionally fused to a heterocycle,
X represents a divalent group selected from O, S, S(O), $S(O)_2$, $NR_4$, $S(NR_4)$, $S(O)(NR_4)$, $S(O)_2(NR_4)$, $NR_4S$, $NR_4S(O)$, $NR_4S(O)_2$, $CH_2$, $CH_2S$, $CH_2S(O)$, $CH_2S(O)_2$, $SCH_2$, $S(O)CH_2$, $S(O)_2CH_2$, $CH_2CH_2$, CH=CH, C≡C, $CH_2O$, $OCH_2$, $NR_4CH_2$, and $CH_2NR_4$,
W represents an $R_5$, $SR_5$, $OR_5$ or $NR_5R_6$ group,
U represents a $CH_2$ or NH group, one or more hydrogen atoms which may be replaced by a $(C_1-C_6)$alkyl group,
V represents C(O), C(S) or $CH_2$,
n represents 0 or 1,
$R_1$ represents a hydrogen atom, or an $OR_7$ or $NR_7R_8$ group,
$R_2$ represents a hydrogen atom, an optionally substituted heterocycle, $NO_2$, $OR_9$ or $NR_9R_{10}$,
$R_3$, $R_4$, $R_{11}$ to $R_{25}$ and $R_{27}$ to $R_{28}$ each represent, independently of each other, a hydrogen atom or a $(C_1-C_6)$alkyl group,
$R_5$ and $R_6$ each represent, independently of each other, a hydrogen atom or a $(C_1-C_6)$alkyl, optionally substituted aryl or optionally substituted benzyl group,
$R_7$, $R_8$, $R_9$ and $R_{10}$ each represent, independently of each other, a hydrogen atom or an optionally substituted $(C_1-C_6)$alkyl or $(C_3-C_{12})$cycloalkyl group or an optionally substituted heterocycle, and
$R_{26}$ represents a $(C_1-C_6)$alkyl group,
for use in the treatment or prevention of pain.

The term "halogen" refers to fluorine, chlorine, bromine or iodine.

The term "$(C_1-C_6)$ alkyl" refers to saturated linear or branched hydrocarbon chains comprising 1 to 6 carbon atoms. It may be a methyl, ethyl, propyl, isopropyl, butyl, isobutyl, sec-butyl, tert-butyl, pentyl or hexyl group.

The term "$(C_1-C_6)$alkoxy" refers to a $(C_1-C_6)$ alkyl chain linked to the rest of the molecule via an oxygen atom. As an example, mention may be made of methoxy, ethoxy, propoxy, isopropoxy, butoxy or tert-butoxy groups.

The term "$(C_1-C_6)$thioalkoxy" refers to a $(C_1-C_6)$ alkyl chain linked to the rest of the molecule via a sulfur atom. As an example, mention may be made of thiomethoxy, thioethoxy, thiopropoxy, thioisopropoxy, thiobutoxy or thio-tert-butoxy groups.

The term "$(C_1-C_6)$haloalkyl" refers to a $(C_1-C_6)$ alkyl chain such as defined above wherein one or more hydrogen atoms are replaced by a halogen atom such as defined above. It may be in particular a trifluoromethyl group.

The term "$(C_1-C_6)$haloalkoxy" refers to a $(C_1-C_6)$alkoxy chain such as defined above wherein one or more hydrogen atoms are replaced by a halogen atom such as defined above. It may be in particular a trifluoromethoxy group.

The term "$(C_1-C_6)$halothioalkoxy" refers to a $(C_1-C_6)$thioalkoxy chain such as defined above wherein one or more hydrogen atoms are replaced by a halogen atom such as defined above. It may be in particular a trifluorothiomethoxy group.

The term "$(C_3-C_{12})$cycloalkyl" refers to cyclic hydrocarbon systems comprising from 3 to 12 carbon atoms and comprising one or more rings, in particular fused rings. As an example, mention may be made of an adamantyl or cyclohexyl group.

The term "aryl" refers to an aromatic hydrocarbon group preferably comprising from 6 to 14 carbon atoms and comprising one or more fused rings, such as, for example, a phenyl or naphthyl group. Advantageously, it is a phenyl group.

The term "heteroaryl" refers to a cyclic aromatic group comprising 5 to 7 atoms included in the ring or a bicyclic aromatic group comprising 8 to 11 atoms included in the rings, wherein 1 to 4 of the atoms included in the rings are a heteroatom selected independently from sulfur, nitrogen and oxygen atoms, and wherein the other atoms included in the rings are carbon atoms. Examples of heteroaryl groups include furyl, thienyl, pyridinyl, and benzothienyl groups.

The term "heterocycle" refers either to a stable monocycle containing from 4 to 7 cyclic atoms, or to a stable bicycle containing from 8 to 11 cyclic atoms, which may be either saturated or unsaturated, wherein 1 to 4 of the cyclic atoms are a heteroatom selected independently from sulfur, nitrogen and oxygen atoms, and wherein the other cyclic atoms are carbon atoms. As an example, mention may be made of furan, pyrrole, thiophene, thiazole, isothiazole, oxadiazole, imidazole, oxazole, isoxazole, pyridine, piperidine, pyrazine, piperazine, tetrahydropyran, pyrimidine, quinazoline, quinoline, quinoxaline, benzofuran, benzothiophene, indoline, indolizine, benzothiazole, benzothienyl, benzopyran, benzoxazole, benzo[1,3]dioxole, benzisoxazole, benzimidazole, chromane, chromene, dihydrobenzofuran, dihydrobenzothienyl, dihydroisoxazole, isoquinoline, dihydrobenzo[1,4]dioxane, imidazo[1,2-a]pyridine, furo[2,3-c]pyridine, 2.3-dihydro-1H-indene, [1,3]dioxolo[4,5-c]pyridine, pyrrolo[1,2-c]pyrimidine, pyrrolo[1,2-a]pyrimidine, tetrahydronaphthalene, benzo[b][1,4]oxazin.

In the context of the present invention, "optionally substituted" means that the group in question is optionally substituted by one or more substituents which may be selected in particular from a halogen atom, $(C_1-C_6)$alkyl, $(C_1-C_6)$haloalkyl, $(C_1-C_6)$haloalkoxy, $(C_1-C_6)$halothioalkoxy, CN, $NO_2$, $OR_{11}$, $SR_{12}$, $NR_{13}R_{14}$, $CO_2R_{15}$, $CONR_{16}R_{17}$, $SO_2R_{18}$, $SO_2NR_{19}R_{20}$, $COR_{21}$, $NR_{22}COR_{23}$, $NR_{24}SO_2R_{25}$, and $R_{26}NR_{27}R_{28}$, wherein $R_{11}$ to $R_{28}$ are such as defined above.

In the present invention, "pharmaceutically acceptable" refers to that which is useful in the preparation of a pharmaceutical composition that is generally safe, nontoxic and neither biologically nor otherwise undesirable and that is acceptable for veterinary and human pharmaceutical use.

"Pharmaceutically acceptable salt or solvate" of a compound refers to salts and solvates which are pharmaceutically acceptable, as defined herein, and which has the desired pharmacological activity of the parent compound.

Acceptable salts for the therapeutic use of the compounds of the present invention include the conventional nontoxic salts of the compounds of the invention such as those formed from pharmaceutically acceptable organic or inorganic acids or from pharmaceutically acceptable organic or inorganic bases. As an example, mention may be made of salts derived from inorganic acids such as hydrochloric acid, hydrobromic acid, phosphoric acid and sulfuric acid, and those derived from organic acids such as acetic acid, trifluoroacetic acid, propionic acid, succinic acid, fumaric acid, malic acid, tartaric acid, citric acid, ascorbic acid, maleic acid, glutamic acid, benzoic acid, salicylic acid, toluenesulfonic acid, methanesulfonic acid, stearic acid and lactic acid. As an example, mention may be made of salts derived from inorganic bases such as soda, potash or calcium hydroxide and salts derived from organic bases such as lysine or arginine.

These salts may be synthesized from the compounds of the invention containing a basic or acidic part and the corresponding acids or bases according to conventional chemical methods well known to the person skilled in the art.

Acceptable solvates for the therapeutic use of the compounds of the present invention include conventional solvates such as those formed during the last step of the preparation of the compounds of the invention due to the presence of solvents. As an example, mention may be made of solvates due to the presence of water or ethanol.

In the context of the present invention, "stereoisomer" refers to a geometric isomer or an optical isomer.

Geometric isomers result from the different position of substituents on a double bond which can then have a Z or E configuration.

Optical isomers result notably from the different position in space of substituents on a carbon atom comprising four different substituents. This carbon atom thus constitutes a chiral or asymmetrical center. Optical isomers include diastereoisomers and enantiomers. Optical isomers that are mirror images of each other but are non-superimposable are enantiomers. Optical isomers that are not mirror images of each other are diastereoisomers.

In the context of the present invention, "tautomer" refers to a constitutional isomer of the compound obtained by prototropy, i.e., by migration of a hydrogen atom and a change in location of a double bond. The different tautomers of a compound are generally interconvertible and are in equilibrium in solution in proportions which may vary according to the solvent used, the temperature or the pH.

According to a first embodiment, $Y_4$=N.

Advantageously, $Y_2$=C—X—Ar and $Y_3$ preferably represents a C—W group.

In particular:
$Y_1$=CH or N, and advantageously CH,
$Y_2$=C—X—Ar,
$Y_3$=C—W, and
$Y_4$=N.

According to a second embodiment, $Y_1$ and/or $Y_4$ represent a nitrogen atom.

In this case, $Y_2$ and $Y_3$ preferably do not represent a nitrogen atom.

In particular:
$Y_1$ and/or $Y_4$=N,
$Y_2$=CH or C—X—Ar, and
$Y_3$=C—W or C—X—Ar.

In particular:
$Y_1$ represents a CH group,
$Y_4$ represents a nitrogen atom,
$Y_2$ represents a CH or a C—X—Ar group, and
$Y_3$ represents a C—X—Ar or a C—W group,
on the condition that:
when $Y_2$=C—X—Ar, then $Y_3$ represents a C—W group, and
when $Y_2$=CH, then $Y_3$ represents a C—X—Ar group.

Advantageously, X represents a divalent group selected from O, S, S(O), S(O)$_2$, NR$_4$, CH$_2$, CH$_2$S, CH$_2$S(O), CH$_2$S(O)$_2$, NHS(O)$_2$, SCH$_2$, S(O)CH$_2$, S(O)$_2$CH$_2$, S(O)$_2$NH, CH$_2$CH$_2$, CH=CH, C≡C, CH$_2$O, OCH$_2$, NR$_4$CH$_2$, and CH$_2$NR$_4$.

In particular, X represents a divalent group selected from S, S(O), S(O)$_2$, NR$_4$, CH$_2$, CH$_2$S, CH$_2$S(O), CH$_2$S(O)$_2$, NHS(O)$_2$, SCH$_2$, S(O)CH$_2$, S(O)$_2$CH$_2$, S(O)$_2$NH, CH$_2$CH$_2$, C≡C, CH$_2$O, OCH$_2$, NR$_4$CH$_2$, and CH$_2$NR$_4$.

More particularly, X may be selected from S, S(O), S(O)$_2$, CH$_2$, CH$_2$S, CH$_2$S(O), CH$_2$S(O)$_2$, NHS(O)$_2$, SCH$_2$, S(O)CH$_2$, S(O)$_2$CH$_2$, S(O)$_2$NH, CH$_2$CH$_2$, CH=CH, and C≡C.

In particular, X may be selected from S, S(O)$_2$, CH$_2$, SCH$_2$, S(O)$_2$CH$_2$, S(O)$_2$NH, CH$_2$S, CH$_2$S(O)$_2$, NHS(O)$_2$, CH$_2$CH$_2$, and C≡C.

X may notably be selected from S, S(O), S(O)$_2$, NR$_4$, CH$_2$, SCH$_2$, S(O)CH$_2$, S(O)$_2$CH$_2$, S(O)$_2$NH, CH$_2$CH$_2$, C≡C, OCH$_2$, and NR$_4$CH$_2$; notably from S, S(O)$_2$, CH$_2$, SCH$_2$, S(O)$_2$CH$_2$, S(O)$_2$NH, CH$_2$CH$_2$, and C≡C, wherein the first atom of these groups is bound to atom C̲ of the C̲—X—Ar chain.

X may be in particular S, S(O)$_2$, SCH$_2$, S(O)$_2$CH$_2$, S(O)$_2$NH, CH$_2$S, CH$_2$S(O)$_2$, or NHS(O)$_2$; and notably S, S(O)$_2$, SCH$_2$, S(O)$_2$CH$_2$, or S(O)$_2$NH, wherein the first atom of these groups is bound to atom C̲ of the C̲—X—Ar chain.

Advantageously, Ar represents a heteroaryl group, such as pyridine, or an aryl group, such as phenyl, optionally substituted by one or more groups selected from a halogen atom, (C$_1$-C$_6$)alkyl, (C$_1$-C$_6$)haloalkyl, (C$_1$-C$_6$)haloalkoxy, (C$_1$-C$_6$)halothioalkoxy, CN, NO$_2$, OR$_{11}$, SR$_{12}$, NR$_{13}$R$_{14}$, CO$_2$R$_{15}$, CONR$_{16}$R$_{17}$, SO$_2$R$_{18}$, SO$_2$NR$_{19}$R$_{20}$, COR$_{21}$, NR$_{22}$COR$_{23}$, and NR$_{24}$SO$_2$R$_{25}$; and/or optionally fused to a heterocycle.

More particularly, Ar may represent an aryl group, such as phenyl, optionally substituted by one or more groups selected from a halogen atom, (C$_1$-C$_6$)alkyl, (C$_1$-C$_6$)haloalkyl, (C$_1$-C$_6$)haloalkoxy, (C$_1$-C$_6$)halothioalkoxy, CN, NO$_2$, OR$_{11}$, SR$_{12}$, NR$_{13}$R$_{14}$, CO$_2$R$_{15}$, CONR$_{16}$R$_{17}$, SO$_2$R$_{18}$, SO$_2$NR$_{19}$R$_{20}$, COR$_{21}$, NR$_{22}$COR$_{23}$, and NR$_{24}$SO$_2$R$_{25}$.

Ar may notably represent an aryl group, such as phenyl, optionally substituted by one or more groups selected from a halogen atom, (C$_1$-C$_6$)alkyl, (C$_1$-C$_6$)haloalkyl, and CONR$_{16}$R$_{17}$, and in particular from a halogen atom such as fluorine, (C$_1$-C$_6$)alkyl such as methyl, and CONR$_{16}$R$_{17}$ such as CONH$_2$.

Ar can also represent a pyridine group.

Ar may notably be selected from the following groups:

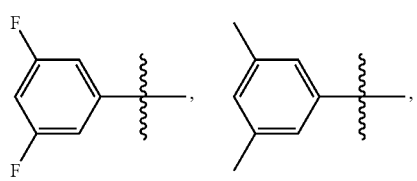

-continued

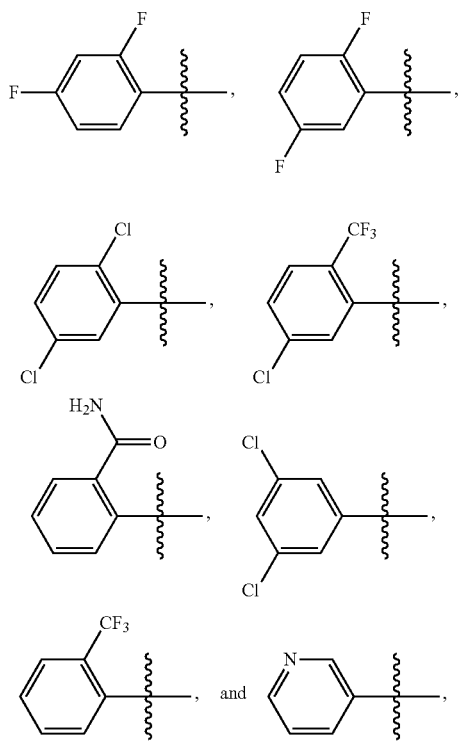

notably from the following groups:

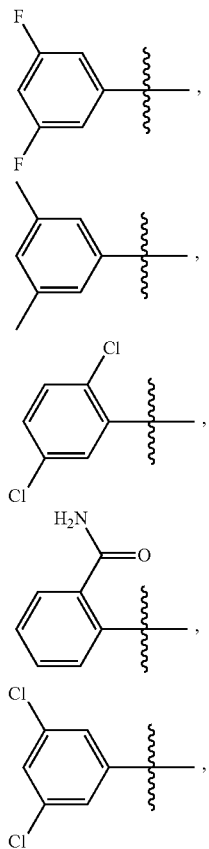

-continued

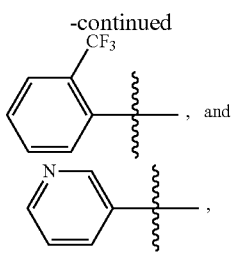

in particular, from the following groups:

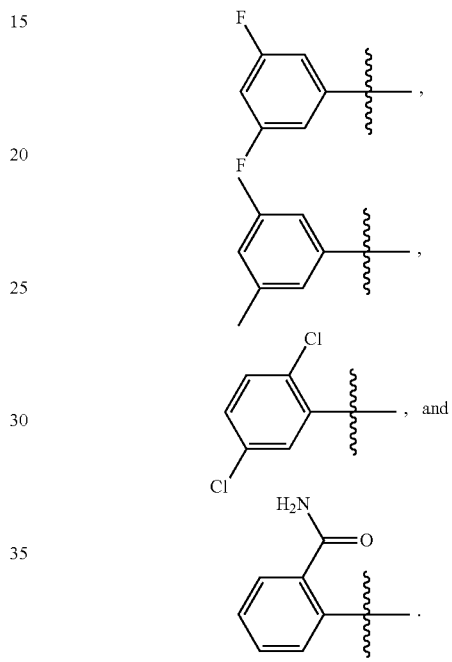

Ar may advantageously represent the group:

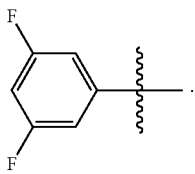 [SMILES: *c1cc(F)cc(F)c1]

W may advantageously represent an $R_5$, $SR_5$, $OR_5$ or $NR_5R_6$ group, and preferably $R_5$, $OR_5$ or $NR_5R_6$, with $R_5$ and $R_6$ representing, independently of each other, a hydrogen atom or a $(C_1$-$C_6)$alkyl group.

W may represent in particular H, OMe, Me, OH or $NH_2$, and notably H.

Advantageously, $R_3$ represents a hydrogen atom.

U may represent more particularly a $CH_2$ or NH group.

Advantageously, n may represent 0.

V may represent more particularly a C(O) or C(S) group, and advantageously a C(O) group.

According to a particular embodiment of the invention:
$R_3$=H,
U=$CH_2$ or NH,
V=C(O) or C(S), and notably C(O), and
n=0 or 1, and notably 0.

According to another particular embodiment of the invention:

V=C(O) or C(S), and notably C(O), and n=0.

According to still another particular embodiment of the invention:

R$_3$=H,

V=C(O) or C(S), and notably C(O), and n=0.

R$_1$ may represent more particularly a hydrogen atom or an NR$_7$R$_8$ group, with R$_7$ notably representing a hydrogen atom and R$_8$ notably representing an optionally substituted (C$_3$-C$_{12}$)cycloalkyl group or an optionally substituted heterocycle.

The (C$_3$-C$_{12}$)cycloalkyl group may be in particular a cyclohexyl. It may be substituted by one or more halogen atoms. It may be in particular the group:

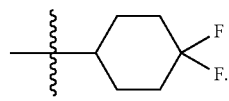

The heterocyclic group may be in particular a tetrahydropyran, notably unsubstituted. It may thus be the following group:

R$_1$ may thus represent more particularly one of the following groups:

H,

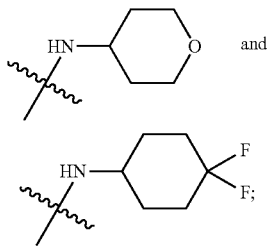

and notably H and

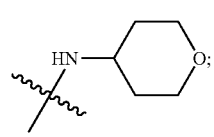 [SMILES: *NC1CCOCC1]

and advantageously

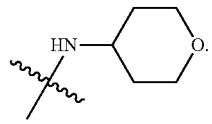 [SMILES: *NC1CCOCC1]

R$_2$ may represent more particularly an optionally substituted heterocycle (notably substituted by (C$_1$-C$_6$)alkyl or NH$_2$), NO$_2$ or NR$_9$R$_{10}$, with notably R$_9$=R$_{10}$=H or else R$_9$ and R$_{10}$ each represent H or an optionally substituted (C$_1$-C$_6$) alkyl.

R$_2$ may represent in particular an optionally substituted heterocycle, notably substituted by (C$_1$-C$_6$)alkyl or NH$_2$. The heterocycle may be in particular a heterocycle with 5 or 6 members comprising at least one nitrogen atom, and in particular one or two. The heterocycle may thus be selected from piperazine, piperidine and pyrrolidine.

R$_2$ may notably represent one of the following groups:

NH$_2$, NH(CH$_2$)$_3$NMe$_2$, NMe(CH$_2$)$_3$NMe$_2$, NO$_2$,

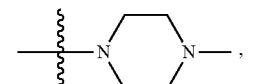

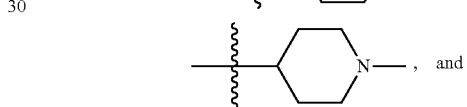

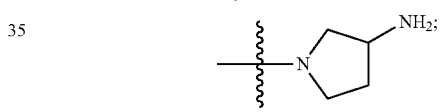

and notably NH$_2$, NO$_2$,

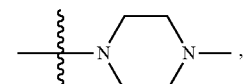

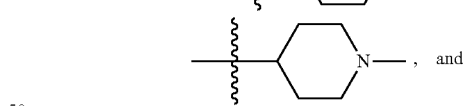

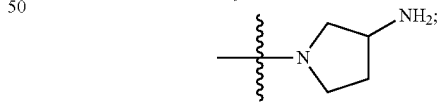

and in particular

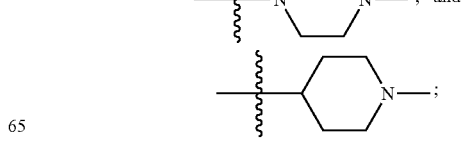

and more particularly
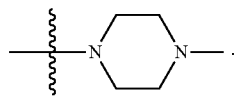 [SMILES: *N1CCN(C)CC1] 5
The compounds of the present invention may be selected from the compounds cited in the following table:
14-2
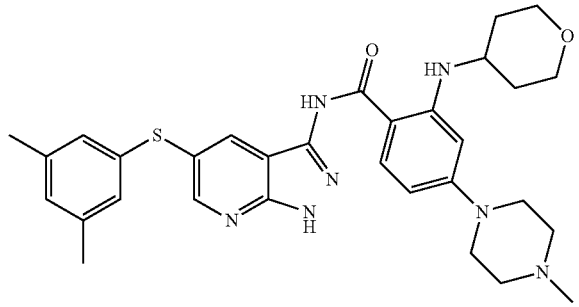
14-10
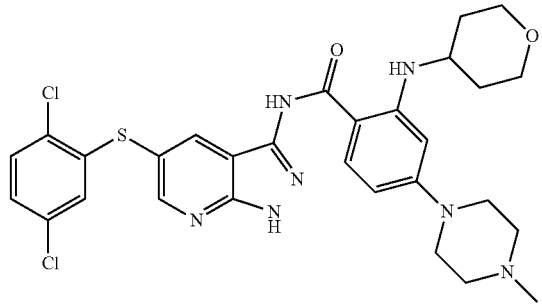 [SMILES: CN1CCN(c2ccc(C(=O)NC(=N)c3cc(Sc4cc(Cl)ccc4Cl)cnc3N)c(NC3CCOCC3)c2)CC1]
14-11
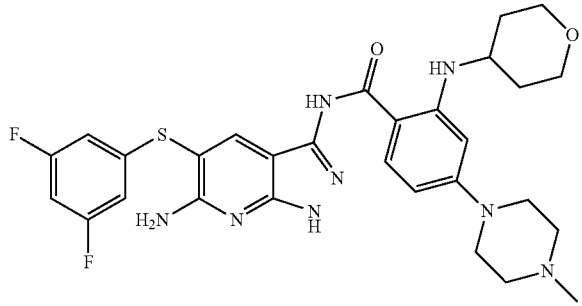 [SMILES: CN1CCN(c2ccc(C(=O)NC(=N)c3cc(Sc4cc(F)cc(F)c4)c(N)nc3N)c(NC3CCOCC3)c2)CC1]
15
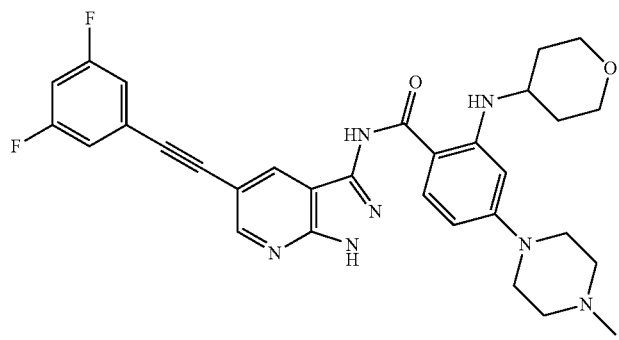 [SMILES: CN1CCN(c2ccc(C(=O)NC(=N)c3cc(C#Cc4cc(F)cc(F)c4)cnc3N)c(NC3CCOCC3)c2)CC1]

-continued
26-4
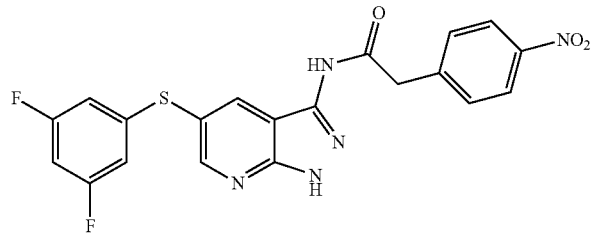 [SMILES: N=C(NC(=O)Cc1ccc([N+](=O)[O-])cc1)c1cc(Sc2cc(F)cc(F)c2)cnc1N]
26-8
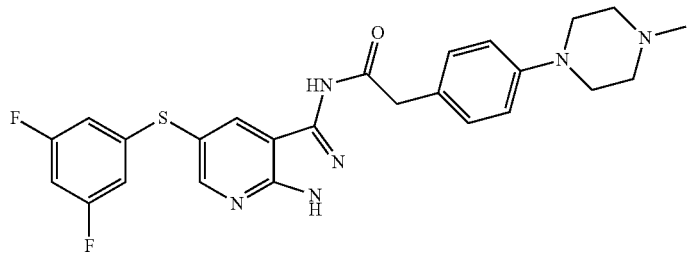 [SMILES: CN1CCN(c2ccc(CC(=O)NC(=N)c3cc(Sc4cc(F)cc(F)c4)cnc3N)cc2)CC1]
27
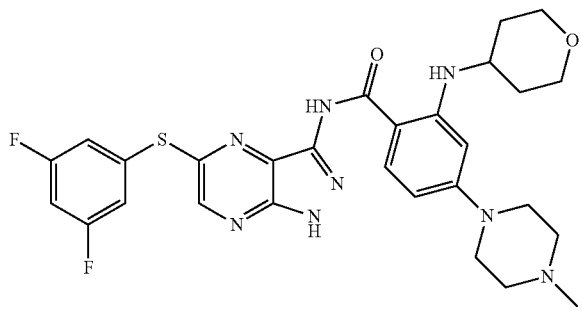 [SMILES: CN1CCN(c2ccc(C(=O)NC(=N)c3nc(Sc4cc(F)cc(F)c4)cnc3N)c(NC3CCOCC3)c2)CC1]
27-1
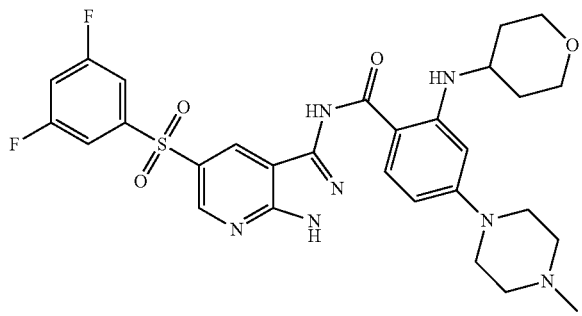
28
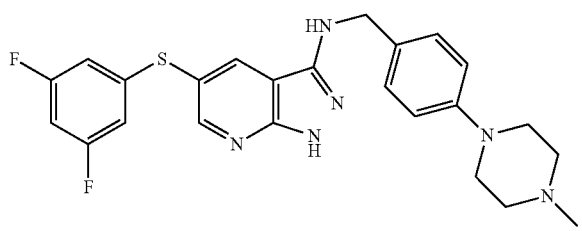 [SMILES: CN1CCN(c2ccc(CNC(=N)c3cc(Sc4cc(F)cc(F)c4)cnc3N)cc2)CC1]
29
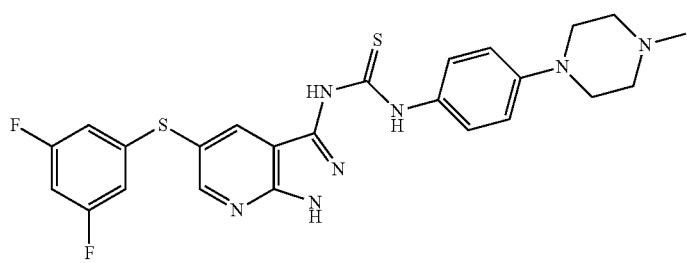 [SMILES: CN1CCN(c2ccc(NC(=S)NC(=N)c3cc(Sc4cc(F)cc(F)c4)cnc3N)cc2)CC1]

29-a
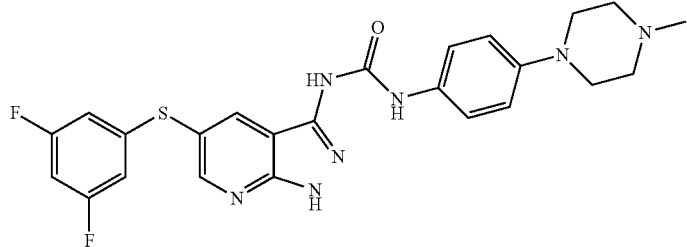 [SMILES: CN1CCN(c2ccc(NC(=O)NC(=N)c3cc(Sc4cc(F)cc(F)c4)cnc3N)cc2)CC1]
30
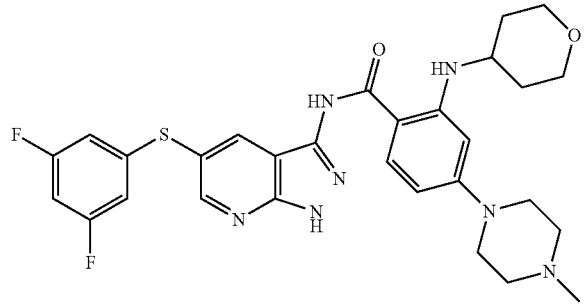 [SMILES: CN1CCN(c2ccc(C(=O)NC(=N)c3cc(Sc4cc(F)cc(F)c4)cnc3N)c(NC3CCOCC3)c2)CC1]
30-1
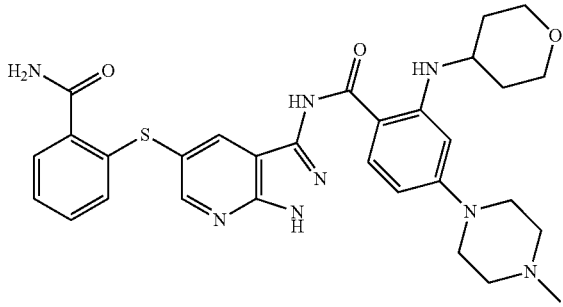 [SMILES: CN1CCN(c2ccc(C(=O)NC(=N)c3cc(Sc4ccccc4C(N)=O)cnc3N)c(NC3CCOCC3)c2)CC1]
30-3
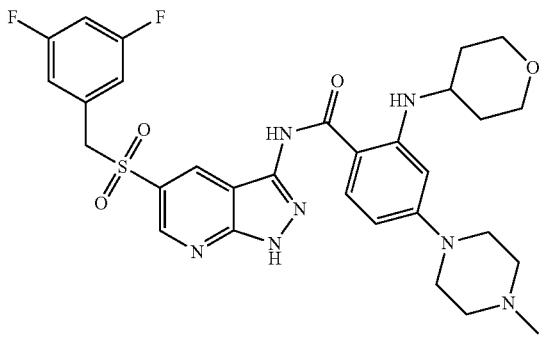 [SMILES: CN1CCN(c2ccc(C(=O)Nc3n[nH]c4ncc(S(=O)(=O)Cc5cc(F)cc(F)c5)cc34)c(NC3CCOCC3)c2)CC1]
30-4
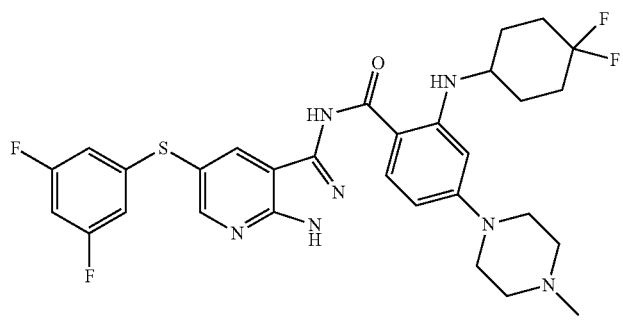 [SMILES: CN1CCN(c2ccc(C(=O)NC(=N)c3cc(Sc4cc(F)cc(F)c4)cnc3N)c(NC3CCC(F)(F)CC3)c2)CC1]

| | |
|---|---|
| 30-5 | 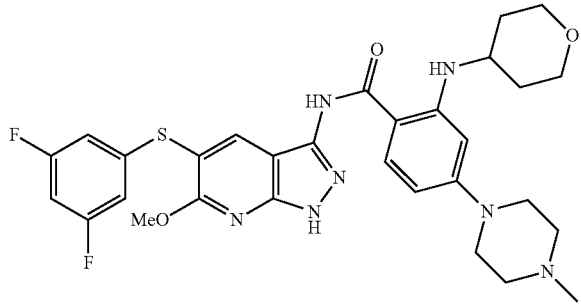 [SMILES: COc1nc2[nH]nc(NC(=O)c3ccc(N4CCN(C)CC4)cc3NC3CCOCC3)c2cc1Sc1cc(F)cc(F)c1] |
| 30-8 | 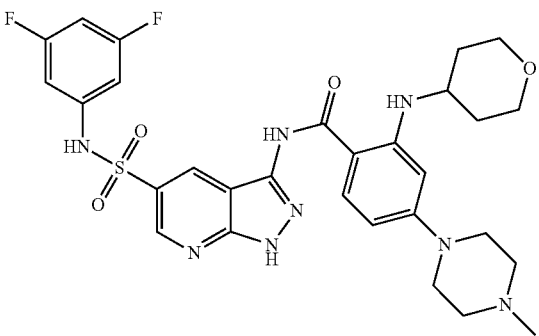 [SMILES: CN1CCN(c2ccc(C(=O)Nc3n[nH]c4ncc(S(=O)(=O)Nc5cc(F)cc(F)c5)cc34)c(NC3CCOCC3)c2)CC1] |
| 30-9 | 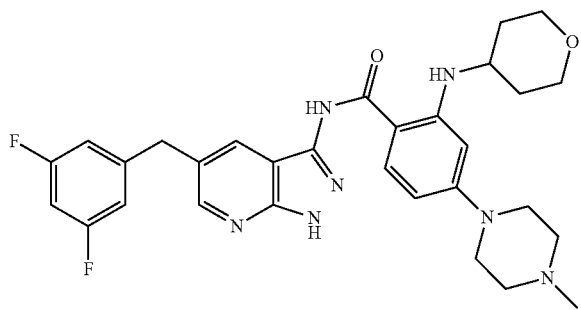 |
| 30-10 | 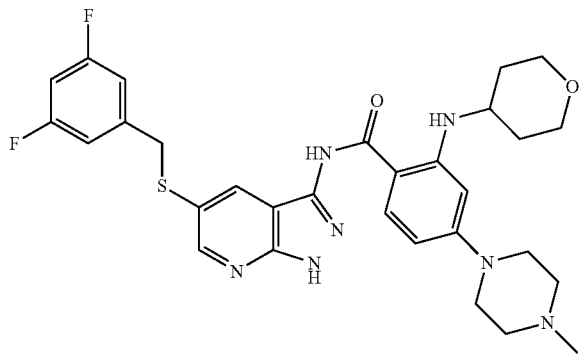 |
| 30-11 | 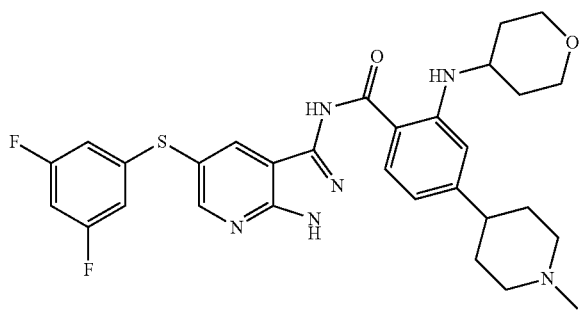 |

30-12
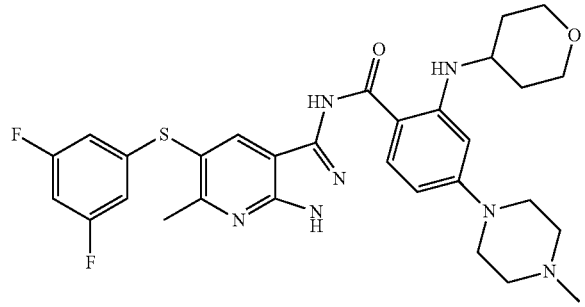 [SMILES: Cc1nc(N)c(C(=N)NC(=O)c2ccc(N3CCN(C)CC3)cc2NC2CCOCC2)cc1Sc1cc(F)cc(F)c1]
30-a
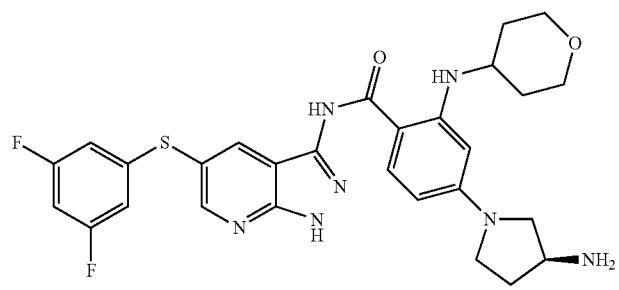 [SMILES: N=C(NC(=O)c1ccc(N2CC[C@H](N)C2)cc1NC1CCOCC1)c1cc(Sc2cc(F)cc(F)c2)cnc1N]
31
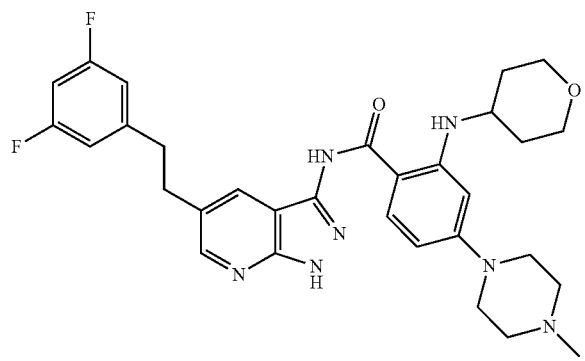 [SMILES: CN1CCN(c2ccc(C(=O)NC(=N)c3cc(CCc4cc(F)cc(F)c4)cnc3N)c(NC3CCOCC3)c2)CC1]
32
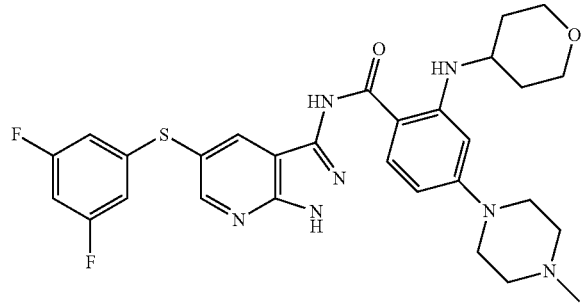 [SMILES: CN1CCN(c2ccc(C(=O)NC(=N)c3cc(Sc4cc(F)cc(F)c4)cnc3N)c(NC3CCOCC3)c2)CC1]
32-1
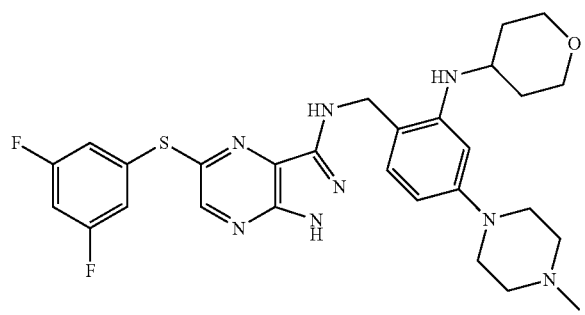 [SMILES: CN1CCN(c2ccc(CNC(=N)c3nc(Sc4cc(F)cc(F)c4)cnc3N)c(NC3CCOCC3)c2)CC1]

33
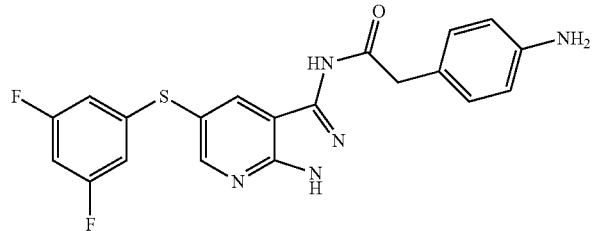
35
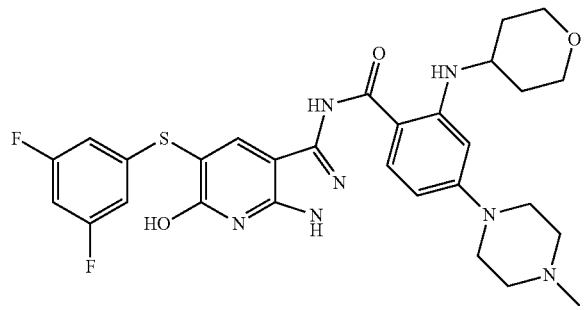 [SMILES: CN1CCN(c2ccc(C(=O)NC(=N)c3cc(Sc4cc(F)cc(F)c4)c(O)nc3N)c(NC3CCOCC3)c2)CC1]
26-12
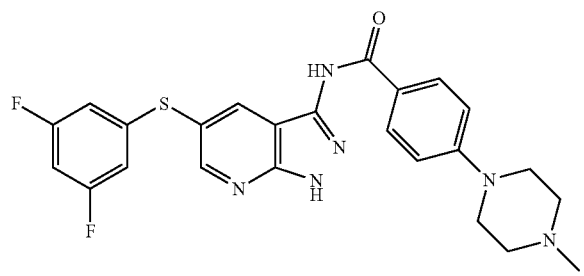 [SMILES: CN1CCN(c2ccc(C(=O)NC(=N)c3cc(Sc4cc(F)cc(F)c4)cnc3N)cc2)CC1]
30-69
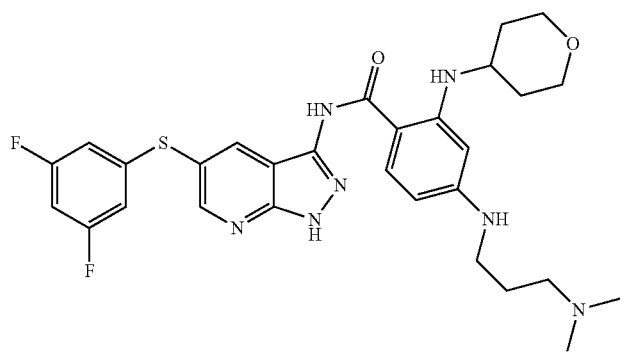 [SMILES: CN(C)CCCNc1ccc(C(=O)Nc2n[nH]c3ncc(Sc4cc(F)cc(F)c4)cc23)c(NC2CCOCC2)c1]
27-2
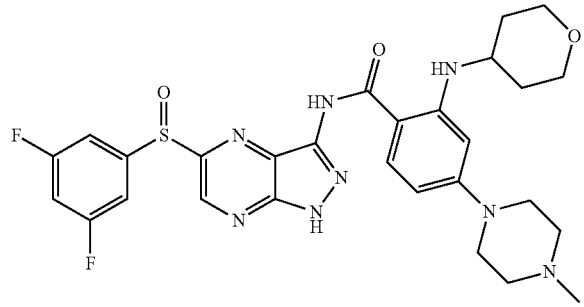 [SMILES: CN1CCN(c2ccc(C(=O)Nc3n[nH]c4ncc(S(=O)c5cc(F)cc(F)c5)nc34)c(NC3CCOCC3)c2)CC1]

27-3 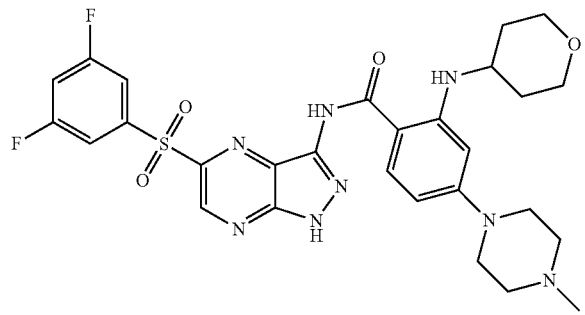 [SMILES: CN1CCN(c2ccc(C(=O)Nc3n[nH]c4ncc(S(=O)(=O)c5cc(F)cc(F)c5)nc34)c(NC3CCOCC3)c2)CC1]
27-4 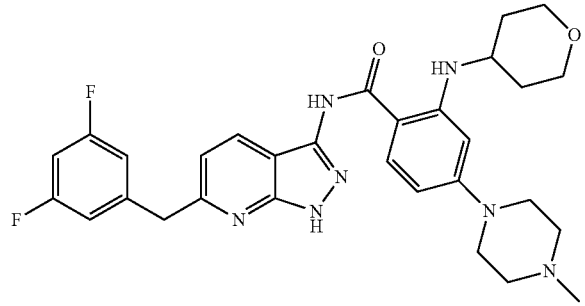 [SMILES: CN1CCN(c2ccc(C(=O)Nc3n[nH]c4nc(Cc5cc(F)cc(F)c5)ccc34)c(NC3CCOCC3)c2)CC1]
30-73 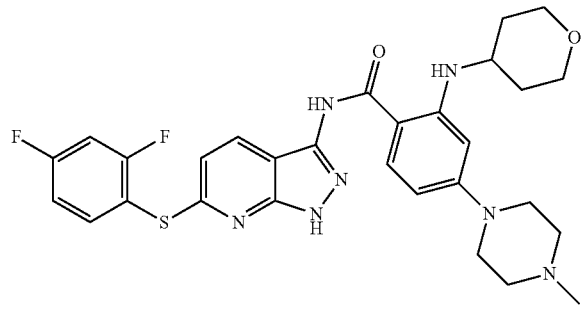 [SMILES: CN1CCN(c2ccc(C(=O)Nc3n[nH]c4nc(Sc5ccc(F)cc5F)ccc34)c(NC3CCOCC3)c2)CC1]
14bis 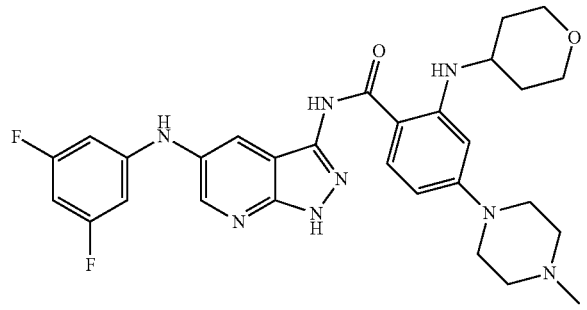 [SMILES: CN1CCN(c2ccc(C(=O)Nc3n[nH]c4ncc(Nc5cc(F)cc(F)c5)cc34)c(NC3CCOCC3)c2)CC1]
30-70 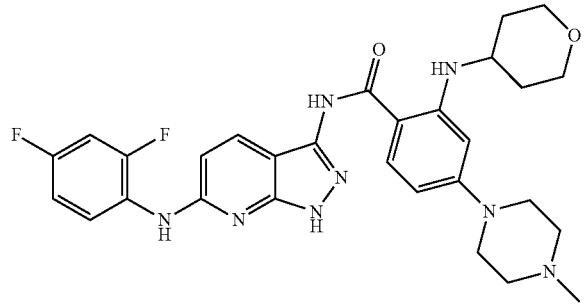 [SMILES: CN1CCN(c2ccc(C(=O)Nc3n[nH]c4nc(Nc5ccc(F)cc5F)ccc34)c(NC3CCOCC3)c2)CC1]

30-71
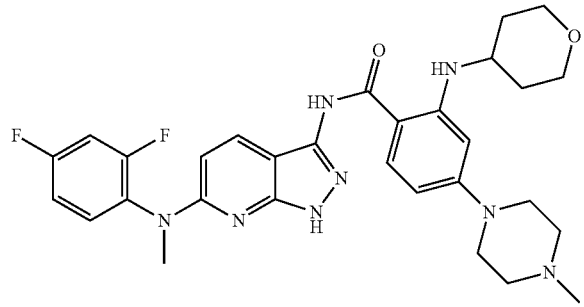 [SMILES: CN1CCN(c2ccc(C(=O)Nc3n[nH]c4nc(N(C)c5ccc(F)cc5F)ccc34)c(NC3CCOCC3)c2)CC1]
30-72
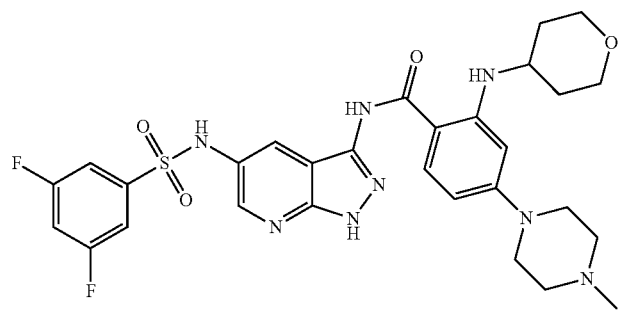 [SMILES: CN1CCN(c2ccc(C(=O)Nc3n[nH]c4ncc(NS(=O)(=O)c5cc(F)cc(F)c5)cc34)c(NC3CCOCC3)c2)CC1]
27-5
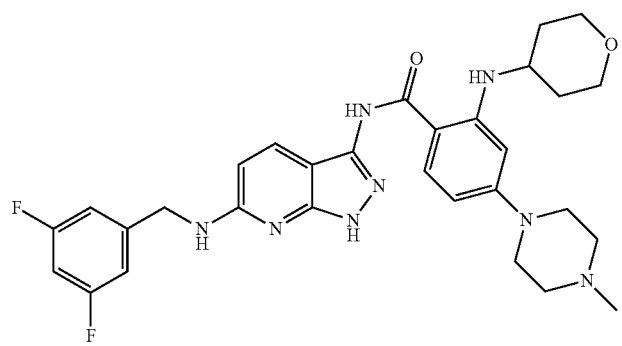 [SMILES: CN1CCN(c2ccc(C(=O)Nc3n[nH]c4nc(NCc5cc(F)cc(F)c5)ccc34)c(NC3CCOCC3)c2)CC1]
30-13
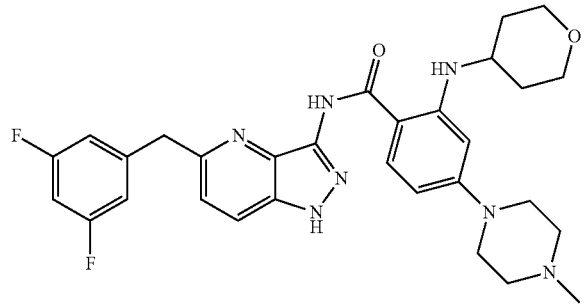
30-14
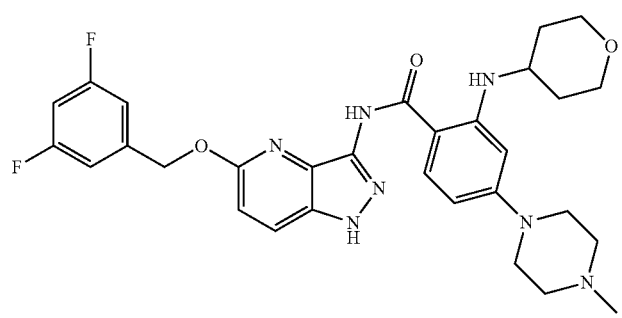

30-15 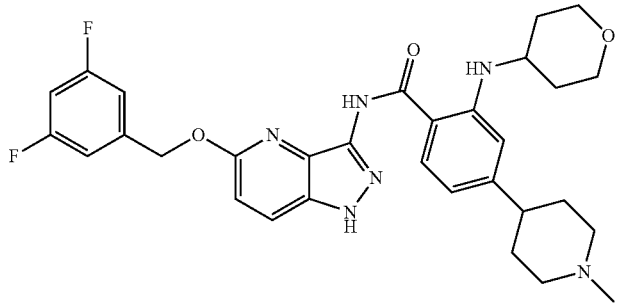 [SMILES: CN1CCC(c2ccc(C(=O)Nc3n[nH]c4ccc(OCc5cc(F)cc(F)c5)nc34)c(NC3CCOCC3)c2)CC1]
30-16 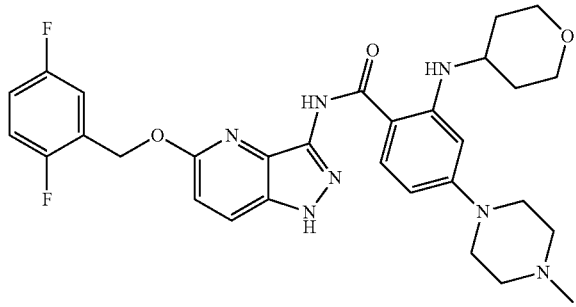 [SMILES: CN1CCN(c2ccc(C(=O)Nc3n[nH]c4ccc(OCc5cc(F)ccc5F)nc34)c(NC3CCOCC3)c2)CC1]
30-17 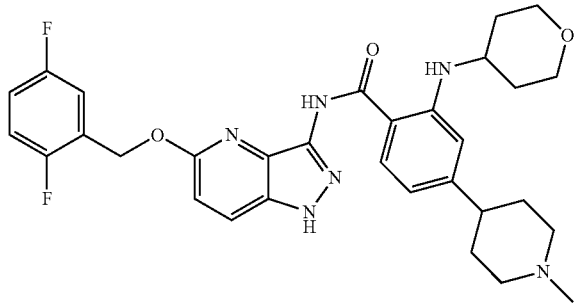
30-18 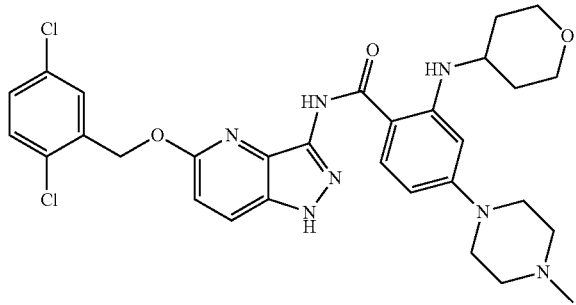 [SMILES: CN1CCN(c2ccc(C(=O)Nc3n[nH]c4ccc(OCc5cc(Cl)ccc5Cl)nc34)c(NC3CCOCC3)c2)CC1]
30-19 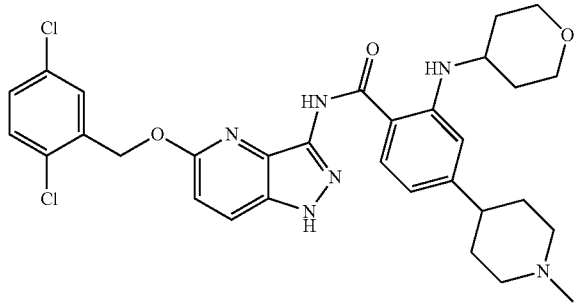 [SMILES: CN1CCC(c2ccc(C(=O)Nc3n[nH]c4ccc(OCc5cc(Cl)ccc5Cl)nc34)c(NC3CCOCC3)c2)CC1]

30-20 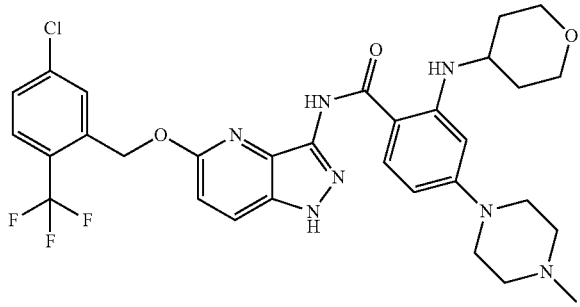 [SMILES: CN1CCN(c2ccc(C(=O)Nc3n[nH]c4ccc(OCc5cc(Cl)ccc5C(F)(F)F)nc34)c(NC3CCOCC3)c2)CC1]
30-21 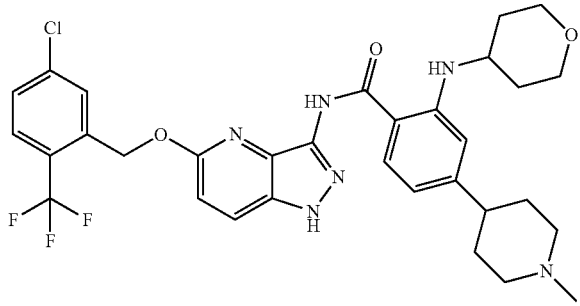 [SMILES: CN1CCC(c2ccc(C(=O)Nc3n[nH]c4ccc(OCc5cc(Cl)ccc5C(F)(F)F)nc34)c(NC3CCOCC3)c2)CC1]
30-22 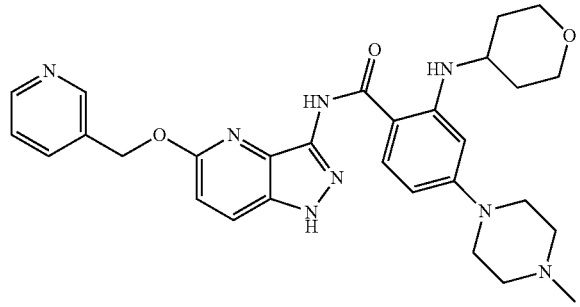
30-23 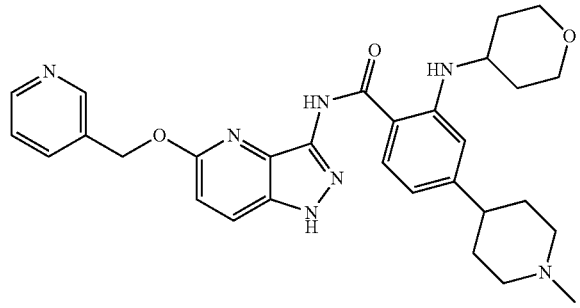 [SMILES: CN1CCC(c2ccc(C(=O)Nc3n[nH]c4ccc(OCc5cccnc5)nc34)c(NC3CCOCC3)c2)CC1]
30-24 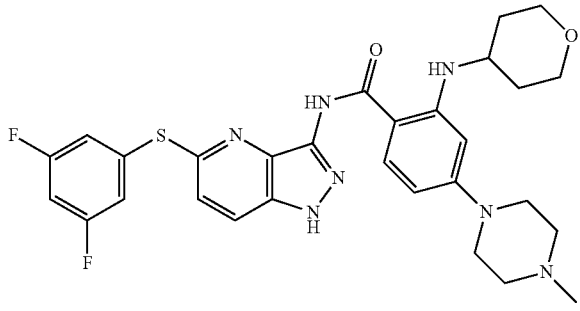 [SMILES: CN1CCN(c2ccc(C(=O)Nc3n[nH]c4ccc(Sc5cc(F)cc(F)c5)nc34)c(NC3CCOCC3)c2)CC1]

30-25
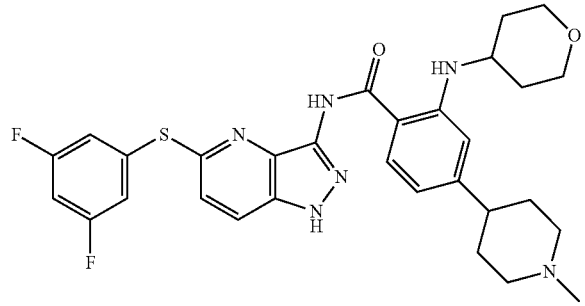 [SMILES: CN1CCC(c2ccc(C(=O)Nc3n[nH]c4ccc(Sc5cc(F)cc(F)c5)nc34)c(NC3CCOCC3)c2)CC1]
30-26
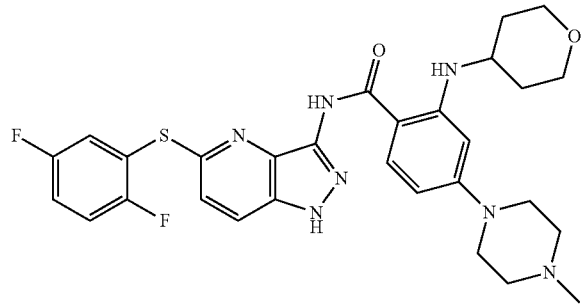 [SMILES: CN1CCN(c2ccc(C(=O)Nc3n[nH]c4ccc(Sc5cc(F)ccc5F)nc34)c(NC3CCOCC3)c2)CC1]
30-27
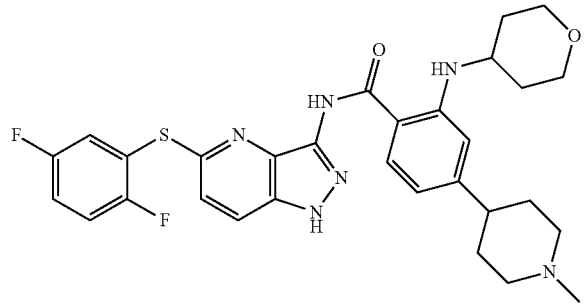 [SMILES: CN1CCC(c2ccc(C(=O)Nc3n[nH]c4ccc(Sc5cc(F)ccc5F)nc34)c(NC3CCOCC3)c2)CC1]
30-28
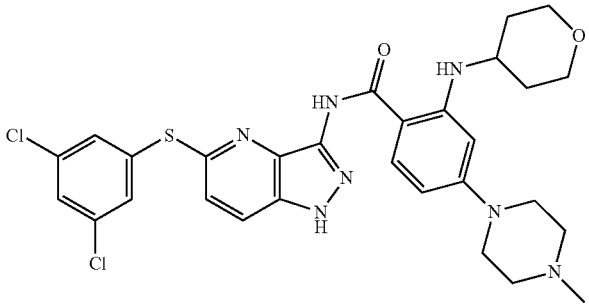 [SMILES: CN1CCN(c2ccc(C(=O)Nc3n[nH]c4ccc(Sc5cc(Cl)cc(Cl)c5)nc34)c(NC3CCOCC3)c2)CC1]
30-29
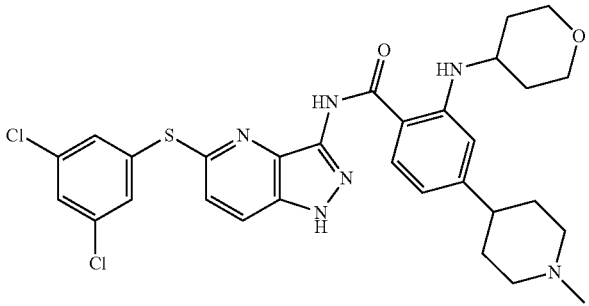 [SMILES: CN1CCC(c2ccc(C(=O)Nc3n[nH]c4ccc(Sc5cc(Cl)cc(Cl)c5)nc34)c(NC3CCOCC3)c2)CC1]

30-30 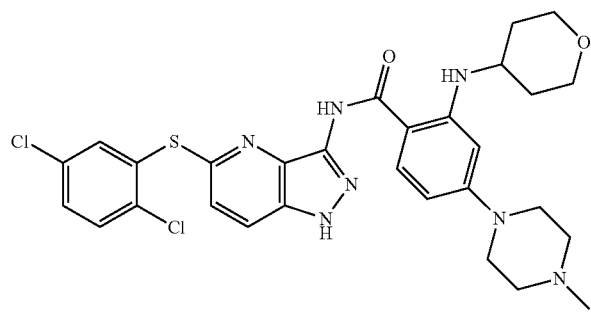 [SMILES: CN1CCN(c2ccc(C(=O)Nc3n[nH]c4ccc(Sc5cc(Cl)ccc5Cl)nc34)c(NC3CCOCC3)c2)CC1]
30-31 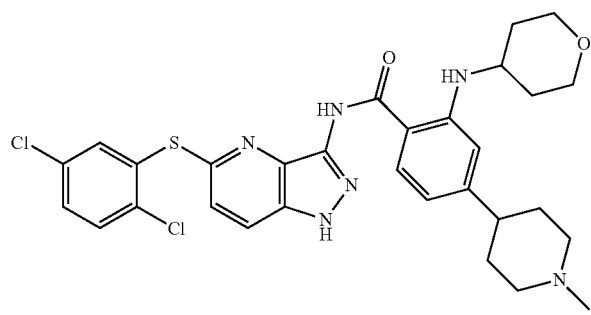 [SMILES: CN1CCC(c2ccc(C(=O)Nc3n[nH]c4ccc(Sc5cc(Cl)ccc5Cl)nc34)c(NC3CCOCC3)c2)CC1]
30-32 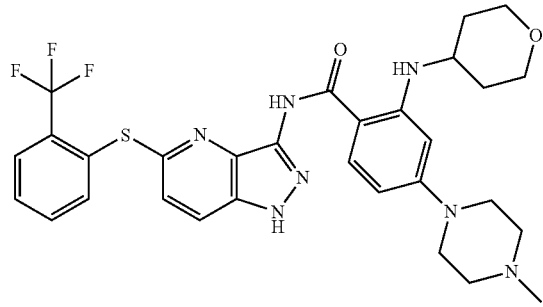 [SMILES: CN1CCN(c2ccc(C(=O)Nc3n[nH]c4ccc(Sc5ccccc5C(F)(F)F)nc34)c(NC3CCOCC3)c2)CC1]
30-33 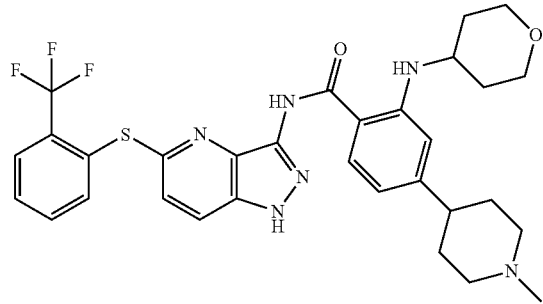 [SMILES: CN1CCC(c2ccc(C(=O)Nc3n[nH]c4ccc(Sc5ccccc5C(F)(F)F)nc34)c(NC3CCOCC3)c2)CC1]
30-34 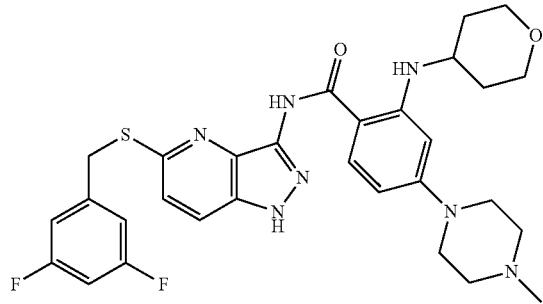 [SMILES: CN1CCN(c2ccc(C(=O)Nc3n[nH]c4ccc(SCc5cc(F)cc(F)c5)nc34)c(NC3CCOCC3)c2)CC1]

30-35 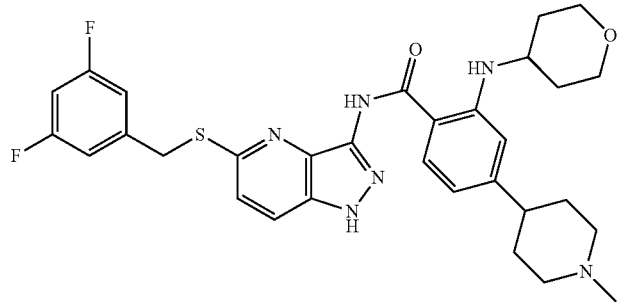 [SMILES: CN1CCC(c2ccc(C(=O)Nc3n[nH]c4ccc(SCc5cc(F)cc(F)c5)nc34)c(NC3CCOCC3)c2)CC1]
30-36 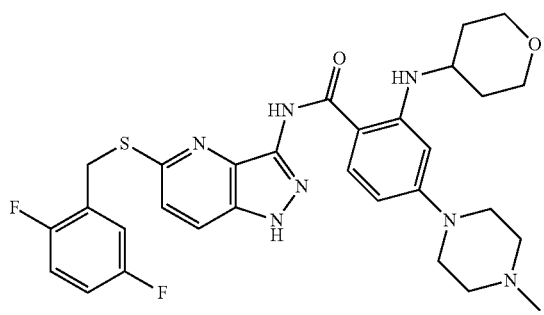 [SMILES: CN1CCN(c2ccc(C(=O)Nc3n[nH]c4ccc(SCc5cc(F)ccc5F)nc34)c(NC3CCOCC3)c2)CC1]
30-37 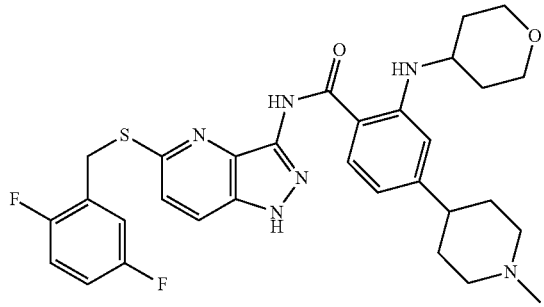 [SMILES: CN1CCC(c2ccc(C(=O)Nc3n[nH]c4ccc(SCc5cc(F)ccc5F)nc34)c(NC3CCOCC3)c2)CC1]
30-38 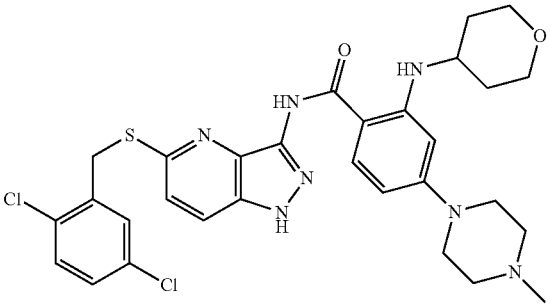 [SMILES: CN1CCN(c2ccc(C(=O)Nc3n[nH]c4ccc(SCc5cc(Cl)ccc5Cl)nc34)c(NC3CCOCC3)c2)CC1]
30-39 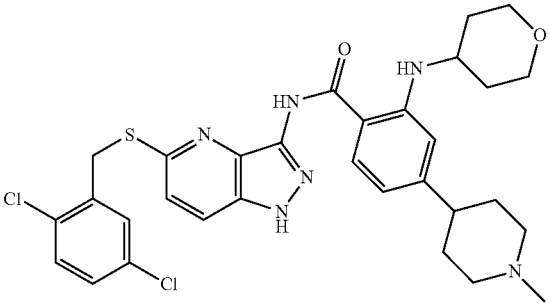

30-40
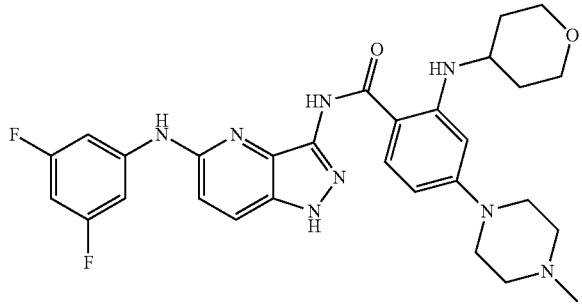 [SMILES: CN1CCN(c2ccc(C(=O)Nc3n[nH]c4ccc(Nc5cc(F)cc(F)c5)nc34)c(NC3CCOCC3)c2)CC1]
30-41
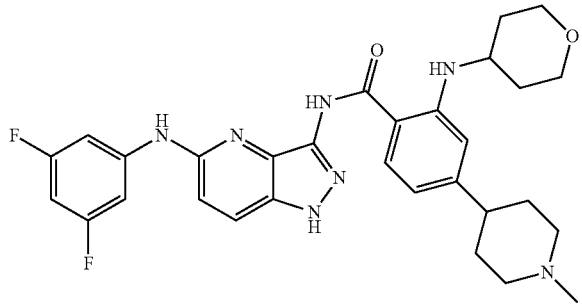
30-42
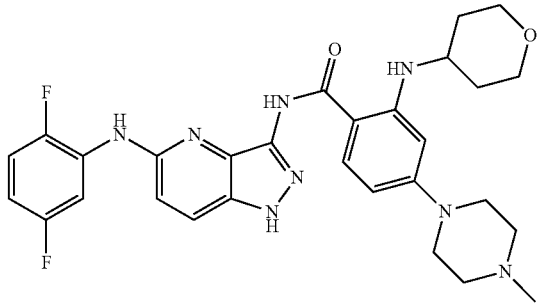
30-43
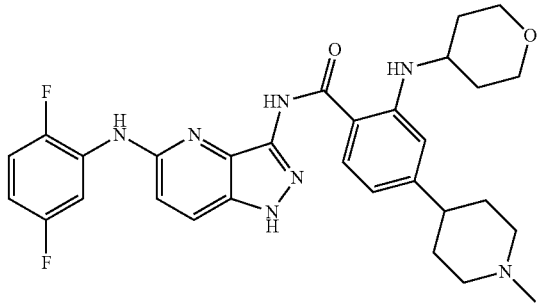 [SMILES: CN1CCN(c2ccc(C(=O)Nc3n[nH]c4ccc(Nc5cc(F)ccc5F)nc34)c(NC3CCOCC3)c2)CC1]
30-44
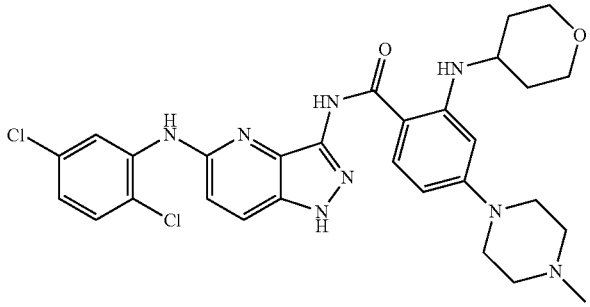 [SMILES: CN1CCN(c2ccc(C(=O)Nc3n[nH]c4ccc(Nc5cc(Cl)ccc5Cl)nc34)c(NC3CCOCC3)c2)CC1]

30-45
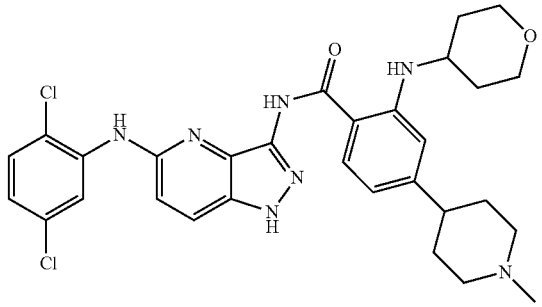
30-46
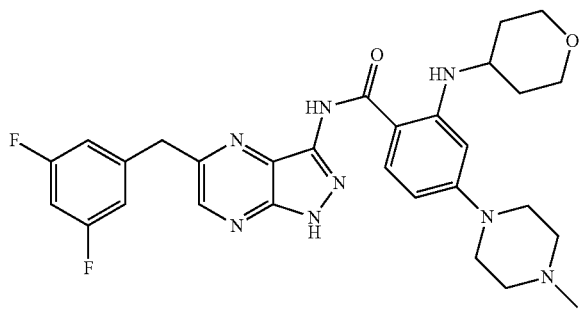
30-47
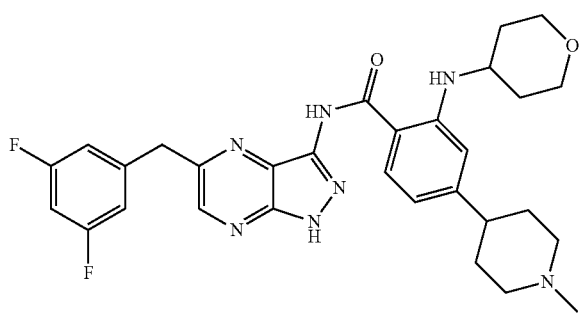
30-48
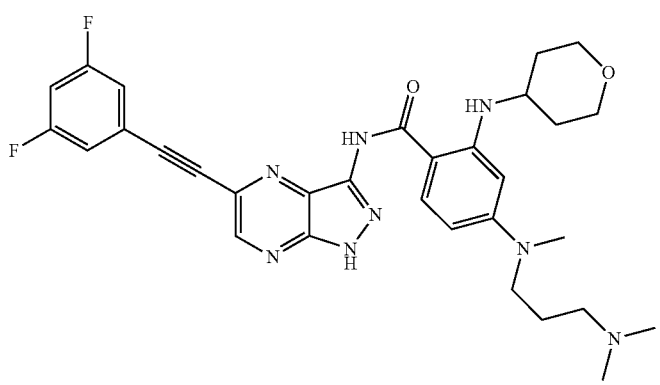 [SMILES: CN(C)CCCN(C)c1ccc(C(=O)Nc2n[nH]c3ncc(C#Cc4cc(F)cc(F)c4)nc23)c(NC2CCOCC2)c1]
30-49
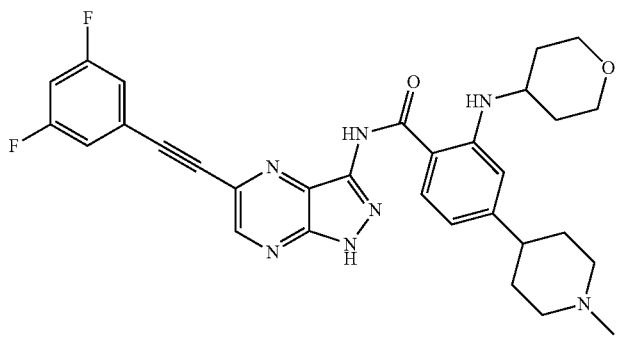 [SMILES: CN1CCC(c2ccc(C(=O)Nc3n[nH]c4ncc(C#Cc5cc(F)cc(F)c5)nc34)c(NC3CCOCC3)c2)CC1]

30-50
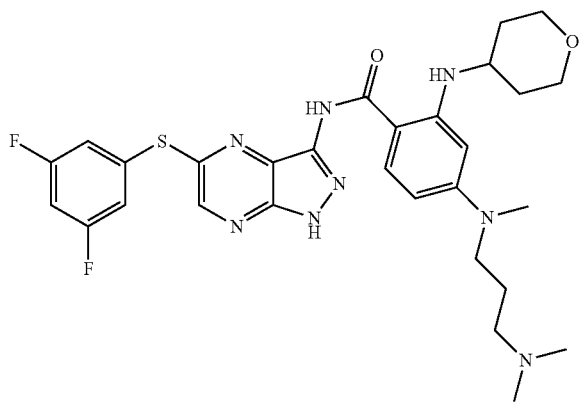 [SMILES: CN(C)CCCN(C)c1ccc(C(=O)Nc2n[nH]c3ncc(Sc4cc(F)cc(F)c4)nc23)c(NC2CCOCC2)c1]
30-51
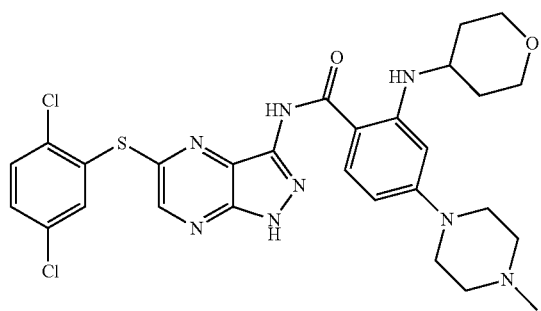 [SMILES: CN1CCN(c2ccc(C(=O)Nc3n[nH]c4ncc(Sc5cc(Cl)ccc5Cl)nc34)c(NC3CCOCC3)c2)CC1]
30-52
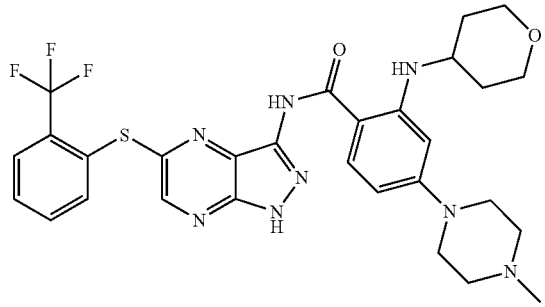 [SMILES: CN1CCN(c2ccc(C(=O)Nc3n[nH]c4ncc(Sc5ccccc5C(F)(F)F)nc34)c(NC3CCOCC3)c2)CC1]
30-53
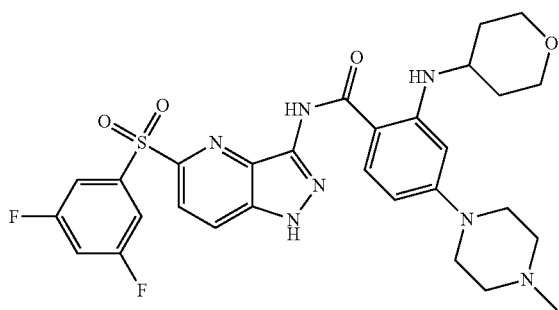 [SMILES: CN1CCN(c2ccc(C(=O)Nc3n[nH]c4ccc(S(=O)(=O)c5cc(F)cc(F)c5)nc34)c(NC3CCOCC3)c2)CC1]

30-54
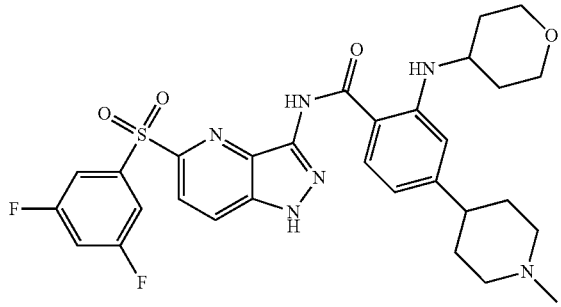
30-55
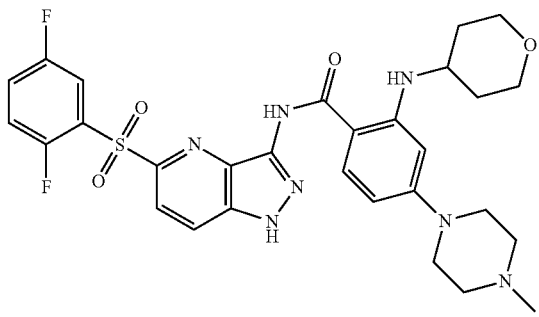 [SMILES: CN1CCN(c2ccc(C(=O)Nc3n[nH]c4ccc(S(=O)(=O)c5cc(F)ccc5F)nc34)c(NC3CCOCC3)c2)CC1]
30-56
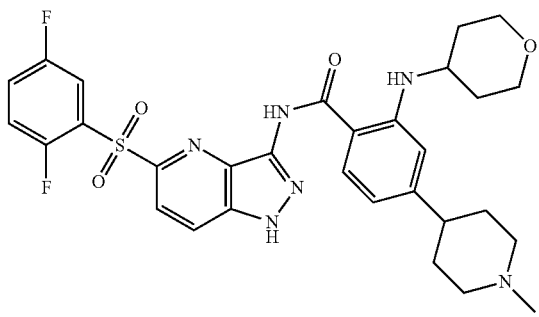 [SMILES: CN1CCC(c2ccc(C(=O)Nc3n[nH]c4ccc(S(=O)(=O)c5cc(F)ccc5F)nc34)c(NC3CCOCC3)c2)CC1]
30-57
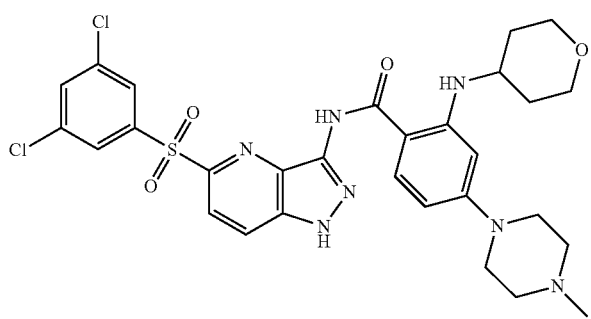 [SMILES: CN1CCN(c2ccc(C(=O)Nc3n[nH]c4ccc(S(=O)(=O)c5cc(Cl)cc(Cl)c5)nc34)c(NC3CCOCC3)c2)CC1]
30-58
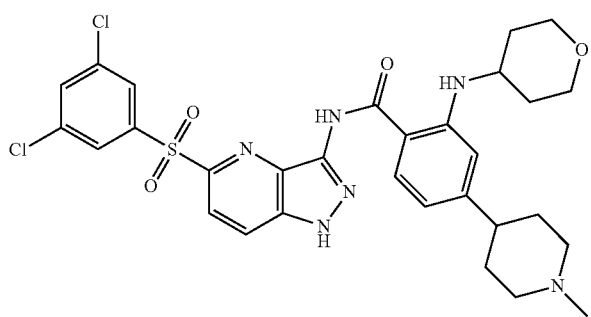 [SMILES: CN1CCC(c2ccc(C(=O)Nc3n[nH]c4ccc(S(=O)(=O)c5cc(Cl)cc(Cl)c5)nc34)c(NC3CCOCC3)c2)CC1]

-continued
39-59
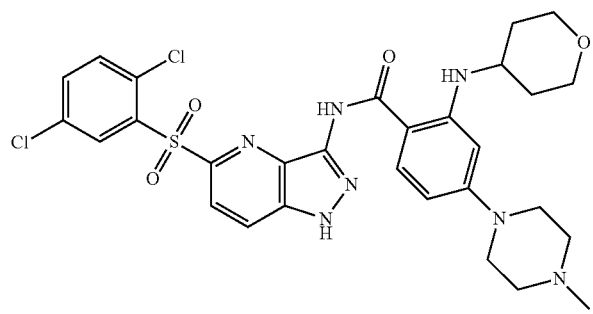 [SMILES: CN1CCN(c2ccc(C(=O)Nc3n[nH]c4ccc(S(=O)(=O)c5cc(Cl)ccc5Cl)nc34)c(NC3CCOCC3)c2)CC1]
30-60
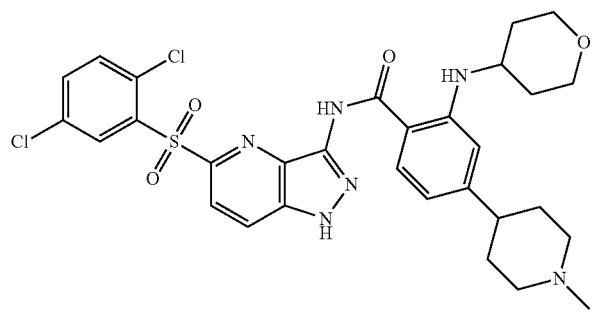
30-61
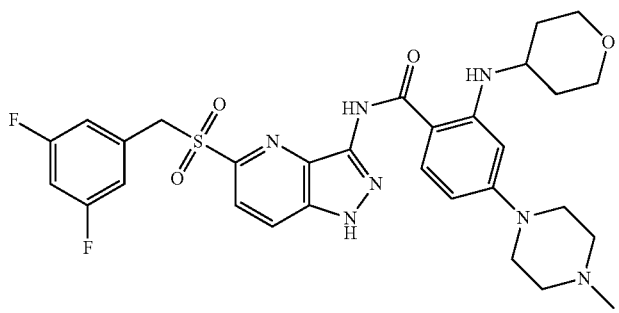 [SMILES: CN1CCN(c2ccc(C(=O)Nc3n[nH]c4ccc(S(=O)(=O)Cc5cc(F)cc(F)c5)nc34)c(NC3CCOCC3)c2)CC1]
30-62
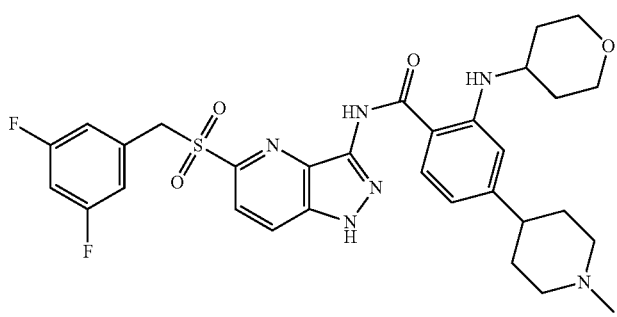 [SMILES: CN1CCC(c2ccc(C(=O)Nc3n[nH]c4ccc(S(=O)(=O)Cc5cc(F)cc(F)c5)nc34)c(NC3CCOCC3)c2)CC1]
30-63
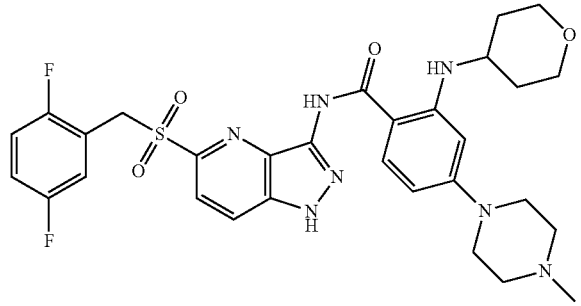 [SMILES: CN1CCN(c2ccc(C(=O)Nc3n[nH]c4ccc(S(=O)(=O)Cc5cc(F)ccc5F)nc34)c(NC3CCOCC3)c2)CC1]

30-64
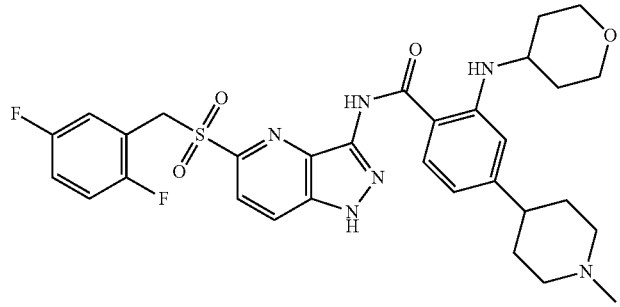 [SMILES: CN1CCC(c2ccc(C(=O)Nc3n[nH]c4ccc(S(=O)(=O)Cc5cc(F)ccc5F)nc34)c(NC3CCOCC3)c2)CC1]
30-65
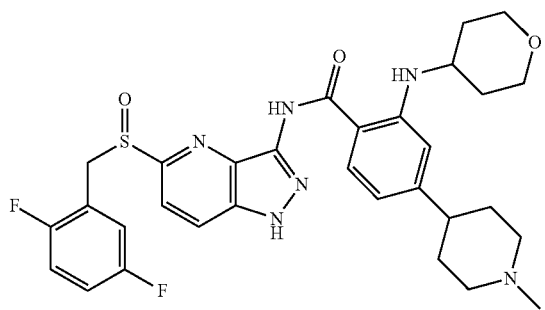 [SMILES: CN1CCC(c2ccc(C(=O)Nc3n[nH]c4ccc(S(=O)Cc5cc(F)ccc5F)nc34)c(NC3CCOCC3)c2)CC1]
30-66
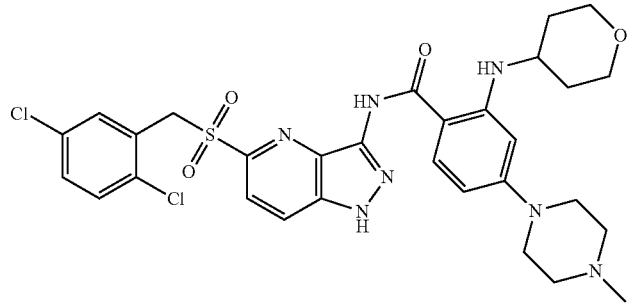 [SMILES: CN1CCN(c2ccc(C(=O)Nc3n[nH]c4ccc(S(=O)(=O)Cc5cc(Cl)ccc5Cl)nc34)c(NC3CCOCC3)c2)CC1]
30-67
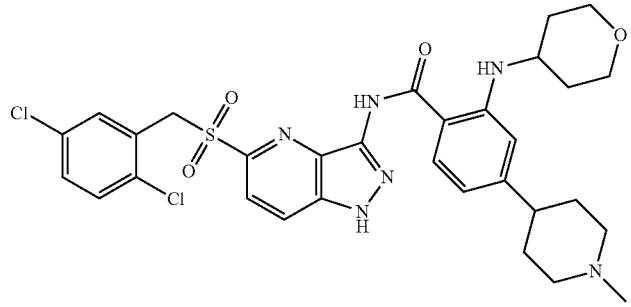
30-68
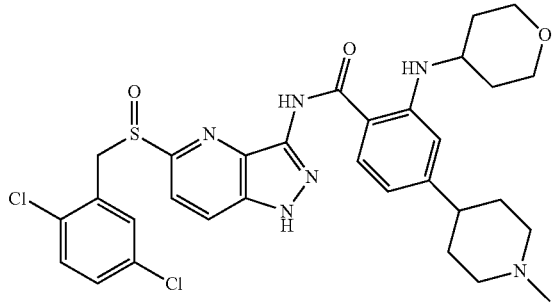 [SMILES: CN1CCC(c2ccc(C(=O)Nc3n[nH]c4ccc(S(=O)Cc5cc(Cl)ccc5Cl)nc34)c(NC3CCOCC3)c2)CC1]

31-1

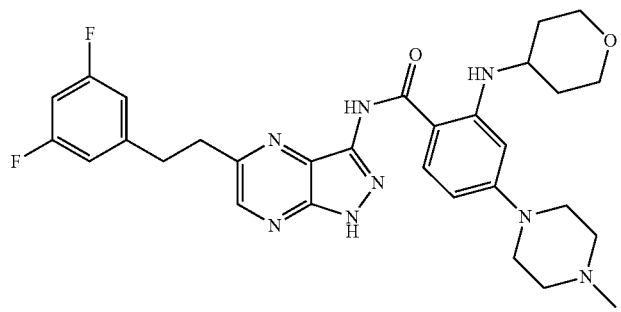 [SMILES: CN1CCN(c2ccc(C(=O)Nc3n[nH]c4ncc(CCc5cc(F)cc(F)c5)nc34)c(NC3CCOCC3)c2)CC1]

The present invention also relates to the use of a compound of formula (I) such as defined above, for the manufacture of a drug, notably intended for the treatment or prevention of pain, in particular pain associated with at least one Trk protein.

The present invention also relates to a method for the treatment or prevention of pain, in particular pain associated with at least one Trk protein comprising the administration to a person in need thereof of an effective dose of a compound of formula (I) such as defined above.

The present invention also relates to a pharmaceutical composition comprising at least one compound of formula (I) such as defined above, and at least one pharmaceutically acceptable excipient for use in the treatment or prevention of pain, in particular pain associated with at least one Trk protein.

The pharmaceutical compositions for use in the treatment or prevention of pain, in particular pain associated with at least one Trk protein according to the invention may be formulated notably for oral administration or for injection, wherein said compositions are intended for mammals, including humans.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

The pharmaceutical compositions for use in the treatment or prevention of pain, in particular pain associated with at least one Trk protein according to the invention may further comprise at least one other active ingredient, such as example an anticancer agent.

The present invention also has as an object a pharmaceutical composition for use in the treatment or prevention of pain, in particular pain associated with at least one Trk protein, comprising:
(i) at least one compound of formula (I) such as defined above, and
(ii) at least one other active ingredient, such as an anticancer agent,
as a combination product for simultaneous, separate or sequential use.

In the context of the invention, the term "treatment" means reversing or alleviating pain.

The term "pain" according to the invention means any kind of pain and in particular nociceptive pain, inflammatory pain, neuropathic pain, idiopathic pain or psychogenic pain, preferably inflammatory or neuropathic pain. The pain according to the invention can also be a combination of two or more of this kind of pains, for example a combination between an inflammatory and a nociceptive pain.

The pain according to the invention can be from any origin. In an embodiment the pain according to the invention is due to cancer, for example bone cancer. In another embodiment the pain according to the invention is due to a nerve injury, as occurs for example in neuropathic pain. In another embodiment, the pain according to the invention is due to an inflammatory state, as occurs for example in rheumatic diseases such as osteoarthritis, lower back pain, lumbar disc herniation and nerve root compression. In another embodiment, the pain according to the invention is associated with functional disorders such as, for instance, fibromyalgia.

According to the invention, "Trk protein" means any member of the Ttrk family, for example TrkA (in particular described in GenBank under the number AB019488), TrkB (in particular described in GenBank under the number AAB33109.1) and TrkC (in particular described in GenBank under the number CAA12029.1), preferentially TrkA.

The Trk protein according to the invention may be in its native form or in a modified form. By "a modified form" is intended a mutated form of the wild-type protein. The mutation may be a point mutation, it may also be a deletion or an insertion of one or more amino acids in the sequence of the Trk protein. Alternatively, the modified Trk protein according to the invention may be a fusion protein, for example obtained after a chromosomal re-arrangement. The modified Trk protein can also result from an alternative splicing.

By the expression "associated with at least one Trk protein" according to the invention, is intended to mean that the pain to be treated is relayed by signaling pathways going through one or more Trk proteins. In particular, the pain will be considered as associated with a Trk protein when it is an inflammatory or a neuropathic pain. The Trk signaling pathways are well known of the skilled person.

The compounds according to the invention have the property of inhibiting or modulating the enzymatic activity of one or more Trk proteins, preferably more than one Trk protein.

By inhibiting or modulating the activity of one or more Trk protein according to the invention, is intended to mean that the compound according to the invention is capable of modulating the activation of at least one Trk protein, which results in a decrease, possibly an inactivation of a Trk signal pathway, itself resulting in a decrease in the feeling of pain. The compounds according to the invention allow for example a reduction in Trk protein activity of more or about 5%, notably more or about 10%, in particular more or about 50%.

The compounds of formula (I) according to the present invention can be prepared by various methods notably summarized in diagrams 1a and 1b below.
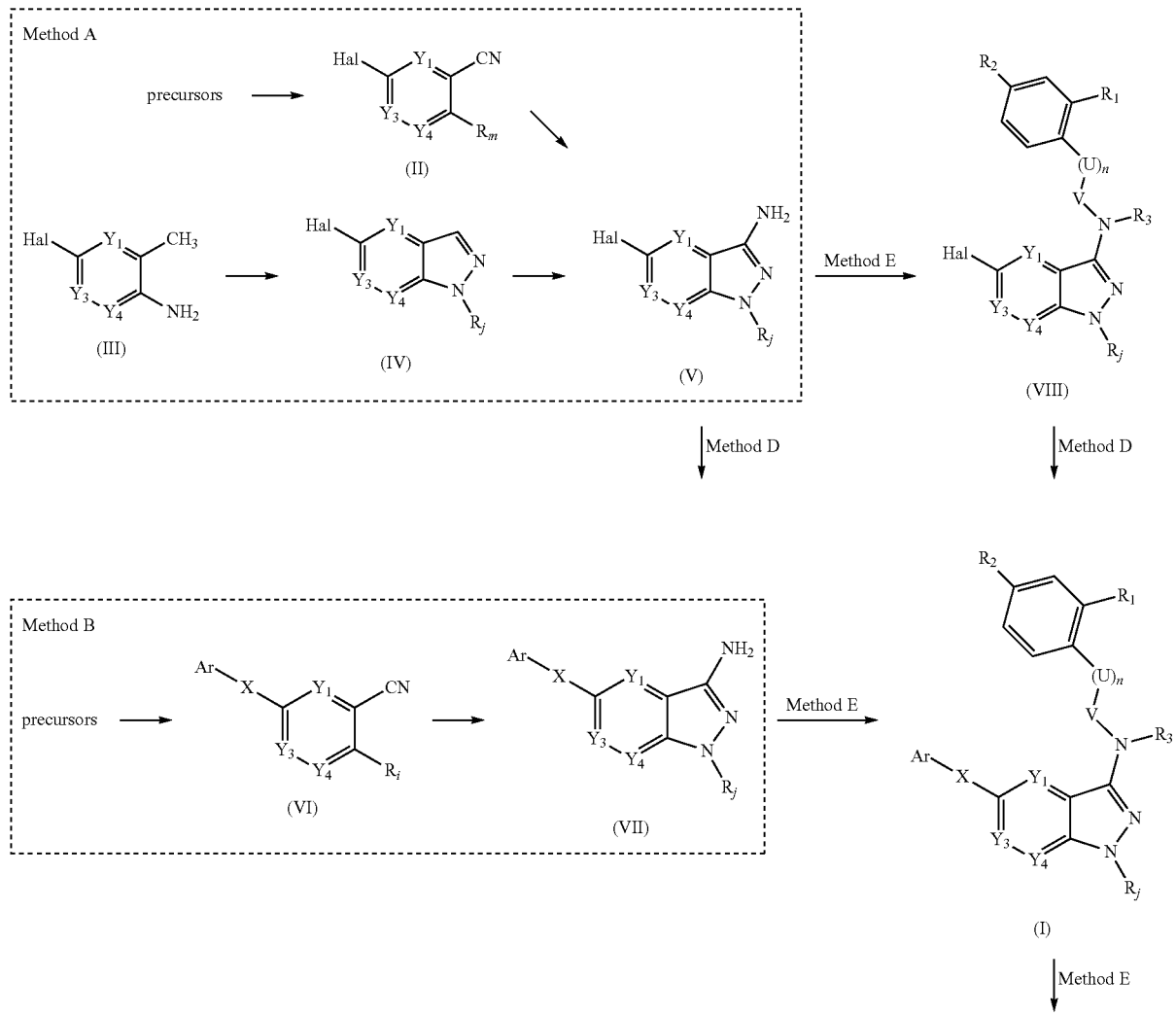
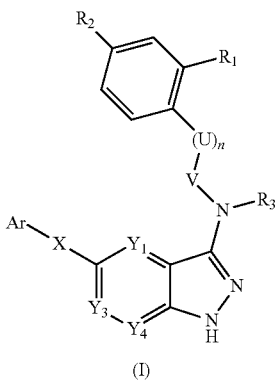
$R_j$ = H or N-protecting group
$R_m$ = Hal, OMe, SO2Me
$R_i$ = NO2, halogen, OH, OMe, SMe, S(O)Me, SO2Me, OMs, OTf or OTs

Diagram 1b

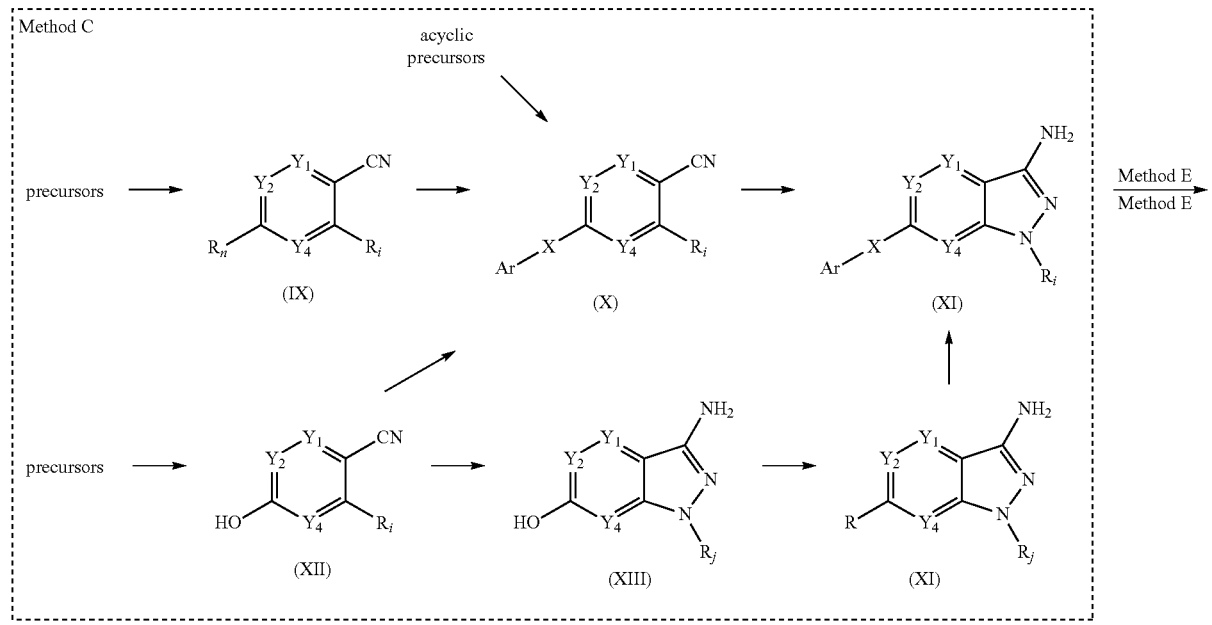

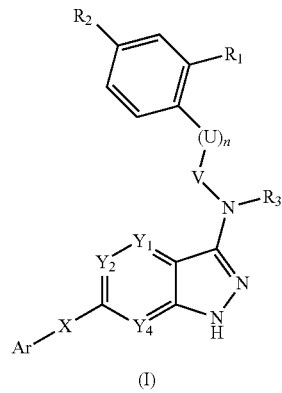

Ri = NO₂, halogen, OH, OMe, SMe, S(O)Me, SO₂Me, OMs, OTf or OTs
Rj = H or N-protecting group
Rn = Hal, OMs, OTs or OTf
(Tf represents an —SO₂CF₃ group and Ts represents a tosyl group

Method A:

According to method A, compounds of formula (I) are obtained by the preliminary synthesis of compounds of general formula (V) characterized by a halogenated heterobicyclic ring having an exocyclic primary amine. These compounds are obtained via the synthesis of intermediates of general formula (II) or (III).

Method A1:

Method A1, presented in diagram 2 (iodized compounds) or 3 (brominated compounds) below, describes the general process giving access to compounds of general formula (V) with W defined as in the description of general formula (I), and notably H, $(C_1\text{-}C_6)$alkyl or aryl, and $R_j$=H or N-protecting group.

Diagram 2

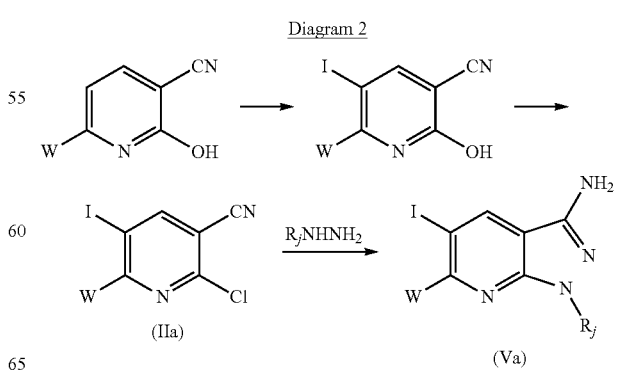

In the context of diagram 2, the optionally substituted 2-chloro-5-iodonicotinonitrile (IIa) is obtained from the corresponding hydroxynicotinonitrile by the successive use of an iodination agent such as N-iodosuccinimide (NIS), or molecular iodine with an inorganic base such as, for example, K$_2$CO$_3$ or Na$_2$CO$_3$, notably in a polar solvent such as hot DMF, followed by treatment with phosphorus oxychloride, pure or diluted in a high boiling-point non-polar solvent, or any other equivalent chlorination agent well known to the person skilled in the art. Reaction temperatures are between −20° C. and 200° C. The compound (IIa) thus obtained is then transformed into optionally substituted 5-iodo-pyrazolo[3,4-b]pyridine-3-amine (Va) by its reaction, preferably under heat, in the presence of a hydrazine optionally carrying an N-protecting group such as trityl, tert-butyl or BOC.

The brominated analogues of general formula (V) as described in diagram 1a may be obtained by the use of the method described in the following references: Witherington et al., Bioorg. Med. Chem. Lett., 2003, 13, 1577-1580 and Lijuan Chen et al., Bioorg. Med. Chem. Lett., 2010, 20, 4273-4278. For reasons of convenience, these molecules were obtained by the use of the reaction sequence presented in following diagram 3.

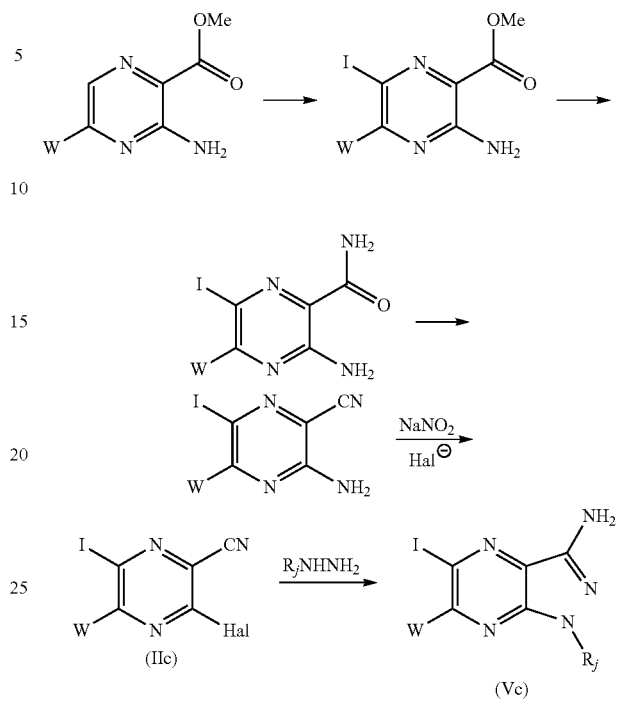

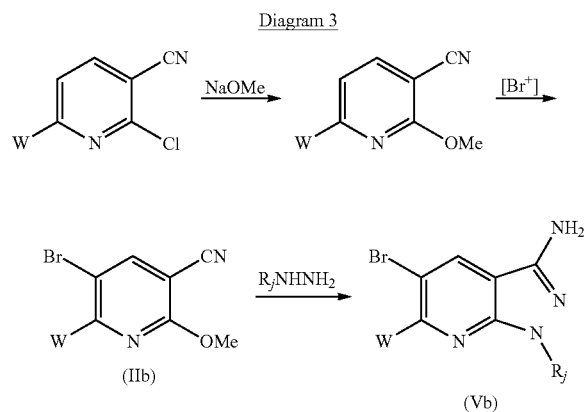

The optionally functionalized 2-methoxy-nicotinotrile is obtained, for example, by reaction of sodium methanolate in methanol at a temperature between −20° C. and the boiling point of the mixture. Alternatively, this compound may be obtained by methylation of 2-hydroxynicotinonitrile or other methods described above. Bromination of 2-methoxy-nicotinonitrile is typically carried out with dibromine in acetic acid at a temperature varying between 20° C. and 110° C. Formation of the pyrazole is typically carried out by reaction of an excess of hydrazine, functionalized or not, at a temperature varying between 20° C. and 100° C. in the presence of a polar solvent such as water, ethanol, tetrahydrofuran (THF) or any other solvent with comparable properties. Alternatively, the use of hydrazine in a saline or hydrated form, without solvent, is also possible.

Method A2:

Method A2 relates to the synthesis of the functionalized pyrazolopyrazines presented in diagram 4 below with R$_j$=H or N-protecting group, Hal=halogen and in particular W=H, (C$_1$-C$_6$)alkyl or aryl.

The optionally functionalized 3-amino-6-iodopyrazine-2-carboxamides are typically obtained in two steps from the corresponding methyl 3-aminopyrazine-2-carboxylates by iodination in the presence of N-iodosuccinimide or molecular iodine optionally in the presence of a cofactor such as KIO$_3$, AgCO$_2$CF$_3$, Ag$_2$SO$_4$, AlCl$_3$, CuCl$_2$ or HgO, followed by a conversion reaction of the methyl ester function into carboxamide, notably by the use of ammonia in a polar solvent such as water, methanol or THF at temperatures varying between 0° C. and 100° C. The carboxamide function of the optionally functionalized 3-amino-6-iodopyrazine-2-carboxamide is then converted into nitrile by the use of dehydration agents such as, in particular, CCl$_4$/PPh$_3$, SOCl$_2$, PhSO$_2$Cl, P$_2$O$_5$, TsCl, COCl$_2$, DCC/py (N,N'-dicyclohexylcarbodiimide/pyridine) or (COCl)$_2$ used as the case may be in the presence of an organic base such as pyridine. The preferred method involves the use of phosphorus oxychloride in dimethylformamide (DMF). Deprotection of the dimethylformimidamide function is carried out by treatment with acid such as aqueous hydrochloric acid or any other reagent with equivalent properties. Formation of the pyrazole ring is carried out by a Sandmeyer reaction, well known to the person skilled in the art, followed by a reaction in the presence of a hydrazine, functionalized or not, under conditions as described in the methods above. Alternatively, the diazonium salt, an intermediate of the Sandmeyer reaction, may be reduced by the use, for example, of tin chloride in an acid medium or any other equivalent agent, in order to form a hydrazine function that can undergo intramolecular cyclization under the effect of heat.

Method A3:

Method A3 aims at obtaining derivatives of general formula (V) featuring a variable function in position 6 of the pyrazolopyridine bicycle. It is detailed in diagram 5 below.

Diagram 5

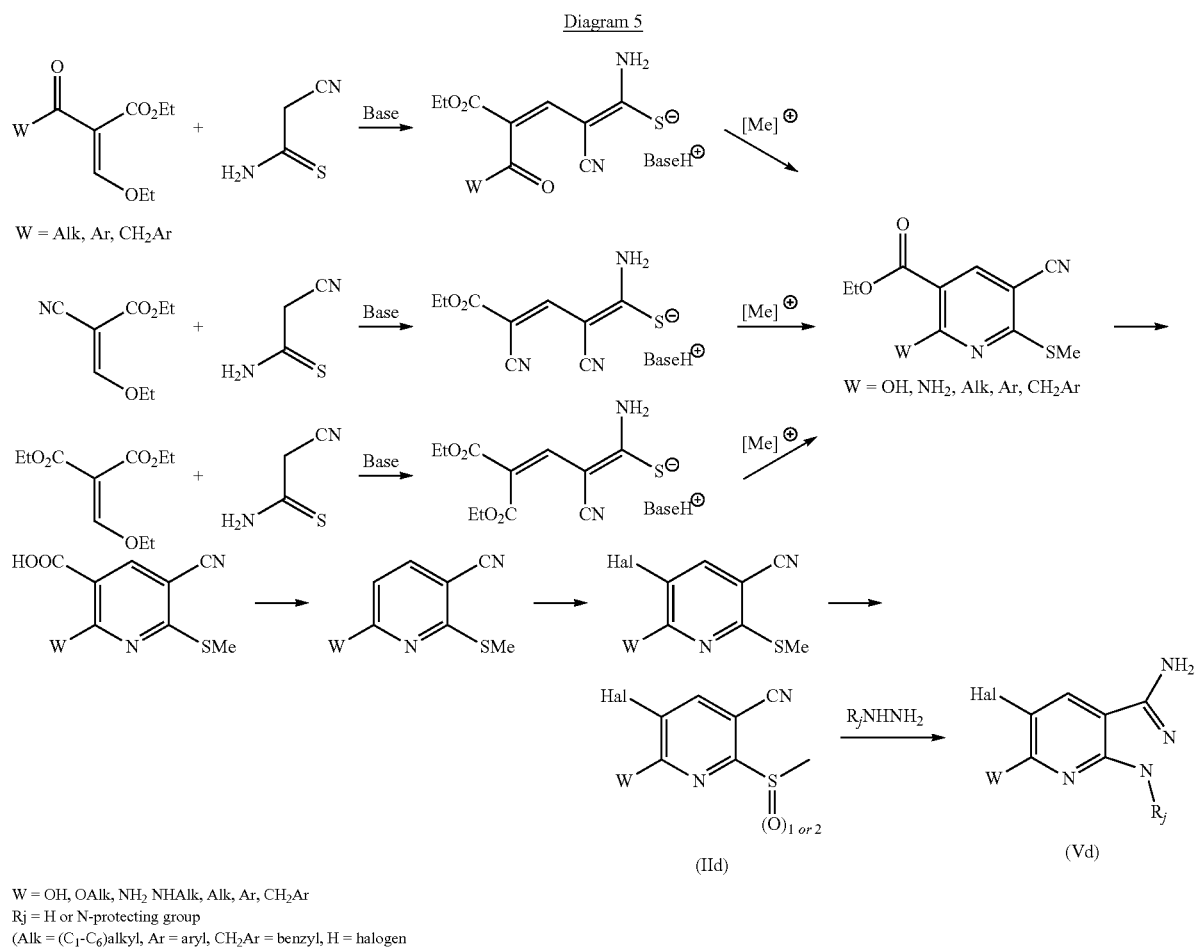

W = OH, OAlk, NH$_2$ NHAlk, Alk, Ar, CH$_2$Ar
Rj = H or N-protecting group
(Alk = (C$_1$-C$_6$)alkyl, Ar = aryl, CH$_2$Ar = benzyl, H = halogen Reaction of the cyanothioacetamide with ethyl 3-ethoxyacrilates variously substituted according to methods described notably by Litrivnor et al. in Russ. Chem. Bull., 1999, 48(1), 195-196 and Tsann-Long Su et al. in J. Med. Chem., 1988, 31, 1209-1215 make it possible to yield access, in two steps, to ethyl 5-cyano-6-(methylthio)nicotinates carrying a variable functionality in position 2. These syntheses are typically carried out, for the first step, in an anhydrous polar solvent such as, for example, ethanol at a temperature ranging between 0° C. and 70° C. in the presence of an organic base such as methylmorpholine, triethylamine, DIPEA (N,N-diisopropylethylamine) or DBU (1,8-diazabicyclo[5,4,0]undec-7-ene). The second step of intramolecular cyclization and of alkylation is typically carried out by the heating to a temperature ranging between 20° C. and 100° C. of a solution of the intermediate thioamidate in a polar solvent, for example ethanol in the presence of a suitable alkylating agent such as alkyl halide or dialkyl sulfate.

The 5-cyano-6-(methylthio)nicotinic acids substituted in position 2 are typically obtained by saponification of the corresponding ethyl esters according to methods well known to the person skilled in the art, notably by the use of hot lithium hydroxide. Decarboxylation of these compounds is carried out by heat treatment in a high boiling-point solvent such as diphenylether at a temperature ranging between 150° C. and 250° C.

Halogenation reactions principally aim at obtaining iodinated, brominated or chlorinated derivatives, more particularly iodinated derivatives. The latter are typically obtained by a molecular iodine treatment in the presence of a silver salt such as, for example, Ag$_2$SO$_4$ in a polar solvent such as ethanol at a temperature ranging between 0° C. and 70° C. Alternative methods, notably those based on other salts such as KIO$_3$, AgCO$_2$CF$_3$, AlCl$_3$, CuCl$_2$ or HgO, or other iodination agents such as N-iodosuccinimide, are also considered. The conceivable bromination methods typically rely on agents such as N-bromosuccinimide or dibromine according to methods well known to the person skilled in the art.

In the case in which W=OH (typically resulting from the use of diethyl 2-(ethoxymethylene)malonate), the corresponding compounds are protected by an alkylation reaction. This reaction is notably carried out by the use of methyl iodide or bromomethane, and silver carbonate in dioxane, THF, acetonitrile or acetone, or any other equivalent agent such as dimethylsulfate. The 5-halo-2-(methylthio) nicotinonitriles obtained are subjected to oxidation of their thiomethoxy function, typically by the use of m-CPBA (m-chloroperbenzoic acid), oxone or any other equivalent agent, to lead to the formation of the corresponding sulfoxide. These compounds, which may contain variable quantities of the corresponding sulfone, are engaged in a reaction in the presence of an optionally substituted hydrazine to form the corresponding 5-halogeno-pyrazolo[3,4-b]pyridin-3-amine carrying a variable functionality in position 6.

Method A4:

Method A4 aims at obtaining derivatives of general formula (V) from the compounds of general formula (III) via intermediate formation of compounds of formula (IV). These compounds are typically obtained by the pathway presented in diagram 6. The following references illustrate the method used: Gueiffier et al. Heterocycles, 1999, 51(7), 1661-1667; Gui-Dong Zhu et al. Bioorg. Med. Chem., 2007, 15, 2441-2452.

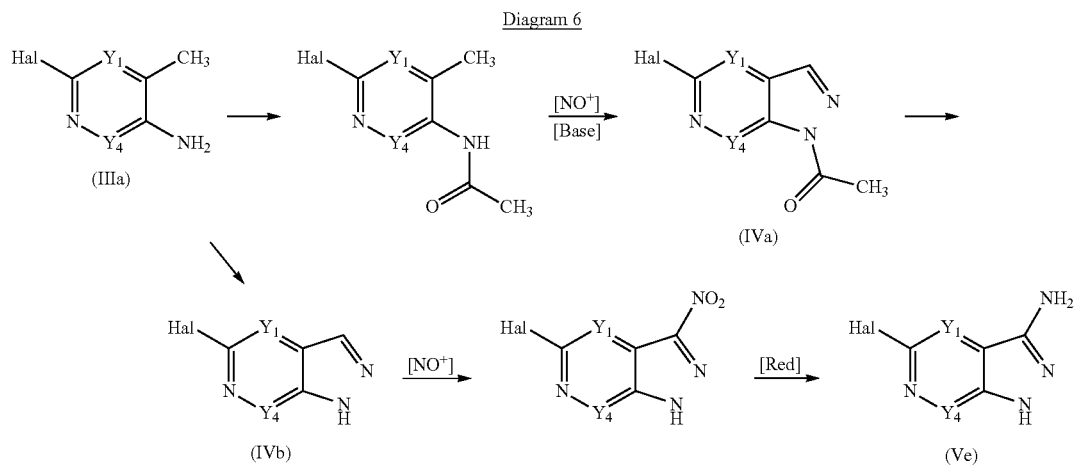

The compounds of general formula (IIIa), acetylated beforehand by one or another of the methods well known to the person skilled in the art, are subjected to the action of isoamyl nitrite, sodium nitrite or any other equivalent organic or inorganic nitrite, in water or acetic acid, for periods typically varying from 1 to 3 days at temperatures varying between 0° C. and 40° C. The compounds of general formula (IVa) thus obtained are deprotected in acidic conditions, for example by the use of hydrochloric acid, before being subjected to the action of nitration agents such as concentrated nitric acid or potassium nitrate in sulfuric acid at temperatures varying between 0° C. and 25° C.

It should be noted that the direct conversion of compounds of general formula (IIIa) into deprotected compounds (IVb) is possible in general.

The nitropyrazoles thus obtained are typically reduced into aminopyrazoles of general formula (Ve) by the use of $SnCl_2$ in hydrochloric acid. Alternative methods include the use of iron, zinc or tin in acidic conditions and methods of catalytic hydrogenation in the presence of complexes of platinum, nickel or Pd/C under an atmosphere of hydrogen or in the presence of equivalent agents such as cyclohexadiene, cyclohexene, sodium borohydride or hydrazine.

Method B:

According to method B, the compounds of formula (I) are obtained by the preliminary synthesis of compounds of general formula (VI) characterized by a functionalized heterobicyclic ring possessing an exocyclic amine. These compounds are obtained via the synthesis of intermediates of general formula (VI).

Method B1:

Method B1 is represented in diagram 7 below, with W notably representing H, $(C_1-C_6)$alkyl, aryl or benzyl.

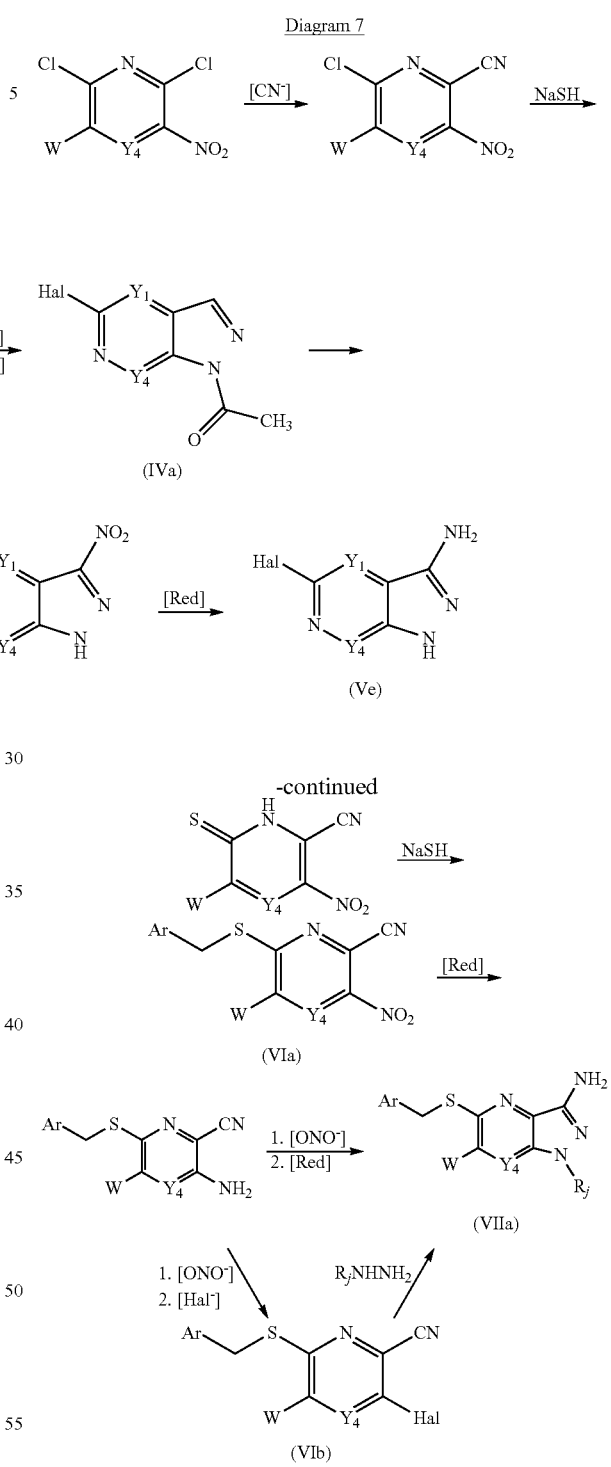

The 3-nitro-6-thioxo-1,6-dihydropyridin-2-carbonitrile and 3-nitro-6-thioxo-1,6-dihydropyrazine-2-carbonitrile derivatives, optionally functionalized in position 5, are typically obtained from the corresponding 2,6-dichloro-3-nitropyridines or 2,6-dichloro-3-nitropyrazines by the successive reactions of a cyanide salt, such as copper cyanide, in a high boiling-point polar solvent such as N-methylpyrrolidone at temperatures ranging between 100° C. and 200° C.; followed by the reaction of aqueous sodium hydrosulfite in a polar solvent. These compounds are then alkylated, for example by the use of a substituted benzyl bromide, in basic medium, according to methods well known to the person skilled in the art. The preferred protocol includes the use of an aprotic and anhydrous polar solvent such as acetone carrid at its boiling point and an organic base such as pyridine, triethylamine or DIPEA, or an inorganic base such as sodium, potassium or calcium carbonate. Reactions for reducing the nitro function in amine are preferentially carried out by the use of $SnCl_2$ in hydrochloric acid. Alternative methods include the use of iron, zinc or tin in acidic conditions and methods of catalytic hydrogenation in the presence of complexes of platinum, nickel or Pd/C under an atmosphere of hydrogen or in the presence of equivalent agents such as cyclohexadiene, cyclohexene, sodium borohydride or hydrazine.

In certain cases, the product of the reduction reaction, in addition to having a primary amine, has a carboxamide function resulting from hydrolysis of the nitrile function. In this case, isolation of the corresponding 3-aminopicolinonitriles or 3-aminopyrazine-2-carbonitriles may be carried out by dehydration of the carboxamide into nitrile via the use of phosphorus oxychloride in the presence of DMF or any other method well known to the person skilled in the art. Lastly, formation of the aminopyrazole ring is carried out preferentially by the formation of a diazonium, obtained by the successive reaction at low temperature of isoamyl nitrite, sodium nitrite or any other equivalent organic or inorganic nitrite, in water, hydrochloric acid, acetic acid or sulfuric acid, at temperatures varying between 0° C. and 20° C., followed by its reduction into hydrazine and intramolecular cyclization activated by heating of the reaction medium. The reduction reaction is preferentially carried out with tin chloride in acidic conditions but may also be carried out by catalytic hydrogenation or any other method well known to the person skilled in the art. In an alternative to this last step, it is conceivable that the intermediate diazonium undergoes a Sandmeyer reaction during which this functional group is substituted by a halogen atom, such as iodine, by the reaction of an adequate salt, such as NaI. If this option is preferred, formation of the aminopyrazole ring is carried out by the use of a hydrazine, functionalized or not, in a polar solvent such as ethanol at temperatures varying between 25° C. and 150° C.

Method B2:

Alternatively, it is possible to take advantage of an aromatic nucleophilic substitution reaction to functionalize the pyridine or pyrazine ring in position 6. In this case the nucleophiles used are phenols, thiophenols, benzyl alcohols or thiobenzyl alcohols as well as anilines or benzylamines, functionalized or not. The general reaction diagram 8a is presented below, notably with W=H, $(C_1-C_6)$alkyl, aryl or benzyl.

Diagram 8a

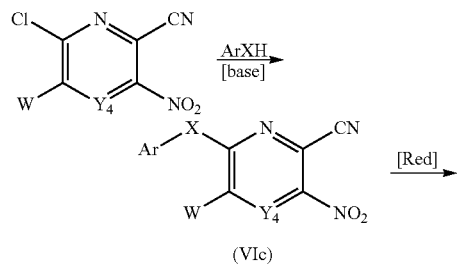

(VIc)

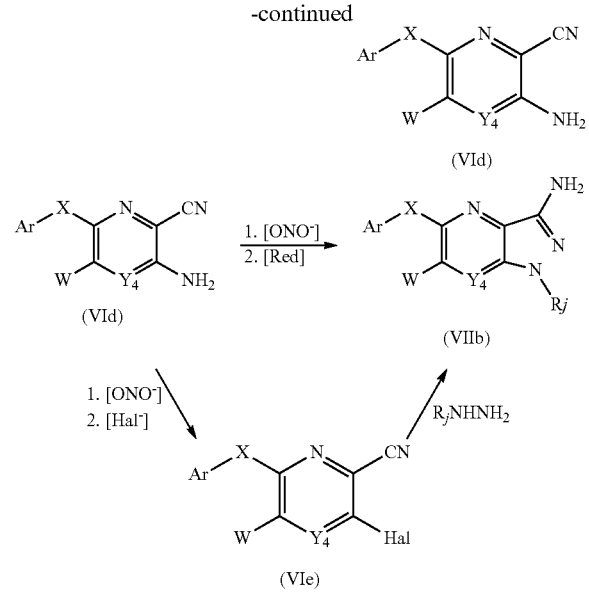

In the case in which X=O or S, the 6-chloro-3-nitropicolinonitriles and 6-chloro-3-nitropyrazine-2-carbonitriles, optionally substituted in position 5, are reacted in the presence of the suitable nucleophile, alcohol or thiol, in a polar solvent such as acetonitrile in the presence of an inorganic base such as potassium or sodium carbonate. Solvents such as DMSO (dimethylsulfoxide), DMF (dimethylformamide), acetone, THF (tetrahydrofuran) or pyridine may also be considered. If necessary, these reactions may be catalyzed by the action of copper and may also be carried out without solvent. Typically, the preferred protocol involves temperatures ranging between 20° C. and 150° C.

Alternatively, the use of bases such as pyridine, DIPEA, diisopropylamine, triethylamine, DBU, potassium tert-butylate, $NEt_3$ or NaH is also possible.

In the case in which X=N, toluene is a preferred solvent and triethylamine (NEt3) the base of choice.

The following steps, up to the compounds of general formula (VIIb), are identical to those documented in method B1 above.

Method B3:

Method B3, presented in diagram 8b below, is a variant of method B2 characterized by a first step resulting from a catalytic coupling reaction between a benzyl boronate, in acid or ester form, and a 6-chloro-3-nitropicolinonitrile or 6-chloro-3-nitropyrazine-2-carbonitrile derivative. It is also well known to the person skilled in the art that catalytic coupling reactions using alternative catalysts and benzyl derivatives are also possible. Among these, the Stille reaction, based on tin complexes, or those based on organozinc compounds may be considered.

Diagram 8b

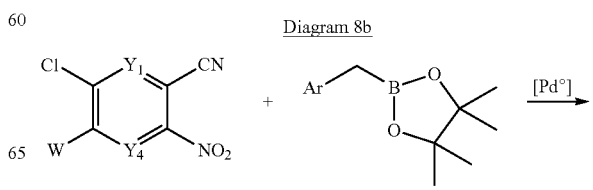

-continued

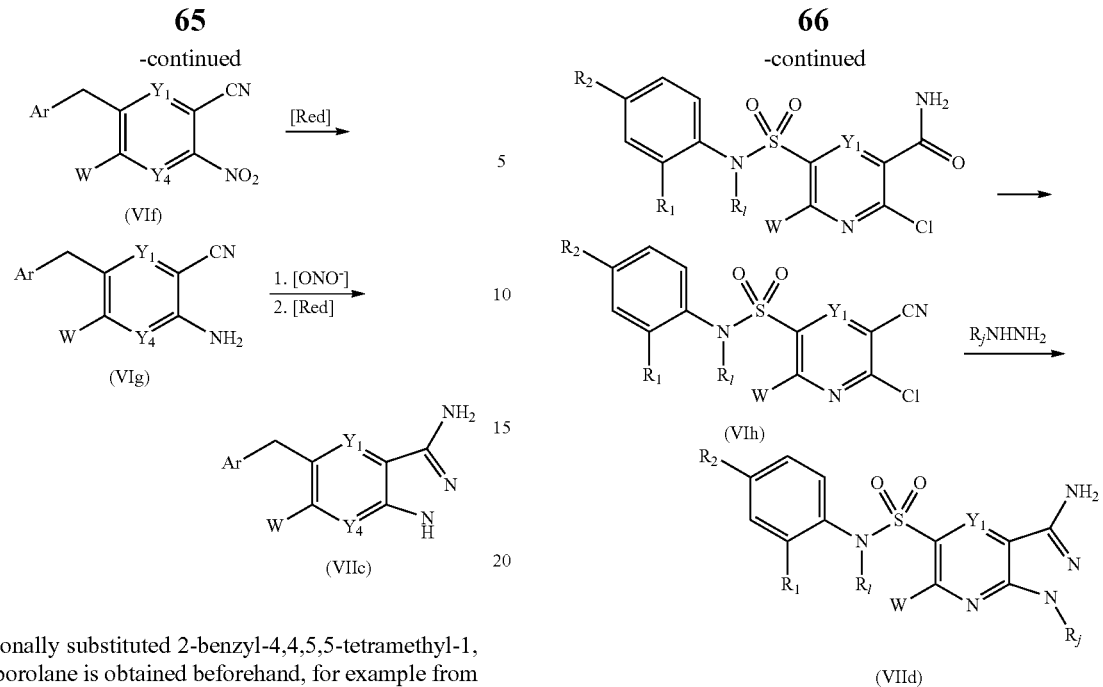

An optionally substituted 2-benzyl-4,4,5,5-tetramethyl-1,3,2-dioxaborolane is obtained beforehand, for example from the corresponding benzyl chloride and octamethyl-bi-dioxaborolane in dioxane in the presence of potassium acetate and Pt(dppf)Cl$_2$ (dppf=1,1'-bis(diphenylphosphino)ferrocene). This compound is brought together with a 6-chloro-3-nitropicolinonitrile, a 6-chloro-3-nitropyrazine-2-carbonitrile optionally substituted in position 5 or a 5-chloro-2-nitronicotinonitrile optionally substituted in position 6 and a palladium catalyst such as Pd(dppf)Cl$_2$ or Pd(PPh$_3$)$_4$, an organic base such as triethylamine or an alcoholate, or an inorganic base such as sodium, potassium or cesium carbonate in a solvent such as toluene, benzene, THF or dioxane. The preferred reaction temperatures are between 20° C. and 100° C. The products of these reactions correspond to substituted 6-benzyl-3-nitropicolinonitrile, 6-benzyl-3-nitropyrazine-2-carbonitrile or 5-benzyl-2-nitronicotinonitrile derivatives for which the following transformation steps are reproduced from method B1 above.

Method B4:

Method B4, presented in diagram 9 below, gives access to pyrazolopyridine and pyrazolopyrazines bicycles featuring optionally functionalized aryl sulfonamide functions, with R$_1$=(C$_1$-C$_6$)alkyl and notably W=H, (C$_1$-C$_6$)alkyl, aryl or benzyl.

Diagram 9

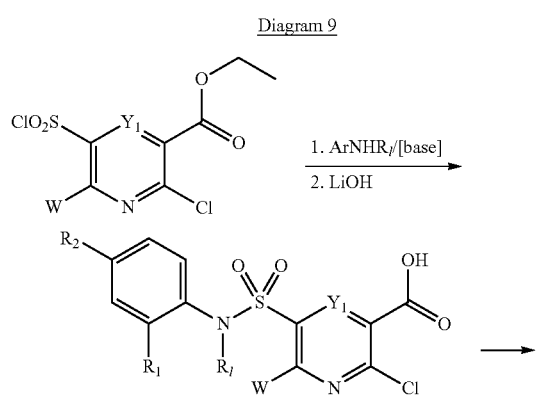

The ethyl 2-chloro-5-(chlorosulfonyl)nicotinate derivatives required for this reaction sequence may be obtained according to the methods described by Levett P. C. et al., Org. Proc. Res. Dev., 2002, 6(6), 767-772; WO 01/98284 and WO 2008/010964.

The formation of sulfonamides is typically carried out by mixing the 2-chloro-5-(chlorosulfonyl)nicotinate of interest with a primary or secondary aniline, optionally functionalized, in an aprotic solvent such as dichloromethane, THF, acetone or acetonitrile in the presence of an organic base such as triethylamine (NEt$_3$), pyridine or DIPEA. The use of an inorganic base such as sodium or potassium carbonate may also be considered. The optimal reaction temperatures are between 0° C. and 70° C.

The saponification reaction of the product thus obtained, notably by the use of lithium hydroxide in a THF/water mixture, gives access to the corresponding 2-chloro-5-(N-phenylsulfamoyl)nicotinic acids.

The corresponding acid chlorides are prepared by treatment with thionyl chloride in toluene under reflux or by any other dehydrochlorination method well known to the person skilled in the art. The reaction of these intermediates with aqueous ammonia makes it possible to form optionally functionalized 2-chloro-5-(N-phenylsulfamoyl)nicotinamides which are then engaged in a dehydration reaction, notably by the use of POCl$_3$, at a temperature ranging between 75° C. and 150° C. The alternative use of agents such as P$_2$O$_5$ or trifluoroacetic anhydride and pyridine may also be considered.

Lastly, these derivatives of general formula (VIh) are reacted in the presence of a hydrazine, functionalized or not, in a polar solvent such as ethanol at temperatures varying between 25° C. and 150° C. to form the corresponding derivatives of general formula (VIId).

Method B5:

Method B5, presented in diagram 10 below, gives access to pyrazolopyridine bicycles featuring optionally functionalized benzyl ether functions, notably with W=H, (C$_1$-C$_6$)alkyl, aryl or benzyl.

Diagram 10

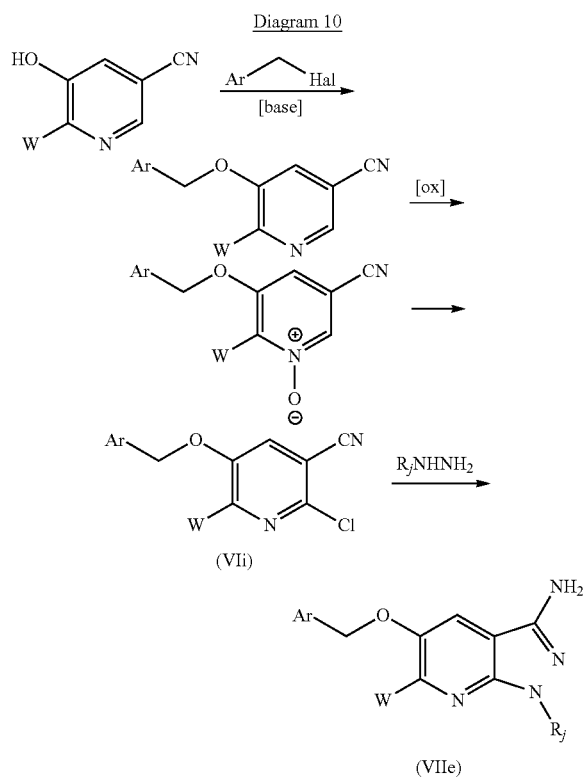

The method described below is inspired by the work of J. Baldwin et al., J. Heterocyclic. Chem., 1980, 17(3), 445-448. The 5-hydroxynicotinonitrile derivatives, optionally functionalized in position 6, are alkylated, typically by the use of an optionally functionalized benzyl halide in the presence of a base. The preferred method requires the use of an aprotic polar solvent such as DMF and a base such as NaH. The optimal reaction temperatures are between 20° C. and 100° C. Alternatively, the solvents which may be used include, for example, THF, DMSO, dioxane, acetonitrile, dichloromethane or acetone and bases such as $^t$BuOK, DIPEA, pyridine, triethylamine, DBU or sodium, potassium or cesium carbonate.

Oxidation of the pyridine ring into pyridine-N-oxide is typically carried out by use of m-CPBA in dichloromethane at room temperature. Nevertheless, many alternative methods are conceivable, notably those based on the use of sodium percarbonate in the presence of a rhenium catalyst, sodium perborate in the presence of acetic acid or the urea-hydrogen peroxide complex.

Treatment of these pyridine-N-oxide derivatives with phosphorus oxychloride leads to the formation of the corresponding 2-chloronicotinonitriles (VI).

Their reaction under heat with a hydrazine, functionalized or not, in a polar solvent such as isopropanol or ethanol leads to the formation of the pyrazolopyridine bicycles (VIIe) sought.

Method B6:

Method B6, presented in diagram 10a below, gives access to optionally functionalized pyrazolopyridine and pyrazolopyrazine bicycles featuring with reversed sulfonamide functions, notably with W=H, $(C_1-C_6)$alkyl, aryl or benzyl.

Diagram 10a

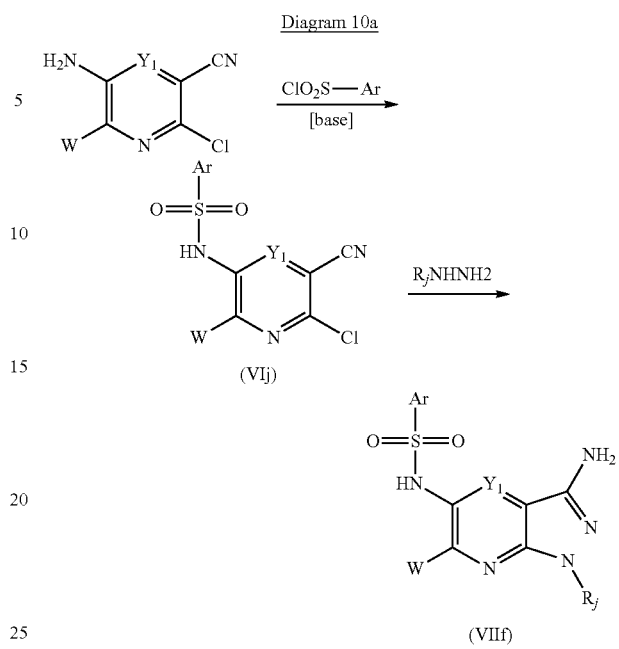

Le method described below consists in forming a sulfonamide function from an aromatic amine and an arylsulfonyl halide, or any other equivalent reagent, in the presence of a base, which can optionally be introduced as solvent or co-solvent. Alternatively, the arylsulfonyl halide or its equivalent can be generated in situ.

Their reaction under heat with a hydrazine, functionalized or not, in a polar solvent such as isopropanol or ethanol leads to the formation the desired pyrazolopyridine and pyrazolopyrazine bicycles (VIIf).

Method C:

Method C aims at the preparation of compounds of general formula (XI) as described in diagram 1.

Method C1:

Method C1, presented in diagram 11 below, is intended for the preparation of pyrazolopyridines and pyrazolopyrazines functionalized at position 6 with $R_n$=halogen, mesylate, tosylate or triflate, X=O, S, NH, N—$(C_1-C_-)$alkyl, and optionally $CH_2$ for (Xc) and (Xd), and $R_j$=H or N-protecting group.

This method can also be used to carry out the synthesis of molecules comprising a diatomic X group corresponding notably to an ArX group representing: —ArCH$_2$NH—, —ArCH$_2$N(R$_4$)—, —ArCH$_2$O—, —ArCH$_2$S—, —ArCH$_2$CH$_2$—, —ArCHCH—, or —ArCC—.

Diagram 11

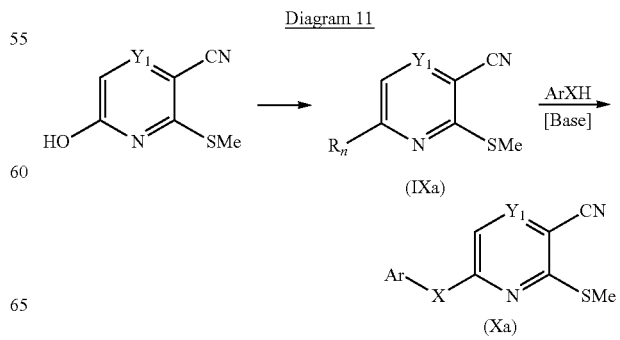

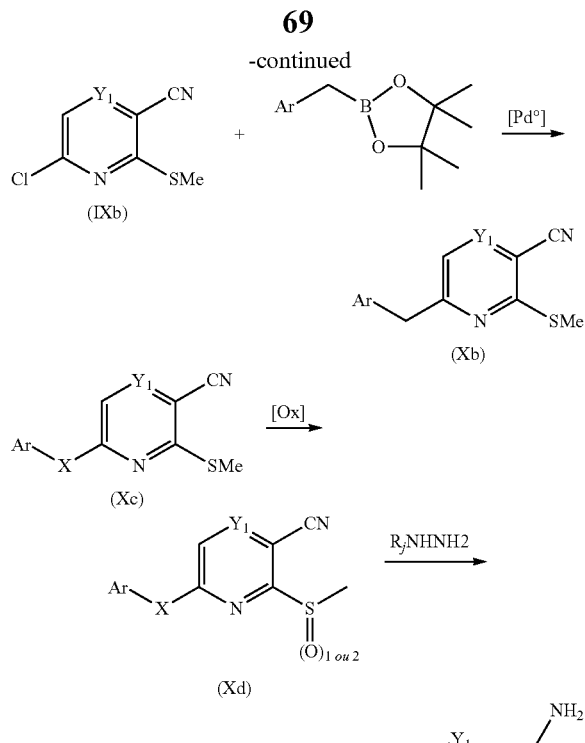

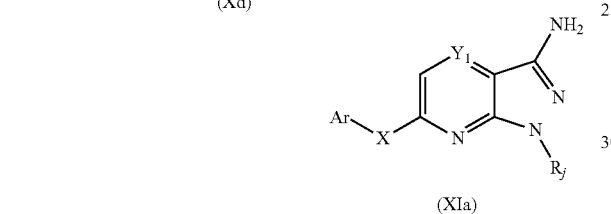

The 6-hydroxy-2-(methylthio)nicotinonitriles or 5-hydroxy-3-(methylthio) pyrazine-2-carbonitriles are subjected to a dehydrochlorination reaction, typically in the presence of phosphorus oxychloride, with or without solvent, at temperatures varying between 70° C. and 180° C. If a solvent is used, a high boiling-point non-polar solvent such as toluene or xylene will be preferred. Alternatively, it is possible to activate the 6-hydroxy-2-(methylthio)nicotinonitriles and 5-hydroxy-3-(methylthio)pyrazine-2-carbonitriles by their derivation into sulfonic esters via the formation of the corresponding tosylates, mesylates or triflates. If this option is preferred, the use of tosyl, mesyl or triflyl chlorides in a solvent such as toluene, dichloromethane, THF, acetonitrile, acetone or dioxane in the presence of an organic or inorganic base gives access to these derivatives.

The 6-chloro-2(methylthio)nicotinonitriles and 5-chloro-3-(methylthio)pyrazine-2-carbonitriles respectively obtained, or their sulfonic ester analogues if this option is preferred, are then reacted with a nucleophile such as a phenol, an aniline or a thiophenol in the context of aromatic nucleophilic substitution. In this case, the reaction is carried out in a polar solvent such as DMSO, DMF, acetone, THF or acetonitrile, in the presence of a base such as potassium tert-butylate or NaH. If necessary, these reactions may be catalyzed by the action of copper and may also be carried out without solvent. Typically, the preferred protocol involves temperatures ranging between 20° C. and 150° C.

Alternatively, the use of organic bases such as pyridine, diisopropylamine, triethylamine or DBU, or inorganic bases such as sodium or potassium carbonate is also possible.

Alternatively, the compounds of formula (IXb) may give rise to a catalytic coupling reaction such as a Suzuki reaction. In this case, these compounds are brought together with an optionally substituted 2-benzyl-4,4,5,5-tetramethyl-1,3,2-dioxaborolane already described in preceding method B3, a palladium catalyst such as Pd(dppf)Cl$_2$ or Pd(PPh$_3$)$_4$, an organic base such as triethylamine or an alcoholate, or an inorganic base such as sodium, potassium or cesium carbonate in a solvent such as toluene, benzene, THF or dioxane. The preferred reaction temperatures are between 20° C. and 100° C.

The derivatives obtained by one or another of these methods are then oxidized, typically by the use of m-CPBA or oxone to form the corresponding methyl sulfoxides or methyl sulfones. These compounds, sometimes obtained as mixtures, are used as-is in the aminopyrazole ring formation reaction by use of an optionally substituted hydrazine in a polar solvent such as ethanol at temperatures varying between 25° C. and 150° C.

Alternatively, it is possible to modify the reaction sequence, notably by reversing the synthesis steps.

Method C2:

Method C2, presented in diagram 12 below, is intended for the preparation of pyrazolopyridines and pyrazolopyridazines functionalized at position 6 with X=O, S, NH, N—(C$_1$-C_)alkyl, or CH$_2$ and R$_j$=H or N-protecting group.

Diagram 12

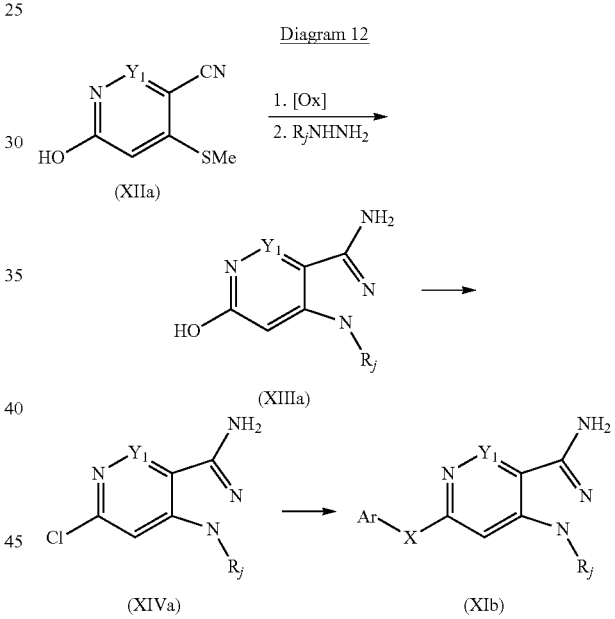

The 6-hydroxy-4-(methylthio)nicotinonitrile or 6-hydroxy-4-(methylthio) pyridazin-3-carbonitrile derivatives are oxidized, typically by the use of m-CPBA or oxone to form the corresponding methyl sulfoxides or methyl sulfones. These compounds, sometimes obtained as mixtures, are used as-is in the aminopyrazole ring formation reaction by use of an optionally substituted hydrazine in a polar solvent such as ethanol at temperatures varying between 25° C. and 150° C.

The pyrazolopyridines and pyrazolopyridazines thus obtained are subjected to a dehydrochlorination reaction, typically in the presence of phosphorus oxychloride, with or without solvent, at temperatures varying between 70° C. and 180° C. If a solvent is used, a high boiling-point non-polar solvent such as toluene or xylene will be preferred. The optionally substituted 6-chloro-pyrazolo[4,3-c]pyridin-3-amine and 6-chloro-pyrazolo[4,3-c]pyridazin-3-amine respectively obtained are then reacted with a nucleophile such as a phenol, an aniline or a thiophenol in the context of aromatic nucleophilic substitution. In this case, the reaction is carried out in a polar solvent such as DMSO, DMF, acetone, THF or acetonitrile, in the presence of a base such as potassium tert-butylate or NaH. If necessary, these reactions may be catalyzed by the action of copper and may also be carried out without solvent. Typically, the preferred protocol involves temperatures ranging between 20° C. and 150° C.

Alternatively, the use of organic bases such as pyridine, diisopropylamine, triethylamine or DBU, or inorganic bases such as sodium or potassium carbonate is also possible.

Alternatively, the compounds of formula (XIVa) may give rise to a catalytic coupling reaction such as a Suzuki reaction. In this case, these compounds are brought together with an optionally substituted 2-benzyl-4,4,5,5-tetramethyl-1,3,2-dioxaborolane described above in preceding method B3, a palladium catalyst such as $Pd(dppf)Cl_2$ or $Pd(PPh_3)_4$, an organic base such as triethylamine or an alcoholate, or an inorganic base such as sodium, potassium or cesium carbonate in a solvent such as toluene, benzene, THF or dioxane. The preferred reaction temperatures are between 20° C. and 100° C.

Method C3:

Method C3, presented in diagram 12a below, is a variant of method C1 based on the regioselective functionalization of 2,6-dichloronicotinonitrile either by an anionic nucleophile such as a phenate or a thiophenate, or by an organometallic such as a benzylzinc chloride. In the latter case, the reaction is catalyzed for example with a palladium(II) complex. The transformation of the chloronicotinonitrile thus obtained in the corresponding pyrazolopyridine, in the case where $Y_1$=CH, is carried out as previously described in method A1.

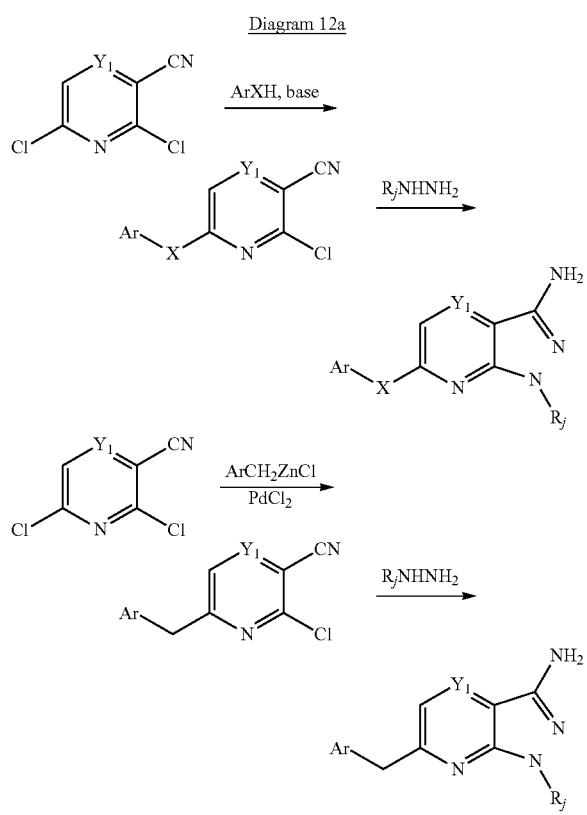

Diagram 12a

Method D:

These methods have as an object the synthesis of compounds of general formula (I) or (VII) by the use of various catalytic coupling methods.

Method D1:

Method D1, presented in diagram 13 below, makes use of the coupling reaction as described in J.A.C.S., 1984, 106, 158 between an organozinc compound prepared in situ and an aryl bromide catalyzed by palladium complexes.

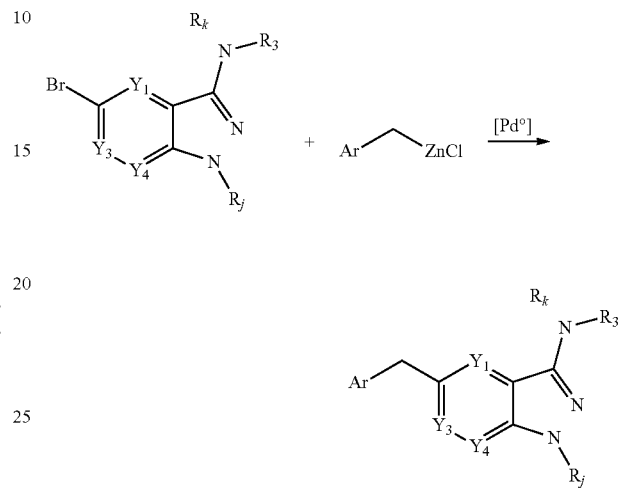

Diagram 13

Rj = H or N-protecting group
$R_k$ = H or $R_2$

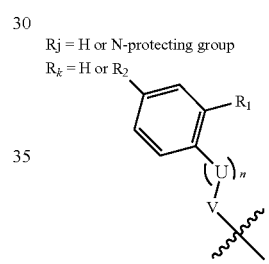

The optionally substituted 3-amino-diazaindazoles or 3-amino-azaindazoles are brought together with a zinc benzyl chloride, optionally substituted, in an aprotic polar solvent such as THF or dioxane, in the presence of a catalytic quantity of a palladium complex such as $(dppf)_2PdCl_2.CH_2Cl_2$. The coupling reaction is carried out at temperatures ranging between 25° C. and 100° C.

Method D2:

Method D2, presented in diagram 14 below, makes use of the coupling reaction as described by Gueiffier A. et al., Tetrahedron, 2006, 62, 6042-6049, between a thiol, in particular a thiophenol or a benzylthiol, and an aryl iodide catalyzed by copper complexes.

Diagram 14

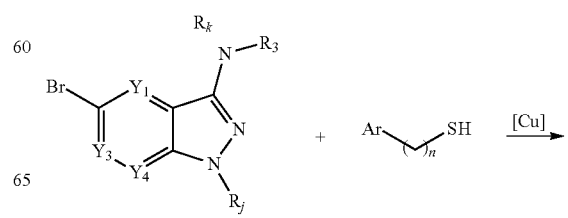

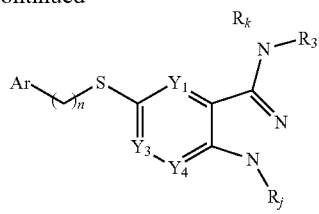

Rj = H or N-protecting group
Rk = H or R2

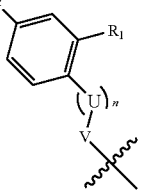

n = 0 or 1

This reaction is typically carried out in a high boiling-point polar solvent such as 2-propanol in the presence of a catalytic quantity of polyethylene glycol, a metal salt such as copper iodide (CuI) and an excess of an inorganic base such as potassium carbonate, calcium carbonate or sodium carbonate. The reaction temperatures typically vary between 50° C. and 100° C.

Method D3:

Method D3, presented in diagram 15 below, makes use of the coupling reaction as described by Sonogashira, K. et al. in Tetrahedron Lett., 1975, 16, 4467-4470 between an acetylene derivative and an aryl halide catalyzed by copper and palladium complexes.

Diagram 15

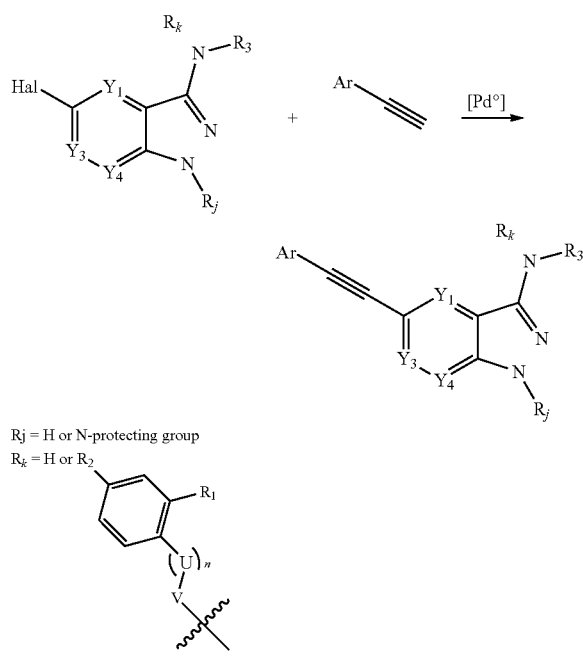

Rj = H or N-protecting group
Rk = H or R2 n = 0 or 1

Such a reaction is typically carried out by the reaction under an inert atmosphere of a heteroaryl halide with a stoichiometric quantity of an optionally substituted ethynylbenzene in the presence of a catalytic quantity of a palladium complex, for example $PdCl_2(PPh_3)_2$ or $Pd(PPh_3)_4$, a catalytic quantity of a copper salt, for example CuI, and an organic base such as triethylamine or DIPEA, or an inorganic base such as potassium or cesium carbonate. The protocol generally involves reaction temperatures ranging between 20° C. and 45° C. in solvents including DMF, THF, dioxane or diethyl ether.

Method E:

The protocols of method E aim at functionalizing the exocyclic amine of aminopyrazole rings by their reaction with an intermediate featuring an electrophile function, optionally generated in situ, such as acid chloride, an isocyanate, a isothiocyanate or an aldehyde.

Method E1:

Method E1, presented in diagram 16 below, aims at the transformation of the primary exocyclic amine function of aminopyrazole compounds into an amide function.

Diagram 16

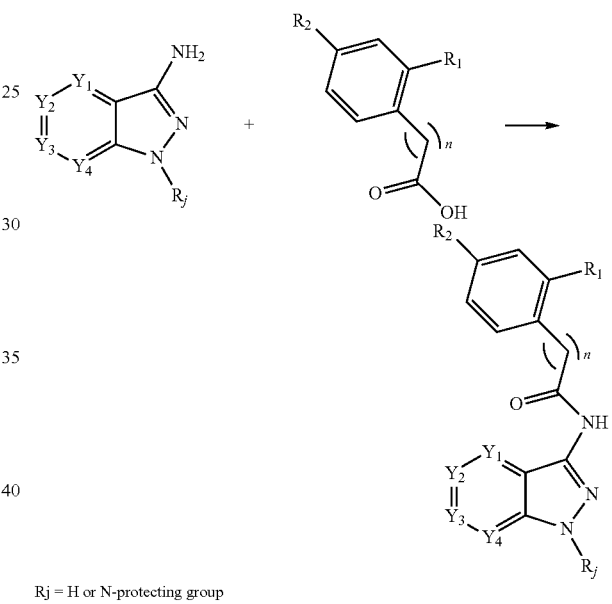

Rj = H or N-protecting group

These compounds are synthesized via the corresponding 3-aminopyrazole by the addition of adequate acid chloride prepared beforehand by the use of oxalyl chloride and a catalytic quantity of DMF in a solvent such as tetrahydrofuran. These acid chlorides may be obtained by the use of alternative methods, such as those based on the use of thionyl chloride or phosphorus oxychloride, well known to the person skilled in the art. The condensation of acid chlorides on aminopyrazoles is typically carried out in an aprotic solvent such as tetrahydrofuran, toluene or dichloromethane in the presence of a base such as DIPEA, pyridine or triethylamine.

Alternatively, the use of a base as a solvent, in particular pyridine, is a possibility.

Alternatively, this type of reaction may be conducted in a biphasic system according to the well-known Schotten-Baumann method.

Alternatively, formation of the amide bond may be carried out from the corresponding 3-aminopyrazole and the acid of interest by the use of peptide coupling conditions using reagents such as HOBt (hydroxybenzotriazole), TBTU (O-(benzotriazol-1-yl)-N,N,N',N'-tetramethyluronium tetrafluoroborate), HATU (2-(1H-7-azabenzotriazol-1-yl)-1,1,3,3-tetramethyluronium hexafluorophosphate), EDCI (1-ethyl-3-(3-dimethylaminopropyl)carbodiimide) or carbonyldiimidazole at a temperature ranging between −20° C. and 100° C. in an aprotic solvent such as tetrahydrofuran, dioxane, dichloromethane or any solvent with similar properties.

Method E2:

Derivatives characterized by the presence of a secondary amine in position 3 of the aminopyrazole ring are synthesized by a reducing amination reaction according to diagram 17 below.

Diagram 17

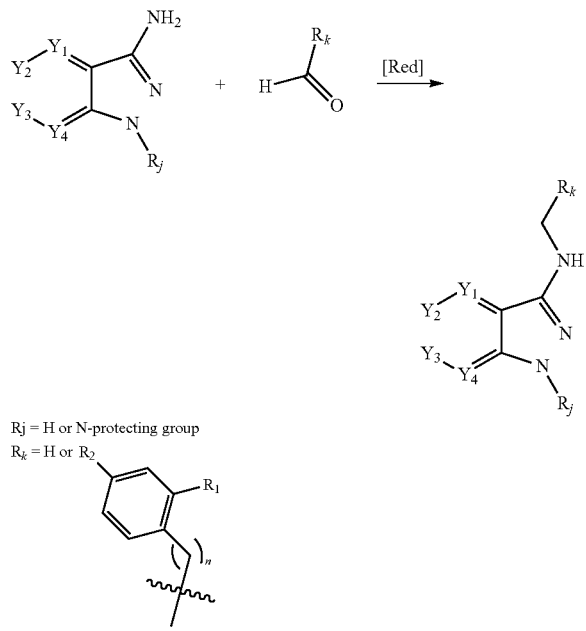

Rj = H or N-protecting group
Rk = H or R2

Reducing amination reactions are typically carried out by mixing adequate stoichiometric quantities of aminopyrazole and aldehyde in a solvent such as DCE (dichloroethane), THF or acetonitrile, optionally in the presence of a quantity of water, TFA (trifluoroacetic acid) or acetic acid, by adding successive fractions of a reducing agent such as NaBH$_4$, NaBH(OAc)$_3$ or NaBH$_3$CN. These reactions are typically carried out at room temperature.

Method E3:

Derivatives carrying a 3-ureido or 3-thioureido function are obtained by the reaction, presented in diagram 18 below, of an aminopyrazole with an isocyanate or isothiocyanate obtained according to methods well known to the person skilled in the art.

Diagram 18

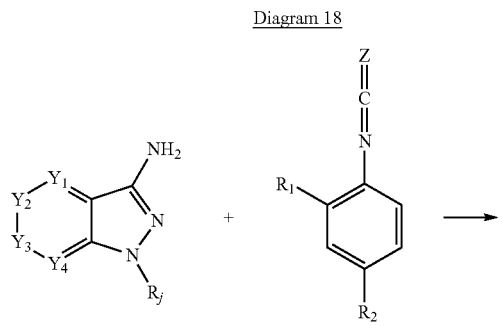

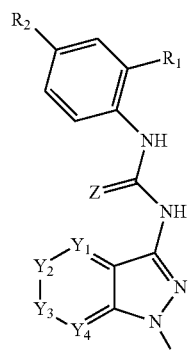

Rj = H or N-protecting group
Z = O or S

In a typical reaction, the reaction mixture is prepared in a polar or non-polar aprotic solvent such as dichloromethane, acetone, DMF, DMA, acetonitrile, THF or dioxane carried at temperatures varying between 20° C. and the boiling point of the chosen solvent. If necessary, recourse to a weakly nucleophilic organic or inorganic base may prove to be necessary. In this case, sodium hydride is a possible option.

Method F: Post-Synthetic Deprotections and Modifications

Method F1: Deprotections

The trifluoroacetate protecting groups are removed by the action of an organic base such as triethylamine or pyridine in a polar solvent such as methanol, ethanol or THF at the reflux temperatures of the solvents used.

The tert-butyl or trityl protecting groups carried by the pyrazole rings are displaced by the action of a strong acid, typically TFA, in a non-polar solvent such as dichloromethane or DCE.

Method F2: Alkyne Reductions

Diagram 19

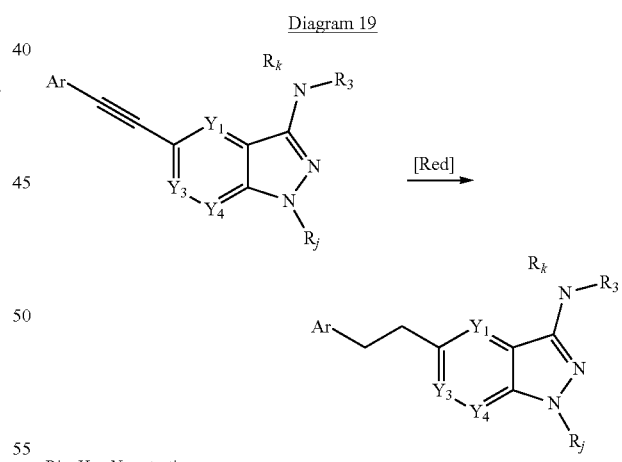

Rj = H or N-protecting group
Rk = H or R2

Reactions for reducing diaryl alkynes into diaryl alkanes are typically carried out by catalytic hydrogenation, under hydrogen pressure, in the presence of catalysts such as $PtO_2$, Pt, Pd/C, Ni or Rh. Alternatively, the use of DIBAL-H (diisobutylaluminum hydride) in the presence or the absence of a catalyst such as $Cp_2TiCl_2$ is conceivable.

Method F3: Oxidation of Sulfides into Sulfones and Sulfoxides

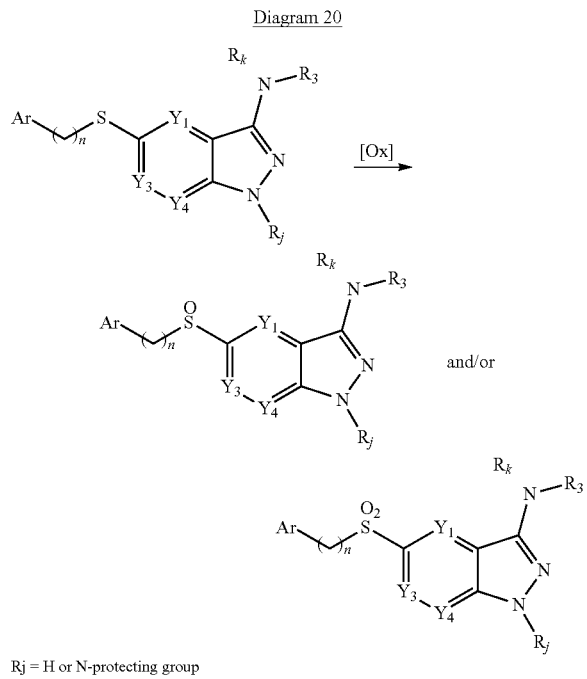

Oxidation reactions of sulfides into sulfoxides are typically carried out via the use of oxone in a mixture of polar solvents such as THF/MeOH or DMF/water. The optimal reaction temperatures are typically between 25° C. and 50° C.

Many alternative methods are available, and some give the possibility of producing semi-oxidized derivatives, namely sulfoxides. Such alternative methods include the use of m-CPBA, $KMnO_4/MnO_2$ in dichloromethane, $H_2O_2$ (30%) in a biphasic medium and the presence of a phase transfer catalyst or a catalyst in the form of a urea complex (UHP).

The combined use of $H_2O_2$ and metal complexes such as $Sc(OTf)_3$ promotes partial oxidation derivatives.

Other known methods include, for example, the use of $CAN/NaBrO_3$ (CAN=ceric ammonium nitrate).

The examples and figures which follow illustrate the invention without limiting its scope in any way.

FIGURES

EXAMPLES

Figure 1A:
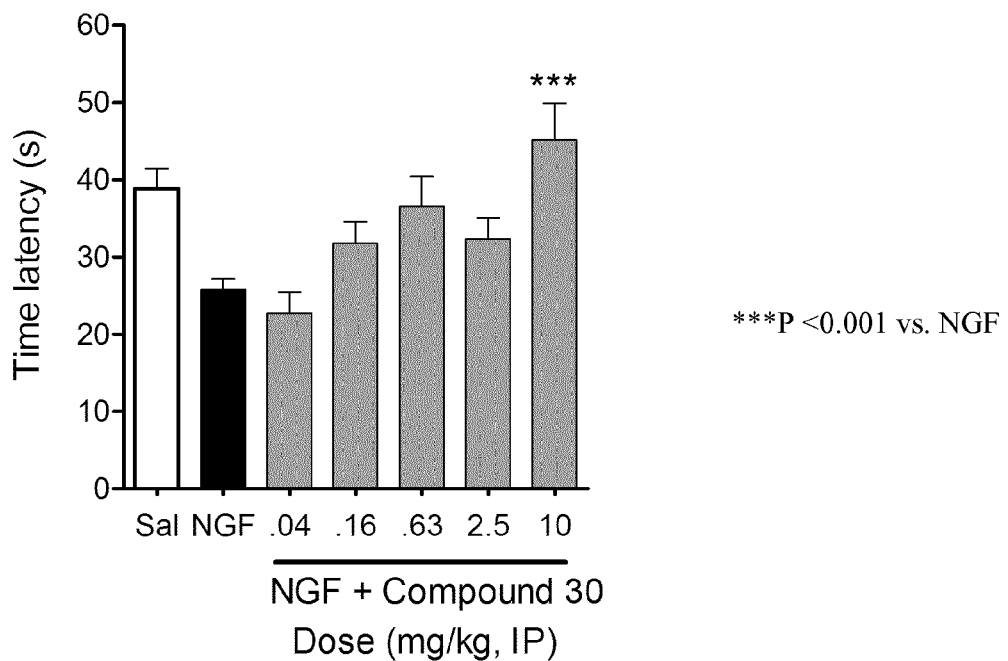
FIG. 1A represents a histogram of the inhibition effect on NGF-induced hyperalgesia (time latency) of Compound 30 administered to a mouse at various doses by intraperitoneal route.

The following abbreviations are used:
DMSO Dimethylsulfoxide
EI Electron impact
ES Electrospray
LCMS Liquid chromatography-mass spectrometry
mg milligram
mL milliliter
NMR Nuclear magnetic resonance I. Synthesis of the Compounds According to the Invention Examples of Method A1

Example 1

5-iodo-1H-pyrazolo[3,4-b]pyridine-3-amine

Example 1a 2-hydroxy-5-iodonicotinonitrile 9 g (0.5 eq) of N-iodosuccinimide at room temperature is added to a solution of 10 g (83 mmol) of 2-hydroxynicotinonitrile in 150 ml of anhydrous dimethylformamide. The reaction mixture is stirred at 60° C. After 30 minutes of stirring, 9 g (0.5 eq) of N-iodosuccinimide is added and then the reaction mixture is stirred at 60° C. for 5 hours. The solvent is evaporated and the precipitate formed is filtered, rinsed with water and with diethyl ether and then dried under vacuum to yield 18.5 g (90%) of 2-hydroxy-5-iodonicotinonitrile in the form of a beige powder.

LCMS (EI, m/z): (M+1) 246.93
$^1$H NMR: δH ppm (400 MHz, DMSO): 12.79 (1H, s, OH), 8.36 (1H, d, $CH_{arom}$), 8.04 (1H, d, $CH_{arom}$).

Example 1b 2-chloro-5-iodonicotinonitrile 30.7 ml (329 mmol) of phosphorus oxychloride at 0° C. and 6 drops of sulfuric acid are added to 9 g (6.6 mmol) of 2-hydroxy-5-iodonicotinonitrile. The reaction mixture is heated at 110° C. for 5 hours and then at room temperature overnight. The reaction mixture is poured in a beaker containing ice and a little water, and a precipitate is formed. The mixture is allowed to gradually return to room temperature and then is filtered and rinsed with water. The solid is dried to yield 6.8 g (70%) of 2-chloro-5-iodonicotinonitrile.

LCMS (EI, m/z): (M+1) 265.45

$^1$H NMR: δH ppm (400 MHz, DMSO): 9.61 (1H, d, $CH_{arom}$), 9.14 (1H, d, $CH_{arom}$).

Example 1

5-iodo-1H-pyrazolo[3,4-b]pyridine-3-amine

Hydrazine (3.86 ml, 79 mmol) is added at room temperature to 7 g (26.5 mmol) of a solution of 2-chloro-5-iodonicotinonitrile in 25 ml of propan-2-ol. The reaction mixture is heated at 85° C. for 7 hours and then at room temperature overnight. The suspended solid is filtered, rinsed with isopropanol and then with ether and dried in an oven at 50° C. to give 6 g (87%) of 5-iodo-1H-pyrazolo[3,4-b]pyridine-3-amine.

LCMS (EI, m/z): (M+1) 260.95

$^1$H NMR: δH ppm (400 MHz, DMSO): 12.12 (1H, bs, NH), 8.51 (1H, d, $CH_{arom}$), 8.45 (1H, d, $CH_{arom}$), 5.64 (2H, bs, $NH_2$).

The following compounds were obtained according to the same method.

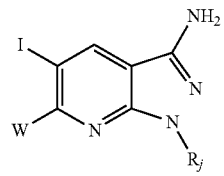

| Ex.** | W | $R_j$ | Compound name | Yield | Mass MH$^+$ |
|---|---|---|---|---|---|
| 1-2 | H | t-butyl | 1-tert-butyl-5-iodo-1H-pyrazolo[3,4-b]pyridin-3-amine | 68% | 317.05 |
| 1-3 | Me | H | 5-iodo-6-methyl-1H-pyrazolo[3,4-b]pyridin-3-amine | 93% | 275.02 |

**$^1$H NMR, DMSO-d$_6$, Ex. 1-2: 8.55 (1H, bs, $CH_{arom}$), 8.42 (1H, bs, $CH_{arom}$), 6.33 (1H, bs, $CH_{arom}$), 1.57 (9H, s, CH); 1-3: 11.92 (1H, s, NH), 8.55 (1H, s, $CH_{arom}$), 5.59 (2H, bs, $NH_2$), 2.66 (3H, s, $CH_3$).

Example 2

5-bromo-1H-pyrazolo[3,4-b]pyridine-3-amine

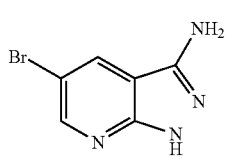 [SMILES: N=C(N)c1cc(Br)cnc1N]

Example 2a 2-methoxy-nicotinonitrile 4.98 g (217 mmol) of sodium is added to 80 ml of anhydrous methanol. The reaction medium is stirred at room temperature for 10 minutes and then 10 g (72.2 mmol) of 2-chloronicotinonitrile is added at 0° C. The reaction medium is stirred at 25° C. for 16 hours. The reaction is hydrolyzed by slowly adding water at 0° C. After returning to room temperature, the precipitate obtained is filtered, rinsed with water and then dried at 50° C. to yield 7.85 g (81%) of 2-methoxy-nicotinonitrile in the form of a yellow solid.

LCMS (EI, m/z): (M+1) 135.04

$^1$H NMR: δH ppm (400 MHz, DMSO): 8.46-8.48 (1H, dd, $CH_{arom}$), 8.25-8.27 (1H, dd, $CH_{arom}$), 7.17-7.20 (1H, dd, $CH_{arom}$), 3.99 (3H, 5, $CH_3$).

Example 2b 5-bromo-2-methoxy-nicotinonitrile 12.23 g (149 mmol) of sodium acetate and then 7.66 ml (149 mmol) of bromine at 0° C. are added to 10 g (74.6 mmol) of a solution of 2-methoxy-nicotinonitrile in 29 ml of acetic acid. The reaction mixture is heated at 70° C. overnight. After returning to room temperature, the reaction medium is added to an ice bath and the precipitate obtained is filtered, rinsed with water and then dried at 50° C. to yield 11.6 g (73%) of 5-bromo-2-methoxy-nicotinonitrile in the form of a white solid.

LCMS (EI, m/z): (M+1) 214.95

$^1$H NMR: δH ppm (400 MHz, DMSO): 8.61 (1H, d, $CH_{arom}$), 8.60 (1H, d, $CH_{arom}$), 3.98 (3H, s, $CH_3$)

Example 2

5-bromo-1H-pyrazolo[3,4-b]pyridine-3-amine 35 ml (23.47 mmol) of hydrazine is added at room temperature to 5 g (23.47 mmol) of 5-bromo-2-methoxynicotinonitrile. The reaction medium is carried at 100° C. for 3 hours. After returning to room temperature, the precipitate obtained is filtered, rinsed with water and then dried at 50° C. to yield 3.6 g (72%) of 5-bromo-1H-pyrazolo[3,4-b]pyridine-3-amine in the form of a yellow solid.

LCMS (EI, m/z): (M+1) 214.05

$^1$H NMR: δH ppm (400 MHz, DMSO): 12.18 (1H, s, NH), 8.38 (1H, d, $CH_{arom}$), 8.37 (1H, d, $CH_{arom}$), 5.66 (2H, 5, NH).

Examples of Method A2

Example 3

5-iodo-1H-pyrazolo[3,4-b]pyrazine-3-amine

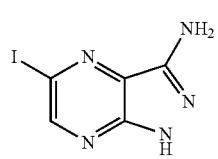 [SMILES: N=C(N)c1nc(I)cnc1N]

Example 3a methyl 3-amino-6-iodopyrazine-2-carboxylate 1.5 equivalents of N-iodosuccinimide are added at room temperature to 5 g (32.7 mmol) of a methyl 3-aminopyrazine-2-carboxylate solution in 25 ml of dimethylformamide. The reaction medium is heated at 65° C. for 1 hour, added together with 0.5 equivalents of N-iodosuccinimide and maintained at 65° C. for 24 hours. After returning to room temperature, the solvent is evaporated and then the product is extracted several times with dichloromethane. The organic phases are combined, washed with 10% sodium bisulfite solution, dried on magnesium sulfate and concentrated to yield 8 g (88%) of methyl 3-amino-6-iodopyrazine-2-carboxylate in the form of a yellow solid.

LCMS (EI, m/z): (M+1) 280
$^1$H NMR: δH ppm (400 MHz, DMSO): 8.50 (1H, 5, $CH_{arom}$), 7.50 (2H, bs, $NH_2$), 3.20 (3H, s, $CH_3$).

Example 3b 3-amino-6-iodopyrazine-2-carboxamide 30 ml of ammonia in water is added under magnetic stirring to 15 g (53.8 mmol) of a solution of methyl 3-amino-6-iodopyrazine-2-carboxylate in 150 ml of methanol. The reaction medium is stirred at 25° C. for 48 hours. After evaporation of the solvents, the precipitate obtained is filtered, rinsed with water and then dried at 50° C. to yield 12.50 g of 3-amino-6-iodopyrazine-2-carboxamide (88%) in the form of a beige solid.

LCMS (EI, m/z): (M+1) 265.02
$^1$H NMR: δH ppm (400 MHz, DMSO): 8.35 (1H, 5, $CH_{arom}$), 7.85 (1H, bs, NH), 7.60 (3H, bs, NH), 3.25 (3H, s, $CH_3$).

Example 3c

N'-(3-cyano-5-iodopyrazine-2-yl)-N,N-dimethyl-formimidamide 13.59 ml (146 mmol) of phosphorus oxychloride is added drop by drop at 0° C. to 11 g (41.7 mmol) of a solution of 3-amino-6-iodopyrazine-2-carboxamide in 80 ml of dimethylformamide. The reaction mixture is stirred at room temperature overnight and then poured in a beaker containing ice and a little water. The pH is adjusted to 8 with 1 N soda solution; a precipitate is formed. The mixture is allowed to gradually return to room temperature and then the solid formed is filtered, rinsed with water and dried at 50° C. to yield 10.50 g of N'-(3-cyano-5-iodopyrazine-2-yl)-N,N-dimethyl formimidamide (84%) in the form of a beige solid.

LCMS (EI, m/z): (M+1) 302.07
$^1$H NMR: δH ppm (400 MHz, DMSO): 8.69 (1H, s, $CH_{arom}$), 8.67 (1H, s, $CH_{ethyl}$), 3.20 (3H, s, $CH_3$), 3.11 (3H, s, $CH_3$).

Example 3d 3-amino-6-iodopyrazine-2-carbonitrile 77 ml (77 mmol) of 1 M hydrochloric acid solution is added to 7.7 g (25.6 mmol) of N'-(3-cyano-5-iodopyrazin-2-yl)-N,N-dimethylformimidamide. The reaction medium is heated at 50° C. for 4 hours and then stirred at room temperature overnight. The precipitate formed is filtered, rinsed with water and dried at 50° C. to yield 6 g (95%) of 3-amino-6-iodopyrazine-2-carbonitrile in the form of a beige solid.

LCMS (EI, m/z): (M+1) 247.0
$^1$H NMR: δH ppm (400 MHz, DMSO): 8.49 (1H, s, $CH_{arom}$), 7.53 (2H, bs, $NH_2$).

Example 3e 3-chloro-6-iodopyrazine-2-carbonitrile 64.3 ml of hydrochloric acid is added at −5° C. to 7.7 g (31.3 mmol) of 3-amino-6-iodopyrazine-2-carbonitrile. At this temperature, a sodium nitrite solution (4.32 g, 62.6 mmol) dissolved in 9 ml of water is added to the reaction mixture and is stirred for 4 hours at −50° C. and then at room temperature overnight. Another equivalent of sodium nitrite is added to the reaction mixture and the precipitate formed is filtered, rinsed with water and dried at 50° C. to yield 3.65 g (44%) of 3-chloro-6-iodopyrazine-2-carbonitrile in the form of a beige solid.

LCMS (EI, m/z): (M+1) 266.49
$^1$H NMR: δH ppm (400 MHz, DMSO): 9.13 (1H, s, $CH_{arom}$)

Example 3

5-iodo-1H-pyrazolo[3,4-b]pyrazine-3-amine 0.74 ml (9.8 mmol) of hydrazine is added to 2.6 g (9.80 mmol) of a solution of 3-chloro-6-iodopyrazine-2-carbonitrile in 15 ml of butanol. The reaction mixture is heated at 110° C. for 5 hours and then left at room temperature overnight. The suspended solid is filtered, rinsed with butanol and then dried in an oven at 50° C. to yield 2.2 g (86%) of 5-iodo-1H-pyrazolo[3,4-b]pyrazine-3-amine in the form of a brown solid.

LCMS (EI, m/z): (M+1) 262.02
$^1$H NMR: δH ppm (400 MHz, DMSO): 12.59 (1H, bs, NH), 8.60 (1H, d, $CH_{arom}$), 5.83 (2H, bs, $NH_2$).

Examples of Method A3

Example 4

5-iodo-6-methoxy-1H-pyrazolo[3,4-b]pyridin-3-amine

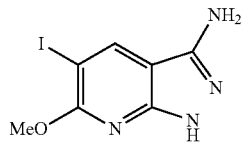 [SMILES: COc1nc(N)c(C(=N)N)cc1I]

Example 4a ethyl 5-cyano-2-hydroxy-6-(methylthio)nicotinate

Ethyl 5-cyano-2-hydroxy-6-(methylthio)nicotinate is obtained by following the procedure of Ya. Yu. Yakunin et al., Russian Chemical Bulletin, 1999, 48(1), 195-6 with a total yield of 34%.

LCMS (EI, m/z): (M−1) 237.22
$^1$H NMR: δH ppm (400 MHz, DMSO): 12.72 (1H, bs, OH), 8.40 (1H, 5, $CH_{arom}$), 4.29 (2H, q, $CH_2$), 2.64 (3H, s, $CH_3$), 1.30 (3H, t, $CH_3$).

Example 4b

5-cyano-2-hydroxy-6-(methylthio)nicotinic acid 4.16 g (2 eq) of lithium hydroxide monohydrate is added at room temperature to a solution of 11.8 g (49.5 mmol) of ethyl 5-cyano-2-hydroxy-6-(methylthio)nicotinate in 100 ml of ethanol and 100 ml of water. The reaction mixture is stirred at 60° C. for 2 hours. The ethanol is evaporated and 1 N aqueous soda is added. The aqueous phase is washed with ethyl acetate and then re-acidified by adding 1 N aqueous hydrogen chloride (pH=1). The precipitate formed is filtered, rinsed with water and with diethyl ether and then dried under vacuum to yield 9.9 g (95%) of 5-cyano-2-hydroxy-6-(methylthio)nicotinic acid in the form of a brown powder.

LCMS (EI, m/z): (M−1) 209.09
$^1$H NMR: δH ppm (400 MHz, DMSO): 8.32 (1H, s, $CH_{arom}$), 2.61 (3H, s, $CH_3$).

Example 4c

6-hydroxy-2-(methylthio)nicotinonitrile

A solution of 6 g (28.5 mmol) of 5-cyano-2-hydroxy-6-(methylthio)nicotinic acid in 35 ml of diphenyl ether is stirred at 250° C. for 4 hours. After returning to room temperature, 100 ml of cyclohexane is added and the reaction medium is triturated for 30 minutes. The solid formed is filtered, rinsed thoroughly with cyclohexane and then dried under vacuum to yield 2.87 g (60%) of 6-hydroxy-2-(methylthio)nicotinonitrile in the form of a brown powder.

LCMS (EI, m/z): (M+1) 167.12
$^1$H NMR: δH ppm (400 MHz, DMSO): 12.16 (1H, bs, OH), 7.92 (1H, d, $CH_{arom}$), 6.46 (1H, d, $CH_{arom}$), 2.59 (3H, s, $CH_3$).

Example 4d

6-hydroxy-5-iodo-2-(methylthio)nicotinonitrile 6 g (1.6 eq) of silver sulfate and 4.58 g (1.5 eq) of iodine are added successively to a solution of 2 g (12 mmol) of 6-hydroxy-2-(methylthio)nicotinonitrile in 200 ml of ethanol. The reaction medium is stirred at room temperature for 2 hours. The solid is filtered and the residue rinsed thoroughly with methanol. The filtrate is evaporated and then taken up in ethyl acetate. The organic phase is washed with water three times, dried on magnesium sulfate and evaporated to yield 3.18 g (90%) of 6-hydroxy-5-iodo-2-(methylthio)nicotinonitrile in the form of a yellow powder.

LCMS (EI, m/z): (M+1) 292.93
$^1$H NMR: δH ppm (400 MHz, DMSO): 12.96 (1H, bs, OH), 8.38 (1H, s, $CH_{arom}$), 2.62 (3H, s, $CH_3$).

Example 4e

5-iodo-6-methoxy-2-(methylthio)nicotinonitrile

905 µl (2 eq) of methyl iodide and 2.1 g (1.05 eq) of silver carbonate are added successively to a solution of 2.12 g (7.26 mmol) of 6-hydroxy-5-iodo-2-(methylthio)nicotinonitrile in 20 ml of 1,4-dioxane. The reaction medium is stirred at 60° C. for 5 hours. The solid is filtered and the residue rinsed thoroughly with methanol. The filtrate is evaporated and the residue purified by silica column chromatography (4:6 dichloromethane/cyclohexane as eluent) to yield 1.52 g (68%) of 5-iodo-6-methoxy-2-(methylthio)nicotinonitrile in the form of a white powder.

LCMS (EI, m/z): (M+1) 306.95
$^1$H NMR: δH ppm (400 MHz, DMSO): 8.50 (1H, s, $CH_{arom}$), 4.04 (3H, 5, $CH_3$), 2.63 (3H, s, $CH_3$).

Example 4f

5-iodo-6-methoxy-2-(methylsulfinyl)nicotinonitrile 1.42 g (1.1 eq) of 70% 3-chloroperbenzoic acid is added to a solution of 1.6 g (5.23 mmol) of 5-iodo-6-methoxy-2-(methylthio)nicotinonitrile in 20 ml of dichloromethane. The reaction medium is stirred at room temperature for 1 hour. Ethyl acetate is added and the organic phase is washed with saturated sodium bicarbonate solution, dried on magnesium sulfate, filtered and evaporated to yield 1.63 g (97%) of 5-iodo-6-methoxy-2-(methylsulfinyl)nicotinonitrile in the form of a white powder which may also contain 5-iodo-6-methoxy-2-(methylsulfonyl)nicotinonitrile in small proportions (<20%). If necessary, the mixture is used as-is in the following steps.

LCMS (EI, m/z): (M+1) 322.95
$^1$H NMR: δH ppm (400 MHz, DMSO): 8.86 (1H, 5, $CH_{arom}$), 4.05 (3H, 5, $CH_3$), 2.95 (3H, s, $CH_3$).

Example 4

5-iodo-6-methoxy-1H-pyrazolo[3,4-b]pyridin-3-amine

294 µl (1.2 eq) of hydrazine monohydrate is added to a solution of 1.63 g (5.05 mmol) of 5-iodo-6-methoxy-2-(methylsulfinyl)nicotinonitrile in 30 ml of 2-propanol. The reaction medium is stirred at 80° C. for 9 hours. After returning to room temperature, the solid formed is filtered and rinsed with 2-propanol to yield 1.14 g (78%) of 5-iodo-6-methoxy-1H-pyrazolo[3,4-b]pyridin-3-amine in the form of a white powder.

LCMS (EI, m/z): (M+1) 291.00
$^1$H NMR: δH ppm (400 MHz, DMSO): 11.87 (1H, 5, NH), 8.49 (1H, 5, $CH_{arom}$), 5.49 (2H, bs, $NH_2$), 3.90 (3H, s, $CH_3$).

Example 5

5-iodo-1H-pyrazolo[3,4-b]pyridine-3,6-diamine

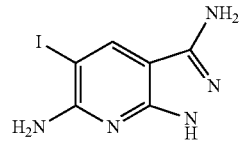

Example 5a

4-methylmorpholinium (2,4)-ethyl-5-amino-2,4-dicyano-5-mercaptopenta-2,4-dienoate 4-methylmorpholinium (2,4)-ethyl-5-amino-2,4-dicyano-5-mercaptopenta-2,4-dienoate is prepared according to the procedure described by V. D. Dyachenko et al., Chemistry of Heterocyclic Compounds, 2005, 41(4), 503-10 with a yield of 50%.

$^1$H NMR: δH ppm (400 MHz, DMSO): 9.60 (1H, bs, NH), 8.66 (1H, s, CH), 8.33 (1H, bs, NH), 7.43 (1H, bs, NH), 4.08 (2H, q, CH$_2$), 3.82-4.02 (2H, m, CH$_2$), 3.55-3.78 (2H, m, CH$_2$), 3.24-3.42 (2H, m, CH$_2$), 3.98-3.17 (2H, m, CH$_2$), 2.81 (3H, s, CH$_3$), 1.19 (3H, t, CH$_3$).

Example 5b ethyl 2-amino-5-cyano-6-(methylthio)nicotinate 2.73 ml (1 eq) of methyl iodide is added to a solution of 14.2 g (43.8 mmol) of 4-methylmorpholinium (2,4)-ethyl-5-amino-2,4-dicyano-5-mercaptopenta-2,4-dienoate in 78 ml of N,N-dimethylformamide. The reaction mixture is stirred at room temperature for 1 hour and then at 75° C. for 20 hours. After returning to room temperature, water is added and the solid formed is filtered and dried under vacuum to yield 10.31 g (100%) of ethyl 2-amino-5-cyano-6-(methylthio)nicotinate in the form of a beige powder.

LCMS (EI, m/z): (M+1) 238.20

$^1$H NMR: δH ppm (400 MHz, DMSO): 8.25 (1H, s, CH$_{arom}$), 8.19 (1H, bs, NH), 7.99 (1H, bs, NH), 4.27 (2H, q, CH$_2$), 2.58 (3H, s, CH$_3$), 1.31 (3H, t, CH$_3$).

Example 5c 2-amino-5-cyano-6-(methylthio)nicotinic acid 3.08 g (2 eq) of lithium hydroxide monohydrate is added at room temperature to a solution of 8.7 g (36.7 mmol) of ethyl 2-amino-5-cyano-6-(methylthio)nicotinate in 87 ml of ethanol and 87 ml of water. The reaction mixture is stirred at 60° C. for 2 hours. The ethanol is evaporated and 1 N aqueous soda is added. The aqueous phase is washed with ethyl acetate and then re-acidified by adding 1 N aqueous hydrogen chloride (pH=1). The precipitate formed is filtered, rinsed with water and with diethyl ether and then dried under vacuum to yield 7.67 g (quantitative) of 2-amino-5-cyano-6-(methylthio)nicotinic acid in the form of a brown powder.

LCMS (EI, m/z): (M+1) 210.16

$^1$H NMR: δH ppm (400 MHz, DMSO): 13.28 (1H, bs, CO$_2$H), 8.21 (1H, 5, CH$_{arom}$), 8.13 (2H, bs, NH$_2$), 2.57 (3H, s, CH$_3$).

Example 5d 6-amino-2-(methylthio)nicotinonitrile

A solution of 3 g (14.3 mmol) of 2-amino-5-cyano-6-(methylthio)nicotinic acid in 30 ml of diphenyl ether is stirred at 255° C. for 60 hours. After returning to room temperature, 60 ml of cyclohexane is added and the reaction medium is triturated for 30 minutes. The solid formed is filtered and then rinsed thoroughly with cyclohexane. The solid is redissolved in ethyl acetate and then the organic phase is washed with water, dried on magnesium sulfate, filtered and then evaporated to yield 1.32 g (55%) of 6-amino-2-(methylthio)nicotinonitrile in the form of a brown powder.

LCMS (EI, m/z): (M+1) 166.13

$^1$H NMR: δH ppm (400 MHz, DMSO): 7.58 (1H, d, CH$_{arom}$), 7.12 (2H, bs, NH$_2$), 6.20 (1H, d, CH$_{arom}$), 2.51 (3H, s, CH$_3$).

Example 5e 6-amino-5-iodo-2-(methylthio)nicotinonitrile 3.75 g (1.5 eq) of silver sulfate and 2.85 g (1.4 eq) of iodine are added successively to a solution of 1.32 g (8.02 mmol) of 6-amino-2-(methylthio)nicotinonitrile in 65 ml of ethanol. The reaction medium is stirred at room temperature for 3 hours. The solid is filtered and the residue rinsed thoroughly with methanol. The filtrate is evaporated and redissolved in ethyl acetate. The organic phase is washed with water three times, dried on magnesium sulfate and evaporated to yield 1.89 g (81%) of 6-amino-5-iodo-2-(methylthio)nicotinonitrile in the form of a brown powder.

LCMS (EI, m/z): (M+1) 291.99

$^1$H NMR: δH ppm (400 MHz, DMSO): 8.13 (1H, s, CH$_{arom}$), 7.19 (1H, broad flat singlet, NH$_2$), 2.51 (3H, s, CH$_3$).

Example 5f 6-amino-5-iodo-2-(methylsulfinyl)nicotinonitrile 1.77 g (1.1 eq) of 70% 3-chloroperbenzoic acid is added to a solution of 1.89 g (6.51 mmol) of 6-amino-5-iodo-2-(methylthio)nicotinonitrile in 60 ml of dichloromethane. The reaction medium is stirred at room temperature for 1 hour. Ethyl acetate is added and the organic phase is washed with saturated sodium bicarbonate solution, dried on magnesium sulfate, filtered and evaporated to yield 1.5 g (75%) of 6-amino-5-iodo-2-(methylsulfinyl)nicotinonitrile in the form of a white powder which may also contain 6-amino-5-iodo-2-(methylsulfonyl)nicotinonitrile in small proportions (<20%). If necessary, the mixture is used as-is in the following steps.

LCMS (EI, m/z): (M+1) 307.98

$^1$H NMR: δH ppm (400 MHz, DMSO): 8.45 (1H, 5, CH$_{arom}$), 7.70 (2H, broad flat singlet, NH$_2$), 2.84 (3H, s, CH$_3$).

Example 5

5-iodo-1H-pyrazolo[3,4-b]pyridine-3,6-diamine

275 μl (2 eq) of hydrazine monohydrate is added to a solution of 872 mg (2.84 mmol) of 6-amino-5-iodo-2-(methylsulfinyl)nicotinonitrile in 11 ml of 2-propanol. The reaction medium is stirred at 80° C. for 3 hours. Water is added and the product is extracted with ethyl acetate. The organic phase is dried on magnesium sulfate, filtered and evaporated. The residue is triturated in a minimum of diisopropyl ether. The solid is filtered to yield 523 mg (67%) of 5-iodo-1H-pyrazolo[3,4-b]pyridin-3,6-diamine in the form of a brown powder.

LCMS (EI, m/z): (M+1) 276.00

$^1$H NMR: δH ppm (400 MHz, DMSO): 11.23 (1H, s, NH), 8.26 (1H, s, CH$_{arom}$), 6.11 (2H, bs, NH$_2$), 5.25 (2H, bs, NH$_2$).

Examples of Method B1

Example 6

5-(3,5-difluorobenzylthio)-1H-pyrazolo[4,3-b]pyridin-3-amine

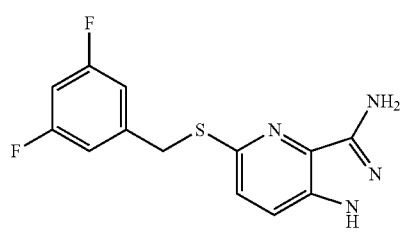 [SMILES: N=C(N)c1nc(SCc2cc(F)cc(F)c2)ccc1N]

Example 6a

6-chloro-3-nitropicolinonitrile 2,6-Dichloro-3-nitropyridine (5.18 mmol, 1 g) is mixed with 5 ml of N-methyl-2-pyrrolidinone in a microwave reactor. The reaction mixture is heated at 180° C. for 15 minutes (6 bars). The crude reaction product is dissolved in ethyl acetate, filtered and washed several times using an aqueous phase. The organic phase is collected, dried on magnesium sulfate and dry concentrated. The crude product thus obtained is purified by silica gel chromatography (heptane/AcOEt) to yield, after concentration, 0.62 g (65%) of a brown oil.

$^1$H NMR: δH ppm (400 MHz, DMSO): 8.81 (1H, d, $CH_{arom}$), 8.18 (1H, d, $CH_{arom}$).

Example 6b

3-nitro-6-thioxo-1,6-dihydropyridine-2-carbonitrile

One equivalent of $NaSH:H_2O$ is added to a solution of 6-chloro-3-nitropicolinonitrile (5.45 mmol, 1 g) in 20 ml of EtOH. The color turns orange. The reaction medium is stirred at room temperature for 30 minutes. The crude reaction product is then concentrated, redissolved in ethyl acetate and extracted several times using an acidic aqueous phase (1 N HCl) and then a neutral phase. The organic phase is concentrated and the crude reaction product recrystallized in acetone to yield 0.64 g (79%) of yellow crystals.

$^1$H NMR: δH ppm (400 MHz, DMSO): 8.71 (1H, d, $CH_{arom}$), 8.27 (1H, d, $CH_{arom}$).

Example 6c

6-(3,5-difluorobenzylthio)-3-nitropicolinonitrile

A mixture of 3-nitro-6-thioxo-1,6-dihydropyridin-2-carbonitrile (4.42 mmol, 1.34 g), 3,5-diflurobenzylbenzylbromide (8.83 mmol, 1.828 g), and $K_2CO_3$ (11.04 mmol, 1.525 g) in 5 ml of acetone is heated at 70° C. for 10 hours and then evaporated under reduced pressure. The residue is purified by silica gel chromatography (AcOEt/heptane) to yield 1.33 g (98%) of the expected product.

LCMS (ES−): m/z 306 (M−H+).

$^1$H NMR: δH ppm (400 MHz, DMSO): 8.53 (1H, d, $CH_{arom}$), 7.91 (1H, d, $CH_{arom}$), 7.21 (2H, m), 7.17 (1H, m), 4.55 (2H, $CH_2$).

Example 6d

3-amino-6-(3,5-difluorobenzylthio)picolinamide

A mixture of 6-(3,5-difluorobenzylthio)-3-nitropicolinonitrile (0.05 g, 0.163 mmol) and $PtO_2$ (0.739 mg, 3.25 μmol) in 10 ml of MeOH is placed under stirring at atmospheric pressure of hydrogen for 2 hours. The catalyst is filtered, the solution is concentrated and the residue thus obtained is purified by silica gel chromatography (AcOEt/heptane) to yield, after concentration, 0.04 g (83%) of white crystals.

LCMS (ES+) m/z: 296 (MH+).

$^1$H NMR: δH ppm (400 MHz, DMSO): 7.84 (1H, broad s, NH), 7.40 (1H, broad s, NH), 7.14 (1H, d, $CH_{arom}$), 7.08 (4H, m, $CH_{arom}$), 6.80 (2H, broad s, $NH_2$), 4.43 (2H, s, $CH_2$).

Example 6e

3-amino-6-(3,5-difluorobenzylthio)picolinonitrile

A mixture of 3-amino-6-(3,5-difluorobenzylthio)picolinoamide (2.37 mmol, 0.7 g) and $P_2Cl_5$ (9.48 mmol, 1.346 g), 20 ml of toluene and 1 ml of ionic solvent (1-butyl-3-methylimidazolium tetrafluoroborate) are placed in a microwave reactor and then heated at 140° C. for 30 minutes. The crude reaction product is then concentrated under reduced pressure and the orange crystals thus obtained are redissolved in ethyl acetate and washed using saturated aqueous $NaHCO_3$ solution. The organic phase is dried on magnesium sulfate and then concentrated to yield 0.7 g of a brown oil. This crude reaction product is purified by silica gel chromatography (AcOEt/heptane+0.1% of $NEt_3$) to yield, after concentration, 0.15 g (23%) of orange crystals.

$^1$H NMR: δH ppm (400 MHz, DMSO): 7.73 (1H, d, $CH_{arom}$), 7.25 (2H, m, $CH_{arom}$), 7.18 (1H, m), 6.85 (1H, d), 5.43 (2H, $CH_2$).

Example 6

5-(3,5-difluorobenzylthio)-1H-pyrazolo[4,3-b]pyridin-3-amine

A solution cooled to 0° C. of $NaNO_2$ in 3 ml of water is added drop by drop to a solution at 0° C. of 3-amino-6-(3,5-difluorobenzylthio)picolinonitrile (1.587 mmol, 0.44 g) in 15 ml of 6 N HCl solution. After 15 minutes, a solution cooled to 0° C. of $SnCl_2.2H_2O$ diluted in 4 ml of 12 N HCl is added drop by drop. The reaction medium is then stirred at 25° C. for 1 hour. The solution is extracted with ethyl acetate and then washed using saturated $NaHCO_3$ solution and then saturated NaCl solution. The organic phase is collected, dried on magnesium sulfate and then concentrated under reduced pressure. The residue is purified by silica gel chromatography (AcOEt/heptane) to yield, after concentration of the organic phases, 0.07 g (15%) of black crystals.

$^1$H NMR: δH ppm (400 MHz, DMSO): 11.64 (1H, s, NH), 7.63 (1H, d, $CH_{arom}$), 7.21 (2H, m, $CH_{arom}$), 7.13 (1H, d, $CH_{arom}$), 7.04 (1H, m, $CH_{arom}$), 5.38 (2H, 5, $NH_2$), 4.51 (2H, s, $CH_2$).

The following compounds are obtained by a similar method:

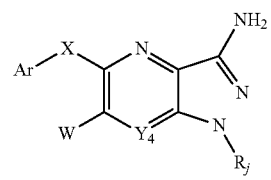

| Ex.** | ArX | W | $Y_4$ | $R_j$ | Compound names | Yield | Mass MH+ |
|---|---|---|---|---|---|---|---|
| 6-2 | 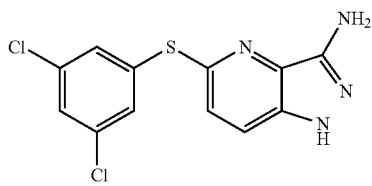 | H | CH | H | 5-(2,5-difluorobenzylthio)-1H-pyrazolo[4,3-b]pyridin-3-amine | 5% 4 steps | 293.0 |
| 6-3 | | H | CH | H | 5-(2,5-dichlorobenzylthio)-1H-pyrazolo[4,3-b]pyridin-3-amine | 3% 4 steps | 324.9 |

**¹H NMR: δH ppm (400 MHz, DMSO): 6-2: 11.65 (1H, s, NH), 7.64 (1H, dd, CHarom, J = 8.8 Hz), 7.42-7.51 (1H, m, CHarom), 7.20-7.25 (1H, m, CHarom), 7.14 (1H, dd, CHarom, J = 8.8 Hz), 7.01-7.11 (1H, m, CHarom), 5.37-5.41 (2H, m, NH2), 4.49 (2H, s). 6-3: 11.65 (1H, s, NH), 7.83 (1H, m, CHarom), 7.61 (1H, dd, CHarom, J = 8.8Hz), 7.50 (1H, m, CHarom), 7.28-7.32 (1H, m, CHarom), 7.10 (1H, dd, CHarom, J = 8.8 Hz), 7.01-7.11 (1H, m, CHarom), 5.42 (2H, s, NH2), 4.47 (2H, s).

Examples of Method B2

Example 7

5-(3,5-dichlorophenylthio)-1H-pyrazolo[4,3-b]pyridin-3-amine

Example 7a 6-(3,5-dichlorophenylthio)-3-nitropicolinonitrile

A mixture of 6-chloro-3-nitropicolinonitrile (3.70 g, 0.02 mol), 3,5-dichlorobenzenethiol (3.60 g, 0.02 mol) and $K_2CO_3$ (5.6 g, 0.04 mol) in 100 ml of acetonitrile is carried at 70° C. for 16 hours. The crude reaction product is diluted in an ethyl acetate fraction and washed using an aqueous phase. The organic phase is dried with sodium sulfate and the residue is purified by silica gel chromatography (AcOEt/petroleum ether) to yield 5.4 g (80%) of a yellow solid.

Example 7b 3-amino-6-(3,5-dichlorophenylthio)picolinonitrile 10 ml of concentrated HCl is added to a solution of 6-(3,5-dichlorophenylthio)-3-nitropicolinonitrile (3.4 g, 0.01 mol) in 50 ml of methanol under stirring. The reaction medium is refluxed, added together with 1.68 g (0.03 mol) of iron and stirred for 10 minutes. After returning to room temperature, the reaction mixture is added together with 100 ml of ethyl acetate and 50 ml of water. The pH is adjusted to 10 using 30% soda solution and the organic phase is extracted and then dried on anhydrous sodium sulfate before being concentrated. The residue is purified by silica gel chromatography (ethyl acetate/petroleum ether) to yield, after concentration of the fractions, 2.82 g (91%) of a yellow solid.

LCMS (m/e): 296 (M+H+). %.

Example 7

5-(3,5-dichlorophenylthio)-1H-pyrazolo[4,3-b]pyridin-3-amine

A solution of 350 mg of $NaNO_2$ (5.07 mmol) in water (2 ml) is added to a stirring solution of 1.5 g of 3-amino-6-(3,5-dichlorophenylthio)picolinonitrile (5.07 mmol) in 100 ml of 50% sulfuric acid at 0° C. The mixture is stirred for 20 minutes at 0-5° C. A solution of 2.9 g of $SnCl_2.2H_2O$ (12.7 mmol, 2.5 eq) in hydrochloric acid (12 N solution, 10 ml) is then added and the solution is stirred for 1 hour at room temperature. The solid formed is filtered and then washed twice with 20 ml of water. The solid is suspended in 100 ml and the pH is adjusted to 10 by adding 30% soda solution. The organic phase is separated and then dried on anhydrous sodium sulfate before being concentrated under vacuum. A light yellow solid is obtained after recrystallization in ethyl acetate (470 mg, 34%).

LCMS m/z 311 (M+H+).

¹H NMR: δH ppm (400 MHz, DMSO): 11.91 (1H, bs, NH), 7.79 (1H, d, $CH_{arom}$), 7.55 (1H, 5, $CH_{arom}$), 7.36 (2H, 5, $CH_{arom}$), 7.33 (1H, m, $CH_{arom}$), 5.42 (2H, 5, $NH_2$).

The following compounds are obtained by a similar method:

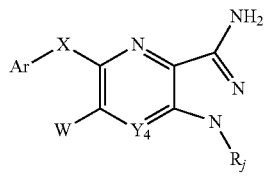

| Ex.** | ArX | Y₄ | W | R_j | Compound names | Yield | Mass MH⁺ |
|---|---|---|---|---|---|---|---|
| 7-1 | 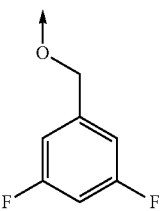 | CH | H | H | 5-(3,5-difluorobenzyloxy)-1H-pyrazolo[4,3-b]pyridin-3-amine | 28% | 277 |
| 7-2 | 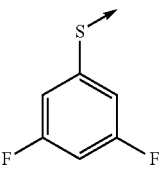 | CH | H | H | 5-(3,5-difluorophenylthio)-1H-pyrazolo[4,3-b]pyridin-3-amine | 33% 3 steps | 278.9 |
| 7-3 | 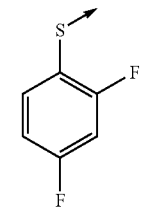 | CH | H | H | 5-(2,4-difluorophenylthio)-1H-pyrazolo[4,3-b]pyridin-3-amine | 24% 3 steps | 279.0 |
| 7-4 | 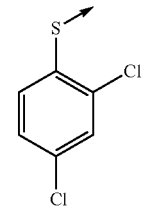 | CH | H | H | 5-(2,4-dichlorophenylthio)-1H-pyrazolo[4,3-b]pyridin-3-amine | 24% 3 steps | 311.0 |
| 7-5 | 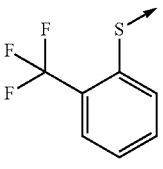 | CH | H | H | 5-(2-(trifluoromethyl)phenylthio)-1H-pyrazolo[4,3-b]pyridin-3-amine | 17% 3 steps | 311.0 |
| 7-6 | 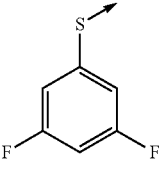 | N | H | H | 5-(3,5-difluorophenylthio)-1H-pyrazolo[3,4-b]pyrazin-3-amine | 6% 7 steps | 279.9 |
| 7-7 | 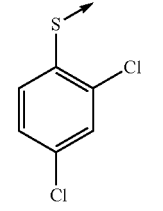 | N | H | H | 5-(2,4-dichlorophenylthio)-1H-pyrazolo[3,4-b]pyrazin-3-amine | 4% 7 steps | 311.9 |
| 7-8 | 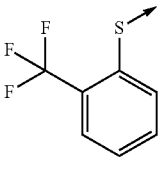 | N | H | H | 5-(2-(trifluoromethyl)phenylthio)-1H-pyrazolo[3,4-b]pyrazin-3-amine | 6% 7 steps | 311.9 |

-continued

| Ex.** | ArX | Y₄ | W | R_j | Compound names | Yield | Mass MH⁺ |
|---|---|---|---|---|---|---|---|
| 7-9 | 3,5-difluorobenzyl-O-CH₂- | CH | H | H | 5-(3,5-difluorobenzyloxy)-1H-pyrazolo[4,3-b]pyridin-3-amine | 6% 3 steps | 277.0 |
| 7-10 | 2,4-difluorobenzyl-O-CH₂- | CH | H | H | 5-(2,5-difluorobenzyloxy)-1H-pyrazolo[4,3-b]pyridin-3-amine | 3% 3 steps | 277.0 |
| 7-11 | 2,4-dichlorobenzyl-O-CH₂- | CH | H | H | 5-(2,5-dichlorobenzyloxy)-1H-pyrazolo[4,3-b]pyridin-3-amine | 32% 3 steps | 309.0 |
| 7-12 | 4-chloro-2-(trifluoromethyl)benzyl-O-CH₂- | CH | H | H | 5-(5-chloro-2-(trifluoromethyl)benzyloxy)-1H-pyrazolo[4,3-b]pyridin-3-amine | 8% 3 steps | 343.1 |
| 7-13 | pyridin-3-ylmethyl-O-CH₂- | CH | H | H | 5-(pyridin-3-ylmethoxy)-1H-pyrazolo[4,3-b]pyridin-3-amine | 6% 3 steps | 342.1 |

¹H NMR: δH ppm (400 M Hz, DMSO): 7-1: 11.61 (1H, s large, NH), 7.73 (1H, d, CHarom), 7.24 (2H, m, CHarom), 7.18 (1H, m, CHarom), 6.86 (1H, d, CHarom). 7-2: 11.95 (1H, sl, NH), 7.78 (1H, d, CHarom, J = 11.6 Hz), 7.33 (1H, d, CHarom, J = 11.6 Hz), 7.19 (1H, t, CHarom), 7.04 (2H, 2d, CHarom, J = 8.8 Hz), 5.51 (2H, s, NH₂). 7-3: 11.80 (1H, sl, NH), 7.70 (1H, d, CHarom, J = 8.8 Hz), 7.60 (1H, t, CHarom), 7.49 (1H, q, CHarom), 7.27-7.33 (1H, m, CHarom), 7.11 (1H, d, CHarom, J = 8.8 Hz), 5.41 (2H, s, NH₂). 7-4: 11.93 (1H, sl, NH), 7.80 (1H, d, CHarom, J = 11.6 Hz), 7.62 (1H, d, CHarom, J = 11.6 Hz), 7.40 (1H, dd, CHarom, J = 11.2 Hz), 7.29 (1H, d, CHarom, J = 11.6 Hz), 7.1 (1H, s, CHarom), 5.51 (2H, s, NH₂). 7-5: 11.86 (1H, sl, NH), 7.87 (1H, d, CHarom, J = 9.6 Hz), 7.73 (1H, d, CHarom, J = 11.6), 7.50-7.68 (2H, m, CHarom), 7.44 (1H, d, CHarom, J = 10.4 Hz), 7.11 (1H, d, CHarom, J = 11.6 Hz), 5.46 (2H, s, NH₂). 7-6: 12.66 (1H, sl, NH), 8.52 (1H, s, CHarom), 7.12-7.20 (1H, m, CHarom), 7.02-7.10 (2H, m, CHarom), 5.90 (2H, s, NH₂). 7-7: 12.70 (1H, s, NH), 8.52 (1H, s, CHarom), 7.60 (1H, d, CHarom, J = 8.8 Hz), 7.38 (1H, dd, CHarom, J = 8.4 Hz), 7.12 (1H, s, CHarom), 5.92 (2H, s, NH₂). 7-8: 12.66 (1H, s, NH), 8.39 (1H, s, CHarom), 7.84 (1H, d, CHarom, J = 7.6 Hz), 7.58 (1H, t, CHarom), 7.50 (1H, t, CHarom), 7.34 (1H, d, CHarom, J = 7.6 Hz), 5.87 (2H, s, NH₂). 7-9: 11.57 (1H, s, NH), 7.74 (1H, d, CHarom, J = 9 Hz), 7.25 (3H, m, CHarom), 6.88 (1H, d, CHarom, J = 9 Hz), 5.44 (2H, s), 5.08 (2H, s). 7-10: 11.58 (1H, s, NH), 7.73 (1H, d, CHarom, J = 12.0 Hz), 7.48-7.58 (1H, m, CHarom), 7.21-7.37 (2H, m, CHarom), 6.85 (1H, d, CHarom, J = 12.0 Hz), 5.44 (2H, s, CH), 5.10 (2H, sl, NH₂). 7-11: 11.60 (1H, sl, NH), 7.70-7.77 (2H, m, CHarom), 7.57 (1H, d, CHarom, J = 11.2 Hz), 7.40-7.50 (1H, m, CHarom), 6.89 (1H, d, CHarom, J = 12.0 Hz), 5.48 (2H, s, CH), 5.06 (2H, sl, NH₂). 7-12: 11.60 (1H, sl, NH), 7.91 (1H, s, CHarom), 7.83 (1H, d, CHarom, J = 11.2 Hz), 7.75 (1H, d, CHarom, J = 12.0 Hz), 7.66 (1H, d, CHarom, J = 9.6 Hz), 6.88 (1H, d, CHarom, J = 12.0 Hz), 5.58 (2H, s, CH), 5.01 (2H, sl, NH₂). 7-13: 11.56 (1H, sl, NH), 8.77 (1H, s, CHarom), 8.55 (1H, s, CHarom), 7.96 (1H, d, CHarom, J = 10.4 Hz), 7.72 (1H, d, CHarom, J = 12.0 Hz), 7.42 (1H, dd, CHarom, J = 10.0 Hz), 6.83 (1H, d, CHarom, J = 11.6 Hz), 5.45 (2H, s, CH), 5.15 (2H, sl, NH₂).

Example 8

N5-(3,5-difluorophenyl)-1H-pyrazolo[4,3-b]pyridine-3,5-diamine

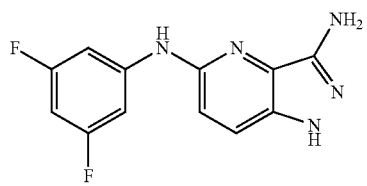 [SMILES: N=C(N)c1nc(Nc2cc(F)cc(F)c2)ccc1N]

Example 8a

6-(3,5-difluorophenylamino)-3-nitropicolinonitrile

A mixture of 6.5 g of 6-chloro-3-nitropicolinonitrile (0.065 mol) and 6.2 g of 3,5-difluoroaniline (0.048 mol) in 100 ml of toluene is heated at 70° C. for 5 hours. The crude reaction product is diluted in an ethyl acetate fraction and washed using saturated NaCl solution. The organic phase is dried with sodium sulfate and the residue purified by silica gel chromatography (AcOEt/petroleum ether) to yield 3.9 g (33%) of a yellow solid.

Example 8b

3-amino-6-(3,5-difluorophenylamino)picolinonitrile 10 ml of concentrated HCl is added to a solution of 6-(3,5-dichlorophenylthio)-3-nitropicolinonitrile (3.9 g, 0.0141 mol) in 150 ml of ethanol under stirring. The reaction medium is refluxed, added together with 2.4 g of iron (0.0423 mol) and stirred at 80° C. for 1 hour. After returning to 0° C. the pH is adjusted to 8 using 1 N soda solution and the reaction medium is filtered on Celite. The reaction mixture is added together with 100 ml of ethyl acetate and 50 ml of methanol. The organic phase is extracted and the aqueous phase is extracted several times by ethyl acetate fractions. The organic phases are combined and then dried on anhydrous sodium sulfate before being concentrated to yield, after concentration, 2.3 g (66%) of a brown solid.

Example 8

5-(3,5-difluorophenylamino)-1H-pyrazolo[4,3-b]pyridin-3-amine

A solution of 713 mg of NaNO$_2$ (10.3 mmol) in water (5 ml) is added, drop by drop, to a stirring solution of 2.3 g of 3-amino-6-(3,5-difluorophenylamino)picolinonitrile (9.4 mmol) in 100 ml of 6 N hydrochloric acid at 0° C. The mixture is stirred for 20 minutes at 0-5° C. A solution of 5.3 g of SnCl$_2$.2H$_2$O (23.5 mmol, 2.5 eq) in hydrochloric acid (12 N solution, 30 ml) is then added drop by drop and the solution is stirred for 1 hour at room temperature. The reaction medium is then cooled at 0° C. and basified to pH 8 using 30% soda solution. The mixture is extracted with ethyl acetate and washed using saturated NaCl solution and the organic phase is dried on anhydrous sodium sulfate before being concentrated under vacuum. The residue is purified by silica column chromatography (AcOEt). A light yellow solid is obtained (530 mg, 22%).

LCMS: m/z 262 (M+H$^+$).

$^1$H NMR: δH ppm (400 MHz, DMSO): 11.47 (s, 1H), 9.45 (s, 1H), 7.65 (m, 3H), 6.87 (d, 1H, J=7.8 Hz), 6.60 (m, 1H), 5.09 (s, 2H).

The following compounds are obtained by a similar method:

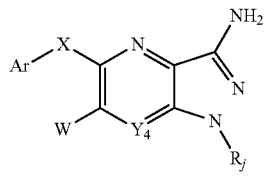

| Ex.** | ArX | Y$_4$ | W | R$_j$ | Compound names | Yield | Mass MH$^+$ |
|---|---|---|---|---|---|---|---|
| 8-1 | HN-(2,4-difluorophenyl) | CH | H | H | N-(2,5-difluorophenyl)-1H-pyrazolo[4,3-b]pyridine-3,5-diamine | 4% 4 steps | 262.0 |
| 8-2 | HN-(2,4-dichlorophenyl) | CH | H | H | N-(2,5-dichlorophenyl)-1H-pyrazolo[4,3-b]pyridine-3,5-diamine | 9% 4 steps | 294.0 |

**$^1$H NMR: δH ppm (400 M Hz, DMSO): 8-1: 11.46 (1H, s, NH), 8.75-8.82 (2H, m, CHarom), 7.65 (1H, dd, CHarom, J = 9.2 Hz), 7.19-7.31 (2H, m, CHarom), 6.67-6.63 (1H, sl, CHarom), 5.06 (2H, s, NH$_2$). 8-2: 11.58 (1H, sl, NH), 8.65 (1H, s, CHarom), 8.35 (1H, s, CHarom), 7.69 (1H, d, CHarom, J = 12.0 Hz), 7.45 (1H, d, CHarom, J = 11.6 Hz), 7.24 (1H, d, CHarom, J = 12.0 Hz), 6.96 (1H, dd, CHarom, J = 11.2 Hz), 5.03 (2H, sl, NH$_2$).

Example of Method B3

Example 9

5-(3,5-difluorobenzyl)-1H-pyrazolo[4,3-b]pyridin-3-amine

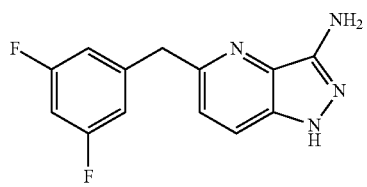 [SMILES: Nc1n[nH]c2ccc(Cc3cc(F)cc(F)c3)nc12]

This compound can be prepared from the following intermediates, according to method B3.

Example 9a 2-(3,5-difluorobenzyl)-4,4,5,5-tetramethyl-1,3,2-dioxaborolane

Example 9b 6-(3,5-difluorobenzyl)-3-nitropicolinonitrile

Example 9c 3-amino-6-(3,5-difluorobenzyl)picolinonitrile

Example of Method B4

Example 10

3-amino-N-(3,5-difluorophenyl)-1H-pyrazolo[3,4-b]pyridine-5-sulfonamide

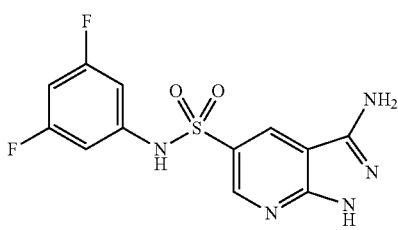 [SMILES: N=C(N)c1cc(S(=O)(=O)Nc2cc(F)cc(F)c2)cnc1N]

Example 10a 5-(N-(3,5-difluorophenyl)sulfamoyl)nicotinic acid 2.74 g (9.64 mmol) of ethyl 2-chloro-5-(chlorosulfonyl)nicotinate in solution in 20 ml of anhydrous dichloromethane is added, drop by drop at 0° C., to a mixture of 623 mg (4.82 mmol) of 3,5-difluoroaniline and 1.68 ml (12.05 mmol) of triethylamine diluted in 10 ml of anhydrous dichloromethane. The solution is stirred at room temperature for 3 hours. The solvent is evaporated to yield a light brown solid. The solid is triturated in 20 ml of methanol, filtered and then rinsed with 3 ml of methanol to yield 2.85 g of a white solid.

This solid is redissolved in 25 ml of tetrahydrofuran and is added together with a solution of 0.421 g (10.04 mmol) of lithium monohydrate hydroxide in 10 ml of water. The reaction mixture is left under stirring for 3 hours at 35° C. and then diluted in water, acidified with 1 N hydrochloric acid and extracted with ethyl acetate. The organic phase is collected, dried on sodium sulfate, filtered and concentrated to yield 1.12 g of 5-(N-(3,5-difluorophenyl)sulfamoyl)nicotinic acid in the form of an orange solid (yield=67%).

$^1$H NMR: δH ppm (400 MHz, DMSO): 8.91 (1H, s, $CH_{arom}$), 8.51 (1H, s, $CH_{arom}$), 7.02 (1H, dd, $CH_{arom}$), 6.83 (2H, d, $CH_{arom}$).

Example 10b 2-chloro-5-(N-(3,5-difluorophenyl)sulfamoyl)nicotinamide 0.288 ml (3.87 mmol) of thionyl chloride and a drop of DMF are added successively to 0.450 g (1.29 mmol) of 2-chloro-5-(N-(3,5-difluorophenyl)sulfamoyl)nicotinic acid in 5 ml of anhydrous toluene. The mixture is placed under stirring, at reflux of toluene, for 2 hours. The acid chloride reaction mixture is then added drop by drop to an iced solution, under stirring, of 4.5 ml of 25% ammonium hydroxide. A release of gas is observed. The reaction medium is left under stirring at room temperature for 30 minutes. The reaction medium is extracted several times with ethyl acetate. The combined organic phases are dried on anhydrous sodium sulfate and then concentrated. 0.315 g of 2-chloro-5-(N-(3,5-difluorophenyl)sulfamoyl)nicotinamide in the form of a light brown solid is obtained (yield=72%).

$^1$H NMR: δH ppm (400 MHz, DMSO): 11.18 (1H, bs, NH), 8.86 (1H, s, $CH_{arom}$), 8.22 (1H, 5, $CH_{arom}$), 8.21 (1H, bs, NH), 7.98 (1H, bs, NH), 6.96 (1H, dd, $CH_{arom}$), 6.79 (2H, d, $CH_{arom}$).

Example 10c 6-chloro-5-cyano-N-(3,5-difluorophenyl)pyridine-3-sulfonamide 3.4 ml (36.2 mmol) of phosphoryl chloride and a drop of concentrated sulfuric acid are added to 0.315 g (0.906 mmol) of 2-chloro-5-(N-(3,5-difluorophenyl) sulfamoyl)nicotinamide. The reaction mixture is stirred for 2 hours at 90° C. and then added drop by drop to ice. The brown solid is filtered, rinsed with water and then dried under vacuum. 0.217 g of 6-chloro-5-cyano-N-(3,5-difluorophenyl)pyridine-3-sulfonamide is obtained in the form of a light brown solid (yield=72%).

$^1$H NMR: δH ppm (400 MHz, DMSO): 11.34 (1H, bs, NH), 9.04 (1H, 5, $CH_{arom}$), 8.92 (1H, 5, $CH_{arom}$), 7.03 (1H, dd, $CH_{arom}$), 6.85 (2H, d, $CH_{arom}$).

Example 10

3-amino-N-(3,5-difluorophenyl)-1H-pyrazolo[3,4-b]pyridine-5-sulfonamide 0.377 ml (2.63 mmol) of 35% hydrazine is added to 0.217 g (0.658 mmol) of 6-chloro-5-cyano-N-(3,5-difluorophenyl)pyridine-3-sulfonamide diluted in 6 ml of isopropanol. The solution is heated at 75° C. for 2 hours. The solvent is evaporated to yield 0.214 g of 3-amino-N-(3,5-difluorophenyl)-1H-pyrazolo[3,4-b]pyridine-5-sulfonamide in the form of a yellow solid (yield=100%).

$^1$H NMR: δH ppm (400 MHz, DMSO): 8.74 (1H, d, CH$_{arom}$), 8.68 (1H, d, CH$_{arom}$), 6.88 (1H, dd, CH$_{arom}$), 6.80 (2H, d, CH$_{arom}$), 6.04 (2H, bs, NH).

Examples of Method B5

Example 11

5-(3,5-difluorobenzyloxy)-1H-pyrazolo[3,4-b]pyridin-3-amine

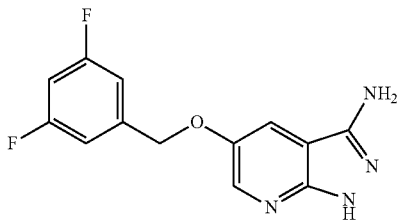 [SMILES: N=C(N)c1cc(OCc2cc(F)cc(F)c2)cnc1N]

This compound can be prepared from the following intermediates, according to method B5.

Example 11a 5-hydroxynicotinonitrile

A mixture of 1 g of 5-methoxynicotinonitrile (7.46 mmol) and 8.62 g of pyridine hydrochloride is heated at 200° C. for 2 hours. The crude reaction product is diluted in a water fraction several times with diethyl ether. The aqueous phase is basified by adding sodium bicarbonate and then extracted again with diethyl ether. The organic phase is dried and then concentrated to yield 850 mg of 5-hydroxynicotinonitrile (95%) in the form of a beige solid.

LCMS: m/z 120.94 (M+H$^+$).

$^1$H NMR: δH ppm (400 MHz, DMSO): 10.79 (s, 1H), 8.46 (s, 1H, CHarom.), 8.42 (s, 1H, CHarom.), 7.60 (s, 1H, CHarom.).

Example 11b 5-(3,5-difluorobenzyloxy)nicotinonitrile 876 mg (2 eq) of sodium hydride is added gradually at 0° C. under nitrogen to a solution of 865 mg of 5-hydroxynicotinonitrile (7.2 mmol) in 15 mL of dimethylacetamide. The mixture is stirred 10 min at 0° C. before adding 2.24 g (1.5 aq) of 3,5-difluorobenzyl bromide. The mixture is placed under stirring for 2.5 additional hours before being diluted in an ethyl acetate fraction and being washed with aqueous fractions. The organic phases are isolated, dried and concentrated. The solid residue obtained is recrystallized in methanol to yield 1.1 g (68% of 5-(3,5-difluorobenzyloxy) nicotinonitrile in the form of a beige powder.

LCMS: m/z 247.11 (M+H$^+$).

$^1$H NMR: δH ppm (400 MHz, DMSO): 8.69 (s, 1H, CH), 8.65 (s, 1H, CH), 8.08 (s, 1H, CH), 7.26 (m, 3H, CH), 5.28 (d, 2H, CH$_2$).

Example 11c 3-cyano-5-(3,5-difluorobenzyloxyl)pyridine 1-oxide 224 mg of m-CPBA is added at 0° C. to a solution in acetonitrile of 250 mg of 5-(3,5-difluorobenzyloxy)nicotinonitrile. The reaction medium is stirred for 20 hours while a precipitate is formed progressivelt. this solid is then filtered and washed to yield 200 mg (75%) of 3-cyano-5-(3,5-difluorobenzyloxyl)pyridine 1-oxide in the form of a white powder.

LCMS: m/z 263.06 (M+H$^+$).

Example 11d 2-chloro-5-(3,5-difluorobenzyloxy)nicotinonitrile

A mixture of 650 mg of 3-cyano-5-(3,5-difluorobenzyloxyl)pyridine 1-oxide in 2.3 mL of POCl$_3$ added with few drops of H$_2$SO$_4$ is heated at 110° C. for 1 h30. The crude reaction medium is then poured in ice and the precipitate thus formed is isolated by filtration and dried under vacuum to yield 600 mg of a beige solid in the form of a mixture of regioisomers comprising mainly the desired 2-chloro-5-(3,5-difluorobenzyloxy)nicotinonitrile which is used without further purification.

LCMS: m/z 281.02 (M+H$^+$).

Example 11

5-(3,5-difluorobenzyloxy)-1H-pyrazolo[3,4-b]pyridin-3-amine 313 mg of hydrazine hydrate (5 eq) is added to a solution of 1.6 g of 2-chloro-5-(3,5-difluorobenzyloxy)nicotinonitrile (450 μmol) in 10 mL of propan-2-ol. The reaction mixture is heated at 100° C. for 6 hours. After return to room temperature leading to a precipitation, the crude reaction medium is filtered, the solid is removed and the filtrate is dry evaporated. It is then purified by chromatography on a silica column eluted with a gradient of ethyl acetate and methanol, whereas the more polar fraction is isolated, concentrated and suspended again in a small fraction of methanol under stirring. The solid thus obtained is isolated and dried to yield 221 mg of 5-(3,5-difluorobenzyloxy)-1H-pyrazolo[3,4-b]pyridin-3-amine in the form of a beige solid which is used without further purification.

LCMS: m/z 277.07 (M+H$^+$).

Example of Method B6

Example 11bis

N-(3-amino-1H-pyrazolo[3,4-b]pyridin-5-yl)-3,5-difluorobenzene-sulfonamide

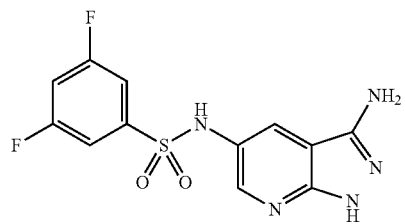 [SMILES: N=C(N)c1cc(NS(=O)(=O)c2cc(F)cc(F)c2)cnc1N]

Example 11bis-a

N-(6-chloro-5-cyanopyridin-3-yl)-3,5-difluorobenzene-sulfonamide 1.132 g (5.32 mmol) of 3,5-difluorobenzene-1-sulfonyle chloride is added under argon to a solution of 545 mg (3.55 mmol) of 5-amino-2-chloronicotinotrile in 20 mL of an anhydrous 1:1 mixture of THF and pyridine. The reaction medium is heated to 70° C. for 3 hours and let 12 additional hours under stirring at room temperature. The solvent is dry evaporated and the crude reaction product is redissolved in ethyl acetate and washed with several aqueous fractions. The organic phase is dried on magnesium sulfate, filtered, concentrated and then purified by silica gel chromatography to yield 784 mg (67%) of N-(6-chloro-5-cyanopyridin-3-yl)-3,5-difluorobenzene-sulfonamide.

$^1$H NMR: δH ppm (400 MHz, DMSO): 11.39 (1H, sl, NH), 8.34 (1H, m, CHarom), 8.10 (1H, m, CHarom), 7.67 (1H, m, CHarom), 7.59 (2H, m, CHarom).

Example 11bis

N-(3-amino-1H-pyrazolo[3,4-b]pyridin-5-yl)-3,5-difluorobenzene-sulfonamide 1.786 g (35.7 mmol) of hydrazine hydrate is added under argon to a solution of 784 mg (2.38 mmol) of N-(6-chloro-5-cyanopyridin-3-yl)-3,5-difluorobenzene-sulfonamide in 6 mL of ethanol. The solution is heated to 100° C. for 20 hours and then cooled to room temperature. The solvent is evaporated to yield 810 mg of N-(3-amino-1H-pyrazolo[3,4-b]pyridin-5-yl)-3,5-difluorobenzene-sulfonamide (100%) which is used without further purification in the following steps.

LCMS: m/z 326.07 (M+H$^+$).

Example of Method C1

Example 12

N6-(2,4-difluorophenyl)-1H-pyrazolo[3,4-b]pyridine-3,6-diamine

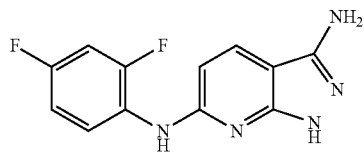 [SMILES: N=C(N)c1ccc(Nc2ccc(F)cc2F)nc1N]

This compound can be prepared from the following intermediates, according to method C1.

Example 12-a 5-cyano-6-(methylthio)pyridin-2-yl trifluoromethanesulfonate 15.26 mL (1.2 eq) of potassium 2-methylpropan-2-olate and then 9.03 g (1.2 eq) of 1,1,1-trifluoro-N-phenyl-N-(trifluoromethylsulfonyl)methanesulfonamide are added dropwise to a solution of 3.5 g (21.06 mmol) of 6-hydroxy-2-(methylthio)nicotinonitrile in 180 mL of tetrahydrofurane under nitrogen. The reaction mixture is stirred at room temperature for 2 h45. Water is added and the product is extracted with ethyl acetate. The organic phase is dried on anhydrous magnesium sulfate, filtered and evaporated to yield an orange solid. The product is purified on a silica gel column (eluent: cyclohexane/dichloromethane 5:5) to yield 5.31 g (85%) of 5-cyano-6-(methylthio)pyridin-2-yltrifluoromethanesulfonate in the form of a yellow solid.

$^1$H NMR: δH ppm (400 MHz, DMSO): 8.57 (1H, d, CH), 7.52 (1H, d, CH), 2.59 (3H, s, CH$_3$).

Example 12-b 6-(2,4-difluorophenylamino)-2-(methylthio)nicotinonitrile 0.81 mL (1.2 eq) of, 4-difluoroaniline and 1.53 g (1.4 eq) of cesium(I) carbonate are added under nitrogen to a solution of 2 g (6.71 mmol) of 5-cyano-6-(methylthio)pyridin-2-yl trifluoromethanesulfonate in 30 mL of 1,4-dioxane. The medium is degased for 5 minutes under argon before adding 0.25 g (0.06 eq) of de 2,2'-bis(diphenylphosphino)-1,1'-binaphthyl and 0.08 g (0.04 eq) of (1E,4E)-1,5-diphenylpenta-1,4-dien-3-one, palladium(II) complex. The reaction medium is stirred at 100° C. for 2 hours. After return to room temperature, ethyl acetate and brine are added. The organic phase is dried on anhydrous magnesium sulfate, filtered and evaporated. The residue obtained is purified on silica gel chromatography (eluent: cyclohexane/ethyl acetate 8:2 then 7:3) to yield 1.52 g (82%) of 6-(2,4-difluorophenylamino)-2-(methylthio)nicotinonitrile in the form of a white solid.

LCMS (IE, m/z): (M+1) 278.06.

$^1$H NMR: δH ppm (400 MHz, DMSO): 9.57 (1H, s, NH), 7.73-7.86 (2H, m, CH), 7.28-7.44 (1H, m, CH), 7.02-7.18 (1H, m, CH), 6.60 (1H, d, CH), 2.41 (3H, s, CH$_3$).

Example 12

N6-(2,4-difluorophenyl)-1H-pyrazolo[3,4-b]pyridine-3,6-diamine 769 mg (3.12 mmol) of m-chloroperbenzoic acid (mCPBA) is added under argon to a stirring solution of 786 mg (2.83 mmol) of 6-(2,4-difluorophenylamino)-2-(methylthio)nicotinonitrile in 25 mL of dichloromethane. The reaction medium is stirred 1 hour at room temperature before adding a fraction of ethyl acetate and washed this organic phase with a NaHCO$_3$ saturated solution. The combined organic phases are dried on magnesium sulfate and dry evaporated. The crude reaction product is dissolved again in 10 mL of propanol and 2 equivalents of hydrazine hydrochloride in water are added. The mixture is heated at 90° C. for 6 hours before being diluted in water and extracted with ethyl acetate. The organic phase is dried on magnesium sulfate and dry evaporated before being purified by silica gel chromatography to yield 495 mg of N6-(2,4-difluorophenyl)-1H-pyrazolo[3,4-b]pyridine-3,6-diamine in the form of a yellow-orange solid (67%).

LCMS (IE, m/z): (M+1) 262.14.

$^1$H NMR: δH ppm (400 MHz, DMSO): 11.40 (1H, s, NH), 8.76 (1H, s, NH), 8.15 (1H, m, CH), 7.81 (1H, d, CH), 7.28 (1H, m, CH), 7.06 (1H, m, CH), 6.55 (1H, d, CH), 5.24 (2H, s, NH$_2$).

The following compound is obtained by a similar method:

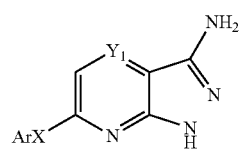

| Ex.** | ArX | Y₁ Compound names | Yield | Masse MH⁺ |
|---|---|---|---|---|
| 12-1 | 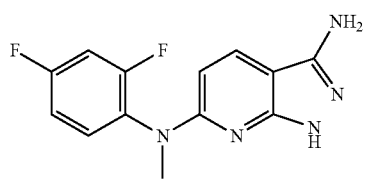 | CH N6-(3,5-difluorobenzyl)-1H-pyrazolo[3,4-b]pyridine-3,6-diamine | 70% | 276.15 |

**¹HNMR, dmso-d₆,Ex.: 12-1: 11.17 (1H, s,NH), 7.66 (1H, d, CH), 7.37 (1H, s,NH), 7.04 (3H, m, CH), 6.24 (1H, d, CH), 5.11 (2H, s, NH₂), 4.52 (2H, s, CH₂).

Example 12bis

N6-(2,4-difluorophenyl)-N6-methyl-1H-pyrazolo[3,4-b]pyridine-3,6-diamine

Example 12bis-a 6-((3,5-difluorophenyl)(methyl)amino)-2-(methylthio) nicotinonitrile 3.05 mL (5.04 mmol) of potassium 2-methylpropan-2-olate and then 286 µL (1.8 eq) of iodomethane are added dropwise under nitrogen to a solution of 700 mg (2.52 mmol) of 6-(2,4-difluorophenylamino)-2-(methylthio)nicotinonitrile in 20 mL of N,N-dimethyl formamide. The reaction medium is stirred at room temperature for 24 hours and then 126 µL (0.8 eq, 2.02 mmol) of iodomethane is added. The reaction medium is stirred at room temperature for 2 additional hours. Water is added and the product is extracted with ethyl acetate. The organic phase is dried on anhydrous magnesium sulfate, filtered, and evaporated to yield 660 mg (90%) of 6-((2,4-difluorophenyl)(methyl)amino)-2-(methylthio)nicotinonitrile in the form of a brown solid.

LCMS (IE, m/z): (M+1) 292.09.

¹H NMR: δH ppm (400 MHz, DMSO): 7.74-7.80 (1H, m, CH), 7.55-7.63 (1H, m, CH), 7.43-7.52 (1H, m, CH), 7.18-7.27 (1H, m, CH), 6.16-6.30 (1H, m, CH), 3.43 (3H, s, CH₃), 2.42 (3H, s, CH₃).

Example 12bis

N6-(2,4-difluorophenyl)-N6-methyl-1H-pyrazolo[3,4-b]pyridine-3,6-diamine 452 mg (1.84 mmol) of mCPBA is added under argon to a stirring solution of 486 mg (1.67 mmol) of 6-((2,4-difluorophenyl)(methyl)amino)-2-(methylthio)nicotinonitrile in 15 mL of dichloromethane. The reaction medium is stirred 30 min at room temperature before adding an ethyl acetate fraction. The organic phase is washed with a NaHCO₃ saturated solution, dried on magnesium sulfate and dry evaporated. The crude reaction product is dissolved again in 6 mL of propanol and 164 µL (3.38 mmol) of hydrazine hydrochloride in water is added. The mixture is heated at 90° C. for 6 hours before being diluted in water and extracted with ethyl acetate. the organic phase is dried on magnesium sulfate and dry evaporated before being purified by silica gel chromatography to yield 328 mg of N6-(2,4-difluorophenyl)-N6-methyl-1H-pyrazolo[3,4-b]pyridine-3,6-diamine in the form of a yellow-orange solid (70%).

LCMS (IE, m/z): (M+1) 276.15.

¹H NMR: δH ppm (400 MHz, DMSO): 11.41 (1H, s, NH), 7.75 (1H, d, CH), 7.51-7.55 (1H, m, CH), 7.40-7.43 (1H, m, CH), 7.17-7.22 (1H, m, CH), 6.03 (1H, d, CH), 5.23 (2H, s, NH₂), 3.28 (3H, s, CH₃).

Example of Method C3

Example 12ter 6-(2,4-difluorophenylthio)-1H-pyrazolo[3,4-b]pyridin-3-amine

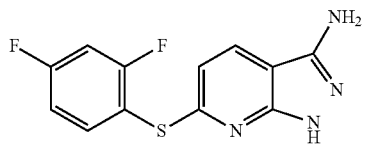 [SMILES: N=C(N)c1ccc(Sc2ccc(F)cc2F)nc1N]

Example 12ter-a 2-chloro-6-(2,4-difluorophenylthio)nicotinonitrile

A solution of 362 mg (1.05 eq) of potassium hydroxide in 10 mL of ethanol is added, under nitrogen, to a solution of 698 µL (6.16 mmol) of 2,4-difluorobenzenethiol in 30 mL of ethanol. The reaction medium is stirred at room temperature for 15 minutes and then cooled in ice before adding a solution of 1.015 g (0.95 eq) of 2,6-dichloronicotinonitrile in 30 mL of ethanol. The reaction medium is stirred for 2 hours at 0-5° C. 63 ml, of a 0.1N HCl solution is added to stop the reaction. Water is added and the producted is extracted with ethyl acetate. The organic phase is dried on anhydrous magnesium sulfate, filtered and evaporated. The residue is purified by silica gel chromatography (eluent: cyclohexane/ethyl acetate 94:6) to yield 1.09 g (66%) of 2-chloro-6-(2,4-difluorophenylthio)-nicotinonitrile in the form of a white solid.

LCMS (IE, m/z): (M+1) 282.98.

$^1$H NMR: δH ppm (400 MHz, DMSO): 8.24 (1H, d, CH), 7.77-7.85 (1H, m, CH), 7.52-7.63 (1H, m, CH), 7.25-7.35 (2H, m, CH), 2.41 (3H, s, CH$_3$).

Example 12ter 6-(2,4-dffluorophenylthio)-1H-pyrazolo[3,4-b]pyridin-3-amine 0.561 mL (11.57 mmol) of hydrazine monohydrate is added under nitrogen to a stirring solution of 1.09 g (3.86 mmol) of 2-chloro-6-(2,4-difluorophenylthio)nicotinonitrile in 15 mL of propanol. The reaction medium is heated at 80° C. for 4 hours. A precipitate is obtained when the reaction medium is returned to room temperature. This precipitate is filtered and rinsed with ethanol. The solid is dissolved in an ethyl acetate fraction and washed with a 1N HCl solution. The organic phase is dried on magnesium sulfate and dry evaporated to yield 420 mg (39%) of 6-(2,4-difluorophenylthio)-1H-pyrazolo[3,4-b]pyridin-3-amine in the form of a yellow solid.

$^1$H NMR: δH ppm (400 MHz, DMSO): 12.10 (1H, s, NH), 8.11 (1H, d, CH), 7.82-7.89 (1H, m, CH), 7.58-7.63 (1H, m, CH), 7.32-7.36 (1H, m, CH), 6.86 (1H, d, CH), 4.59 (2H, s, NH$_2$).

The following compound is obtained by a similar method:

solution of 416 mg of palladium(II) chloride (510 mmol) and 883 mg of 2,6-dichloronicotinonitrile (5.1 mmol) in 2 mL of anhydrous THF. The reaction is refluxed for 7 hours, then cooled to room temperature. A 1N soda aqueous solution is added and the product is extracted with several successive ethyl acetate fractions. The organic phases are dried on magnesium sulfate and dry evaporated before being purified by silica gel chromatography to yield 680 mg of a mixture of 2-chloro-6-(3,5-difluorobenzyl)-nicotinonitrile and by-products which is used without further purification in the following step.

The previous mixture is dissolved in 10 mL of isopropanol under stirring and 750 µL of 35% hydrazine hydrate is added. The solution is heated at 80° C. for 4 hours. The solvent is dry evaporated and the product is purified by silica gel chromatography (dichloromethane/methanol 9:1) to yield 290 mg of 6-(3,5-difluorobenzyl)-1H-pyrazolo[3,4-b]pyridin-3-amine (64%).

LCMS (IE, m/z): (M+1) 261.16.

$^1$H NMR: δH ppm (400 MHz, DMSO): 11.82 (1H, s, NH), 8.01 (1H, d, CH), 6.99-7.04 (3H, m, CH), 6.91 (1H, d, CH), 5.49 (2H, s, NH$_2$), 4.12 (2H, s, CH$_2$).

Example of Method D1

Example 13

5-(3,5-difluorobenzyl)-1H-pyrazolo[3,4-b]pyridine-3-amine

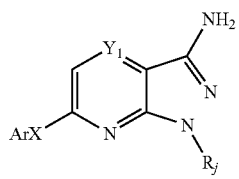

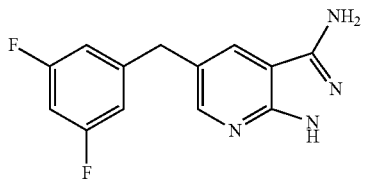

| Ex.** | ArX | Y$_1$ | R$_j$ | Compound names | Yield | Mass MH$^+$ |
|---|---|---|---|---|---|---|
| 12ter-1 | (2,4-difluorophenoxy) | CH | H | 6-(2,4-difluorophenoxy)-1H-pyrazolo[3,4-b]pyridin-3-amine | ND | 263.06 |

Example 12quater 6-(3,5-difluorobenzyl)-1H-pyrazolo[3,4-b]pyridin-3-amine

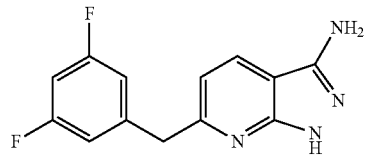 [SMILES: N=C(N)c1ccc(Cc2cc(F)cc(F)c2)nc1N]

17.35 mL of a 0.5M solution in THF of (3,5-difluorobenzyl)zinc chloride (8.58 mmol) is added under argon to a 0.575 g (0.704 mmol) of (dppf)$_2$PdCl$_2$.CH$_2$Cl$_2$ and 28 ml (14.08 mmol) of 3,5-difluorobenzyl zinc (II) chloride are added to 1.5 g (7.04 mmol) of a solution of 5-bromo-1H-pyrazolo[3,4-b]pyridin-3-amine in 10 ml of tetrahydrofuran. The reaction medium is heated at 90° C. for 18 hours. After returning to room temperature, the reaction is hydrolyzed by slowly adding water at 0° C. After filtration of the precipitate formed, the solid is rinsed with tetrahydrofuran and the aqueous filtrate is extracted several times with ethyl acetate. The organic phases are combined, dried on magnesium sulfate and concentrated. The residue is purified by silica chromatography (95:4.5:0.5 and then 95:4:1 dichloromethane/methanol/ammonium as eluent) to yield 1.7 g (93%) of 5-(3,5-difluorobenzyl)-1H-pyrazolo[3,4-b]pyridine-3-amine in the form of a beige solid.

LCMS (EI, m/z): (M+1) 261.41.

$^1$H NMR: δH ppm (400 MHz, DMSO): 11.87 (1H, s, NH), 8.31 (1H, d, CH$_{arom}$), 7.92 (1H, d, CH$_{arom}$), 6.98-7.08 (3H, m, CH$_{arom}$), 5.47 (2H, 5, NH), 4.04 (2H, 5, CH$_2$).

The following compounds are obtained by a similar method:

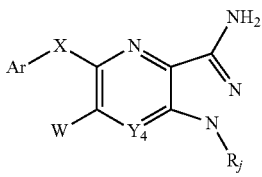

0.7 g (2.68 mmol) of 5-iodo-1H-pyrazolo[3,4-b]pyridine-3-amine, 0.74 g (5.36 mmol) of anhydrous potassium carbonate and 0.10 g of copper iodide (0.536 mmol) are mixed in a 50 ml round-bottom flask. 15 ml of propan-2-ol, 0.01 g (0.2 mmol) of polyethylene glycol and 0.43 g (2.95 mmol) of 3,5-difluorothiophenol are then added. The reaction mixture is heated at 80° C. for 2 hours. The solvent is evaporated and the solid formed is filtered, rinsed with water and then with pentane and dried in an oven at 50° C. to yield 0.75 g (100%) of 5-(3,5-diflurophenylthio)-1H-pyrazolo[3,4-b]pyrazin-3-amine in the form of a brown solid.

LCMS (EI, m/z): (M+1) 280.03.

$^1$H NMR: δH ppm (400 MHz, DMSO): 12.65 (1H, bs, NH), 8.52 (1H, s, CH$_{arom}$), 7.18 (1H, t, CH$_{arom}$), 7.05-7.18 (2H, m, CH$_{arom}$), 5.89 (2H, 5, NH).

| Ex.** | ArX | Y$_4$ | W | R$_j$ | Compound names | Yield | Mass MH$^+$ |
|---|---|---|---|---|---|---|---|
| 13-1 | 3,5-difluorobenzyl | CH | H | H | 5-(3,5-difluorobenzyl)-1H-pyrazolo[4,3-b]pyridin-3-amine | 8% 4 steps | 261.1 |
| 13-2 | 3,5-difluorobenzyl | N | H | H | 5-(3,5-difluorobenzyl)-1H-pyrazolo[3,4-b]pyrazin-3-amine | 21% 3 steps | 262.1 |

**$^1$H NMR: δH ppm (400 MHz, DMSO): 13-1: 11.61 (1H, sl, NH), 7.65 (1H, d, CHarom, J = 11.6 Hz), 7.20 (1H, d, CHarom, J = 11.2 Hz), 6.95-7.10 (3H, m, CHarom), 5.32 (2H, sl, NH$_2$), 4.18 (2H, s, CH$_2$). 13-2: 12.31 (1H, sl, NH), 8.44 (1H, s, CHarom), 7.03-7.08 (3H, m, CHarom), 5.61 (2H, sl, NH$_2$), 4.25 (2H, s, CH$_2$).

Examples of Method D2

Example 14

5-(3,5-difluorophenylthio)-1H-pyrazolo[3,4-b]pyrazin-3-amine

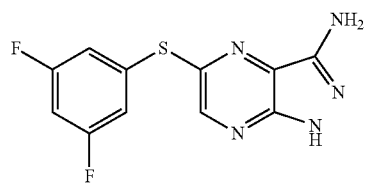 [SMILES: N=C(N)c1nc(Sc2cc(F)cc(F)c2)cnc1N]

The following derivatives were obtained according to the same method:

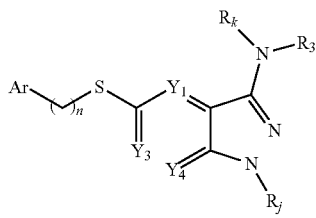

| Ex.** | Ar | $R_k$ | n | $Y_1, Y_3, Y_4$ | $R_3$ | $R_j$ | Compound name | Yield | Mass MH+ |
|---|---|---|---|---|---|---|---|---|---|
| 14-1 | 2-carbamoylphenyl (benzamide with ortho attachment) | H | 0 | CH, CH, N | H | H | 2-(3-amino-1H-pyrazolo[3,4-b]pyridin-5-ylthio)benzamide | ND | ND |
| 14-2 | 3,5-dimethylphenyl | 2-(tetrahydro-2H-pyran-4-ylamino)-4-(4-methylpiperazin-1-yl)benzoyl | 0 | CH, CH, N | H | H | N-(5-(3,5-dimethylphenylthio)-1H-pyrazolo[3,4-b]pyridin-3-yl)-4-(4-methylpiperazin-1-yl)-2-(tetrahydro-2H-pyran-4-ylamino)benzamide | ND | ND |
| 14-3 | 3,5-difluorophenyl | H | 0 | CH, CH, N | H | H | 5-(3,5-difluorophenylthio)-1H-pyrazolo[3,4-b]pyridin-3-amine | 45% | (M + 1) 279.28 |
| 14-4 | 2,5-dichlorophenyl | H | 0 | CH, C—OMe, N | H | H | 5-(2.5-dichlorophenylthio)-6-methoxy-1H-pyrazolo[3,4-b]pyridin-3-amine | 80% | ND |
| 14-5 | 2,5-dichlorophenyl | H | 0 | CH, C—NH$_2$, N | H | H | 5-(2.5-dichlorophenylthio)-1H-pyrazolo[3,4-b]pyridine-3,6-diamine | 35% | ND |
| 14-6 | 3,5-difluorobenzyl | H | 0 | CH, CH, N | H | $^t$Bu | 1-tert-butyl-5-(3,5-difluorobenzylthio)-1H-pyrazolo[3,4-b]pyridin-3-amine | ND | (M + 1) 293.08 |
| 14-7 | 3,5-difluorophenyl | H | 0 | CH, CMe, N | H | H | 5-(3,5-difluorophenylthio)-6-methyl-1H-pyrazolo[3,4-b]pyridin-3-amine | ND | (M + 1) 293.06 |
| 14-8 | 3,5-difluorophenyl | H | 0 | CH, C—OMe, N | H | H | 5-(3,5-difluorophenylthio)-6-methoxy-1H-pyrazolo[3,4-b]pyridin-3-amine | 28% | (M + 1) 610.30 |

-continued

| Ex.** | Ar | $R_k$ | n | $Y_1, Y_3, Y_4$ | $R_3$ | $R_j$ | Compound name | Yield | Mass MH+ |
|---|---|---|---|---|---|---|---|---|---|
| 14-9 | 3,5-difluorophenyl | H | 0 | CH, CH, N | H | tBu | 1-tert-butyl-5-(3,5-difluorophenylthio)-1H-pyrazolo[3,4-b]pyridin-3-amine | 79% | (M + 1) 335.26 |
| 14-10 | 2,5-dichlorophenyl | 2-(tetrahydro-2H-pyran-4-ylamino)-4-(4-methylpiperazin-1-yl)benzoyl | 0 | CH, CH, N | H | H | N-(5-(2,5-dichlorophenylthio)-1H-pyrazolo[3,4-b]pyridin-3-yl)-4-(4-methylpiperazin-1-yl)-2-(tetrahydro-2H-pyran-4-ylamino)benzamide | 31% | (M + 1) 612.37 |
| 14-11 | 3,5-difluorophenyl | 2-(tetrahydro-2H-pyran-4-ylamino)-4-(4-methylpiperazin-1-yl)benzoyl | 0 | CH, C—NH$_2$, N | H | H | N-(6-amino-5-(3,5-difluorophenylthio)-1H-pyrazolo[3,4-b]pyridin-3-yl)-4-(4-methylpiperazin-1-yl)-2-(tetrahydro-2H-pyran-4-ylamino)benzamide | 68% | ND |

$^1$H NMR, DMSO-d$_6$, Ex.: 14-3: 12.65 (1H, bs, NH), 8.52 (1H, s, CHarom), 7.18 (1H, t, CH$_{arom}$), 7.05-7.18 (2H, m, CH$_{arom}$), 5.89 (2H, s, NH). 14-6: 8.21 (2H, bs, CH$_{arom}$), 7.07 (1H, m, CH$_{arom}$), 6.90 (2H, m, CH$_{arom}$), 6.27 (2H, bs, NH), 4.03 (2H, s, CH), 1.63 (9H, s, CH). 14-7: 12.16 (1H, bs, NH), 8.39 (1H, s, CH$_{arom}$), 7.00-7.08 (1H, m, CH$_{arom}$), 6.64-6.72 (2H, m, CH$_{arom}$), 5.73 (2H, bs, NH$_2$), 2.54 (3H, s, CH$_3$). 14-9: 8.51 (1H, bs, CH$_{arom}$), 8.35 (1H, bs, CH$_{arom}$), 7.02 (1H, m, CH$_{arom}$), 6.72 (2H, bs, CH$_{arom}$), 6.52 (2H, bs, NH), 1.67 (9H, s, CH). (ND: not determined).

Example 14bis

N-(5-(3,5-difluorophenylamino)-1H-pyrazolo[3,4-b]pyridin-3-yl)-4-(4-methylpiperazin-1-yl)-2-(tetrahydro-2H-pyran-4-ylamino)benzamide

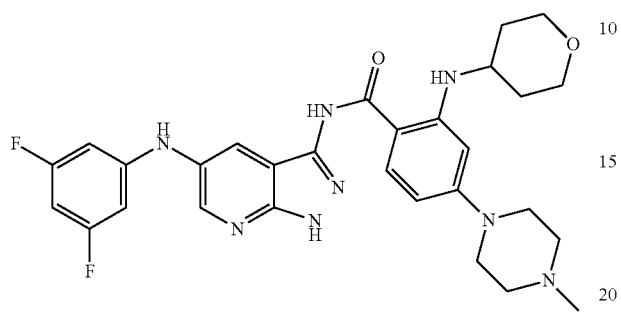

A solution of 225 mg of N-(5-iodo-1-trityl-1H-pyrazolo[3,4-b]pyridin-3-yl)-4-(4-methylpiperazin-1-yl)-2-(tetrahydro-2H-pyran-4-ylamino)benzamide (0.25 mmol), 36 mg of difluoroaniline (0.275 mmol), 19 mg of R-(+)-2,2'-bis(diphenylphosphino)-1,1'-binaphtyle (0.030 mmol), 11 mg (0.013 mmol) of tris(dibenzylideneacetone)dipalladium(0) and 75 mg (0.75 mmol) of sodium tert-butoxide in 10 mL of THF is refluxed under argon overnight. The crude reaction medium is cooled, extracted with ethyl acetate and washed with water. The organic phase is dried on magnesium sulfate and purified by silica gel chromatography to yield N-(5-(3,5-difluorophenylamino)-1-trityl-1H-pyrazolo[3,4-b]pyridin-3-yl)-4-(4-methylpiperazin-1-yl)-2-(tetrahydro-2H-pyran-4-ylamino)benzamide which is used in the following step without further purification.

The product thus obtained is dissolved in 10 mL of dichloromethane at 0° C. and 56 mg (0.5 mmol) of TFA is added. The reaction medium is stirred for 4 hours. Water is added and the pH of the reaction medium is adjusted to 7 with a NaHCO$_3$ solution. The aqueous phase is collected, basified (pH 9-10) with a concentrated K$_2$CO$_3$ solution and extracted with dichloromethane. The organic phase is collected, dried on magnesium sulfate and dry concentrated to yield 40 mg of N-(5-(3,5-difluorophenylamino)-1H-pyrazolo[3,4-b]pyridin-3-yl)-4-(4-methylpiperazin-1-yl)-2-(tetrahydro-2H-pyran-4-ylamino)benzamide.

LCMS (IE, m/z): (M+1) 562.12.

$^1$H NMR: δH ppm (400 MHz, DMSO): 13.45 (1H, sl, NH), 10.47 (1H, sl, NH), 8.65 (1H, 5, CH$_{arom}$), 8.55 (1H, 5, CH$_{arom}$), 8.14 (1H, d, NH), 7.77 (1H, d, CH$_{arom}$), 7.26 (2H, m, CH$_{arom}$), 7.05 (1H, m, CH$_{arom}$), 6.25 (1H, d, CH$_{arom}$), 6.14 (1H, 5, NH), 6.77 (1H, 5, NH), 3.82-3.84 (2H, dt, CH), 3.72 (1H, m, CH), 3.47-3.52 (2H, m, CH), 3.28-3.34 (4H, m, CH), 2.43 (4H, m, CH), 2.23 (3H, s, CH$_3$), 1.94-1.97 (2H, m, CH), 1.37-1.39 (2H, m, CH).

Examples of Method D3

Example 15

N-(5-((3,5-difluorophenyl)ethynyl)-1H-pyrazolo[3,4-b]pyridin-3-yl)-4-(4-methylpiperazin-1-yl)-2-(tetrahydro-2H-pyran-4-ylamino)benzamide

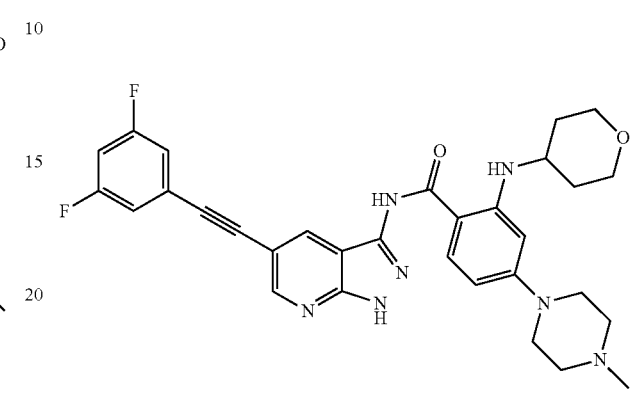

0.94 mg (0.926 mmol) of triethylamine is added to 400 mg (0.712 mmol) of N-(5-iodo-1H-pyrazolo[3,4-b]pyridin-3-yl)-4-(4-methylpiperazin-1-yl)-2-(tetrahydro-2H-pyran-4-ylamino)benzamide, 67.8 mg (0.356 mmol) of CuI and 50 mg (0.071 mmol) of Pd(PPh$_3$)$_2$Cl$_2$ under argon in 12 ml of anhydrous dioxane under stirring. The reaction is heated for 3.5 hours at 100° C. The reaction mixture is diluted with 30 ml of water and extracted with ethyl acetate. The organic phase is dried on sodium sulfate, filtered and concentrated. The residue obtained is purified by silica gel chromatography (dichloromethane/methanol) to yield 152 mg of N-(5-((3,5-difluorophenyl)ethynyl)-1H-pyrazolo[3,4-b]pyridin-3-yl)-4-(4-methylpiperazin-1-yl)-2-(tetrahydro-2H-pyran-4-ylamino)benzamide in the form of a yellow solid (yield=37%).

LCMS (EI, m/z): (M+1) 572.17.

$^1$H NMR: δH ppm (400 MHz, DMSO): 13.57 (1H, bs, NH), 10.56 (1H, bs, NH), 8.68 (1H, 5, CH$_{arom}$), 8.43 (1H, 5, CH$_{arom}$), 8.13 (1H, d, NH), 7.80 (1H, d, CH$_{arom}$), 7.38 (2H, m, CH$_{arom}$), 6.27 (1H, d, CH$_{arom}$), 6.15 (1H, d, CH$_{arom}$), 3.84-3.82 (2H, dt, CH), 3.70 (1H, m, CH), 3.45-3.50 (2H, m, CH), 3.21-3.33 (4H, m, CH), 2.42-2.46 (4H, m, CH), 2.28 (3H, s, CH$_3$), 1.94-1.97 (2H, m, CH), 1.37-1.39 (2H, m, CH).

The following derivative was obtained according to the same method:

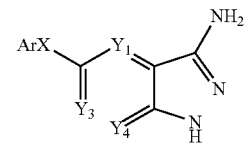

| Ex.** | ArX | $Y_1, Y_3, Y_4$ | Compound name | Yield | Mass MH+ |
|---|---|---|---|---|---|
| 15-1 | 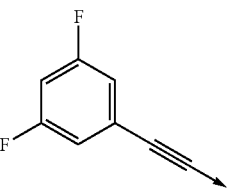 | N, CH, N | 5((3,5-difluorophenyl)ethynyl)-1H-pyrazolo[3,4-b]pyrazin-3-amine | 6% 6 steps | 272.1 |

**$^1$H NMR, dmso-d$_6$, Ex.: 15-1: 12.71 (1H, sl, NH), 8.66 (1H, s, CHarom), 7.40-7.47 (3H, m, CHarom), 6.01 (2H, sl, NH$_2$).

Examples of Method E

The protocols comprising method E aim at functionalizing the exocyclic amine of the aminopyrazole rings by their reaction with an intermediate featuring an electrophilic function, optionally generated in situ, such as acid chloride, isocyanate, isothiocyanate or aldehyde.

Preparation of the Reaction Intermediates

Example 16

2-(N-(4,4-difluorocyclohexyl)-2,2,2-trifluoroacetamido)-4-(4-methyl piperazin-1-yl)benzoic acid

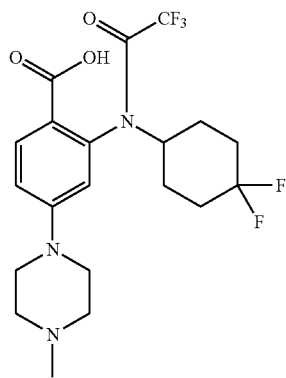 [SMILES: CN1CCN(c2ccc(C(=O)O)c(N(C(=O)C(F)(F)F)C3CCC(F)(F)CC3)c2)CC1]

Example 16a tert-butyl 4-(4-methylpiperazin-1-yl)-2-nitrobenzoate

This compound was previously described in WO 2008/74749.

5.28 ml (47.6 mmol) of 1-methylpiperazine is added to 4.1 g (17 mmol) of tert-butyl 4-fluoro-2-nitrobenzoate. The reaction mixture is stirred without solvent for 5 hours. 150 ml of water is added to the reaction mixture and it is stirred for 24 hours. The precipitate formed is filtered, rinsed with water and dried under vacuum to yield 4.9 g (90%) of tert-butyl 4-(4-methylpiperazin-1-yl)-2-nitrobenzoate in the form of a yellow solid.

LCMS (EI, m/z): (M+1) 322.37.

$^1$H NMR: δH ppm (400 MHz, DMSO): 7.69 (1H, d, CH$_{arom}$), 7.30 (1H, d, CH$_{arom}$), 7.20 (1H, dd, CH$_{arom}$), 3.38 (4H, m, CH), 2.40 (4H, m, CH), 2.22 (3H, s, CH$_3$), 1.45 (9H, s, CH$_3$).

Example 16b tert-butyl 2-amino-4-(4-methylpiperazin-1-yl)benzoate

This compound was previously described in WO 2008/74749.

0.160 g (1.500 mmol) of palladium on carbon (10%) and 15.19 ml (150 mmol) of cyclohexene are added to a solution of 4.82 g (15 mmol) of tert-butyl 4-(4-methylpiperazin-1-yl)-2-nitrobenzoate in 100 ml of ethanol. The reaction mixture is heated at a temperature of 80° C. for 8 hours. The reaction mixture is filtered and then rinsed with ethanol to yield 4.2 g (yield=96%) of tert-butyl 2-amino-4-(4-methylpiperazin-1-yl)benzoate in the form of a yellow solid.

LCMS (EI, m/z): (M+1) 292.39.

$^1$H NMR: δH ppm (400 MHz, DMSO): 7.44 (1H, d, CH$_{arom}$), 6.40 (2H, bs, NH$_2$), 6.19 (1H, dd, CH$_{arom}$), 6.12 (1H, d, CH$_{arom}$), 3.17 (4H, m, CH), 2.40 (4H, m, CH), 2.22 (3H, s, CH$_3$), 1.49 (9H, s, CH$_3$).

Example 16c tert-butyl 2-(4,4-difluorocyclohexylamino)-4-(4-methylpiperazin-1-yl)benzoate 1.045 ml (13.57 mmol) of trifluoroacetic acid, 1 g (7.46 mmol) of 4,4-difluorocyclohexanone and 2.158 g (8.20 mmol) of tetramethylammonium triacetoxyborohydride are added to 1.521 g (5.22 mmol) of tert-butyl 2-amino-4-(4-methylpiperazin-1-yl)benzoate dissolved in 60 ml of dichloromethane. The reaction is left under stirring at room temperature for 24 hours. The solvent is evaporated and then the crude reaction product is redissolved in 30 ml of ethyl acetate. The solution is successively washed with 0.5 M HCl solution, 0.5 M soda solution and finally with saturated NaHCO$_3$ solution. The organic phase is dried on sodium sulfate, filtered and concentrated to obtain 2.2 g of tert-butyl 2-(4,4-difluorocyclohexylamino)-4-(4-methylpiperazin-1-yl)benzoate in the form of a light brown gum (yield=72%).

LCMS (EI, m/z): (M+1) 410.3.

$^1$H NMR: δH ppm (400 MHz, DMSO): 7.73 (1H, bs, NH), 7.58 (1H, m, CH$_{arom}$), 7.77 (1H, m, CH$_{arom}$), 6.09 (1H, bs, CH$_{arom}$), 3.37 (4H, m, CH), 3.27 (4H, m, CH), 2.47 (4H, m, CH), 2.25 (3H, s, CH), 1.99 (4H, s, CH), 1.40 (9H, s, CH).

Example 16d tert-butyl 2-(N-(4,4-difluorocyclohexyl)-2,2,2-trifluoroacetamido)-4-(4-methylpiperazin-1-yl)benzoate 0.99 ml (6.98 mmol) of trifluoroacetic anhydride and 1.12 ml (8.06 mmol) of triethylamine are added to 2.2 g (5.3 mmol)

of tert-butyl 2-(4,4-difluorocyclohexylamino)-4-(4-methylpiperazin-1-yl)benzoate dissolved in 40 ml of dichloromethane. The reaction is left under stirring at room temperature for 3 hours. The solvent is evaporated and then the crude reaction product is taken up in 30 ml of ethyl acetate. The solution is washed with saturated NaHCO$_3$ solution. The organic phase is dried on sodium sulfate, filtered and concentrated to obtain 2.5 g of tert-butyl 2-(N-(4,4-difluorocyclohexyl)-2,2,2-trifluoroacetamido)-4-(4-methylpiperazin-1-yl)benzoate in the form of a light brown gum (yield=92%).

LCMS (EI, m/z): (M+1) 506.26.

$^1$H NMR: δH ppm (400 MHz, DMSO): 7.84 (1H, m, CH$_{arom}$), 7.09 (1H, m, CH$_{arom}$), 6.89 (1H, bs, CH$_{arom}$), 3.45-3.39 (8H, m, CH), 2.83 (4H, m, CH), 2.20 (4H, m, CH), 2.05 (3H, s, CH), 1.46 (9H, s, CH).

Example 16

2-(N-(4,4-difluorocyclohexyl)-2,2,2-trifluoroacetamido)-4-(4-methyl piperazin-1-yl)benzoic acid 7.62 ml (99 mmol) of trifluoroacetic acid is added to 2.5 g (4.95 mmol) of tert-butyl 2-(N-(4,4-difluorocyclohexyl)-2,2,2-trifluoroacetamido)-4-(4-methylpiperazin-1-yl)benzoate dissolved in 30 ml of dichloromethane. The reaction is left under stirring at room temperature overnight. The solvent is evaporated and then the crude reaction product is redissolved in 30 ml of ethyl acetate. The solvents are evaporated, the solid formed is redissolved in ethyl ether and the solvent is evaporated again. This operation is repeated three times until a light brown solid is obtained. 2.2 g of 2-(N-(4,4-difluorocyclohexyl)-2,2,2-trifluoroacetamido)-4-(4-methylpiperazin-1-yl)benzoic acid in the form of a trifluoroacetic salt is obtained (yield=79%).

LCMS (EI, m/z): (M+1) 450.1.

$^1$H NMR: δH ppm (400 MHz, DMSO): 10.01 (1H, bs, OH), 7.92 (1H, m, CH$_{arom}$), 7.13 (1H, m, CH$_{arom}$), 7.01 (1H, bs, CH$_{arom}$), 4.39 (1H, m, CH), 3.12-3.52 (8H, m, CH), 2.86 (3H, s, CH), 1.75-2.0 (8H, m, CH).

The following compounds are also obtained by this method:

4-(4-methylpiperazin-1-yl)-2-(2,2,2-trifluoro-N-(tetrahydro-2H-pyran-4-yl) acetamido)benzoic acid This compound was previously described in WO 2008/74749, WO 2009/13126 and WO 2010/69966.

LCMS (EI, m/z): (M+1) 416.40.

$^1$H NMR: δH ppm (400 MHz, DMSO): 12.60 (1H, bs, OH), 10.08 (1H, bs, OH), 7.90 (1H, d, CH$_{arom}$), 7.13 (1H, dd, CH$_{arom}$), 6.90 (1H, d, CH$_{arom}$), 4.40 (1H, m, CH), 4.10 (2H, m, CH), 3.70-3.90 (2H, m, CH), 3.59-3.62 (4H, m, CH), 3.30-3.32 (4H, m, CH), 2.87 (3H, s, CH$_3$), 1.87-1.98 (1H, m, CH), 1.59-1.60 (1H, m, CH), 1.00-1.54 (2H, m, CH).

4-((3-(dimethylamino)propyl)(methyl)amino)-2-(2,2,2-trifluoro-N-(tetrahydro-2H-pyran-4-yl)acetamido)benzoic acid This compound was previously described in WO 2009/13126 and WO 2008/74749.

Example 17

(S)-2-(2,2,2-trifluoro-N-(tetrahydro-2H-pyran-4-yl)acetamido)-4-(3-(2,2,2-trifluoroacetamido)pyrrolidin-1-yl)benzoic acid

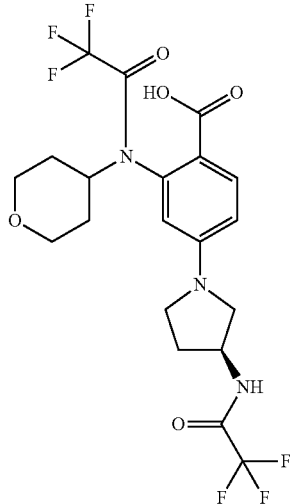 [SMILES: O=C(O)c1ccc(N2CC[C@H](NC(=O)C(F)(F)F)C2)cc1N(C(=O)C(F)(F)F)C1CCOCC1]

Example 17a tert-butyl (S)-4-(3-(tert-butoxycarbonylamino)pyrrolidin-1-yl)-2-(tetrahydro-2H-pyran-4ylamino)benzoate This compound was obtained by reproducing example 16d using tert-butyl (S)-pyrrolidin-3-ylcarbamate.

Example 17b (S)-4-(3-aminopyrrolidin-1-yl)-2-(tetrahydro-2H-pyran-4-ylamino)benzoic acid 19.7 ml (25 eq) of trifluoroacetic acid is added to a solution of 4.72 g (10.23 mmol) of tert-butyl (S)-4-(3-(tert-butoxycarbonylamino)pyrrolidin-1-yl)-2-(tetrahydro-2H-pyran-4-ylamino)benzoate in 100 ml of dichloromethane. The reaction medium is stirred at room temperature for 30 hours. The solvents are evaporated and the residue is redissolved in diethyl ether and triturated until a solid is obtained. The solid formed is filtered and dried under vacuum to yield 4.3 g (100%) of a yellow powder of (S)-4-(3-aminopyrrolidin-1-yl)-2-(tetrahydro-2H-pyran-4-ylamino)benzoic acid in the form of a trifluoroacetic acid salt.

LCMS (EI, m/z): (M+1) 306.22.

Example 17

(S)-2-(2,2,2-trifluoro-N-(tetrahydro-2H-pyran-4-yl)acetamido)-4-(3-(2,2,2-trifluoroacetamido)pyrrolidin-1-yl)benzoic acid 1.74 ml (3.5 eq) of triethylamine and 1.6 ml (2.1 eq) of trifluoroacetic anhydride are added to a solution of 1.5 g (3.58 mmol) of (S)-4-(3-aminopyrrolidin-1-yl)-2-(tetrahydro-2H-pyran-4-ylamino)benzoic acid in the form of a trifluoroacetic acid salt in 40 ml of dichloromethane at 0° C. The reaction medium is stirred at room temperature for 24 hours. Water (10 ml) is added drop by drop and then the organic phase is washed with saturated sodium chloride solution, dried on magnesium sulfate, filtered and evaporated. The residue is purified by silica gel chromatography (96:4 dichloromethane/methanol as eluent) to yield 250 mg (14%) of (S)-2-(2,2,2-trifluoro-N-(tetrahydro-2H-pyran-4-yl)acetamido)-4-(3-(2,2,2-trifluoroacetamido)pyrrolidin-1-yl)benzoic acid in the form of a yellow powder.

LCMS (EI, m/z): (M+1) 498.07.

Example 18

2-(2-fluoroethoxy)-4-(4-methylpiperazin-1-yl)benzoic acid

This compound can be prepared from the following intermediates.

Example 18a tert-butyl 4-fluoro-2-(2-fluoroethoxyl)benzoate

Example 18b tert-butyl 2-(2-fluoroethoxy)-4-(4-methylpiperazin-1-yl)benzoate The following compound was also obtained by this method:

2-(2-fluoroethoxy)-4-(4-(1-methylpiperidin-4-yl) piperazin-1-yl)benzoic acid

Example 19

4-(4-methylpiperazin-1-yl)-2-(2,2,2-trifluoro-N-(2-fluoroethyl)-acetamido)-benzoic acid This compound can be prepared from the following intermediates.

Example 19a tert-butyl 4-fluoro-2-(2-fluoroethylamino)benzoate

Example 19b tert-butyl 4-fluoro-2-(2,2,2-trifluoro-N-(2-fluoroethyl)acetamido)benzoate

Example 19c tert-butyl 4-(4-methylpiperazin-1-yl)-2-(2,2,2-trifluoro-N-(2-fluoroethyl)-acetamido)-benzoate The following compound was also obtained by this method:

4-((3-(dimethylamino)propyl)(methyl)amino)-2-(2,2,2-trifluoro-N-(2-fluoroethyl) acetamido)benzoic acid

Example 20

4-(1-methylpiperidin-4-yl)-2-(2,2,2-trifluoro-N-(tetrahydro-2H-pyran-4-yl)acetamido)benzoic acid hydrotrifloroacetate

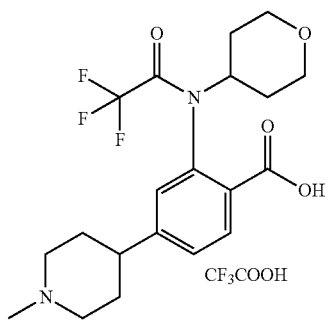 [SMILES: CN1CCC(c2ccc(C(=O)O)c(N(C(=O)C(F)(F)F)C3CCOCC3)c2)CC1 ; "CF3COOH"]

This compound can be prepared from the following intermediates.

Example 20a tert-butyl 2-nitro-4-(pyridin-4-yl)benzoate 1.67 g of bis(triphenylphosphine)palladium(II)chloride (2.38 mmol) and 15.8 g of sodium carbonate (149 mmol) are added to a solution of 18 g of tert-butyl 4-bromo-2-nitrobenzoate (59.6 mmol) and 10.98 g of pyridine-4-ylboronic acid (89 mmol) in a mixture of 200 ml of dimethoxyethane and 100 mL of water. The reaction medium is heated at 100° C. for 24 hours and then concentrated under reduced pressure. The residue obtained is purified by flash chromatography (CH$_2$Cl$_2$/AcOEt: 100:0 to 70:30, 30 min). The product is isolated in the form of an oil which crystallizes to yield 14.64 g (82%) of crystals.

MS (m/z): (M+1) 301.0.

$^1$H NMR: δH ppm (400 MHz, DMSO): 8.73 (2H, d, CHarom, J=6.0 Hz), 8.44 (1H, s, CHarom), 8.24 (1H, dd, CHarom, J=8.0 Hz), 7.97 (1H, d, CHarom, J=8.0 Hz), 7.85 (2H, dd, CHarom, J=4.4 Hz), 1.54 (9H, s).

Example 20b 4-(4-(tert-butoxycarbonyl)-3-nitrophenyl)-1-methylpyridinium iodide 7.55 mL od iodomethane (121 mmol) is added to a solution of 16.2 g of tert-butyl 2-nitro-4-(pyridin-4-yl)benzoate (60.6 mmol) in 20 mL of acetone. The reaction medium is heated at 60° C. for 4 hours and then at room temperature overnight. After dry concentration, 27 g of orange crystals are isolated (100%).

MS (m/z): (M+1) 315.0.

$^1$H NMR: δH ppm (400 MHz, DMSO): 9.14 (2H, d, CHarom, J=6.4 Hz), 8.71 (1H, s, CHarom), 8.63 (2H, d, CHarom, J=6.4 Hz), 8.47 (1H, dd, CHarom, J=8.0 Hz), 8.08 (1H, d, CHarom, J=8.0 Hz), 4.37 (3H, s, CH), 1.54 (9H, s).

Example 20c tert-butyl 2-amino-4-(1-methylpiperidin-4-yl)benzoate 0.48 g of platine (IV) oxide (2.12 mmol) is added to a solution of 26.8 g of 4-(4-(tert-butoxycarbonyl)-3-nitrophenyl)-1-methylpyridinium iodide (60.6 mmol) in 200 mL of methanol placed in a reactor made in stainless steel. The reaction medium is brought under 5 bar of hydrogen for 24 h. The catalyst is filtered and the filtrate is concentrated under reduced pressure to yield 24.8 g (98%) of white crystals.

MS (m/z): (M+1) 291.1.

$^1$H NMR: δH ppm (400 MHz, DMSO): 9.18 (1H, s, HI), 7.60 (1H, d, CHarom, J=8.4 Hz), 6.54-6.40 (3H, m, CHarom), 6.39 (1H, d, CHarom, J=8.0 Hz), 3.48-3.53 (2H, m, CH), 3.06 (2H, t, CH), 2.81 (3H, s, CH), 2.60-2.70 (1H, m, CH), 1.89-1.97 (2H, m, CH), 1.70-1.80 (2H, m, CH), 1.52 (9H, s).

Example 20d tert-butyl 4-(1-methylpiperidin-4-yl)-2-(tetrahydro-2H-pyran-4-ylamino)benzoate 7.18 mL of 2,2,2-trifluoroacetic acid (93 mmol), 4.11 mg of dihydro-2H-pyran-4(3H)-one (44.5 mmol) and then 14.5 g of tetramethylammonium triacetoxyborohydride (53.8 mmol) are successively added to a solution of 15 g of tert-butyl 2-amino-4-(1-methylpiperidin-4-yl)benzoate in 200 mL of dichloromethane under stirring. The reaction medium is stirred at room temperature for 2 h and then taken up with a 1N soda solution. The organic phase is isolated, dried on magnesium sulfate and then dried concentrated. The residue contained always HI. It is thus taken up in dichloromethane and washed with 100 mL of a 1H soda solution. The organic phase is decanted, dried on magnesium sulfate and dry concentrated to yield 14.6 g of a yellow solid (quantitative yield).

MS (m/z): (M+1) 375.2.

$^1$H NMR: δH ppm (400 MHz, DMSO): 7.69 (1H, d, CHarom, J=8.4 Hz), 7.63 (1H, d, CHarom, J=7.6 Hz), 6.65 (1H, s, CHarom), 6.44 (1H, dd, CHarom, J=8.4 Hz), 3.74-3.86 (2H, m, CH), 3.66-3.71 (1H, m, CH), 3.51 (2H, t, CH), 3.05-3.12 (2H, m, CH), 2.6-2.5 (1H, m, CH), 2.42 (3H, s, CH), 2.30-2.40 (2H, m, CH), 1.89-1.97 (2H, m, CH), 1.64-1.77 (4H, m, CH), 1.52 (9H, s), 1.33-1.45 (2H, m, CH).

Example 20e tert-butyl 4-(1-methylpiperidin-4-yl)-2-(2,2,2-trifluoro-N-(tetrahydro-2H-pyran-4-yl)acetamido)benzoate 6.35 mL of triethylamine and 5.50 mL of 2,2,2-trifluoroacetic anhydride (39.6 mmol) are added at 0° C. to a solution of 11.4 g of tert-butyl 4-(1-methylpiperidin-4-yl)-2-(tetrahydro-2H-pyran-4-ylamino)benzoate (30.4 mmol) in 240 mL of dichloromethane under stirring. The reaction medium is stirred at room temperature for 1 h and then 100 mL of water is added dropwise. The organic phase is decanted, dried on magnesium sulfate and dry concentrated. The residue is taken up in a mixture of ethanol/diethyl ether to yield a solid which is filtered on a fritted disc and 12.06 g of white crystals is isolated. The filtrate is concentrated (4.5 g) and then purified by flash chromatography on silica (CH$_2$Cl$_2$/meOH: 95:5 to 90:10, 20 min). The product obtained is recrystallized in diethyl ether to yield 1.04 g of additional white crystals (global yield=74%).

MS (m/z): (M+1) 471.1.

$^1$H NMR: δH ppm (400 MHz, DMSO): 9.45 (1H, sl, NH), 7.96 (1H, d, CHarom, J=8 Hz), 7.51 (1H, d, CHarom, J=8 Hz), 7.31 (1H, s, CHarom), 4.6-4.5 (1H, m, CH), 3.90-3.75 (2H, m, CH), 3.5-3.35 (4H, m, CH), 3.1-2.85 (3H, m, CH), 2.79 (3H, s, CH$_3$), 2.1-1.95 (3H, 3, CH), 1.9-1.75 (2H, m, CH), 1.55-1.40 (11H, m), 1.0-0.85 (1H, m, CH).

Example 20

4-(1-methylpiperidin-4-yl)-2-(2,2,2-trifluoro-N-(tetrahydro-2H-pyran-4-yl)acetamido)benzoic acid hydrotrifluoroacetate 6.33 mL of 2,2,2-trifluoroacetic acid (82 mmol) is added under stirring to a solution of 3.2 g of tert-butyl 4-(1-methylpiperidin-4-yl)-2-(2,2,2-trifluoro-N-(tetrahydro-2H-pyran-4-yl)acetamido)benzoate (5.47 mmol) (in the form of a salt of trifluoroacetic acid) in 30 mL of dichloromethane. The reaction medium is stirred at room temperature for 16 h, and then evaporated under reduced pressure. The residue is taken up in ethanol, and the white solid formed is filtered on a fritted disc to yield 1.61 g (53%) of white crystals.

MS (m/z): (M+1) 415.1.

$^1$H NMR: δH ppm (400 MHz, DMSO): 13.39 (1H, sl, COOH), 9.46 (1H, sl, COOH du TFA), 7.99 (1H, d, CHarom, J=8.4 Hz), 7.49 (1H, d, CHarom, J=8.4 Hz), 7.30 (1H, s, CHarom), 4.53 (1H, m, CH), 3.74-3.86 (2H, m, CH), 3.35-3.45 (5H, m, CH), 2.90-3.01 (3H, m, CH), 2.76 (3H, s, CH), 1.65-2.04 (5H, m, CH), 1.44-1.54 (2H, m, CH).

Example 21

1-(4-isothiocyanatophenyl)-4-methylpiperazine

This compound was prepared by adapting the method described in EP1215208.

The following compound was also obtained by this method:

tert-butyl 2-isothiocyanato-5-(4-methylpiperazin-1-yl)phenylcarbamate

Example 22 tert-butyl 2-isocyanato-5-(4-methylpiperazin-1-yl)phenylcarbamate

This compound can be prepared from the following intermediates.

Example 22a tert-butyl 5-(4-methylpiperazin-1-yl)-2-nitrophenylcarbamate

Example 22b tert-butyl 2-amino-5-(4-methylpiperazin-1-yl)phenylcarbamate

Example 22 tert-butyl 2-isocyanato-5-(4-methylpiperazin-1-yl)phenylcarbamate

Example 23

4-(4-methylpiperazin-1-yl)-2-(tetrahydro-2H-pyran-4-ylamino)benzaldehyde

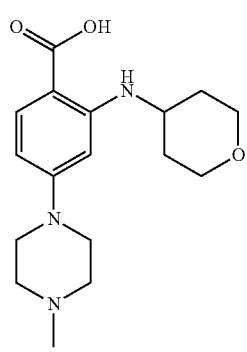 [SMILES: CN1CCN(c2ccc(C(=O)O)c(NC3CCOCC3)c2)CC1]

Example 23a (4-(4-methylpiperazin-1-yl)-2-(tetrahydro-2H-pyran-4-ylamino)phenyl)methanol 500 mg (1.060 mmol) of 4-(4-methylpiperazine-1-yl)-2-(2,2,2-trifluoro-N-(tetrahydro-2H-pyran-4-yl)acetamido)benzoic acid dissolved in 5 ml of tetrahydrofuran is added at 0° C. to a suspension of 201 mg (5.30 mmol) of LiAlH$_4$ in 9 ml of tetrahydrofuran. The reaction mixture is stirred at 0° C. for 1 hour and then at room temperature for 3 hours. The reaction mixture is cooled at 0° C. and then, drop by drop, 200 μl water, then 200 μl of soda solution (15% by weight) and finally 1 ml of water are added. The reaction mixture is stirred at room temperature for 2 hours and then filtered and rinsed with tetrahydrofuran. The filtrate is concentrated to yield 250 mg (yield=77%) of (4-(4-methylpiperazine-1-yl)-2-(tetrahydro-2H-pyran-4-ylamino)phenyl)methanol in the form of a white solid.

LCMS (EI, m/z): (M+1) 306.14.

$^1$H NMR: $\delta_{H\ ppm}$ (400 MHz, DMSO): 6.85 (1H, d, CH$_{arom}$), 6.20 (1H, d, CH$_{arom}$), 6.10 (1H, d, CH$_{arom}$), 4.95 (1H, bs, OH), 4.87 (1H, d, NH), 4.37 (2H, d, CH$_2$), 3.83-3.86 (2H, m, CH), 3.56 (1H, m, CH), 3.46-3.56 (3H, m, CH), 3.45 (1H, m, CH), 3.05-3.07 (4H, m, CH), 2.41-2.44 (4H, m, CH), 2.21 (3H, s, CH$_3$), 1.89-1.92 (2H, m, CH).

Example 23

4-(4-methylpiperazin-1-yl)-2-(tetrahydro-2H-pyran-4-ylamino)benzaldehyde 85 mg (0.982 mmol) of manganese dioxide is added at room temperature to a solution of (4-(4-methylpiperazine-1-yl)-2-(tetrahydro-2H-pyran-4-ylamino)phenyl)methanol (100 mg, 0.327 mmol) in a mixture of ethyl acetate (10 ml) and dichloromethane (9 ml). The reaction mixture is placed in an ultrasonic bath for 5 hours. The reaction mixture is filtered, the solvents are evaporated and the crude product is purified by chromatography to yield 50.0 mg (yield=50.3%) of (4-(4-methylpiperazine-1-yl)-2-(tetrahydro-2H-pyran-4-ylamino)benzaldehyde in the form of a white solid. LCMS (EI, m/z): (M+1) 304.19.

$^1$H NMR: $\delta_{H\ ppm}$ (400 MHz, DMSO): 9.43 (1H, d, CH), 7.32 (1H, d, CH$_{arom}$), 6.36 (1H, d, CH$_{arom}$), 6.08 (1H, d, CH$_{arom}$), 3.94-3.99 (2H, m, CH), 3.77 (1H, m, CH), 3.61-3.63 (2H, m, CH), 3.42-3.45 (4H, m, CH), 2.57-2.60 (4H, m, CH), 2.36 (3H, s, CH$_3$), 2.04-2.08 (2H, m, CH), 1.51-1.60 (2H, m, CH).

Example 24

2-(4-(4-methylpiperazin-1-yl)phenyl)acetic acid

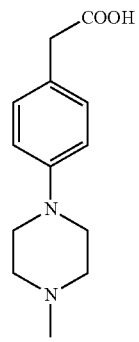 [SMILES: CN1CCN(c2ccc(CC(=O)O)cc2)CC1]

Example 24a 2,2,2-trichloro-1-(4-(4-methylpiperazin-1-yl)phenyl)ethanol 1.0 ml (10.00 mmol) of trichloroacetic acid and, in small portions, 1.854 g (10 mmol) of sodium 2,2,2-trichloroacetate are added at room temperature to a solution of 1.362 g (6.67 mmol) of 4-(4-methylpiperazine-1-yl)benzaldehyde in 13.5 ml of dimethylformamide. The reaction mixture is stirred for 3 hours at room temperature. The solvent is concentrated and the crude reaction product extracted with ethyl acetate. The organic phase is washed using saturated sodium bicarbonate solution. The organic phases are combined, dried on magnesium sulfate and then concentrated to yield 1.760 g (yield=82%) of 2,2,2-trichloro-1-(4-(4-methylpiperazine-1-yl)phenyl)ethanol in the form of a white solid.

LCMS (EI, m/z): (M+1) 324.04.

$^1$H NMR: $\delta_{H\ ppm}$ (400 MHz, DMSO): 7.41 (2H, d, CH$_{arom}$), 7.02 (1H, bs, OH), 6.90 (2H, d, CH$_{arom}$), 5.08 (1H, bs, CH), 3.14-3.16 (4H, m, CH), 2.42-2.47 (4H, m, CH), 2.21 (3H, s, CH$_3$).

Example 24

2-(4-(4-methylpiperazin-1-yl)phenyl)acetic acid 0.559 g (14.77 mmol) of sodium borohydride is added quickly to 2.294 g (7.35 mmol) of dibenzyl diselenide in 28 ml of ethanol. The reaction mixture is stirred at room temperature for 1 hour. 2.266 g (7 mmol) of 2,2,2-trichloro-1-(4-(4-methylpiperazine-1-yl)phenyl)ethanol and 1.680 g (42.0 mmol) of sodium hydroxide are then added. The reaction mixture is stirred at 35° C. for 24 hours. The solvent is concentrated and the crude product extracted with ethyl acetate after adding a pH 5 aqueous phase. The organic phases are combined, dried on magnesium sulfate and then concentrated to yield 2-(4-(4-methylpiperazine-1-yl)phenyl)acetic acid which is used without additional purification.

LCMS (EI, m/z): (M+1) 235.294.

Example 25

2-(4-(4-methylpiperazin-1-yl)-2-nitrophenyl) acetic acid

This compound can be prepared from the following intermediates.

Example 25a diethyl 2-(4-fluoro-2-nitrophenyl)malonate

Example 25b diethyl 2-(4-(4-methylpiperazin-1-yl)-2-nitrophenyl) malonate

Example of Method E1

Example 26

N-(5-(3,5-difluorophenylthio)-1H-pyrazolo[3,4-b]pyridin-3-yl)-4-(4-methylpiperazin-1-yl)-2-(2,2,2-trifluoro-N-(tetrahydro-2H-pyran-4-yl) acetamido) benzamide 0.95 ml (11.21 mmol) of oxalyl chloride and 2 drops of anhydrous dimethylformamide are added to 2.97 g (5.61 mmol) of a solution of 4-(4-methylpiperazin-1-yl)-2-(2,2,2-trifluoro-N-(tetrahydro-2H-pyran-4-yl)acetamido)benzoic acid in 95 ml of dichloromethane. The reaction mixture is stirred for 2 hours at room temperature. The solvents are evaporated, the solid formed is taken up in toluene and the solvent evaporated. This operation is repeated three times until a white solid is obtained. The acid chloride is dissolved in 35 ml of anhydrous tetrahydrofuran at −20° C. and then the solution formed is added to a solution containing 1.56 g (5.61 mmol) of 5-(3,5-difluorophenylthio)-1H-pyrazolo[3,4-b]pyridin-3-amine and 3.71 ml (21.30 mmol) of N-ethyl-N-isopropylpropan-2-amine in 30 ml of anhydrous tetrahydrofuran. The reaction mixture is stirred for 3 hours at −20° C. and then overnight at room temperature. The precipitate obtained is filtered and rinsed with tetrahydrofuran and water and then dried to yield 2 g (53%) of N-(5-(3,5-difluorophenylthio)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide.

LCMS (EI, m/z): (M+1) 676.20.

$^1$H NMR: δH ppm (400 MHz, DMSO): 13.66 (1H, bs, NH), 11.08 (1H, bs, NH), 8.61 (1H, s, $CH_{arom}$), 8.46 (1H, s, $CH_{arom}$), 7.83 (1H, d, $CH_{arom}$), 7.05-7.10 (2H, m, $CH_{arom}$), 6.83-6.89 (3H, m, $CH_{arom}$), 4.39-4.44 (1H, m, CH), 3.83-3.85 (1H, m, CH), 3.69-3.72 (1H, m, CH), 3.59-3.62 (1H, m, CH), 3.30-3.32 (4H, m, $CH_2$), 2.30-2.44 (4H, m, $CH_2$), 2.27 (3H, s, $CH_3$), 1.87-1.90 (1H, m, CH), 1.59-1.60 (1H, m, CH), 1.49-1.50 (1H, m, CH), 1.20-1.40 (1H, m, CH).

The following derivatives were obtained according to the same method:

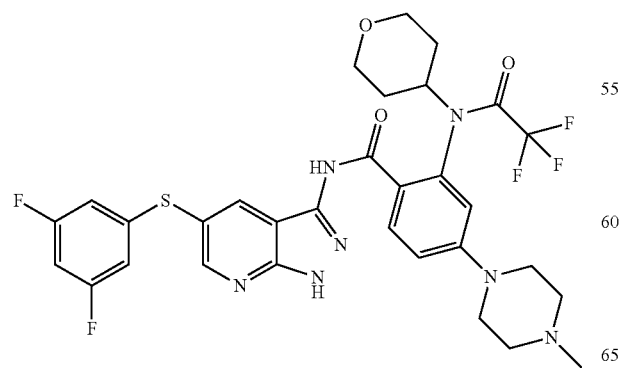

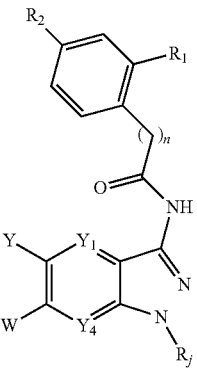

| Ex.** | Y | R₁ | R₂ | n | W | R_j | Y₁, Y₄ | Compound names | Yield | Mass MH⁺ |
|---|---|---|---|---|---|---|---|---|---|---|
| 26-1 | 2-carbamoylphenylthio | tetrahydropyran-4-yl with N-trifluoroacetyl | 4-methylpiperazin-1-yl | 0 | H | H | CH, N | N-(5-(2-carbamoylphenylthio)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-2 | 3,5-difluorophenylsulfonyl | tetrahydropyran-4-yl with N-trifluoroacetyl | 4-methylpiperazin-1-yl | 0 | H | H | CH, N | N-(5-(3,5-difluorophenylsulfonyl)-1H-pyrazolo[3,4-b]pyridin-3-yl)-4-(4-methylpiperazin-1-yl)-2-(tetrahydro-2H-pyran-4-ylamino)benzamide | ND | ND |
| 26-3 | I | tetrahydropyran-4-yl with N-trifluoroacetyl | 4-methylpiperazin-1-yl | 0 | H | H | CH, N | N-(5-iodo-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-4 | 3,5-difluorophenylthio | H | NO₂ | 1 | H | H | CH, N | N-(5-(3,5-difluorophenylthio)-1H-pyrazolo[3,4-b]pyridin-3-yl)-2-(4-nitrophenyl)acetamide | ND | 442.21 |
| 26-5 | 3,5-difluorobenzylsulfonyl | tetrahydropyran-4-yl with N-trifluoroacetyl | 4-methylpiperazin-1-yl | 0 | H | H | CH, N | N-(5-(3,5-difluorobenzylsulfonyl)-1H-pyrazolo[3,4-b]pyridin-3-yl)-4-(4-methylpiperazin-1-yl)-2-(2,2,2-trifluoro)-N-(tetrahydro)-2H-pyran-4-yl)acetamido)benzamide | ND | ND |
| 26-6 | 3,5-difluorophenylthio | 4,4-difluorocyclohexyl with N-trifluoroacetyl | 4-methylpiperazin-1-yl | 0 | H | H | CH, N | 2-(N-(4,4-difluorocyclohexyl)-2,2,2-trifluoroacetamido)-N-(5-(3,5-difluorophenylsulfonyl)-1H-pyrazolo[3,4-b]pyridin-3-yl)-4-(4-methylpiperazin-1-yl)benzamide | ND | ND |

| Ex.** | Y | R₁ | R₂ | n | W | Rⱼ | Y₁, Y₄ | Compound names | Yield | Mass MH⁺ |
|---|---|---|---|---|---|---|---|---|---|---|
| 26-7 | 3,5-difluorobenzyl | 4,4-difluorocyclohexyl with N-trifluoroacetyl | 4-methylpiperazin-1-yl | 0 | H | H | CH, N | N-(5-(3,5-difluorobenzyl)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | 22% | 676.2 |
| 26-8 | 3,5-difluorophenylthio | H | 4-methylpiperazin-1-yl | 1 | H | H | CH, N | N-(5-(3,5-difluorophenylthio)-1H-pyrazolo[3,4-b]pyridin-3-yl)-2-(4-(4-methylpiperazin-1-yl)phenyl)acetamide | ND | 495.17 |
| 26-9 | I | tetrahydropyran-4-yl with N-trifluoroacetyl | 4-methylpiperazin-1-yl | 0 | OMe | H | CH, N | N-(5-iodo-6-methoxy-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | ND | 688.18 |
| 26-10 | I | tetrahydropyran-4-yl with N-trifluoroacetyl | 4-methylpiperazin-1-yl | 0 | NH₂ | H | CH, N | N-(6-amino-5-iodo-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | ND | 673.06 |
| 26-11 | 3,5-difluorophenylthio | tetrahydropyran-4-yl with N-trifluoroacetyl | (S)-3-(2,2,2-trifluoroacetamido)pyrrolidin-1-yl | 1 | H | H | CH, N | (S)-N-(5-(3,5-difluorophenylthio)-1H-pyrazolo[3,4-b]pyridin-3-yl)-2-(2,2,2-trifluoro-N-(tetrahydro-2H-pyran-4-yl)acetamido)-4-(3-(2,2,2-trifluoroacetamido)pyrrolidin-1-yl)benzamide | ND | ND |
| 26-12 | 3,5-difluorophenylthio | H | 4-methylpiperazin-1-yl | 0 | H | H | CH, N | N-(5-(3,5-difluorophenylthio)-1H-pyrazolo[3,4-b]pyridin-3-yl)-4-(4-methylpiperazin-1-yl)benzamide | 46% | 481.38 |

-continued

| Ex.** | Y | R₁ | R₂ | n | W | R_j | Y₁, Y₄ | Compound names | Yield | Mass MH⁺ |
|---|---|---|---|---|---|---|---|---|---|---|
| 26-13 | 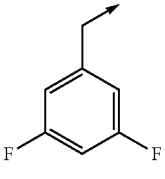 | 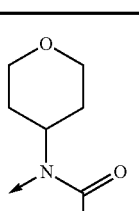 | 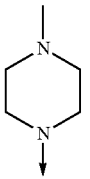 | 0 | H | H | N, CH | N-(5-(3,5-difluorobenzyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 35% | 658.1 |
| 26-14 | 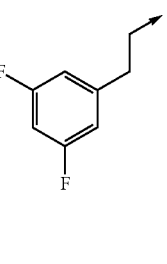 | 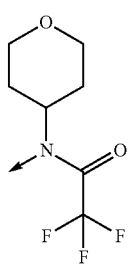 | 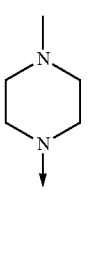 | 0 | H | H | N, CH | N-(5-(3,5-difluorobenzyloxy)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 63% | 674.1 |
| 26-15 | 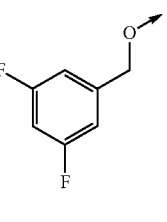 | 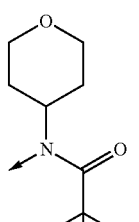 | 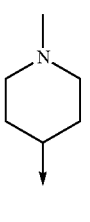 | 0 | H | H | N, CH | N-(5-(3,5-difluorobenzyloxy)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | 673.1 |
| 26-16 | 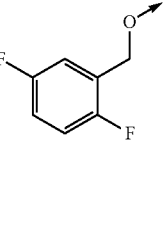 | 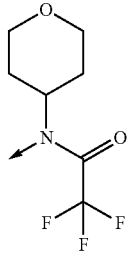 | 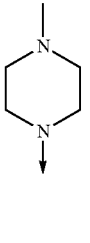 | 0 | H | H | N, CH | N-(5-(2,5-difluorobenzyloxy)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 62% | 674.2 |
| 26-17 | 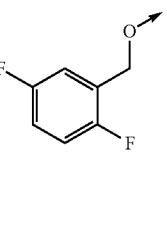 | 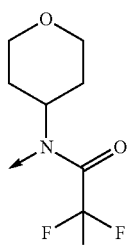 | 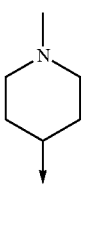 | 0 | H | H | N, CH | N-(5-(2,5-difluorobenzyloxy)-1H-pyrazolo[4,3-b]pyridin-3-yl)-4-(1-methylpiperidin-4-yl)-2-(2,2,2-trifluoro)-N-(tetrahydro-2H-pyran-4-yl)acetamido)benzamide | ND | 673.3 |

| Ex.** | Y | R₁ | R₂ | n | W | Rⱼ | Y₁, Y₄ | Compound names | Yield | Mass MH⁺ |
|---|---|---|---|---|---|---|---|---|---|---|
| 26-18 | 2,5-dichlorobenzyloxy | N-(tetrahydro-2H-pyran-4-yl)-trifluoroacetamide | 4-methylpiperazin-1-yl | 0 | H | H | N, CH | N-(5-(2,5-dichlorobenzyloxy)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-19 | 2,5-dichlorobenzyloxy | N-(tetrahydro-2H-pyran-4-yl)-trifluoroacetamide | 1-methylpiperidin-4-yl | 0 | H | H | N, CH | N-(5-(2,5-dichlorobenzyloxy)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-20 | 5-chloro-2-(trifluoromethyl)benzyloxy | N-(tetrahydro-2H-pyran-4-yl)-trifluoroacetamide | 4-methylpiperazin-1-yl | 0 | H | H | N, CH | N-(5-(5-chloro-2-(trifluoromethyl)benzyloxy)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 55% | 740.2 |
| 26-21 | 5-chloro-2-(trifluoromethyl)benzyloxy | N-(tetrahydro-2H-pyran-4-yl)-trifluoroacetamide | 1-methylpiperidin-4-yl | 0 | H | H | N, CH | N-(5-(5-chloro-2-(trifluoromethyl)benzyloxy)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | 739.3 |
| 26-22 | pyridin-3-ylmethoxy | N-(tetrahydro-2H-pyran-4-yl)-trifluoroacetamide | 4-methylpiperazin-1-yl | 0 | H | H | N, CH | 4-(4-methylpiperazin-1-yl)-N-(5-(pyridin-3-ylmethoxy)-1H-pyrazolo[4,3-b]pyridin-3-yl)-2-(2,2,2-trifluoro-N-(tetrahydro-2H-pyran-4-yl)acetamido)benzamide | 90% | 639.2 |

-continued

| Ex.** | Y | R₁ | R₂ | n | W | Rⱼ | Y₁, Y₄ | Compound names | Yield | Mass MH⁺ |
|---|---|---|---|---|---|---|---|---|---|---|
| 26-23 | pyridin-3-ylmethoxy | N-(tetrahydro-2H-pyran-4-yl)trifluoroacetamide | 1-methylpiperidin-4-yl | 0 | H | H | N, CH | 4-(1-methylpiperidin-4-yl)-N-(5-(pyridin-3-ylmethoxy)-1H-pyrazolo[4,3-b]pyridin-3-yl)-2-(2,2,2-trifluoro-N-(tetrahydro-2H-pyran-4-yl)acetamido)benzamide | ND | 638.2 |
| 26-24 | 3,5-difluorophenylthio | N-(tetrahydro-2H-pyran-4-yl)trifluoroacetamide | 4-methylpiperazin-1-yl | 0 | H | H | N, CH | N-(5-(3,5-difluorophenylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-25 | 3,5-difluorophenylthio | N-(tetrahydro-2H-pyran-4-yl)trifluoroacetamide | 1-methylpiperidin-4-yl | 0 | H | H | N, CH | N-(5-(3,5-difluorophenylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 50% | ND |
| 26-26 | 2,5-difluorophenylthio | N-(tetrahydro-2H-pyran-4-yl)trifluoroacetamide | 4-methylpiperazin-1-yl | 0 | H | H | N, CH | N-(5-(2,5-difluorophenylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-27 | 2,5-difluorophenylthio | N-(tetrahydro-2H-pyran-4-yl)trifluoroacetamide | 1-methylpiperidin-4-yl | 0 | H | H | N, CH | N-(5-(2,5-difluorophenylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |

| Ex.** | Y | R₁ | R₂ | n | W | R_j | Y₁, Y₄ | Compound names | Yield | Mass MH⁺ |
|---|---|---|---|---|---|---|---|---|---|---|
| 26-28 | 3,5-dichlorophenylthio | N-(tetrahydro-2H-pyran-4-yl), N-C(O)CF₃ | 4-methylpiperazin-1-yl | 0 | H | H | N, CH | N-(5-(3,5-dichlorophenylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-29 | 3,5-dichlorophenylthio | N-(tetrahydro-2H-pyran-4-yl), N-C(O)CF₃ | 1-methylpiperidin-4-yl | 0 | H | H | N, CH | N-(5-(3,5-dichlorophenylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-30 | 2,5-dichlorophenylthio | N-(tetrahydro-2H-pyran-4-yl), N-C(O)CF₃ | 4-methylpiperazin-1-yl | 0 | H | H | N, CH | N-(5-(2,5-dichlorophenylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-31 | 2,5-dichlorophenylthio | N-(tetrahydro-2H-pyran-4-yl), N-C(O)CF₃ | 1-methylpiperidin-4-yl | 0 | H | H | N, CH | N-(5-(2,5-dichlorophenylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-32 | 2-(trifluoromethyl)phenylthio | N-(tetrahydro-2H-pyran-4-yl), N-C(O)CF₃ | 4-methylpiperazin-1-yl | 0 | H | H | N, CH | 4-(4-methylpiperazin-1-yl)-2-(2,2,2-trifluoro-N-(tetrahydro-2H-pyran-4-yl)acetamido)-N-(5-(2-(trifluoromethyl)phenylthio)-1H-pyrazolo[4,3-b]pyridin-3-yl)benzamide | ND | ND |

-continued

| Ex.** | Y | R₁ | R₂ | n | W | R_j | Y₁, Y₄ | Compound names | Yield | Mass MH⁺ |
|---|---|---|---|---|---|---|---|---|---|---|
| 26-33 | 2-(trifluoromethyl)phenylthio | N-(tetrahydro-2H-pyran-4-yl)-2,2,2-trifluoroacetamide | 1-methylpiperidin-4-yl | 0 | H | H | N, CH | 4-(1-methylpiperidin-4-yl)-2-(2,2,2-trifluoro-N-(tetrahydro-2H-pyran-4-yl)acetamido)-N-(5-(2-(trifluoromethyl)phenylthio)-1H-pyrazolo[4,3-b]pyridin-3-yl)benzamide | ND | ND |
| 26-34 | 3,5-difluorobenzylthio | N-(tetrahydro-2H-pyran-4-yl)-2,2,2-trifluoroacetamide | 4-methylpiperazin-1-yl | 0 | H | H | N, CH | N-(5-(3,5-difluorobenzylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-35 | 3,5-difluorobenzylthio | N-(tetrahydro-2H-pyran-4-yl)-2,2,2-trifluoroacetamide | 1-methylpiperidin-4-yl | 0 | H | H | N, CH | N-(5-(3,5-difluorobenzylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 73% | ND |
| 26-36 | 2,5-difluorobenzylthio | N-(tetrahydro-2H-pyran-4-yl)-2,2,2-trifluoroacetamide | 4-methylpiperazin-1-yl | 0 | H | H | N, CH | N-(5-(2,5-difluorobenzylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-37 | 2,5-difluorobenzylthio | N-(tetrahydro-2H-pyran-4-yl)-2,2,2-trifluoroacetamide | 1-methylpiperidin-4-yl | 0 | H | H | N, CH | N-(5-(2,5-difluorobenzylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |

| Ex.** | Y | R₁ | R₂ | n | W | Rⱼ | Y₁, Y₄ | Compound names | Yield | Mass MH⁺ |
|---|---|---|---|---|---|---|---|---|---|---|
| 26-38 | 2,5-dichlorobenzylthio | N-(tetrahydro-2H-pyran-4-yl)-trifluoroacetamide | 4-methylpiperazin-1-yl | 0 | H | H | N, CH | N-(5-(2,5-dichlorobenzylthio)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-39 | 2,5-dichlorobenzylthio | N-(tetrahydro-2H-pyran-4-yl)-trifluoroacetamide | 1-methylpiperidin-4-yl | 0 | H | H | N, CH | N-(5-(2,5-dichlorobenzylthio)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-40 | 3,5-difluorophenylamino | N-(tetrahydro-2H-pyran-4-yl)-trifluoroacetamide | 4-methylpiperazin-1-yl | 0 | H | H | N, CH | N-(5-(3,5-difluorophenylamino)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 79% | 659.2 |
| 26-41 | 3,5-difluorophenylamino | N-(tetrahydro-2H-pyran-4-yl)-trifluoroacetamide | 1-methylpiperidin-4-yl | 0 | H | H | N, CH | N-(5-(3,5-difluorophenylamino)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | 658.2 |
| 26-42 | 2,5-difluorophenylamino | N-(tetrahydro-2H-pyran-4-yl)-trifluoroacetamide | 4-methylpiperazin-1-yl | 0 | H | H | N, CH | N-(5-(2,5-difluorophenylamino)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | 659.2 |

-continued

| Ex.** | Y | R₁ | R₂ | n | W | R_j | Y₁, Y₄ | Compound names | Yield | Mass MH⁺ |
|---|---|---|---|---|---|---|---|---|---|---|
| 26-43 | 2,5-difluorophenyl-NH- | N-(tetrahydropyran-4-yl)-N-(trifluoroacetyl) | 1-methylpiperidin-4-yl | 0 | H | H | N, CH | N-(5-(3,5-difluorophenylamino)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | 658.2 |
| 26-44 | 2,5-dichlorophenyl-NH- | N-(tetrahydropyran-4-yl)-N-(trifluoroacetyl) | 4-methylpiperazin-1-yl | 0 | H | H | N, CH | N-(5-(2,5-dichlorophenylamino)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 26% | 691.2 |
| 26-45 | 2,5-dichlorophenyl-NH- | N-(tetrahydropyran-4-yl)-N-(trifluoroacetyl) | 1-methylpiperidin-4-yl | 0 | H | H | N, CH | N-(5-(2,5-dichlorophenylamino)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 98% | 692.2 |
| 26-46 | 3,5-difluorobenzyl | N-(tetrahydropyran-4-yl)-N-(trifluoroacetyl) | 4-methylpiperazin-1-yl | 0 | H | H | N, N | N-(5-(3,5-difluorobenzyl)-1H-pyrazolo[3,4-b]pyrazin-3-yl)-4-(4-methylpiperazin-1-yl)-2-(2,2,2-trifluoro-N-(tetrahydro-2H-pyran-4-yl)acetamido)benzamide | ND | ND |
| 26-47 | 3,5-difluorobenzyl | N-(tetrahydropyran-4-yl)-N-(trifluoroacetyl) | 1-methylpiperidin-4-yl | 0 | H | H | N, N | N-(5-(3,5-difluorobenzyl)-1H-pyrazolo[3,4-b]pyrazin-3-yl)-4-(1-methylpiperidin-4-yl)-2-(2,2,2-trifluoro-N-(tetrahydro-2H-pyran-4-yl)acetamido)benzamide | ND | ND |

| Ex.** | Y | R₁ | R₂ | n | W | R_j | Y₁, Y₄ | Compound names | Yield | Mass MH⁺ |
|---|---|---|---|---|---|---|---|---|---|---|
| 26-48 | 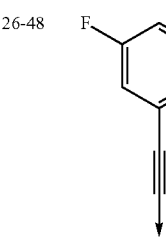 | 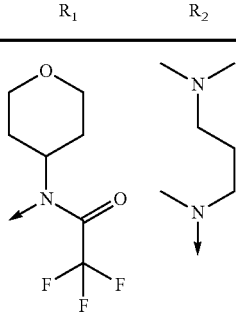 |  | 0 | H | H | N, N | N-(5-((3,5-difluorophenyl)ethynyl)-1H-pyrazolo[3,4-b]pyrazin-3-yl)-4-((3-(dimethylamino)propyl)(methyl)amino)-2-(2,2,2-trifluoro-N-(tetrahydro-2H-pyran-4-yl)acetamido)benzamide | ND | ND |
| 26-49 | 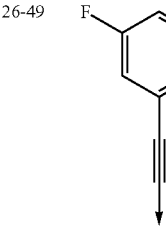 | 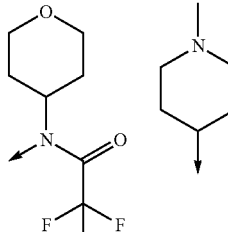 | 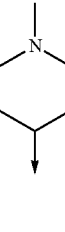 | 0 | H | H | N, N | N-(5-((3,5-difluorophenyl)ethynyl)-1H-pyrazolo[3,4-b]pyrazin-3-yl)-4-(1-methylpiperidin-4-yl)-2-(2,2,2-trifluoro-N-(tetrahydro-2H-pyran-4-yl)acetamido)benzamide | ND | ND |
| 26-50 | 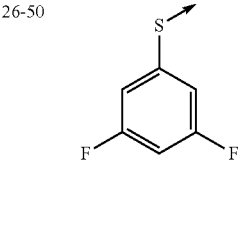 | 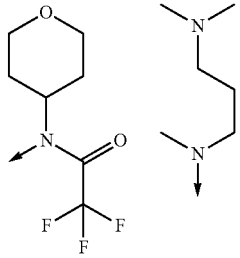 | 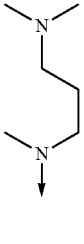 | 0 | H | H | N, N | N-(5-(3,5-difluorophenylthio)-1H-pyrazolo[3,4-b]pyrazin-3-yl)-4-((3-(dimethylamino)propyl)(methyl)amino)-2-(2,2,2-trifluoro-N-(tetrahydro-2H-pyran-4-yl)acetamido)benzamide | 43% | 693.2 |
| 26-51 | 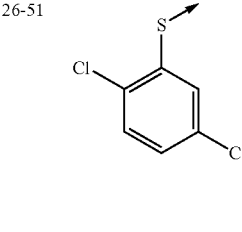 | 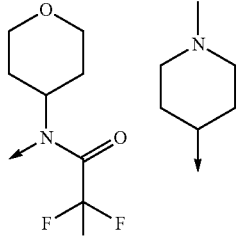 | 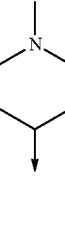 | 0 | H | H | N, N | N-(5-(2,5-dichlorophenylthio)-1H-pyrazolo[3,4-b]pyrazin-3-yl)-4-(4-methylpiperazin-1-yl)-2-(2,2,2-trifluoro-N-(tetrahydro-2H-pyran-4-yl)acetamido)benzamide | ND | ND |
| 26-52 | 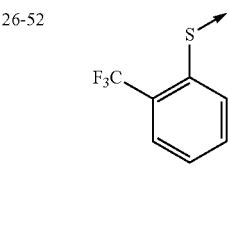 | 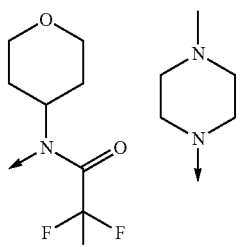 | 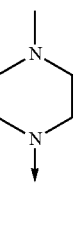 | 0 | H | H | N, CH | 4-(4-methylpiperazin-1-yl)-2-(2,2,2-trifluoro-N-(tetrahydro-2H-pyran-4-yl)acetamido)-N-(5-(2-(trifluoromethyl)phenylthio)-1H-pyrazolo[3,4-b]pyrazin-3-yl)benzamide | 66% | 709.1 |

| Ex.** | Y | R₁ | R₂ | n | W | R_j | Y₁, Y₄ | Compound names | Yield | Mass MH⁺ |
|---|---|---|---|---|---|---|---|---|---|---|
| 26-53 | 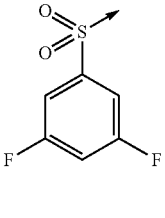 | 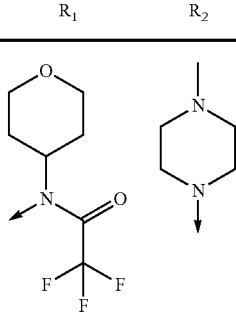 |  | 0 | H | H | N, CH | N-(5-(3,5-difluorophenylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 28% | 708.2 |
| 26-54 | 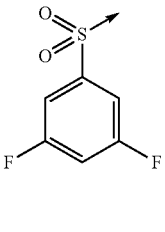 | 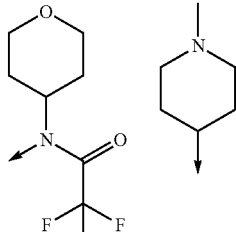 |  | 0 | H | H | N, CH | N-(5-(3,5-difluorophenylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 74% | 707.2 |
| 26-55 | 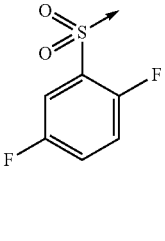 | 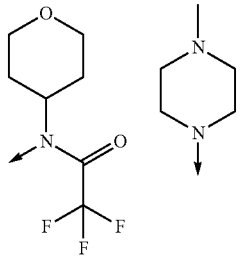 |  | 0 | H | H | N, CH | N-(5-(2,5-difluorophenylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-56 | 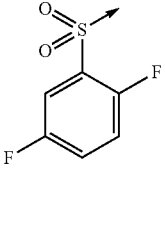 | 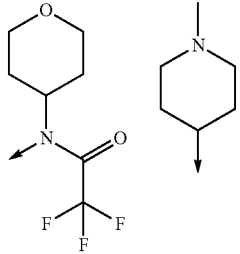 |  | 0 | H | H | N, CH | N-(5-(2,5-difluorophenylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-57 | 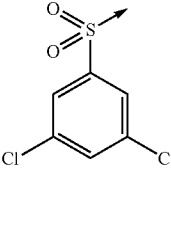 | 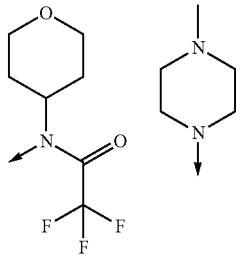 |  | 0 | H | H | N, CH | N-(5-(3,5-dichlorophenylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |

| Ex.** | Y | R$_1$ | R$_2$ | n | W | R$_j$ | Y$_1$, Y$_4$ | Compound names | Yield | Mass MH$^+$ |
|---|---|---|---|---|---|---|---|---|---|---|
| 26-58 | 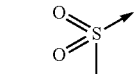 | 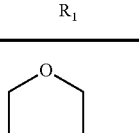 |  | 0 | H | H | N, CH | N-(5-(3,5-dichlorophenylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-59 | 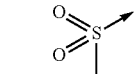 | 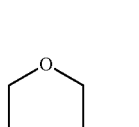 | 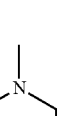 | 0 | H | H | N, CH | N-(5-(2,5-dichlorophenylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | ND | ND |
| 26-60 | 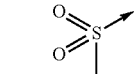 | 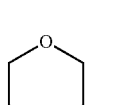 |  | 0 | H | H | N, CH | N-(5-(2,5-dichlorophenylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-61 | 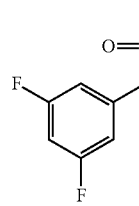 | 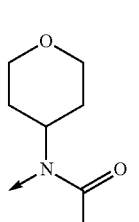 | 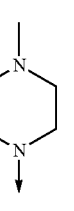 | 0 | H | H | N, CH | N-(5-(3,5-difluorobenzylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 94% | ND |
| 26-62 | 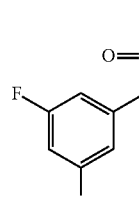 | 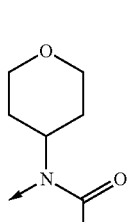 | 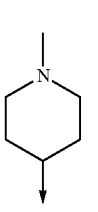 | 0 | H | H | N, CH | N-(5-(3,5-difluorobenzylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 99% | ND |

-continued

| Ex.** | Y | R₁ | R₂ | n | W | R_j | Y₁, Y₄ | Compound names | Yield | Mass MH⁺ |
|---|---|---|---|---|---|---|---|---|---|---|
| 26-63 | 2,5-difluorobenzylsulfonyl | tetrahydropyran-4-yl with N-CO-CF₃ | 4-methylpiperazin-1-yl | 0 | H | H | N, CH | N-(5-(2,5-difluorobenzylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 60% | ND |
| 26-64 | 2,5-difluorobenzylsulfonyl | tetrahydropyran-4-yl with N-CO-CF₃ | 1-methylpiperidin-4-yl | 0 | H | H | N, CH | N-(5-(2,5-difluorobenzylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 36% | ND |
| 26-65 | 2,5-difluorobenzylsulfinyl | tetrahydropyran-4-yl with N-CO-CF₃ | 1-methylpiperidin-4-yl | 0 | H | H | N, CH | N-(5-(2,5-difluorobenzylsulfinyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | ND | ND |
| 26-66 | 2,5-dichlorobenzylsulfonyl | tetrahydropyran-4-yl with N-CO-CF₃ | 4-methylpiperazin-1-yl | 0 | H | H | N, CH | N-(5-(2,5-dichlorobenzylsulfonyl)-1H-pyrazolo[4,3-b]pyridin-3-yl)-4-(4-methylpiperazin-1-yl)-2-(2,2,2-trifluoro-N-(tetrahydro-2H-pyran-4-yl)acetamido)benzamide | 52% | ND |
| 26-67 | 2,5-dichlorobenzylsulfonyl | tetrahydropyran-4-yl with N-CO-CF₃ | 1-methylpiperidin-4-yl | 0 | H | H | N, CH | N-(5-(2,5-dichlorobenzylsulfonyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 90% | ND |

-continued

| Ex.** | Y | R₁ | R₂ | n | W | R_j | Y₁, Y₄ | Compound names | Yield | Mass MH⁺ |
|---|---|---|---|---|---|---|---|---|---|---|
| 26-68 | 2,5-dichlorobenzylsulfinyl group | tetrahydropyran-4-yl with N-trifluoroacetyl | 1-methylpiperidin-4-yl | 0 | H | H | N, CH | N-(5-(2,5-dichlorobenzylsulfinyl)-1H-pyrazolo[4,3-b]pyridin-3-yl)-4-(1-methylpiperidin-4-yl)-2-(2,2,2-trifluoro-N-(tetrahydro-2H-pyran-4-yl)acetamido)benzamide | 50% | ND |
| 26-69 | I | tetrahydropyran-4-yl with N-trifluoroacetyl | 1-methylpiperazin-4-yl | 0 | H | C(Ph)₃ | CH, N | N-(5-iodo-1-trityl-1H-pyrazolo[3,4-b]pyridin-3-yl)-4-(4-methylpiperazin-1-yl)-2-(tetrahydro-2H-pyran-4-ylamino)benzamide | 67% | 900.23 |
| 26-70 | 3,5-difluorophenylsulfonamido group | tetrahydropyran-4-yl with N-trifluoroacetyl | 1-methylpiperazin-4-yl | 0 | H | H | CH, N | N-(5-(3,5-difluorophenylsulfonamido)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | 11% | ND |

¹H NMR, dmso-d₆, Ex.: 26-4: 13.64 (1H, sl, NH), 11.26 (1H, sl, NH), 8.68 (1H, d, CH_arom), 8.58 (1H, d, CH_arom), 8.20 (2H, d, CH_arom), 7.64 (2H, d, CH_arom), 7.03 (1H, m, CH_arom), 6.78 (2H, m, CH_arom), 3.95 (2H, m, CH₂). 26-8: 13.59 (1H, sl, NH), 11.05 (1H, sl, NH), 8.68 (1H, d, CH_arom), 8.57 (1H, d, CH_arom), 7.19 (2H, d, CH_arom), 6.99-7.08 (1H, m, CH_arom), 6.88 (2H, d, CH_arom), 6.75-6.79 (2H, m, CH_arom), 3.61 (2H, m, CH₂), 3.07-3.09 (4H, m, CH), 2.41-2.44 (4H, m, CH), 2.20 (3H, s, CH₃). 26-9: 13.17 (1H, sl, NH), 10.90 (1H, sl, NH), 8,55 (1H, s, CHarom), 7,79 (1H, d, CHarom), 7,07 (1H, dd, CHarom), 6.90 (1H, d, CHarom), 4.40-4.50 (1H, m, CH), 3.96 (3H, s, CH₃), 3.82-3.89 (1H, m, CH), 3.74-3.80 (1H, m, CH), 3.34-3.41 (2H, m, CH), 3.28-3.33 (4H, m, 2*CH₂), 2.43-2.47 (4H, m, 2*CH₂), 2.23 (3H, s, CH₃). 1.85-1.92 (1H, m, CH), 1.58-1.63 (1H, m, CH), 1.45-1.53 (1H, m, CH), 1.22-1.33 (1H, m, CH). 26-10: 12.48 (1H, sl, NH), 10.72 (1H, sl, NH), 8.30 (1H, s, CHarom), 7.77 (1H, d, CHarom), 7.06 (1H, dd, CHarom), 6.88 (1H, d, CHarom), 6.40 (2H, sl, NH₂), 4.40-4.50 (1H, m, CH), 3.82-3.89 (1H, m, CH), 3.74-3.80 (1H, m, CH), 3.34-3.41 (2H, m, CH), 3.28-3.33 (4H, m, 2*CH₂), 2.43-2.47 (4H, m, 2*CH₂), 2.23 (3H, s, CH₃), 1.85-1.92 (1H, m, CH), 1.58-1.65 (1H, m, CH), 1.45-1.55 (1H, m, CH), 1.22-1.34 (1H, m, CH). (ND: not determined). 26-14: 12.99 (1H, sl, NH), 10.25 (1H, s, NH), 7.96 (1H, d, CHarom, J = 9.2 Hz), 7.90-7.80 (1H, m, CHarom), 7.23-7.16 (3H, m, CHarom), 7.12-7.08 (1H, m, CHarom), 6.96 (1H, d, CHarom, J = 8.8 Hz), 6.87 (1H, s, CHarom), 5.31 (2H, s), 4.49-4.42 (1H ,m), 3.86-3.75 (2H, m), 3.45 (1H, m), 3.37 (1H, m), 3.35 (4H, s), 2.42 (4H, s), 2.22 (3H, s), 1.90-1.75 (2H, m), 1.53-1.49 (1H, m), 1.31-1.25 (1H, m). 26-16: 13.00 (1H, s, NH), 10.27 (1H, s, NH), 7.95 (1H, d, CHarom, J = 8.8 Hz), 7.89-7.84 (1H, m, CHarom), 7.50-7.40 (1H, m, CHarom), 7.35-7.20 (2H, m, CHarom), 7.12-7.09 (1H, m, CHarom), 6.94 (1H, d, CHarom, J = 8.8 Hz), 6.87 (1H, s, CHarom), 5.30 (2H, s), 4.52-4.43 (1H, m), 3.85-3.75 (2H, m), 3.46-3.43 (1H, m), 3.36 (5H, s), 2.45 (4H, s), 2.22 (3H, s), 1.92-1.82 (2H, m), 1.60-1.52 (1H, m), 1.33-1.26 (1H, m). 26-20: 13.01 (1H, s, NH), 10.22 (1H, s, NH), 7.97 (1H, d, CHarom, J = 8.8 Hz), 7.90-7.78 (3H, m, CHarom), 7.68-7.64 (1H, m, CHarom), 7.12-7.08 (1H, m, CHarom), 6.97 (1H, d, CHarom, J = 8.8 Hz), 6.85 (1H, s, CHarom), 5.43 (2H, s), 4.45-4.40 (1H, m), 3.86-3.70 (2H, m), 3.46-3.42 (1H, m), 3.30-3.28 (5H, m), 2.46 (4H, s), 2.23 (3H, s), 1.90 (1H, d, J = 11.2 Hz), 1.77 (1H, d, J = 11.2 Hz), 1.58-1.50 (1H, m), 1.30-1.20 (1H, m).

In certain cases, the major product of these reactions corresponds to the disubstituted product characterized by the additional functionalization of the pyrazole ring. In these cases, this product is isolated and transformed into a mono-substituted product by treatment with a base as described below.

Example 27

N-(5-(3,5-difluorophenylthio)-1-H-pyrazolo[3,4-b]pyrazine-3-yl)-4-(4-methylpiperazine-1-yl)-2-(tetrahydro-2H-pyran-4-ylamino)benzamide

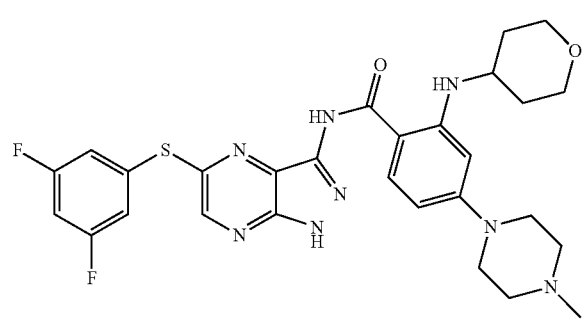

Example 27a

N-(5-(3,5-difluorophenylthio)-1-(4-(4-methylpiperazine-1-yl)-2-(2,2,2-trifluoro-N-(tetrahydro-2H-pyran-4-yl)acetamido)benzoyl)-1H-pyrazolo[3,4-b]pyrazine-3-yl)-4-(4-methylpiperazine-1-yl)-2-(2,2,2-trifluoro-N-(tetrahydro-2H-pyran-4-yl)acetamido)benzamide 1.51 ml (17.90 mmol) of oxalyl chloride and 2 drops of anhydrous dimethylformamide are added to 4.74 g (8.95 mmol) of a solution of 4-(4-methylpiperazine-1-yl)-2-(2,2,2-trifluoro-N-(tetrahydro-2H-pyran-4-yl)acetamido)benzoic acid in 60 ml of dichloromethane. The reaction mixture is stirred for 2 hours at room temperature. The solvents are evaporated, the solid formed is taken up in toluene and the solvent is evaporated; this operation is repeated three times until a white solid is obtained.

The acid chloride is added at 0° C. in small fractions to 1 g (3.58 mmol) of 5-(3,5-difluorophenylthio)-1H-pyrazolo[3,4-b]pyrazine-3-amine dissolved in 15 ml of pyridine. The reaction mixture is stirred at 25° C. overnight at room temperature. After evaporation of the solvent, the residue is purified by silica gel chromatography (90:10 dichloromethane/methanol and then 90:9:1 and then 90:5:5 dichloromethane/methanol/ammonium as eluent) to yield N-(5-(3,5-difluorophenylthio)-1-(4-(4-methylpiperazine-1-yl)-2-(2,2,2-trifluoro-N-(tetrahydro-2H-pyran-4-yl)acetamido)benzoyl)-1H-pyrazolo[3,4-b]pyrazine-3-yl)-4-(4-methylpiperazine-1-yl)-2-(2,2,2-trifluoro-N-(tetrahydro-2H-pyran-4-yl)acetamido)benzamide.

LCMS (EI, m/z): (M+1) 1074.64.

Example 27

N-(5-(3,5-difluorophenylthio)-1-H-pyrazolo[3,4-b]pyrazine-3-yl)-4-(4-methylpiperazine-1-yl)-2-(tetrahydro-2H-pyran-4-ylamino)benzamide 0.27 ml (1.95 mmol) of triethylamine is added to 0.21 g (0.19 mmol) of a solution of N-(5-(3,5-difluorophenylthio)-1-(4-(4-methylpiperazine-1-yl)-2-(2,2,2-trifluoro-N-(tetrahydro-2H-pyran-4-yl)acetamido)benzoyl)-1H-pyrazolo[3,4-b]pyrazine-3-yl)-4-(4-methylpiperazine-1-yl)-2-(2,2,2-trifluoro-N-(tetrahydro-2H-pyran-4-yl)acetamido)benzamide in 5 ml of methanol. The reaction medium is heated at 65° C. for 4 hours, and then overnight at room temperature. After evaporation of the solvent, the product is extracted several times with ethyl acetate. The organic phases are combined, washed with saturated sodium bicarbonate solution, dried on magnesium sulfate and concentrated. The residue is purified by silica gel chromatography (95:4:1 dichloromethane/methanol/ammonium as eluent) to yield 0.065 g (57%) of N-(5-(3,5-difluorophenylthio)-1-H-pyrazolo[3,4-b]pyrazine-3-yl)-4-(4-methylpiperazine-1-yl)-2-(tetrahydro-2H-pyran-4-ylamino)benzamide in the form of a yellow solid.

LCMS (EI, m/z): (M−1) 579.21.

$^1$H NMR: δH ppm (400 MHz, DMSO): 13.95 (1H, bs, NH), 10.25 (1H, bs, NH), 8.62 (1H, s, $CH_{arom}$), 8.27 (1H, d, NH), 7.80 (1H, d, $CH_{arom}$), 7.17-7.27 (3H, m, $CH_{arom}$), 6.27 (1H, d, $CH_{arom}$), 6.12 (1H, d, $CH_{arom}$), 3.79-3.82 (2H, m, CH), 3.67 (1H, m, CH), 3.45-3.50 (2H, m, CH), 3.26-3.29 (4H, m, CH), 2.42-2.44 (4H, m, CH), 2.22 (3H, s, $CH_3$), 1.90-1.93 (2H, m, CH), 1.31-1.36 (2H, m, CH).

The following compounds were obtained by the same method:

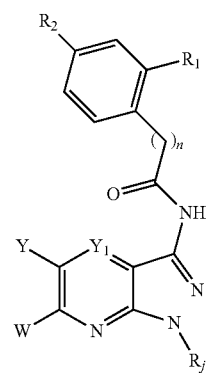

| Ex.** | Y | $R_1$ | $R_2$ | $Y_1$ | n | W | $R_j$ | Compound names | Yield | Mass |
|---|---|---|---|---|---|---|---|---|---|---|
| 27-1 | O=S(=O) 3,5-difluorophenyl | tetrahydro-2H-pyran-4-yl-NH | 4-methylpiperazin-1-yl | CH | 0 | H | H | N-(5-(3,5-difluorophenylsulfonyl)-1H-pyrazolo[3,4-b]pyridin-3-yl)-4-(4-methylpiperazin-1-yl)-2-(tetrahydro-2H-pyran-4-ylamino)benzamide | 18.6% | (M + H) 612.13 |

-continued

| Ex.** | Y | $R_1$ | $R_2$ | $Y_1$ | n | W | $R_j$ | Compound names | Yield | Mass |
|---|---|---|---|---|---|---|---|---|---|---|
| 27-2 | 3,5-difluorophenyl sulfinyl group | tetrahydropyran-4-ylamino | 4-methylpiperazin-1-yl | N | 0 | H | H | N-(5-(3,5-difluorophenylsulfinyl)-1H-pyrazolo[3,4-b]pyrazin-3-yl)-4-(4-methylpiperazin-1-yl)-2-(tetrahydro-2H-pyran-4-ylamino)benzamide | ND | (M + Na) 619.6 |
| 27-3 | 3,5-difluorophenyl sulfonyl group | tetrahydropyran-4-ylamino | 4-methylpiperazin-1-yl | N | 0 | H | H | N-(5-(3,5-difluorophenylsulfonyl)-1H-pyrazolo[3,4-b]pyrazin-3-yl)-4-(4-methylpiperazin-1-yl)-2-(tetrahydro-2H-pyran-4-ylamino)benzamide | ND | (M + H) 613.5 |
| 27-4 | H | tetrahydropyran-4-ylamino | 4-methylpiperazin-1-yl | CH | 0 | 3,5-difluorobenzyl | H | N-(6-(3,5-difluorobenzyl)-1H-pyrazolo[3,4-b]pyridin-3-yl)-4-(4-methylpiperazin-1-yl)-2-(tetrahydro-2H-pyran-4-ylamino)benzamide | 24% | (M + H) 562.00 |
| 27-5 | H | tetrahydropyran-4-ylamino | 4-methylpiperazin-1-yl | CH | 0 | 3,5-difluorobenzylamino | H | N-(6-(3,5-difluorobenzylamino)-1H-pyrazolo[3,4-b]pyridin-3-yl)-4-(4-methylpiperazin-1-yl)-2-(tetrahydro-2H-pyran-4-ylamino)benzamide | ND | (M − H) 275.1 |

Reactions carried out in pyridine often make it possible to modify the regioisomer distribution of the products. The following example is characteristic of a reaction of this type.

Example 27-bis

N-(5-(N-(3,5-difluorophenyl)sulfamoyl)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide

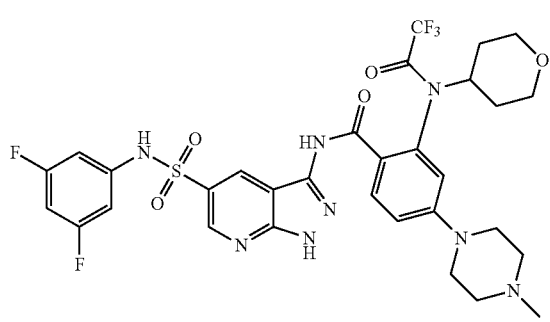 [SMILES: CN1CCN(c2ccc(C(=O)NC(=N)c3cc(S(=O)(=O)Nc4cc(F)cc(F)c4)cnc3N)c(N(C(=O)C(F)(F)F)C3CCOCC3)c2)CC1]

0.224 ml (2.63 mmol) of oxalyl chloride and 2 drops of anhydrous dimethylformamide are added to 0.697 g (1.316 mmol) of a solution of 4-(4-methylpiperazin-1-yl)-2-(2,2,2-trifluoro-N-(tetrahydro-2H-pyran-4-yl)acetamido)benzoic acid in 20 ml of dichloromethane. The reaction mixture is stirred for 2 hours at room temperature. The solvents are evaporated, the solid formed is redissolved in toluene and the solvent is evaporated. This operation is repeated three times until a white solid is obtained.

The acid chloride is dissolved in 5 ml of anhydrous pyridine and then the solution formed is added to a solution of 0.214 g (0.658 mmol) of 3-amino-N-(3,5-difluorophenyl)-1H-pyrazolo[3,4-b]pyridine-5-sulfonamide in 5 ml of pyridine at 0° C. The reaction mixture is stirred for 3 hours at 0° C., and then overnight at room temperature. The pyridine is evaporated and the crude reaction product is redissolved in toluene and then dry concentrated. The reaction mixture is diluted with saturated $NaHCO_3$ solution and extracted with ethyl acetate. The organic phase is dried on $MgSO_4$, filtered and concentrated and the crude product is used directly in the deprotection reaction with no purification or characterization.

The following compounds were obtained by the same method:

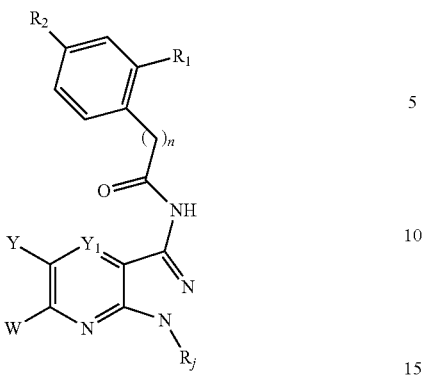

| Ex.** | Y | R₁ | R₂ | Y₁ | n | W | R$_j$ | Compound names | Yield | Mass |
|---|---|---|---|---|---|---|---|---|---|---|
| 27bis-1 | H | tetrahydropyran-4-yl with N-C(O)CF₃ | 4-methylpiperazin-1-yl | CH | 0 | S-(2,4-difluorophenyl) | H | N-(6-(2,4-difluorophenylthio)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | ND | 676.18 (M + H) |
| 27bis-2 | H | tetrahydropyran-4-yl with N-C(O)CF₃ | 4-methylpiperazin-1-yl | CH | 0 | HN-(2,4-difluorophenyl) | H | N-(6-(2,4-difluorophenylamino)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | 28% | 657.13 (M − H) |
| 27bis-3 | H | tetrahydropyran-4-yl with N-C(O)CF₃ | 4-methylpiperazin-1-yl | CH | 0 | N(Me)-(2,4-difluorophenyl) | H | N-(6-((2,4-difluorophenyl)(methyl)amino)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide | ND | 671.05 (M − H) |

Example of Method E2

Example 28

5-(3,5-difluorophenylthio)-N-(4-(4-methylpiperazin-1-yl)benzyl)-1H-pyrazolo[3,4-b]pyridin-3-amine

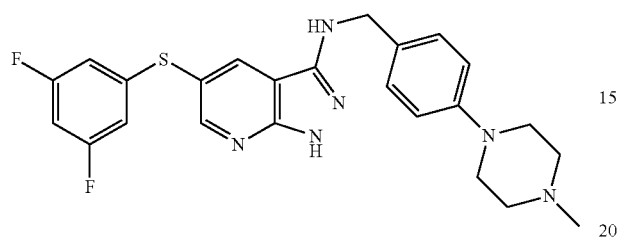

The following derivative was obtained according to the same method:

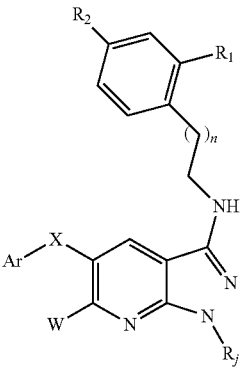

| Ex.** | ArX | R$_1$ | R$_2$ | n | W | R$_j$ | Compound name | Yield | Mass MH$^+$ |
|---|---|---|---|---|---|---|---|---|---|
| 28-1 | ![S-3,5-difluorophenyl] | NO$_2$ | ![4-methylpiperazin-1-yl] | 0 | H | H | 5-(3,5-difluorophenylthio)-N-(4-(4-methylpiperazin-1-yl)-2-nitrobenzyl)-1H-pyrazolo[3,4-b]pyridin-3-amine | 91% | 512.16 |

**$^1$H NMR, DMSO-d$_6$, Ex.: 28-1: 12.43 (1H, bs, NH), 8.49 (1H, d, CH$_{arom}$), 8.47 (1H, d, CH$_{arom}$), 7.51 (1H, d, CH$_{arom}$), 7.45 (1H, m, CH$_{arom}$), 7.27 (1H, m, CH$_{arom}$), 7.03-7.08 (1H, m, CH$_{arom}$), 7.00 (1H, t, NH), 6.77-6.80 (2H, m, CH$_{arom}$), 4.63 (2H, d, CH), 3.19-3.21 (4H, m, CH), 2.42-2.45 (4H, m, CH), 2.21 (3H, s, CH$_3$).

41.5 μl of trifluoroacetic acid (0.539 mmol) and, in small fractions, 129 mg (0.611 mmol) of sodium triacetoxyborohydride are added to a solution of 100 mg (0.35 mmol) of 5-(3,5-difluorophenylthio)-1H-pyrazolo[3,4-b]pyridin-3-amine and 81 mg (0.395 mmol) of 4-(4-methylpiperazin-1-yl)benzaldehyde in 20 ml of a 1:1 mixture of dichloromethane and tetrahydrofuran. The reaction medium is stirred for 16 hours at room temperature. An additional fraction of 125 μl of trifluoroacetic acid and 388 mg of sodium triacetoxyborohydride are added and the reaction medium is stirred for an additional 24 hours. The solvent is then concentrated and the reaction medium extracted with ethyl acetate and washed using saturated sodium bicarbonate solution. The organic phases are combined, dried on magnesium sulfate and then concentrated to yield a yellow oil. A trituration of this oil in methanol leads to the isolation of 135 mg of a yellow solid.

LCMS (EI, m/z): (M+1) 467.57.

$^1$H NMR: δH ppm (400 MHz, DMSO): 12.43 (1H, bs, NH), 8.49 (1H, d, CH$_{arom}$), 8.47 (1H, d, CH$_{arom}$), 7.25 (2H, d, CH$_{arom}$), 7.03-7.08 (1H, m, CH$_{arom}$), 6.89 (2H, d, CH$_{arom}$), 6.76-6.77 (3H, m, NH and CH$_{arom}$), 4.34 (2H, d, CH), 3.08 (4H, m, CH), 2.44 (4H, m, CH), 2.21 (3H, s, CH$_3$).

Example 29

1-(5-(3,5-difluorophenylthio)-1H-pyrazolo[3,4-b]pyridin-3-yl)-3-(4-(4-methylpiperazin-1-yl)phenyl)thiourea

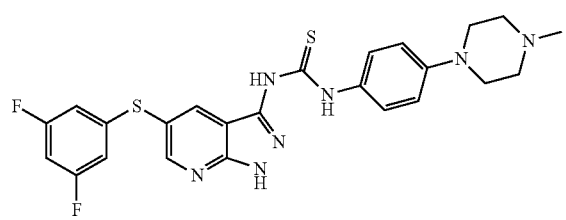 [SMILES: CN1CCN(c2ccc(NC(=S)NC(=N)c3cc(Sc4cc(F)cc(F)c4)cnc3N)cc2)CC1]

0.507 g (2.17 mmol) of 1-(4-isothiocyanatophenyl)-4-methylpiperazine is added at 25° C. to 0.540 g (2.17 mmol) of 3,5-difluorophenylthio-1H-pyrazolo[3,4-b]pyridin-3-amine dissolved in 12 ml of anhydrous dimethylacetamide. The mixture is left under stirring for 15 hours at 85° C. The reaction is treated by adding 20 ml of water and then is extracted with ethyl acetate. The organic phase is dried on sodium sulfate, filtered and concentrated. The product is purified by silica chromatography (15:1 dichloromethane/methanol as eluent) to yield 0.156 g (yield=15%) of 1-(1-tert-butyl-5-(3,5-difluorophenylthio)-1H-pyrazolo[3,4-b]pyridin-3-yl)-3-(4-(4-methylpiperazin-1-yl)phenyl)thiourea in the form of a light brown solid.

LCMS (EI, m/z): (M+1) 512.08.

¹H NMR: δH ppm (400 MHz, DMSO): 13.69 (1H, bs, NH), 11.50 (1H, bs, NH), 11.19 (1H, bs, NH), 8.96 (1H, d, CH$_{arom}$), 8.66 (1H, d, CH$_{arom}$), 7.41 (2H, d, CH$_{arom}$), 7.10 (1H, ddd, CH$_{arom}$), 6.95 (2H, d, CH$_{arom}$), 6.89 (2H, bd, CH$_{arom}$), 3.13-3.16 (4H, m, CH), 2.45-2.47 (4H, m, CH), 2.23 (3H, s, CH).

Example 29-bis 1-(5-(3,5-difluorophenylthio)-1H-pyrazolo[3,4-b]pyridin-3-yl)-3-(4-(4-methylpiperazin-1-yl)phenyl)urea

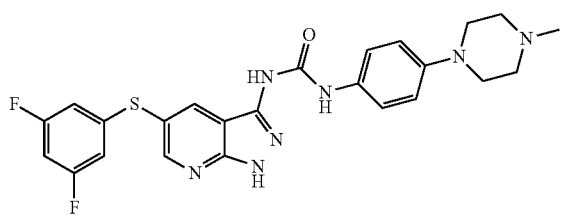 [SMILES: CN1CCN(c2ccc(NC(=O)NC(=N)c3cc(Sc4cc(F)cc(F)c4)cnc3N)cc2)CC1]

0.048 g (1.19 mmol) of sodium hydride is added at 0° C. to 0.200 g (0.598 mmol) of 1-tert-butyl-5-(3,5-difluorophenylthio)-1H-pyrazolo[3,4-b]pyridin-3-amine dissolved in 10 ml of anhydrous dimethylacetamide. The reaction is left under stirring for 10 minutes. 0.130 g (0.598 mmol) of 1-(4-isocyanatophenyl)-4-methylpiperazine is then added at 0° C. The mixture is left under stirring for 3 hours at room temperature. The reaction is treated by adding 20 ml of water drop by drop at 0° C. and then is extracted with ethyl acetate. The organic phase is dried on sodium sulfate, filtered and concentrated. The product is purified by silica chromatography to yield 0.150 g (yield=45%) of 1-(1-tert-butyl-5-(3,5-difluorophenylthio)-1H-pyrazolo[3,4-b]pyridin-3-yl)-3-(4-(4-methylpiperazin-1-yl)phenyl)urea in the form of a light brown solid.

LCMS (EI, m/z): (M+1) 552.21.

¹H NMR: δH ppm (400 MHz, DMSO): 8.92 (1H, bs, NH), 8.58 (1H, bs, NH), 8.51 (1H, bs, CH$_{arom}$), 8.30 (1H, bs, CH.), 7.31 (2H, d, CH$_{arom}$), 7.05 (1H, m, CH.), 6.83-6.85 (2H, m, CH$_{arom}$), 3.03-3.08 (4H, m, CH), 2.45-2.48 (4H, m, CH), 2.21 (3H, s, CH), 1.76 (9H, s, CH).

A solution of 0.150 g (0.272 mmol) of 1-(1-tert-butyl-5-(3,5-difluorophenylthio)-1H-pyrazolo[3,4-b]pyridin-3-yl)-3-(4-(4-methylpiperazin-1-yl)phenyl)urea dissolved in 20 ml of TFA (trifluoroacetic acid) is refluxed for 3 hours. The solvent is evaporated and the crude reaction product is diluted with saturated NaHCO$_3$ solution and extracted with ethyl acetate. The organic phase is dried on MgSO$_4$, filtered and concentrated. The solid obtained is triturated in methanol, filtered and dried. 110 mg (82%) of 1-(5-(3,5-difluorophenylthio)-1H-pyrazolo[3,4-b]pyridin-3-yl)-3-(4-(4-methylpiperazin-1-yl)phenyl)urea in the form of a beige solid is obtained.

LCMS (EI, m/z): (M+1): 496.06.

¹H NMR: δH ppm (400 MHz, DMSO): 10.85 (1H, bs, NH), 9.57 (1H, bs, NH), 8.57 (1H, bs, CH.), 8.30 (1H, bs, CH.), 7.39 (2H, d, CH.), 6.99 (1H, m, CH.), 6.89 (2H, d, CH$_{arom}$), 6.70 (2H, bd, CH$_{arom}$), 3.03-3.08 (4H, m, CH), 2.45-2.48 (4H, m, CH), 2.21 (3H, s, CH).

Examples of Method F

Examples of Method F1

Deprotection

Example 30

N-(5-(3,5-difluorophenylthio)-1-H-pyrazolo[3,4-b]pyridine-3-yl)-4-(4-methylpiperazine-1-yl)-2-(tetrahydro-2H-pyran-4-ylamino)benzamide 9.08 ml (65.1 mmol) of triethylamine is added to 2 g (2.96 mmol) of a solution of N-(5-(3,5-difluorophenylthio)-1H-pyrazolo[3,4-b]pyridin-3-yl)-4-(4-methylpiperazin-1-yl)-2-(2,2,2-trifluoro-N-(tetrahydro-2H-pyran-4-yl)acetamido)benzamide in 65 ml of methanol. The reaction medium is heated at 65° C. for 2 hours, and then overnight at room temperature. The precipitate formed is filtered, rinsed with pentane, with water and then with diethyl ether, and then is dried under vacuum to yield 0.73 g (43%) of (N-(5-(3,5-difluorophenylthio)-1-H-pyrazolo[3,4-b]pyridine-3-yl)-4-(4-methylpiperazine-1-yl)-2-(tetrahydro-2H-pyran-4-ylamino)benzamide in the form of a white solid.

LCMS (EI, m/z): (M+1) 580.23.

¹H NMR: δH ppm (400 MHz, DMSO): 13.59 (1H, bs, NH), 10.56 (1H, bs, NH), 8.61 (1H, 5, CH$_{arom}$), 8.50 (1H, 5, CH$_{arom}$), 8.17 (1H, d, NH), 7.80 (1H, d, CH$_{arom}$), 7.07 (1H, m, CH$_{arom}$), 6.86 (2H, m, CH$_{arom}$), 6.23 (1H, d, CH$_{arom}$), 6.13 (1H, d, CH$_{arom}$), 3.79-3.82 (2H, dt, CH), 3.60 (1H, m, CH), 3.45-3.50 (2H, m, CH), 3.21-3.33 (4H, m, CH), 2.42-2.46 (4H, m, CH), 2.22 (3H, s, CH$_3$), 1.91-1.94 (2H, m, CH), 1.35-1.38 (2H, m, CH).

The following derivatives were obtained according to the same method:

| Ex.** | ArX | R₁ | R₂ | (U)ₙ | V | Y₁,Y₂,Y₃,Y₄ | R₃ | Compound name | Yield | Mass |
|---|---|---|---|---|---|---|---|---|---|---|
| 30-1 | 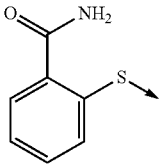 | 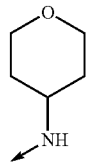 | 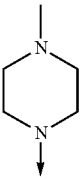 | n = 0 | CO | CH, CXAr, CH, N | H | N-(5-(2-carbamoylphenylthio)-1H-pyrazolo[3,4-b]pyridin-3-yl)-4-(4-methylpiperazin-1-yl)-2-(tetrahydro-2H-pyran-4-ylamino)benzamide | ND | ND |
| 30-2 | I | 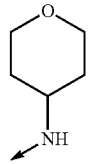 | 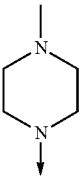 | n = 0 | CO | CH, CXAr, CH, N | H | N-(5-iodo-1H-pyrazolo[3,4-b]pyridin-3-yl)-4-(4-methylpiperazin-1-yl)-2-(tetrahydro-2H-pyran-4-ylamino)benzamide | ND | ND |
| 30-3 | 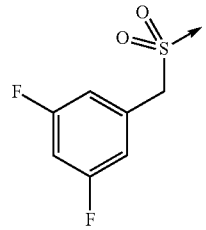 | 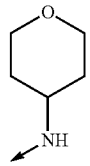 | 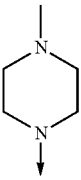 | n = 0 | CO | CH, CXAr, CH, N | H | N-(5-(3,5-difluorobenzylsulfonyl)-1H-pyrazolo[3,4-b]pyridin-3-yl)-4-(4-methylpiperazin-1-yl)-2-(tetrahydro-2H-pyran-4-ylamino)benzamide | ND | (M + 1) 626.14 |
| 30-4 | 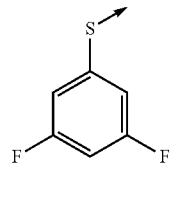 | 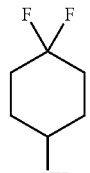 | 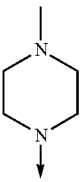 | n = 0 | CO | CH, CXAr, CH, N | H | 2-(4,4-difluorocyclohexyl-amino)-N-(5-(3,5-difluorophenylthio)-1H-pyrazolo[3,4-b]pyridin-3-yl)-4-(4-methylpiperazin-1-yl)benzamide | ND | ND |
| 30-5 | 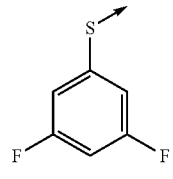 | 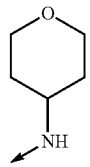 | 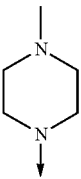 | n = 0 | CO | CH, CXAr, COMe, N | H | N-(5-(3,5-difluorophenylthio)-6-methoxy-1H-pyrazolo[3,4-b]pyridin-3-yl)-4-(4-methylpiperazin-1-yl)-2-(tetrahydro-2H-pyran-4-ylamino)benzamide | ND | 610.20 |
| 30-6 | I | 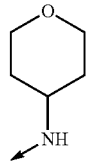 | 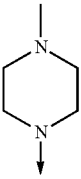 | n = 0 | CO | CH, CXAr, COMe, N | H | N-(5-iodo-6-methoxy-1H-pyrazolo[3,4-b]pyridin-3-yl)-4-(4-methylpiperazin-1-yl)-2-(tetrahydro-2H-pyran-4-ylamino)benzamide | ND | 592.12 |
| 30-7 | I | 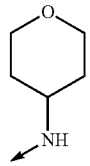 | 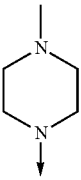 | n = 0 | CO | CH, CXAr, CNH₂, N | H | N-(6-amino-5-iodo-1H-pyrazolo[3,4-b]pyridin-3-yl)-4-(4-methylpiperazin-1-yl)-2-(tetrahydro-2H-pyran-4-ylamino)benzamide | ND | (M − 1) 574.87 |

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-8 | 3,5-difluorophenyl-NH-SO₂- | tetrahydropyran-4-yl-NH- | 4-methylpiperazin-1-yl | n = 0 | CO | CH, CXAr, CH, N | H | N-(5-(N-(3,5-difluorophenyl)sulfamoyl)-1H-pyrazolo[3,4-b]pyridin-3-yl)-4-(4-methylpiperazin-1-yl)-2-(tetrahydro-2H-pyran-4-ylamino)benzamide | 30% (2 steps) | (M + 1) 627.20 |
| 30-9 | 3,5-difluorobenzyl | tetrahydropyran-4-yl-NH- | 4-methylpiperazin-1-yl | n = 0 | CO | CH, CXAr, CH, N | H | N-(5-(3,5-difluorobenzyl)-1H-pyrazolo[3,4-b]pyridin-3-yl)-4-(4-methylpiperazin-1-yl)-2-(tetrahydro-2H-pyran-4-ylamino)benzamide | 20% | (M + 1) 562.42 |
| 30-10 | 3,5-difluorobenzylthio | tetrahydropyran-4-yl-NH- | 4-methylpiperazin-1-yl | n = 0 | CO | CH, CXAr, CH, N | H | N-(5-(3,5-difluorobenzylthio)-1H-pyrazolo[3,4-b]pyridin-3-yl)-4-(4-methylpiperazin-1-yl)-2-(tetrahydro-2H-pyran-4-ylamino)benzamide | 20.6% | (M + 1) 594.11 |
| 30-11 | 3,5-difluorophenylthio | tetrahydropyran-4-yl-NH- | 1-methylpiperidin-4-yl | n = 0 | CO | CH, CXAr, CH, N | H | N-(5-(3,5-difluorophenylthio)-1H-pyrazolo[3,4-b]pyridin-3-yl)-4-(1-methylpiperidin-4-yl)-2-(tetrahydro-2H-pyran-4-ylamino)benzamide | 59.4% (2 steps) | (M + 1) 579.11 |
| 30-12 | 3,5-difluorophenylthio | tetrahydropyran-4-yl-NH- | 4-methylpiperazin-1-yl | n = 0 | CO | CH, CXAr, CCH₃, N | H | N-(5-(3,5-difluorophenylthio)-6-methyl-1H-pyrazolo[3,4-b]pyridin-3-yl)-4-(4-methylpiperazin-1-yl)-2-tetrahydro-2H-pyran-4-ylamino)benzamide | 45% | (M + 1) 579.11 |
| 30-13 | 3,5-difluorobenzyl | tetrahydropyran-4-yl-NH- | 4-methylpiperazin-1-yl | n = 0 | CO | N, ArXC, CH, CH | H | N-(5-(3,5-difluorobenzyl)-1H-pyrazolo[4,3-b]pyridin-3-yl)-4-(4-methylpiperazin-1-yl)-2-(tetrahydro-2H-pyran-4-ylamino)benzamide | 70% | 562.27 |
| 30-14 | 3,5-difluorobenzyloxy | tetrahydropyran-4-yl-NH- | 4-methylpiperazin-1-yl | n = 0 | CO | N, ArXC, CH, CH | H | N-(5-(3,5-difluorobenzyloxy)-1H-pyrazolo[4,3-b]pyridin-3-yl)-4-(4-methylpiperazin-1-yl)-2-(tetrahydro-2H-pyran-4-ylamino)benzamide | 55% | 578.27 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-15 | 3,5-difluorobenzyl-O- | tetrahydropyran-4-yl-NH | 1-methylpiperidin-4-yl | n = 0 | CO | N, ArXC, CH, CH | H | N-(5-(3,5-difluorobenzyloxy)-1H-pyrazolo[4,3-b]pyridin-3-yl)-4-(1-methylpiperidin-4-yl)-2-(tetrahydro-2H-pyran-4-ylamino)benzamide | 49% 2 steps | 577.27 |
| 30-16 | 2,5-difluorobenzyl-O- | tetrahydropyran-4-yl-NH | 4-methylpiperazin-1-yl | n = 0 | CO | N, ArXC, CH, CH | H | N-(5-(2,5-difluorobenzyloxy)-1H-pyrazolo[4,3-b]pyridin-3-yl)-4-(4-methylpiperazin-1-yl)-2-(tetrahydro-2H-pyran-4-ylamino)benzamide | 61% | 578.27 |
| 30-17 | 2,5-difluorobenzyl-O- | tetrahydropyran-4-yl-NH | 1-methylpiperidin-4-yl | n = 0 | CO | N, ArXC, CH, CH | H | N-(5-(2,5-difluorobenzyloxy)-1H-pyrazolo[4,3-b]pyridin-3-yl)-4-(1-methylpiperidin-4-yl)-2-(tetrahydro-2H-pyran-4-ylamino)benzamide | 54% 2 steps | 577.27 |
| 30-18 | 2,5-dichlorobenzyl-O- | tetrahydropyran-4-yl-NH | 4-methylpiperazin-1-yl | n = 0 | CO | N, ArXC, CH, CH | H | N-(5-(2,5-dichlorobenzyloxy)-1H-pyrazolo[4,3-b]pyridin-3-yl)-4-(4-methylpiperazin-1-yl)-2-(tetrahydro-2H-pyran-4-ylamino)benzamide | 10% 2 steps | 610.01 |
| 30-19 | 2,5-dichlorobenzyl-O- | tetrahydropyran-4-yl-NH | 1-methylpiperidin-4-yl | n = 0 | CO | N, ArXC, CH, CH | H | N-(5-(2,5-dichlorobenzyloxy)-1H-pyrazolo[4,3-b]pyridin-3-yl)-4-(1-methylpiperidin-4-yl)-2-(tetrahydro-2H-pyran-4-ylamino)benzamide | 40% 2 steps | 609.03 |
| 30-20 | 5-chloro-2-(trifluoromethyl)benzyl-O- | tetrahydropyran-4-yl-NH | 4-methylpiperazin-1-yl | n = 0 | CO | N, ArXC, CH, CH | H | N-(5-(5-chloro-2-(trifluoromethyl)benzyloxy)-1H-pyrazolo[4,3-b]pyridin-3-yl)-4-(4-methylpiperazin-1-yl)-2-(tetrahydro-2H-pyran-4-ylamino)benzamide | 64% | 644.24 |
| 30-21 | 5-chloro-2-(trifluoromethyl)benzyl-O- | tetrahydropyran-4-yl-NH | 1-methylpiperidin-4-yl | n = 0 | CO | N, ArXC, CH, CH | H | N-(5-(5-chloro-2-(trifluoromethyl)benzyloxy)-1H-pyrazolo[4,3-b]pyridin-3-yl)-4-(1-methylpiperidin-4-yl)-2-(tetrahydro-2H-pyran-4-ylamino)benzamide | 39% 2 steps | 643.24 |

-continued

| Ex.** | ArX | R₁ | R₂ | (U)ₙ | V | Y₁,Y₂,Y₃,Y₄ | R₃ | Compound name | Yield | Mass |
|---|---|---|---|---|---|---|---|---|---|---|
| 30-22 | (pyridin-3-ylmethoxy) | tetrahydropyran-4-yl-NH | 4-methylpiperazin-1-yl | n = 0 | CO | N, ArXC, CH, CH | H | 4-(4-methylpiperazin-1-yl)-N-(5-(pyridin-3-ylmethoxy)-1H-pyrazolo[4,3-b]pyridin-3-yl)-2-(tetrahydro-2H-pyran-4-ylamino)benzamide | 30% | 543.28 |
| 30-23 | (pyridin-3-ylmethoxy) | tetrahydropyran-4-yl-NH | 1-methylpiperidin-4-yl | n = 0 | CO | N, ArXC, CH, CH | H | 4-(1-methylpiperidin-4-yl)-N-(5-(pyridin-3-ylmethoxy)-1H-pyrazolo[4,3-b]pyridin-3-yl)-2-(tetrahydro-2H-pyran-4-ylamino)benzamide | 67% 2 steps | 542.29 |
| 30-24 | 3,5-difluorophenylthio | tetrahydropyran-4-yl-NH | 4-methylpiperazin-1-yl | n = 0 | CO | N, ArXC, CH, CH | H | N-(5-(3,5-difluorophenylthio)-1H-pyrazolo[4,3-b]pyridin-3-yl)-4-(4-methylpiperazin-1-yl)-2-(tetrahydro-2H-pyran-4-ylamino)benzamide | 65% 2 steps | 580.23 |
| 30-25 | 3,5-difluorophenylthio | tetrahydropyran-4-yl-NH | 1-methylpiperidin-4-yl | n = 0 | CO | N, ArXC, CH, CH | H | N-(5-(3,5-difluorophenylthio)-1H-pyrazolo[4,3-b]pyridin-3-yl)-4-(1-methylpiperidin-4-yl)-2-(tetrahydro-2H-pyran-4-ylamino)benzamide | 56% 2 steps | 579.23 |
| 30-26 | 2,5-difluorophenylthio | tetrahydropyran-4-yl-NH | 4-methylpiperazin-1-yl | n = 0 | CO | N, ArXC, CH, CH | H | N-(5-(2,5-difluorophenylthio)-1H-pyrazolo[4,3-b]pyridin-3-yl)-4-(4-methylpiperazin-1-yl)-2-(tetrahydro-2H-pyran-4-ylamino)benzamide | 27% 2 steps | 580.23 |
| 30-27 | 2,5-difluorophenylthio | tetrahydropyran-4-yl-NH | 1-methylpiperidin-4-yl | n = 0 | CO | N, ArXC, CH, CH | H | N-(5-(2,5-difluorophenylthio)-1H-pyrazolo[4,3-b]pyridin-3-yl)-4-(1-methylpiperidin-4-yl)-2-(tetrahydro-2H-pyran-4-ylamino)benzamide | 54% 2 steps | 579.23 |
| 30-28 | 3,5-dichlorophenylthio | tetrahydropyran-4-yl-NH | 4-methylpiperazin-1-yl | n = 0 | CO | N, ArXC, CH, CH | H | N-(5-(3,5-dichlorophenylthio)-1H-pyrazolo[4,3-b]pyridin-3-yl)-4-(4-methylpiperazin-1-yl)-2-(tetrahydro-2H-pyran-4-ylamino)benzamide | 31% 2 steps | 612.17 |
| 30-29 | 3,5-dichlorophenylthio | tetrahydropyran-4-yl-NH | 1-methylpiperidin-4-yl | n = 0 | CO | N, ArXC, CH, CH | H | N-(5-(3,5-dichlorophenylthio)-1H-pyrazolo[4,3-b]pyridin-3-yl)-4-(1-methylpiperidin-4-yl)-2-(tetrahydro-2H-pyran-4-ylamino)benzamide | 43% 2 steps | 611.17 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-30 | 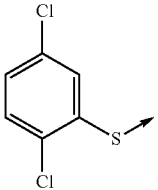 | 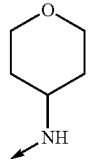 | 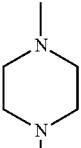 | n = 0 | CO | N, ArXC, CH, CH | H | N-(5-(2,5-dichlorophenylthio)-1H-pyrazolo[4,3-b]pyridin-3-yl)-4-(4-methylpiperazin-1-yl)-2-(tetrahydro-2H-pyran-4-ylamino)benzamide | 31% 2 steps | 612.20 |
| 30-31 | 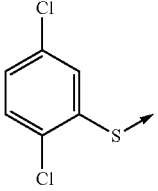 | 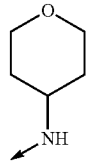 | 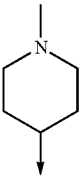 | n = 0 | CO | N, ArXC, CH, CH | H | N-(5-(2,5-dichlorophenylthio)-1H-pyrazolo[4,3-b]pyridin-3-yl)-4-(1-methylpiperidin-4-yl)-2-(tetrahydro-2H-pyran-4-ylamino)benzamide | 57% 2 steps | 611.18 |
| 30-32 | 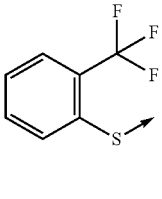 | 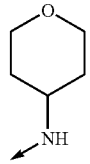 | 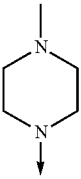 | n = 0 | CO | N, ArXC, CH, CH | H | 4-(4-methylpiperazin-1-yl)-2-(tetrahydro-2H-pyran-4-ylamino)-N-(5-(2-(trifluoromethyl)phenylthio)-1H-pyrazolo[4,3-b]pyridin-3-yl)benzamide | 38% 2 steps | 612.24 |
| 30-33 | 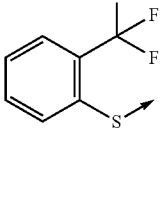 | 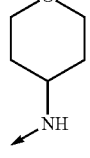 | 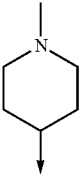 | n = 0 | CO | N, ArXC, CH, CH | H | 4-(1-methylpiperidin-4-yl)-2-(tetrahydro-2H-pyran-4-ylamino)-N-(5-(2-(trifluoromethyl)phenylthio)-1H-pyrazolo[4,3-b]pyridin-3-yl)benzamide | 57% 2 steps | 611.24 |
| 30-34 | 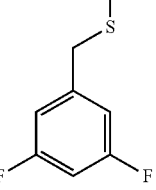 | 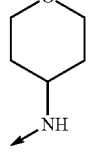 | 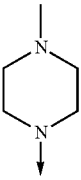 | n = 0 | CO | N, ArXC, CH, CH | H | N-(5-(3,5-difluorobenzylthio)-1H-pyrazolo[4,3-b]pyridin-3-yl)-4-(4-methylpiperazin-1-yl)-2-(tetrahydro-2H-pyran-4-ylamino)benzamide | 21% 2 steps | 594.25 |
| 30-35 | 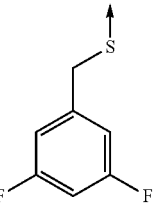 | 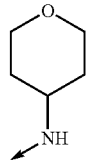 | 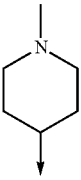 | n = 0 | CO | N, ArXC, CH, CH | H | N-(5-(3,5-difluorobenzylthio)-1H-pyrazolo[4,3-b]pyridin-3-yl)-4-(1-methylpiperidin-4-yl)-2-(tetrahydro-2H-pyran-4-ylamino)benzamide | 91% 2 steps | 593.25 |
| 30-36 | 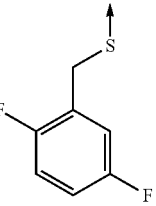 | 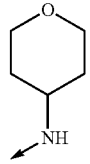 | 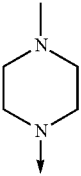 | n = 0 | CO | N, ArXC, CH, CH | H | N-(5-(2,5-difluorobenzylthio)-1H-pyrazolo[4,3-b]pyridin-3-yl)-4-(4-methylpiperazin-1-yl)-2-(tetrahydro-2H-pyran-4-ylamino)benzamide 2,2,2-trifluoroacetate | 86% 2 steps | 594.25 |

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-37 | 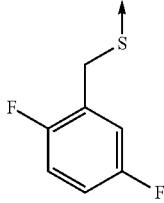 | 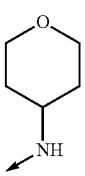 | 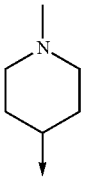 | n = 0 | CO | N, ArXC, CH, CH | H | N-(5-(2,5-difluorobenzylthio)-1H-pyrazolo[4,3-b]pyridin-3-yl)-4-(1-methylpiperidin-4-yl)-2-(tetrahydro-2H-pyran-4-ylamino)benzamide | 55% 2 steps | 593.25 |
| 30-38 | 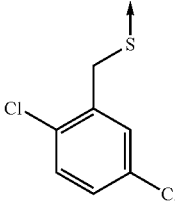 | 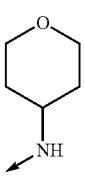 | 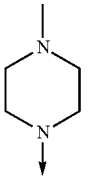 | n = 0 | CO | N, ArXC, CH, CH | H | N-(5-(2,5-dichlorobenzylthio)-1H-pyrazolo[4,3-b]pyridin-3-yl)-4-(4-methylpiperazin-1-yl)-2-(tetrahydro-2H-pyran-4-ylamino)benzamide | 24% 2 steps | 626.19 |
| 30-39 | 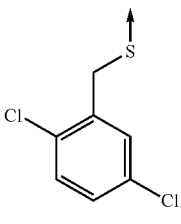 | 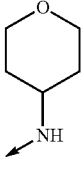 | 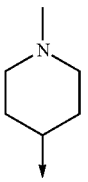 | n = 0 | CO | N, ArXC, CH, CH | H | N-(5-(2,5-dichlorobenzylthio)-1H-pyrazolo[4,3-b]pyridin-3-yl)-4-(1-methylpiperidin-4-yl)-2-(tetrahydro-2H-pyran-4-ylamino)benzamide | 50% 2 steps | 625.19 |
| 30-40 | 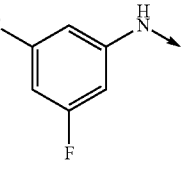 | 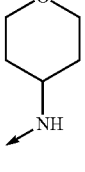 | 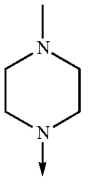 | n = 0 | CO | N, ArXC, CH, CH | H | N-(5-(3,5-difluorophenylamino)-1H-pyrazolo[4,3-b]pyridin-3-yl)-4-(4-methylpiperazin-1-yl)-2-(tetrahydro-2H-pyran-4-ylamino)benzamide | 70% 2 steps | 563.27 |
| 30-41 | 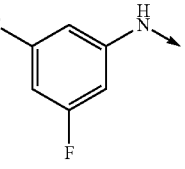 | 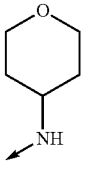 | 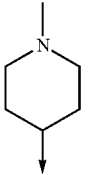 | n = 0 | CO | N, ArXC, CH, CH | H | N-(5-(3,5-difluorophenylamino)-1H-pyrazolo[4,3-b]pyridin-3-yl)-4-(1-methylpiperidin-4-yl)-2-(tetrahydro-2H-pyran-4-ylamino)benzamide | 27% 2 steps | 562.27 |
| 30-42 | 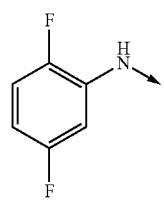 | 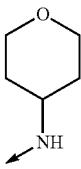 | 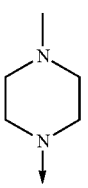 | n = 0 | CO | N, ArXC, CH, CH | H | N-(5-(2,5-difluorophenylamino)-1H-pyrazolo[4,3-b]pyridin-3-yl)-4-(4-methylpiperazin-1-yl)-2-(tetrahydro-2H-pyran-4-ylamino)benzamide | 37% 2 steps | 563.27 |
| 30-43 | 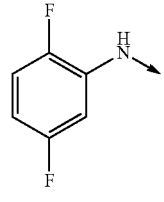 | 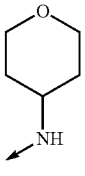 | 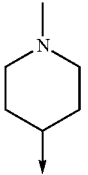 | n = 0 | CO | N, ArXC, CH, CH | H | N-(5-(2,5-difluorophenylamino)-1H-pyrazolo[4,3-b]pyridin-3-yl)-4-(1-methylpiperidin-4-yl)-2-(tetrahydro-2H-pyran-4-ylamino)benzamide | 41% 2 steps | 562.27 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-44 | 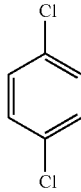 | 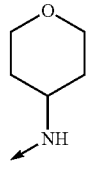 | 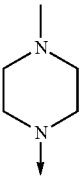 | n = 0 | CO | N, ArXC, CH, CH | H | N-(5-(2,5-dichlorophenylamino)-1H-pyrazolo[4,3-b]pyridin-3-yl)-4-(4-methylpiperazin-1-yl)-2-(tetrahydro-2H-pyran-4-ylamino)benzamide | 74% | 595.21 |
| 30-45 | 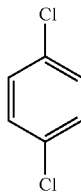 | 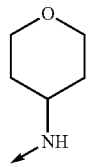 | 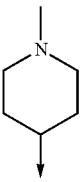 | n = 0 | CO | N, ArXC, CH, CH | H | N-(5-(2,5-dichlorophenylamino)-1H-pyrazolo[4,3-b]pyridin-3-yl)-4-(1-methylpiperidin-4-yl)-2-(tetrahydro-2H-pyran-4-ylamino)benzamide | 33% | 594.21 |
| 30-46 | 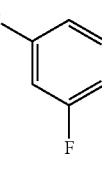 | 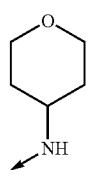 | 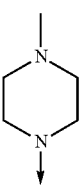 | n = 0 | CO | N, ArXC, CH, N | H | N-(5-(3,5-difluorobenzyl)-1H-pyrazolo[3,4-b]pyrazin-3-yl)-4-(4-methylpiperazin-1-yl)-2-(tetrahydro-2H-pyran-4-ylamino)benzamide | 12% 2 steps | 563.07 |
| 30-47 | 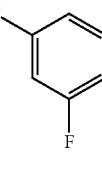 | 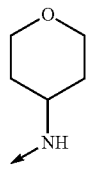 | 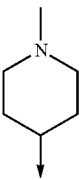 | n = 0 | CO | N, ArXC, CH, N | H | N-(5-(3,5-difluorobenzyl)-1H-pyrazolo[3,4-b]pyrazin-3-yl)-4-(1-methylpiperidin-4-yl)-2-(tetrahydro-2H-pyran-4-ylamino)benzamide | 15% 2 steps | 562.04 |
| 30-48 | 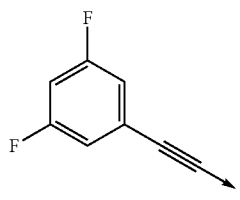 | 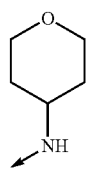 | 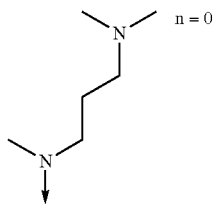 | n = 0 | CO | N, ArXC, CH, N | H | N-(5-((3,5-difluorophenyl)ethynyl)-1H-pyrazolo[3,4-b]pyrazin-3-yl)-4-((3-(dimethylamino)propyl)(methyl)amino)-2-(tetrahydro-2H-pyran-4-ylamino)benzamide | 12% 2 steps | 589.24 |
| 30-49 | 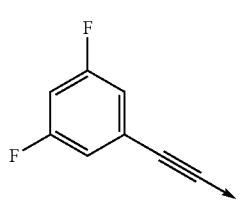 | 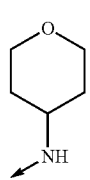 | 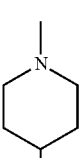 | n = 0 | CO | N, ArXC, CH, N | H | N-(5-((3,5-difluorophenyl)ethynyl)-1H-pyrazolo[3,4-b]pyrazin-3-yl)-4-(1-methylpiperidin-4-yl)-2-(tetrahydro-2H-pyran-4-ylamino)benzamide | 16% 2 steps | 572.07 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-50 | 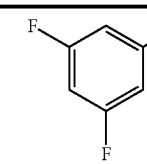 | 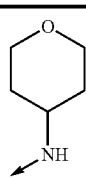 | 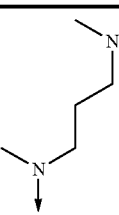 | n = 0 | CO | N, ArXC, CH, N | H | N-(5-(3,5-difluorophenylthio)-1H-pyrazolo[3,4-b]pyrazin-3-yl)-4-((3-(dimethylamino)propyl)(methyl)amino)-2-(tetrahydro-2H-pyran-4-ylamino)benzamide | 27% | 597.26 |
| 30-51 | 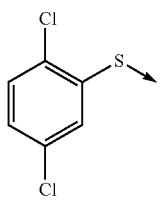 | 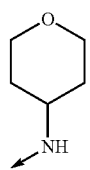 | 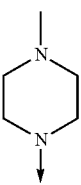 | n = 0 | CO | N, ArXC, CH, N | H | N-(5-(2,5-dichlorophenylthio)-1H-pyrazolo[3,4-b]pyrazin-3-yl)-4-(4-methylpiperazin-1-yl)-2-(tetrahydro-2H-pyran-4-ylamino)benzamide | 23% 2 steps | 613.16 |
| 30-52 |  | 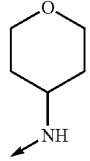 | 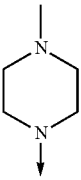 | n = 0 | CO | N, ArXC, CH, N | H | 4-(4-methylpiperazin-1-yl)-2-(tetrahydro-2H-pyran-4-ylamino)-N-(5-(2-(trifluoromethyl)phenylthio)-1H-pyrazolo[3,4-b]pyrazin-3-yl)benzamide | 64% | 613.23 |
| 30-53 | 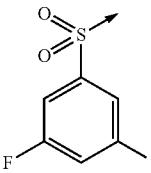 | 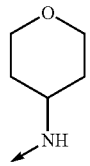 | 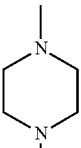 | n = 0 | CO | N, ArXC, CH, CH | H | N-(5-(3,5-difluorophenylsulfonyl)-1H-pyrazolo[4,3-b]pyridin-3-yl)-4-(4-methylpiperazin-1-yl)-2-tetrahydro-2H-pyran-4-ylamino)benzamide | 64% | 612.22 |
| 30-54 | 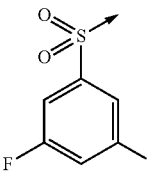 | 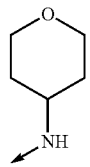 | 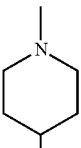 | n = 0 | CO | N, ArXC, CH, CH | H | N-(5-(3,5-difluorophenylsulfonyl)-1H-pyrazolo[4,3-b]pyridin-3-yl)-4-(1-methylpiperidin-4-yl)-2-(tetrahydro-2H-pyran-4-ylamino)benzamide | 48% | 611.22 |
| 30-55 | 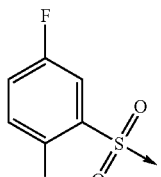 | 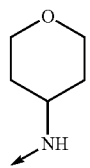 | 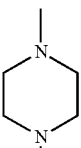 | n = 0 | CO | N, ArXC, CH, CH | H | N-(5-(2,5-difluorophenylsulfonyl)-1H-pyrazolo[4,3-b]pyridin-3-yl)-4-(4-methylpiperazin-1-yl)-2-(tetrahydro-2H-pyran-4-ylamino)benzamide | 50% 2 steps | 612.22 |
| 30-56 | 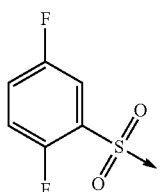 | 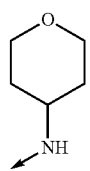 | 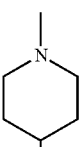 | n = 0 | CO | N, ArXC, CH, CH | H | N-(5-(2,5-difluorophenylsulfonyl)-1H-pyrazolo[4,3-b]pyridin-3-yl)-4-(1-methylpiperidin-4-yl)-2-(tetrahydro-2H-pyran-4-ylamino)benzamide | 28% 2 steps | 611.22 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-57 | 3,5-dichlorophenylsulfonyl | tetrahydropyran-4-ylamino | 4-methylpiperazin-1-yl | n = 0 | CO | N, ArXC, CH, CH | H | N-(5-(3,5-dichlorophenylsulfonyl)-1H-pyrazolo[4,3-b]pyridin-3-yl)-4-(4-methylpiperazin-1-yl)-2-(tetrahydro-2H-pyran-4-ylamino)benzamide | 29% 2 steps | 644.16 |
| 30-58 | 3,5-dichlorophenylsulfonyl | tetrahydropyran-4-ylamino | 1-methylpiperidin-4-yl | n = 0 | CO | N, ArXC, CH, CH | H | N-(5-(3,5-dichlorophenylsulfonyl)-1H-pyrazolo[4,3-b]pyridin-3-yl)-4-(1-methylpiperidin-4-yl)-2-(tetrahydro-2H-pyran-4-ylamino)benzamide | 28% 2 steps | 643.17 |
| 30-59 | 2,5-dichlorophenylsulfonyl | tetrahydropyran-4-ylamino | 4-methylpiperazin-1-yl | n = 0 | CO | N, ArXC, CH, CH | H | N-(5-(2,5-dichlorophenylsulfonyl)-1H-pyrazolo[4,3-b]pyridin-3-yl)-4-(4-methylpiperazin-1-yl)-2-(tetrahydro-2H-pyran-4-ylamino)benzamide | 21% 2 steps | 644.16 |
| 30-60 | 2,5-dichlorophenylsulfonyl | tetrahydropyran-4-ylamino | 1-methylpiperidin-4-yl | n = 0 | CO | N, ArXC, CH, CH | H | N-(5-(2,5-dichlorophenylsulfonyl)-1H-pyrazolo[4,3-b]pyridin-3-yl)-4-(1-methylpiperidin-4-yl)-2-(tetrahydro-2H-pyran-4-ylamino)benzamide | 36% 2 steps | 643.17 |
| 30-61 | 3,5-difluorobenzylsulfonyl | tetrahydropyran-4-ylamino | 4-methylpiperazin-1-yl | n = 0 | CO | N, ArXC, CH, CH | H | N-(5-(3,5-difluorobenzylsulfonyl)-1H-pyrazolo[4,3-b]pyridin-3-yl)-4-(4-methylpiperazin-1-yl)-2-(tetrahydro-2H-pyran-4-ylamino)benzamide | 66% | 626.24 |
| 30-62 | 3,5-difluorobenzylsulfonyl | tetrahydropyran-4-ylamino | 1-methylpiperidin-4-yl | n = 0 | CO | N, ArXC, CH, CH | H | N-(5-(3,5-difluorobenzylsulfonyl)-1H-pyrazolo[4,3-b]pyridin-3-yl)-4-(1-methylpiperidin-4-yl)-2-(tetrahydro-2H-pyran-4-ylamino)benzamide | 67% | 625.24 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-63 | 2,5-difluorobenzyl sulfonyl | tetrahydropyran-4-yl-NH | 4-methylpiperazin-1-yl | n = 0 | CO | N, ArXC, CH, CH | H | N-(5-(2,5-difluorobenzylsulfonyl)-1H-pyrazolo[4,3-b]pyridin-3-yl)-4-(4-methylpiperazin-1-yl)-2-(tetrahydro-2H-pyran-4-ylamino)benzamide | 74% | 626.24 |
| 30-64 | 2,5-difluorobenzyl sulfonyl | tetrahydropyran-4-yl-NH | 1-methylpiperidin-4-yl | n = 0 | CO | N, ArXC, CH, CH | H | N-(5-(2,5-difluorobenzylsulfonyl)-1H-pyrazolo[4,3-b]pyridin-3-yl)-4-(1-methylpiperidin-4-yl)-2-(tetrahydro-2H-pyran-4-ylamino)benzamide | 58% | 625.24 |
| 30-65 | 2,5-difluorobenzyl sulfinyl | tetrahydropyran-4-yl-NH | 1-methylpiperidin-4-yl | n = 0 | CO | N, ArXC, CH, CH | H | N-(5-(2,5-difluorobenzylsulfinyl)-1H-pyrazolo[4,3-b]pyridin-3-yl)-4-(1-methylpiperidin-4-yl)-2-(tetrahydro-2H-pyran-4-ylamino)benzamide 2,2,2-trifluoroacetate | 31% 2 steps | 629.24 |
| 30-66 | 2,5-dichlorobenzyl sulfonyl | tetrahydropyran-4-yl-NH | 4-methylpiperazin-1-yl | n = 0 | CO | N, ArXC, CH, CH | H | N-(5-(2,5-dichlorobenzylsulfonyl)-1H-pyrazolo[4,3-b]pyridin-3-yl)-4-(4-methylpiperazin-1-yl)-2-(tetrahydro-2H-pyran-4-ylamino)benzamide | 55% | 658.18 |
| 30-67 | 2,5-dichlorobenzyl sulfonyl | tetrahydropyran-4-yl-NH | 1-methylpiperidin-4-yl | n = 0 | CO | N, ArXC, CH, CH | H | N-(5-(2,5-dichlorobenzylsulfonyl)-1H-pyrazolo[4,3-b]pyridin-3-yl)-4-(1-methylpiperidin-4-yl)-2-(tetrahydro-2H-pyran-4-ylamino)benzamide | 57% | 657.18 |
| 30-68 | 2,5-dichlorobenzyl sulfinyl | tetrahydropyran-4-yl-NH | 1-methylpiperidin-4-yl | n = 0 | CO | N, ArXC, CH, CH | H | N-(5-(2,5-dichlorobenzylsulfinyl)-1H-pyrazolo[4,3-b]pyridin-3-yl)-4-(1-methylpiperidin-4-yl)-2-(tetrahydro-2H-pyran-4-ylamino)benzamide | 20% | 641.19 |
| 30-69 | 3,5-difluorophenylthio | tetrahydropyran-4-yl-NH | (3-dimethylamino)propyl(methyl)amino | n = 0 | CO | CH, ArXC, CH, N | H | N-(5-(3,5-difluorophenylthio)-1H-pyrazolo[3,4-b]pyridin-3-yl)-4-((3-(dimethylamino)propyl)(methyl)amino)-2-(tetrahydro-2H-pyran-4-ylamino)benzamide | 57% | 596.26 |

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 30-70 | (structure: 2,4-difluorophenylamino) | (tetrahydropyran-4-yl-NH) | (4-methylpiperazin-1-yl) | n = 0 | CO | CH, CH, ArXC, N | H | N-(6-(2,4-difluorophenylamino)-1H-pyrazolo[3,4-b]pyridin-3-yl)-4-(4-methylpiperazin-1-yl)-2-(tetrahydro-2H-pyran-4-ylamino)benzamide | 33% | 561.19 (M − 1) |
| 30-71 | (structure: N-methyl-2,4-difluorophenylamino) | (tetrahydropyran-4-yl-NH) | (4-methylpiperazin-1-yl) | n = 0 | CO | CH, CH, ArXC, N | H | N-(6-((2,4-difluorophenyl)(methyl)amino)-1H-pyrazolo[3,4-b]pyridin-3-yl)-4-(4-methylpiperazin-1-yl)-2-(tetrahydro-2H-pyran-4-ylamino)benzamide | ND | 577.26 (M + 1) |
| 30-72 | (structure: 3,5-difluorophenylsulfonamido) | (tetrahydropyran-4-yl-NH) | (4-methylpiperazin-1-yl) | n = 0 | CO | CH, ArXC, CH, N | H | N-(5-(3,5-difluorophenylsulfonamido)-1H-pyrazolo[3,4-b]pyridin-3-yl)-4-(4-methylpiperazin-1-yl)-2-(tetrahydro-2H-pyran-4-ylamino)benzamide | 74% | 627.19 (M + 1) |
| 30-73 | (structure: 2,4-difluorophenylthio) | (tetrahydropyran-4-yl-NH) | (4-methylpiperazin-1-yl) | n = 0 | CO | CH, CH, ArXC, N | H | N-(6-(2,4-difluorophenylthio)-1H-pyrazolo[3,4-b]pyridin-3-yl)-4-(4-methylpiperazin-1-yl)-2-(tetrahydro-2H-pyran-4-ylamino)benzamide | 42% (2 steps) | (M + 1) 580.23 |

¹H NMR, DMSO-d₆, Ex.: 30-3: 13.86 (1H, bs, NH), 10.70 (1H, bs, NH), 8.67 (2H, bs, CH_arom), 8.10 (1H, d, NH), 7.77 (1H, d, CH_arom), 7.22 (1H, m, CH_arom), 6.95 (2H, d, CH_arom), 6.26 (1H, d, CH_arom), 6.16 (1H, bs, CH_arom), 4.85 (2H, bs, CH), 3.82-3.86 (2H, dt, CH), 3.70 (1H, m, CH), 3.47-3.53 (2H, m, CH), 3.28-3.32 (4H, m, CH), 2.42-2.46 (4H, m, CH), 2.20 (3H, s, CH₃), 1.94-1.98 (2H, m, CH), 1.34-1.41 (2H, m, CH).; 30-5: 13.25 (1H, bs, NH), 10.48 (1H, bs, NH), 8.42 (1H, s, CH_arom), 8.11 (1H, d, NH), 7.76 (1H, d, CH_arom), 7.00-7.10 (1H, m, CH_arom), 6.79-6.87 (2H, m, CH_arom), 6.23 (1H, dd, CH_arom), 6.12 (1H, d, CH_arom), 3.94 (3H, s, CH₃), 3.75-3.83 (2H, m, CH), 3.63-3.71 (1H, m, CH), 3.42-3.52 (2H, m, CH), 3.22-3.32 (4H, m, 2*CH₂), 2.36-2.48 (4H, m, 2*CH₂), 2.22 (3H, s, CH₃). 30-6: 13.10 (1H, bs, NH), 10.38 (1H, bs, NH), 8.56 (1H, s, CH_arom), 8.12 (1H, d, NH), 7.75 (1H, d, CH_arom), 6.23 (1H, dd, CH_arom), 6.14 (1H, d, CH_arom), 3.97 (3H, s, CH₃), 3.80-3.86 (2H, m, CH), 3.62-3.74 (1H, m, CH), 3.40-3.55 (2H, m, CH), 3.22-3.32 (4H, m, 2*CH₂), 2.36-2.48 (4H, m, 2*CH₂), 2.23 (3H, s, CH₃), 1.90-1.99 (2H, m, CH), 1.32-1.45 (2H, m, CH). 30-7: 12.43 (1H, bs, NH), 10.22 (1H, bs, NH), 8.32 (1H, s, CH_arom), 8.13 (1H, d, NH), 7.73 (1H, d, CH_arom), 6.37 (2H, bs, NH₂), 6.22 (1H, dd, CH_arom), 6.13 (1H, d, CH_arom), 3.78-3.86 (2H, m, CH), 3.65-3.74 (1H, m, CH), 3.44-3.54 (2H, m, CH), 3.22-3.32 (4H, m, 2*CH₂), 2.36-2.48 (4H, m, 2*CH₂), 2.23 (3H, s, CH₃), 1.90-1.99 (2H, m, CH), 1.32-1.45 (2H, m, CH). 30-8: 13.79 (1H, bs, NH), 10.91 (1H, bs, NH), 10.69 (1H, bs, NH), 8.83 (1H, S, CH_arom), 8.76 (1H, S, CH_arom), 8.18 (1H, d, NH), 7.80 (1H, d, CH_arom), 6.82-6.75 (3H, m, CH_arom), 6.26 (1H, d, CH_arom), 6.15 (1H, d, CH_arom), 3.87-3.82 (2H, dt, CH), 3.72 (1H, m, CH), 3.32-3.29 (4H, m, CH), 2.42-2.46 (4H, m, CH), 2.28 (3H, s, CH₃), 1.97-1.95 (2H, m, CH), 1.43-1.36 (2H, m, CH). 30-13: 12.99 (1H, s, NH), 9.92 (1H, s, NH), 8.38 (1H, d, NH, J = 7.6 Hz), 7.92 (1H, d, CHarom, J = 8.4 Hz), 7.84 (1H, d, CHarom, J = 9.2 Hz), 7.32 (1H, s, CHarom), 7.07-7.00 (3H, m, CHarom), 6.26 (1H, d, CHarom), 6.14 (1H, s, CHarom), 4.21 (2H, s), 3.82-3.76 (2H, m), 3.69-3.63 (1H, m), 3.48 (2H, t), 3.28 (4H, s), 2.46 (4H, s), 2.25 (3H, s), 2.00-1.90 (2H, m), 1.37-1.26 (2H, m). 30-14: 12.96 (1H, sl, NH), 9.84 (1H, s, NH), 8.34 (1H, d, NH, J = 7.6 Hz), 7.96 (1H, d, CHarom, J = 9.2 Hz), 7.81 (1H, d, CHarom, J = 8.8 Hz), 7.25 (1H, s, CHarom), 7.23 (1H, s, CHarom), 7.17 (1H, t, CHarom), 6.96 (1H, d, CHarom, J = 9.2 Hz), 6.25 (1H, d, CHarom), 5.35 (2H, s), 3.82-3.77 (2H, m), 3.67 (1H, sl), 3.46 (2H, t), 3.29 (4H, s), 2.50 (4H, s), 2.29 (3H, s), 1.93-1.88 (2H, m), 1.35-1.25 (2H, m). 30-15: 13.01 (1H, sl, NH), 10.11 (1H, sl, NH), 7.99 (1H, sl, NH), 7.97 (1H, d, CHarom, J = 9.2 Hz), 7.84 (1H, d, CHarom, J = 8.4 Hz), 7.25-7.14 (3H, m, CHarom), 6.97 (1H, d, CHarom, J = 8.8 Hz), 6.67 (1H, sl, NH), 6.51 (1H, d, CHarom, J = 8.0 Hz), 5.35 (2H, s, CHarom), 3.83-3.78 (2H, m, m), 3.47 (2H, t), 2.87 (2H, d, J = 11.2 Hz), 2.45-2.40 (1H, m), 2.19 (3H, s), 2.00-1.87 (4H, m), 1.75-1.65 (4H, m), 1.34-1.28 (2H, m). 30-16: 12.95 (1H, sl, NH), 9.85 (1H, s, NH), 8.33 (1H, d, NH, J = 7.6 Hz), 7.95 (1H, d, CHarom, J = 8.8 Hz), 7.81 (1H, d, CHarom, J = 8.8 Hz), 7.48 (1H, q, CHarom), 7.31-7.20 (2H, m, CHarom), 6.93 (1H, d, CHarom, J = 9.2 Hz), 6.25 (1H, d, CHarom, J = 9.2 Hz), 6.14 (1H, d, CHarom), 5.35 (2H, s), 3.47 (2H, t), 3.28 (4H, s), 2.44 (4H, s), 2.29 (3H, s), 1.94-1.88 (2H, m), 1.36-1.27 (2H, m). 30-17: 13.06 (1H, sl, NH), 10.12 (1H, sl, NH), 7.93 (1H, sl, NH), 7.86 (2H, d, CHarom, J = 8.4 Hz), 7.51-7.44 (1H, m, CHarom), 7.30-7.20 (2H, m, CHarom), 6.90 (1H, s, CHarom), 6.64 (1H, sl, CHarom), 6.49 (1H, sl, CHarom), 5.37 (2H, s, CHarom), 3.83-3.76 (2H, m, CH), 3.46 (2H, t), 2.86 (2H, d, J = 10.4 Hz), 2.44-2.38 (1H, m), 2.19 (3H, s), 1.99-1.90 (4H, m), 1.75-1.65 (4H, m), 1.40-1.30 (2H, m). 30-18: 12.94 (1H, sl, NH), 9.81 (1H, s, NH), 8.32 (1H, d, CHarom, J = 7.7 Hz), 7.96 (1H, d, CHarom, J = 9 Hz), 7.81 (1H, d, CHarom, J = 9 Hz), 7.71 (1H, d, NH), 7.51 (1H, d, CHarom, J = 8.6 Hz), 7.43 (1H, dd, CHarom, J = 8.6 Hz), 6.97 (1H, m, CHarom), 6.24 (1H, d, CHarom, J = 8.9 Hz), 6.13 (1H, s, CHarom), 5.39 (2H, s), 3.82-3.74 (2H, m), 3.72-3.62 (1H, m), 3.46 (2H, t), 3.28-3.22 (4H, m), 2.46-2.40 (4H, m), 2.22 (3H, s), 1.95-1.87 (2H, m), 1.37-1.26 (2H, m). 30-19: 13.01 (1H, sl, NH), 10.09 (1H, s, NH), 7.97 (2H, d, CHarom, J = 9 Hz), 7.83 (1H, d, CHarom, J = 8.2 Hz), 7.71 (1H, dd, NH), 7.50 (1H, d, CHarom, J = 7.4 Hz), 7.43 (1H, dd, CHarom, J = 8.6 Hz), 6.98 (1H, d, CHarom, J = 9 Hz), 6.67 (1H, s, CHarom), 6.51 (1H, d, CHarom, J = 8.2 Hz), 5.38 (2H, s), 3.84-3.75 (2H, m), 3.72-3.62 (1H, m), 3.46 (2H, t), 2.86 (2H, d), 2.43 (1H, m), 2.19 (3H, s), 1.99-1.88 (4H, m), 1.74-1.64 (4H, m), 1.38-1.26 (2H, m). 30-20: 12.97 (1H, sl, NH), 9.82 (1H, s, NH), 8.32 (1H, d, NH, J = 8.0 Hz), 7.97 (1H, d, CHarom, J = 8.8 Hz), 7.81 (1H, d, CHarom), 7.80-7.76 (2H, m, CHarom), 7.64 (1H, d, CHarom, J = 8.4 Hz), 6.96 (1H, d, CHarom, J = 8.8 Hz), 6.24 (1H, d, CHarom), 6.13 (1H, s, CHarom), 5.47 (2H, s), 3.81-3.76 (2H, m), 3.66 (1H, sl), 3.46 (2H, t), 3.26 (4H, s), 2.43 (4H, s), 2.29 (3H, s), 1.93-1.88 (2H, m), 1.35-1.25 (2H, m). 30-21: 13.03 (1H, s, NH), 10.08 (1H, s, NH), 8.00-7.95 (2H, m, CHarom), 7.87-7.75 (3H, m, CHarom), 7.63 (1H, d, CHarom, J = 8.4 Hz), 6.97 (1H, d, CHarom, J = 8.8 Hz), 6.67 (1H, s, CHarom), 6.51 (1H, d, CHarom, J = 8.0 Hz), 5.47 (2H, s, CHarom), 3.83-3.76 (2H, m), 3.68-3.64 (1H, m), 3.47 (2H, t), 2.87 (2H, d, J = 11.2 Hz), 2.45-2.40 (1H, m), 2.20 (3H, s), 2.00-1.87 (4H, m), 1.74-1.65 (4H, m), 1.36-1.25 (2H, m). 30-22: 12.93 (1H, s, NH), 9.86 (1H, s, NH), 8.70 (1H, s, CHarom), 8.51 (1H, dd, CHarom, J = 5.2 Hz), 8.38 (1H, d, NH, J = 8.0 Hz), 7.96-7.90 (2H, m, CHarom), 7.84 (1H, d, CHarom, J = 8.8 Hz), 7.73-7.33 (1H, m, CHarom), 6.91 (1H, d, CHarom, J = 8.8 Hz), 6.27 (1H, d, CHarom, J = 8.8 Hz), 6.15 (1H, d, CHarom), 5.35 (2H, s), 3.83-3.77 (2H, m), 3.70-3.64 (1H, m), 3.47 (2H, t), 3.59 (4H, s), 2.59 (4H, s), 2.34 (3H, s), 1.95-1.88 (2H, m), 1.40-1.28 (2H, m). 30-23: 13.03 (1H, s, NH), 10.17 (1H, s, NH), 8.70 (1H, s, CHarom), 8.52 (1H, dd, CHarom, J = 4.8 Hz), 8.06 (1H, d, NH, J = 7.6 Hz), 7.96 (1H, d, CHarom, J = 8.8 Hz), 7.94-7.88 (2H, m, CHarom), 7.37-7.34 (1H, m, CHarom), 6.93 (1H, d, CHarom, J = 9.2 Hz), 6.69 (1H, s, CHarom), 6.52 (1H, d, CHarom, J = 8.0 Hz), 5.36 (2H, s), 3.83-3.79 (2H, m), 3.68-3.64 (1H, m), 3.46 (2H, t), 3.25-3.15 (2H, m), 2.65-2.55 (3H, m), 2.54 (3H, s), 2.00-1.85 (6H, m), 1.41-1.28 (2H, m). 30-24: 13.21 (1H, s, NH), 10.00 (1H, s, NH), 8.30 (1H, d, NH, J = 7.6 Hz), 8.00 (1H, d, CHarom, J = 8.8 Hz), 7.79 (1H, d, CHarom, J = 9.2 Hz), 7.33 (1H, d, CHarom, J = 8.8 Hz), 7.26-7.16 (3H, m, CHarom), 6.24 (1H, d, CHarom), 4.06-3.99 (2H, m), 3.67 (1H, sl), 3.47 (2H, t), 3.28 (4H, s), 2.47 (4H, s), 2.25 (3H, s), 1.94-1.88 (2H, m), 1.37-1.26 (2H, m). 30-25: 13.26 (1H, s, NH), 10.28 (1H, s, NH), 8.02 (1H, d, CHarom, J = 8.8 Hz), 7.97 (1H, d, NH, J = 7.6 Hz), 7.83 (1H, d, CHarom, J = 8.0 Hz), 7.34 (1H, d, CHarom, J = 8.8 Hz), 7.27-7.17 (3H, m, CHarom), 6.68 (1H, s, CHarom), 6.51 (1H, d, CHarom, J = 8.0 Hz), 3.85-3.78 (2H, m), 3.71-3.65 (1H, m), 3.47 (2H, t), 2.87 (2H, d, J = 11.2 Hz), 2.48-2.40 (1H, m), 2.19 (3H, s), 1.98-1.88 (4H, m), 1.74-1.66 (4H, m), 1.36-1.27 (2H, m). 30-26: 13.12 (1H, s, NH), 9.95 (1H, s, NH), 8.32 (1H, d, NH, J = 7.6 Hz), 7.93 (1H, d, CHarom, J = 8.8 Hz), 7.79 (1H, d, CHarom, J = 8.8 Hz), 7.73 (1H, t, CHarom), 7.52-7.40 (2H, m, CHarom), 7.12 (1H, d, CHarom, J = 8.8 Hz), 6.25 (1H, d, CHarom, J = 8.8 Hz), 6.13 (1H, s, CHarom), 3.83-3.77 (2H, m), 3.69 (1H, sl), 3.48 (2H, t), 3.28 (4H, s), 2.44 (4H, s), 2.27 (3H, s), 1.96-1.89 (2H, m), 1.37-1.27 (2H, m). 30-27: 13.17

-continued

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|

(1H, s, NH), 10.21 (1H, s, NH), 7.99-7.92 (2H, m, CHarom et NH), 7.81 (1H, d, CHarom, J = 8.4 Hz), 7.77-7.70 (1H, m, CHarom), 7.51-7.40 (2H, m, CHarom), 7.13 (1H, dd, CHarom, J = 8.8 Hz), 6.69 (1H, s, CHarom), 6.51 (1H, d, CHarom, J = 8.4 Hz), 3.85-3.78 (2H, m), 3.72-3.67 (1H, m), 3.48 (2H, t), 2.87 (2H, d, J = 11.2 Hz), 2.47-2.40 (1H, m), 2.20 (3H, s), 1.96-1.87 (4H, m), 1.75-1.65 (4H, m), 1.38-1.28 (2H, m). 30-28: 13.31 (1H, sl, NH), 9.95 (1H, s, NH), 8.31 (1H, d, NH, J = 7.6 Hz), 7.99 (1H, d, CHarom, J = 7.6 Hz), 7.78 (1H, d, CHarom, J = 9.2 Hz), 7.58-7.49 (3H, m, CHarom), 7.31 (1H, d, CHarom, J = 8.8 Hz), 6.24 (1H, d, CHarom, J = 8.8 Hz), 6.10 (1H, s, CHarom), 3.83-3.76 (2H, m), 3.70-3.60 (1H, m), 3.45 (2H, t), 3.21 (4H, s), 2.43 (4H, s), 2.22 (3H, s), 1.94-1.86 (2H, m), 1.38-1.28 (2H, m). 30-29: 13.26 (1H, s, NH), 10.25 (1H, s, NH), 8.01 (1H, d, CHarom, J = 8.8 Hz), 7.94 (1H, d, NH, J = 7.6 Hz), 7.82 (1H, d, CHarom, J = 8.4 Hz), 7.59-7.54 (3H, m, CHarom), 7.32 (1H, d, CHarom, J = 8.8 Hz), 6.67 (1H, s, CHarom), 6.54 (1H, d, CHarom, J = 7.6 Hz), 3.84-3.78 (2H, m), 3.71-3.62 (1H, m), 3.47 (2H, t), 2.87 (2H, d, J = 11.2 Hz), 2.45-2.41 (1H, m), 2.19 (3H, s), 1.96-1.90 (4H, m), 1.74-1.68 (4H, m), 1.34-1.27 (2H, m). 30-30: 13.23 (1H, s, NH), 9.98 (1H, s, NH), 8.29 (1H, d, NH, J = 7.6 Hz), 8.01 (1H, d, CHarom, J = 8.8 Hz), 7.79 (1H, d, CHarom, J = 8.8 Hz), 7.62 (1H, d, CHarom, J = 8.4 Hz), 7.52 (1H, s, CHarom), 7.44 (1H, d, CHarom, J = 7.6 Hz), 7.24 (1H, d, CHarom, J = 8.4 Hz), 6.25 (1H, d, CHarom, J = 8.0 Hz), 6.12 (1H, d, CHarom), 3.82-3.75 (2H, m), 3.73-3.67 (1H, m), 3.47 (2H, t), 3.27 (4H, s), 2.43 (4H, s), 2.22 (3H, s), 1.95-1.87 (2H, m), 1.35-1.28 (2H, m). 30-31: 13.28 (1H, s, NH), 10.25 (1H, s, NH), 8.02 (1H, d, CHarom, J = 8.8 Hz), 7.95 (1H, d, NH, J = 7.6 Hz), 7.81 (1H, d, CHarom, J = 8.0 Hz), 7.61 (1H, d, CHarom, J = 8.4 Hz), 7.56 (1H, s, CHarom), 7.43 (1H, d, CHarom, J = 8.4 Hz), 7.25 (1H, d, CHarom, J = 8.8 Hz), 6.68 (1H, s, CHarom), 6.51 (1H, d, CHarom, J = 7.2 Hz), 3.84-3.78 (2H, m), 3.69-3.61 (1H, m), 3.47 (2H, t), 2.87 (2H, d, J = 11.2 Hz), 2.47-2.41 (1H, m), 2.20 (3H, s), 2.00-1.90 (4H, m), 1.76-1.69 (4H, m), 1.40-1.30 (2H, m). 30-32: 13.16 (1H, s, NH), 9.95 (1H, s, NH), 8.33 (1H, d, NH, J = 8.0 Hz), 7.93 (1H, d, CHarom, J = 8.8 Hz), 7.89 (1H, d, CHarom, J = 9.2 Hz), 7.70-7.63 (2H, m, CHarom), 7.60 (1H, t, CHarom), 6.97 (1H, d, CHarom, J = 8.8 Hz), 6.25 (1H, d, CHarom, J = 9.2 Hz), 6.14 (1H, s, CHarom), 3.83-3.78 (2H, m), 3.68 (1H, sl), 3.48 (2H, t), 3.28 (4H, s), 2.44 (4H, s), 2.23 (3H, s), 1.95-1.90 (2H, m), 1.38-1.28 (2H, m). 30-33: 13.21 (1H, s, NH), 10.22 (1H, s, NH), 7.99 (1H, d, NH, J = 7.6 Hz), 7.94 (1H, d, CHarom, J = 9.2 Hz), 7.89 (1H, d, CHarom, J = 7.2 Hz), 7.82 (1H, d, CHarom, J = 8.4 Hz), 7.71-7.57 (3H, m, CHarom), 6.98 (1H, d, CHarom, J = 8.8 Hz), 6.69 (1H, s, CHarom), 6.52 (1H, d, CHarom, J = 8.0 Hz), 3.85-3.79 (2H, m), 3.72-3.62 (1H, m), 3.48 (2H, t), 2.87 (2H, d, J = 11.2 Hz), 2.47-2.41 (1H, m), 2.19 (3H, s), 2.00-1.90 (4H, m), 1.76-1.69 (4H, m), 1.40-1.30 (2H, m). 30-34: 13.07 (1H, s, NH), 10.11 (1H, s, NH), 8.32 (1H, d, NH, J = 7.6 Hz), 7.90-7.85 (2H, m, CHarom), 7.22 (1H, d, CHarom, J = 8.8 Hz), 7.19 (1H, s, CHarom), 7.17 (1H, s, CHarom), 7.03 (1H, t, CHarom), 6.30 (1H, d, CHarom, J = 8.4 Hz), 6.19 (1H, s, CHarom), 4.43 (2H, s), 4.02 (2H, sl), 3.80-3.74 (2H, m), 3.67 (1H, sl), 3.44 (2H, t), 3.10 (1H, m), 2.84 (3H, s), 1.89-1.84 (2H, m), 1.30-1.14 (2H, m). 30-35: 13.08 (1H, s, NH), 10.28 (1H, s, NH), 7.96 (1H, d, NH, J = 7.6 Hz), 7.88 (1H, d, CHarom, J = 8.8 Hz), 7.86 (1H, d, CHarom, J = 6.8 Hz), 7.22 (1H, d, CHarom, J = 8.8 Hz), 7.18 (1H, s, CHarom), 7.17 (1H, s, CHarom), 7.02 (1H, t, CHarom), 6.66 (1H, s, CHarom), 6.51 (1H, d, CHarom, J = 8.4 Hz), 4.43 (2H, s), 3.80-3.74 (2H, m), 3.64 (1H, sl), 3.44 (2H, t), 2.89-2.84 (2H, m), 2.43 (4H, sl), 2.20 (3H, s), 1.98-1.95 (2H, m), 1.72-1.69 (4H, m), 1.29-1.20 (2H, m). 30-36: 13.10 (1H, sl, NH), 10.11 (1H, s, NH), 9.73 (1H, sl, COOH), 8.34 (1H, sl, NH), 7.92-7.86 (2H, m, CHarom), 7.47-7.40 (1H, m, CHarom), 7.23 (1H, d, CHarom, J = 8.8 Hz), 7.20-7.13 (1H, m, CHarom), 7.11-7.05 (1H, m, CHarom), 6.31 (1H, dd, CHarom, J = 9.2 Hz), 6.20 (1H, s, CHarom), 4.41 (2H, s), 4.04 (2H, d, J = 8.8 Hz), 3.81-3.75 (2H, m), 3.70-3.66 (1H, m), 3.51 (2H, d, J = 11.2 Hz), 3.44 (2H, t), 3.16-2.97 (4H, m), 2.87 (1H, s), 1.91-1.84 (2H, m), 1.34-1.22 (2H, m). 30-37: 13.09 (1H, s, NH), 10.29 (1H, s, NH), 7.97 (1H, d, NH, J = 7.6 Hz), 7.90-7.86 (2H, m, CHarom), 7.47-7.41 (1H, m, CHarom), 7.23 (1H, d, CHarom, J = 8.8 Hz), 7.19-7.13 (1H, m, CHarom), 7.11-7.05 (1H, m, CHarom), 6.67 (1H, s, CHarom), 6.52 (1H, d, CHarom, J = 8.0 Hz), 4.41 (2H, s), 3.79-3.74 (2H, m), 3.66-3.62 (1H, m), 3.44 (2H, t), 2.86 (2H, d, J = 11.2 Hz), 2.45-2.40 (1H, m), 2.19 (3H, s), 2.00-1.85 (4H, m), 1.74-1.65 (4H, m), 1.33-1.23 (2H, m). 30-38: 13.02 (1H, s, NH), 10.04 (1H, s, NH), 8.28 (1H, d, NH, J = 8.0 Hz), 7.88-7.84 (2H, m, CHarom), 7.74 (1H, m, CHarom), 7.43 (1H, d, CHarom, J = 8.8 Hz), 7.29 (1H, dd, CHarom, J = 8.4 Hz), 7.22 (1H, d, CHarom, J = 8.8 Hz), 6.25 (1H, dd, CHarom, J = 9.2 Hz), 6.12 (1H, s, CHarom), 4.50 (2H, s), 3.78-3.74 (2H, m), 3.66-3.62 (1H, m), 3.44 (2H, t), 3.26 (4H, s), 2.43 (4H, s), 2.22 (3H, s), 1.91-1.84 (2H, m), 1.35-1.23 (2H, m). 30-39: 13.09 (1H, s, NH), 10.32 (1H, s, NH), 8.28 (1H, d, NH, J = 8.0 Hz), 7.90 (2H, D, CHarom), 7.74 (1H, s, CHarom), 7.43 (1H, d, CHarom, J = 8.4 Hz), 7.29 (1H, dd, CHarom, J = 8.4 Hz), 7.25 (1H, d, CHarom, J = 8.8 Hz), 6.67 (1H, s, CHarom), 6.54 (1H, dd, CHarom, J = 8.4 Hz), 4.51 (2H, s), 3.79-3.76 (2H, m), 3.70-3.64 (1H, m), 3.44 (2H, t), 2.95-2.92 (2H, m), 2.52-2.51 (1H, m), 2.27 (3H, s), 2.13-2.01 (2H, m), 1.90-1.87 (2H, m) 1.77-1.69 (4H, m), 1.32-1.24 (2H, m). 30-40: 12.77 (1H, s, NH), 9.86 (1H, s, NH), 9.60 (1H, s, NH), 8.40 (1H, d, NH, J = 7.6 Hz), 7.86 (1H, d, CHarom, J = 8.8 Hz), 7.83 (1H, d, CHarom, J = 9.2 Hz), 7.56 (1H, d, CHarom, J = 8.8 Hz), 6.93 (1H, d, CHarom, J = 9.2 Hz), 6.55 (1H, t, CHarom), 6.23 (1H, dd, CHarom, J = 9.2 Hz), 6.13 (1H, s, CHarom), 3.82-3.75 (2H, m), 3.69-3.61 (1H, m), 3.46 (2H, t), 3.27 (4H, s), 2.44 (4H, s), 2.29 (3H, s), 1.96-1.88 (2H, m), 1.38-1.26 (2H, m). 30-41: 12.85 (1H, s, NH), 10.13 (1H, s, NH), 9.62 (1H, s, NH), 8.03 (1H, d, NH, J = 7.2 Hz), 7.90-7.84 (2H, m, CHarom), 7.57 (1H, d, CHarom, J = 10.4 Hz), 6.95 (1H, d, CHarom, J = 8.8 Hz), 6.68 (1H, s, CHarom), 6.60-6.50 (2H, m, CHarom), 3.83-3.78 (2H, m), 3.68-3.63 (1H, m), 3.46 (2H, t), 2.87 (2H, d, J = 11.2 Hz), 2.45-2.40 (1H, m), 2.20 (3H, s), 2.00-1.92 (4H, m), 1.75-1.65 (4H, m), 1.37-1.27 (2H, m). 30-42: 12.77 (1H, s, NH), 9.87 (1H, s, NH), 9.02 (1H, s, NH), 8.80-8.72 (1H, m, CHarom), 8.41(1H, d, NH, J = 7.6 Hz), 7.86 (1H, d, CHarom, J = 8.8 Hz), 7.83 (1H, d, CHarom, J = 9.2 Hz), 7.28 (1H, d, CHarom, J = 9.2 Hz), 7.22-7.15 (1H, m, CHarom), 6.63-6.57 (1H, m, CHarom), 6.23 (1H, d, CHarom, J = 8.8 Hz), 6.13 (1H, s, CHarom), 3.83-3.75 (2H, m), 3.70-3.64 (1H, m), 3.46 (2H, t), 3.27 (4H, s), 2.44 (4H, s), 2.23 (3H, s), 1.95-1.88 (2H, m), 1.39-1.26 (2H, m). 30-43: 12.84 (1H, s, NH), 10.13 (1H, s, NH), 9.05 (1H, sl, NH), 8.81-8.74 (1H, m, CHarom), 8.05 (1H, d, NH, J = 7.2 Hz), 7.89-7.84 (1H, m, CHarom), 7.30 (1H, d, CHarom, J = 8.8 Hz), 7.23-7.15 (1H, m, CHarom), 6.67 (1H, s, CHarom), 6.64-6.58 (1H, m, CHarom), 6.51 (1H, d, CHarom, J = 8.4 Hz), 3.83-3.76 (2H, m), 3.68-3.64 (1H, m), 3.47 (2H, t), 2.89 (2H, d, J = 10.8 Hz), 2.45-2.40 (1H, m), 2.21 (3H, s), 2.01-1.91 (4H, m), 1.74-1.66 (4H, m), 1.38-1.27 (2H, m). 30-44: 12.80 (1H, s, NH), 10.16 (1H, s, NH), 8.89 (1H, s, CHarom), 8.52 (1H, s, NH), 8.34 (1H, d, NH, J = 7.6 Hz), 7.89 (1H, d, CHarom, J = 9.2 Hz), 7.81 (1H, d, CHarom, J = 9.2 Hz), 7.41 (1H, d, CHarom, J = 8.8 Hz), 7.35 (1H, d, CHarom, J = 9.2 Hz), 6.89 (1H, dd, CHarom, J = 8.4 Hz), 6.21 (1H, d, CHarom, J = 9.2 Hz), 6.11 (1H, s, CHarom), 3.83-3.75 (2H, m), 3.66-3.60 (1H, m), 3.46 (2H, t), 3.25 (4H, s), 2.44 (4H, s), 2.23 (3H, s), 1.95-1.87 (2H, m), 1.37-1.26 (2H, m). 30-45: 12.86 (1H, s, NH), 10.10 (1H, s, NH), 8.91 (1H, s, CHarom), 8.54 (1H, s, NH), 8.00 (1H, d, NH, J = 7.6 Hz), 7.90 (1H, d, CHarom, J = 9.2 Hz), 7.85 (1H, d, CHarom, J = 8.0 Hz), 7.64 (1H, d, CHarom, J = 8.4 Hz), 7.37 (1H, d, CHarom, J = 9.2 Hz), 6.88 (1H, dd, CHarom, J = 8.4 Hz), 6.64 (1H, s, CHarom), 6.48 (1H, d, CHarom, J = 8.4Hz), 3.83-3.77 (2H, m), 3.67-3.60 (1H, m), 3.47 (2H, t), 2.88 (2H, d, J = 11.2 Hz), 2.45-2.38 (1H, m), 2.21 (3H, s), 2.00-1.87 (4H, m), 1.75-1.65 (4H, m), 1.37-1.26 (2H, m). 30-46: 13.74 1H, sl, NH), 10.14 (1H, s, NH), 8.62 (1H, s, CHarom), 8.33 (1H, d, NH, J = 8.7 Hz), 7.12-7.03 (3H, m, CHarom), 6.26 (1H, d, CHarom, J = 8.8 Hz), 6.13 (1H, s, CHarom), 4.31 (2H, s), 4.14-4.07 (4H, m), 3.68 (1H, sl), 3.28 (4H, s), 2.43 (4H, s), 2.23 (3H, s), 1.92 (2H, d, J = 12.4 Hz), 1.38-1.26 (2H, m). 30-47: 13.80 (1H, sl, NH), 10.41 (1H, s, NH), 8.64 (1H, s, CHarom), 8.02 (1H, d, NH), 7.85 (1H, d, CHarom, J = 8.1 Hz), 7.12-7.03 (3H, m, CHarom), 6.69 (1H, s, CHarom), 6.52 (1H, d, CHarom, J = 8.1 Hz), 4.30 (2H, s), 3.81 (2H, d, J = 11.1 Hz), 3.68 (1H, sl), 3.48 (2H, t), 2.87 (2H, d, J = 10.5 Hz), 2.47-2.39 (1H, m), 2.19 (3H, s), 2-1.88 (4H, m), 1.76-1.66 (4H, m), 1.39-1.27 (2H, m). 30-48: 13.99 (1H, sl, NH), 10.17 (1H, s, NH), 8.34 (1H, d, CHarom), 8.29 (1H, dl, NH), 7.78 (1H, d, CHarom, J = 8.9 Hz), 7.54-7.41 (3H, m, CHarom), 6.07 (1H, d, CHarom, J = 8.9 Hz), 5.87 (1H, s, CHarom), 3.82 (2H, dl), 3.62 (1H, sl), 3.51-3.37 (4H, m), 2.97 (3H, s), 2.28-2.19 (2H, m), 2.15 (6H, s), 2-1.90 (4H, m), 1.71-1.61 (4H, m), 1.42-1.28 (2H, m). 30-49: 14.06 (1H, sl, NH), 10.56 (1H, s, NH), 8.85 (1H, s, CHarom), 7.97 (1H, sl, NH), 7.85 (1H, d, CHarom, J = 8.1 Hz), 7.50-7.40 (3H, m, CHarom), 6.71 (1H, s, CHarom), 6.54 (1H, d, CHarom, J = 8.1 Hz), 3.83-3.76 (2H, m), 3.70 (1H, sl), 3.48 (2H, t), 2.88 (2H, d, J = 10.6 Hz), 2.48-2.40 (1H, m), 2.20 (3H, s), 2.01-1.89 (4H, m), 1.76-1.66 (4H, m), 1.40-1.28 (2H, m). 30-50: 13.94 (1H, sl, NH), 10.11 (1H, sl, NH), 8.59 (1H, s, CHarom), 8.30 (1H, sl, NH), 7.76 (1H, d, CHarom, J = 9.2 Hz), 7.48 (1H, d, CHarom, J = 9.2 Hz), 7.27-7.13 (3H, m, CHarom), 6.04 (1H, dd, CHarom, J = 9.2 Hz), 5.85 (1H, s, CHarom), 3.87-3.76 (2H, m), 3.66-3.55 (1H, m), 3.49-3.26 (4H, m), 2.96 (3H, s), 2.22 (2H, t), 2.14 (6H, s), 1.97-1.89 (4H, m), 1.69-1.60 (4H, q), 1.40-1.28 (2H, m). 30-51: 13.95 (1H, sl, NH), 10.17 (1H, sl, NH), 8.54 (1H, s, CHarom), 8.28 (1H, sl, NH), 7.78 (1H, d, CHarom, J = 9.2 Hz), 7.59 (1H, d, CHarom, J = 9.2 Hz), 7.42-7.38 (2H, m, CHarom), 6.23 (1H, d, CHarom, J = 8.0 Hz), 6.11 (1H, s, CHarom), 3.82-3.77 (2H, m), 3.66 (1H, sl), 3.46 (2H, t), 3.26 (4H, s), 2.43 (4H, s), 2.22 (3H, s), 1.92-1.88 (2H, m), 1.34-1.24 (2H, m). 30-52: 13.97 (1H, sl, NH), 10.20 (1H, s, NH), 8.38 (1H, sl, NH), 8.27 (1H, d, NH), 7.88 (1H, d, CHarom, J = 7.2 Hz), 7.78 (1H, d, CHarom, J = 9.2 Hz), 7.66-7.55 (3H, m, CHarom), 6.26 (1H, dd, CHarom, J = 9.2 Hz), 6.13 (1H, s, CHarom), 3.85-3.76 (2H, m), 3.75-3.63 (1H, m), 3.48 (2H, t), 3.37-3.26 (4H, m), 2.61-2.52 (4H, m), 2.32 (3H, sl), 1.96-1.88 (4H, m), 1.39-1.26 (2H, m). 30-53: 13.64 (1H, s, NH), 10.20 (1H, s, NH), 8.30 (1H, d, CHarom, J = 8.8 Hz), 8.23 (1H, d, CHarom, J = 8.0 Hz), 8.19 (1H, d, CHarom, J = 8.8 Hz), 7.81 (1H, d, CHarom, J = 9.2 Hz), 7.75-7.65 (3H, m, CHarom), 6.28 (1H, d, CHarom, J = 8.8 Hz), 6.14 (1H, s, CHarom), 3.83-3.77 (2H, m), 3.70-3.64 (1H, m), 3.48 (2H, t), 3.29 (4H, s), 2.44 (4H, s), 2.23 (3H, s), 1.95-1.89 (2H, m), 1.38-1.26 (2H, m). 30-54: 13.64 (1H, sl, NH), 10.48 (1H, sl, NH), 8.32 (1H, d, CHarom, J = 8.8 Hz), 8.19 (1H, d, CHarom, J = 8.8 Hz), 7.91 (1H, sl, NH), 7.85 (1H, d, CHarom, J = 8.4 Hz), 7.77-7.65 (3H, m, CHarom), 6.71 (1H, s, CHarom), 6.54 (1H, d, CHarom, J = 8.4 Hz), 3.86-3.80 (2H, m), 3.71-3.64 (1H, m), 3.48 (2H, t), 2.89 (2H, d, J = 11.2 Hz), 2.45-2.40 (1H, m), 2.21 (3H, s), 2.00-1.90 (4H, m), 1.75-1.65 (4H, m), 1.38-1.27 (2H, m). 30-55: 13.64 (1H, s, NH), 10.16 (1H, s, NH), 8.29 (1H, d, CHarom, J = 8.8 Hz), 8.24 (1H, d, NH, J = 7.6 Hz), 8.17 (1H, d, CHarom, J = 8.8 Hz), 8.09 (1H, t, CHarom), 7.88-7.85 (1H, m, CHarom), 7.81 (1H, d, CHarom, J = 9.2 Hz), 7.67 (1H, q, CHarom), 6.28 (1H, d, CHarom, J = 8.8 Hz), 6.14 (1H, s, CHarom), 3.83-3.75 (2H, m), 3.72-3.67 (1H, m), 3.48 (2H, t), 3.29 (4H, s), 2.44 (4H, s), 2.23 (3H, s), 1.96-1.89 (2H, m), 1.35-1.28 (2H, m). 30-56: 13.67 (1H, s, NH), 10.43 (1H, s, NH), 8.31 (1H, d, CHarom, J = 8.8 Hz), 8.18 (1H, d, CHarom, J = 8.8 Hz), 8.13-8.05 (1H, m, CHarom), 7.92 (1H, d, NH, J = 7.6 Hz), 7.90-7.82 (2H, m, CHarom), 7.66 (1H, q, CHarom), 6.71 (1H, s, CHarom), 6.54 (1H, d, CHarom, J = 8.4 Hz), 3.85-3.80 (2H, m), 3.73-3.65 (1H, m), 3.49 (2H, t), 2.89 (2H, d, J = 11.2 Hz), 2.48-2.42 (1H, m), 2.21 (3H, s), 1.99-1.90 (4H, m), 1.76-1.68 (4H, m), 1.37-1.27 (2H, m). 30-57: 13.66 (1H, s, NH), 10.17 (1H, s, NH), 8.30 (1H, d, CHarom, J = 8.8 Hz), 8.24-8.16 (2H, m, CHarom et NH), 8.03-7.97 (3H, m, CHarom), 7.81 (1H, d, CHarom, J = 9.2 Hz), 6.28 (1H, d, CHarom, J = 7.2 Hz), 6.14 (1H, s, CHarom), 3.83-3.77 (2H, m), 3.71-3.67 (1H, m), 3.48 (2H, t), 3.29 (4H, s), 2.44 (4H, s), 2.23 (3H, s), 1.96-1.89 (2H, m), 1.34-1.28 (2H, m). 30-58: 13.71 (1H, s, NH), 10.45 (1H, s, NH), 8.32 (1H, d, CHarom, J = 9.2 Hz), 8.22 (1H, d, CHarom, J = 8.8 Hz), 8.02-7.96 (2H, m, CHarom), 7.86-7.81 (1H, m, NH), 7.83 (1H, d, CHarom), 6.71 (1H, s, CHarom), 6.54 (1H, d, CHarom, J = 7.6 Hz), 3.85-3.78 (2H, m), 3.72-3.65 (1H, m), 3.48 (2H, t), 2.88 (2H, d, J = 11.2 Hz), 2.48-2.44 (1H, m), 2.21 (3H, s), 1.97-1.87 (4H, m), 1.76-1.70 (4H, m), 1.36-1.28 (2H, m). 30-59: 13.69 (1H, s, NH), 10.04 (1H, s, NH), 8.34 (1H, d, NH, J = 8.8 Hz), 8.26-8.16 (3H, m, CHarom), 7.81 (1H, dd, CHarom, J = 8.4 Hz), 7.74 (1H, d, CHarom, J = 9.2 Hz), 7.66 (1H, d, CHarom, J = 8.4 Hz), 6.24 (1H, dd, CHarom, J = 9.2 Hz), 6.10 (1H, d, CHarom), 3.82-3.76 (2H, m), 3.68-3.62 (1H, m), 3.48 (2H, t), 3.27 (4H, s), 2.43 (4H, s), 2.22 (3H, s), 1.93-1.86 (2H, m), 1.31-1.21 (2H, m). 30-60: 13.74 (1H, s, NH), 10.31 (1H, s, NH), 8.35 (1H, d, CHarom, J = 8.8 Hz), 8.25 (1H, d, CHarom, J = 8.8 Hz), 8.21 (1H, s, CHarom), 7.85 (1H, d, NH, J = 7.2 Hz), 7.81 (1H, dd, CHarom, J = 8.8 Hz), 7.76 (1H, d, CHarom, J = 8.0 Hz), 7.66 (1H, d, CHarom, J = 8.4 Hz), 6.67 (1H, s, CHarom), 6.50 (1H, d, CHarom, J = 8.0 Hz), 3.85-3.78 (2H, m), 3.68-3.62 (1H, m), 3.48 (2H, t), 2.87 (2H, d, J = 11.2 Hz), 2.46-2.40 (1H, m), 2.20 (3H, s), 1.97-1.87 (4H, m), 1.75-1.67 (4H, m), 1.32-1.24 (2H, m). 30-61: 13.61 (1H, s, NH), 10.32 (1H, s, NH), 8.71 (1H, d, NH, J = 8.0 Hz), 7.87 (1H, d, CHarom, J = 9.2 Hz), 7.80 (1H, d, CHarom, J = 8.8 Hz), 7.17 (1H, t, CHarom), 7.05-7.02 (2H, m, CHarom), 6.29 (1H, d, CHarom, J = 9.2 Hz), 6.14 (1H, s, CHarom), 4.93 (2H, s), 3.74-3.68 (3H, m), 3.43 (2H, t), 3.29 (4H, s), 2.44 (4H, s), 2.28 (3H, s), 1.90-1.84 (2H, m), 1.28-1.20 (2H, m). 30-62: 13.67 (1H, sl, NH), 10.59 (1H, s, NH), 8.23 (1H, d, CHarom, J = 8.8 Hz), 8.10 (1H, d, NH, J = 7.6 Hz), 7.92 (1H, d, CHarom, J = 8.0 Hz), 7.82 (1H, d, CHarom, J = 8.8 Hz), 7.17 (1H, t, CHarom), 7.05-7.02 (2H, m, CHarom), 6.71 (1H, d, CHarom), 6.56 (1H, d, CHarom, J = 8.0 Hz), 4.94 (2H, s), 3.77-3.70 (3H, m), 3.43 (2H, t), 2.87 (2H, d, J = 11.2 Hz), 2.45-2.40 (1H, m), 2.20 (3H, s), 1.98-1.91 (4H, m), 1.89-1.95 (2H, m), 1.75-1.67 (4H, m), 1.30-1.20 (2H, m). 30-63: 13.63 (1H, sl, NH), 10.28 (1H, sl, NH), 8.37 (1H, d, NH, J = 8.0 Hz), 8.24 (1H, d, CHarom, J = 8.8 Hz), 7.88-7.82 (2H, m, CHarom), 7.24-7.17 (2H, m, CHarom), 6.29 (1H, d, CHarom, J = 9.2 Hz), 6.14 (1H, s, CHarom), 4.87 (2H, s), 3.75-3.70 (3H, m), 3.43 (2H, t), 3.28 (4H, s), 2.45 (4H, s), 2.23 (3H, s), 1.90-1.85 (2H, m), 1.32-1.20 (2H, m). 30-64: 13.69 (1H, sl, NH), 10.55 (1H, s, NH), 8.26 (1H, d, CHarom, J = 8.8 Hz), 8.05 (1H, d, NH, J = 7.6 Hz), 7.90 (1H, d, CHarom, J = 8.4 Hz), 7.86 (1H, d, CHarom, J = 8.8 Hz), 7.24-7.15 (3H, m, CHarom), 6.70 (1H, s, CHarom), 6.56 (1H, d, CHarom, J = 8.0 Hz), 4.88 (2H, s), 3.80-3.65 (3H, m), 3.43 (2H, t), 2.87 (2H, d, J = 11.2 Hz), 2.46-2.40 (1H, m), 2.20 (3H, s), 2.00-1.86 (4H, m), 1.75-1.67 (4H, m), 1.29-1.23 (2H, m). 30-65: 13.49 (1H, sl, NH), 10.45 (1H, s, NH), 9.31 (1H, sl, COOH), 8.21 (1H, d, CHarom, J = 8.8 Hz), 8.06 (1H, d, NH), 7.92 (1H, d, CHarom, J = 8.4 Hz), 7.57 (1H, d, CHarom, J = 8.8 Hz), 7.17-7.11 (2H, m, CHarom), 6.96-6.91 (1H, m, CHarom), 6.67 (1H, s, CHarom), 6.53 (1H, d, CHarom, J = 8.0 Hz), 4.51 (1H, d, J = 13.2 Hz), 4.20 (1H, d, J = 13.2 Hz), 3.81-3.76 (2H, m), 3.71-3.62 (1H, m), 3.56-3.41 (4H, m), 3.08 (2H, t), 2.83 (3H, s), 2.45-2.40 (1H, m), 2.07-2.00 (2H, m), 1.95-1.86 (4H, m), 1.41-1.29 (2H, m). 30-66: 13.62 (1H, sl, NH), 10.22 (1H, sl, NH), 8.36 (1H, d, NH, J = 7.6 Hz), 8.23 (1H, d, CHarom, J = 8.8 Hz), 7.85 (1H, d, CHarom, J = 9.2 Hz), 7.80 (1H, d, CHarom, J = 8.8 Hz), 7.48 (1H, s, CHarom), 7.45-7.37 (2H, m, CHarom), 6.29 (1H, d, CHarom, J = 7.2 Hz), 6.14 (1H, s, CHarom), 4.97 (2H, s), 3.76-3.70 (3H, m), 3.44 (2H, t), 3.28 (4H, s), 2.44 (4H, s), 2.23 (3H, s), 1.91-1.86 (2H, m), 1.30-1.24 (2H, m). 30-67: 13.67 (1H, sl, NH), 10.49 (1H, s, NH), 8.25 (1H, d, CHarom, J = 8.8Hz), 8.02 (1H, d, NH, J = 7.2 Hz), 7.89 (1H, d, CHarom, J = 8.0 Hz), 7.82 (1H, d, CHarom, J = 8.8 Hz), 7.49 (1H, s, CHarom), 7.45-7.35 (2H, m, CHarom), 6.70 (1H, s, CHarom), 6.56 (1H, d, CHarom, J = 8.0 Hz), 4.97 (2H, s), 3.78-3.64 (3H, m), 3.44 (2H, t), 2.88 (2H, d, J = 11.2 Hz), 2.45-2.40 (1H, m), 2.20 (3H, s), 1.98-1.86 (4H, m), 1.76-1.66 (4H, m), 1.32-1.22 (2H, m). 30-68: 13.46 (1H, s, NH), 10.36 (1H, s, NH), 8.21 (1H, d, CHarom, J = 8.8 Hz), 8.00 (1H, d, NH, J = 7.6 Hz), 7.86 (1H, d, CHarom, J = 8.4 Hz), 7.59 (1H, d, CHarom, J = 8.8 Hz), 7.43-7.33 (2H, m, CHarom), 7.28 (1H, s, CHarom), 6.69 (1H, s, CHarom), 6.54 (1H, d, CHarom, J = 7.6 Hz), 4.58 (1H, d, J = 12.8 Hz), 4.30 (1H, d, J = 12.8 Hz), 3.78-3.75 (2H, m), 3.70-3.65 (2H, m), 3.46 (2H, m), 2.92-2.88 (2H, m), 2.45-2.40 (1H, m), 2.24 (3H, s), 2.05-1.95 (2H, m), 1.93-1.89 (2H, m), 1.77-1.70 (4H, m), 1.34-1.24 (2H, m). (ND: not determined).

Example 30-bis (S)-4-(3-aminopyrrolidin-1-yl)-N-(5-(3,5-difluorophenylthio)-1H-pyrazolo[3,4-b]pyridin-3-yl)-2-(tetrahydro-2H-pyran-4-ylamino)benzamide

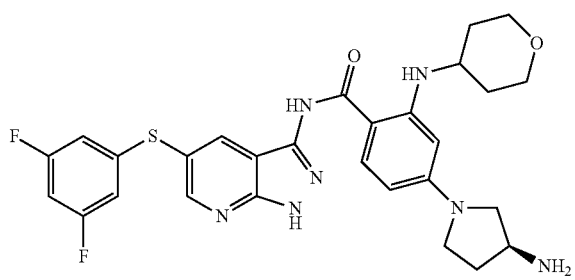 [SMILES: N=C(NC(=O)c1ccc(N2CC[C@H](N)C2)cc1NC1CCOCC1)c1cc(Sc2cc(F)cc(F)c2)cnc1N]

876 µl (20 eq) of triethylamine is added to a solution of 238 mg (0.314 mmol) of (S)—N-(5-(3,5-difluorophenylthio)-1H-pyrazolo[3,4-b]pyridin-3-yl)-2-(2,2,2-trifluoro-N-(tetrahydro-2H-pyran-4-yl)acetamido)-4-(3-(2,2,2-trifluoroacetamido)pyrrolidin-1-yl)benzamide in 6 ml of methanol. The reaction medium is stirred at 65° C. for 4 hours. After returning to room temperature, 8 ml of n-butanol and 260 mg (6 eq) of potassium carbonate are added. The reaction medium is stirred at 80° C. for 24 hours. After returning to room temperature, the solvents are evaporated, water is added and the product is extracted with dichloromethane. The organic phase is washed with saturated sodium chloride solution, dried on magnesium sulfate, filtered and evaporated. The residue is purified by silica gel chromatography (8:2 dichloromethane/methanol as eluent) to yield 87 mg (yield=49%) of (S)-4-(3-aminopyrrolidin-1-yl)-N-(5-(3,5-difluorophenylthio)-1H-pyrazolo[3,4-b]pyrazine-3-yl)-2-(tetrahydro-2H-pyran-4-ylamino)benzamide in the form of a brown powder.

LCMS (EI, m/z): (M+1) 566.24.

$^1$H NMR: δH ppm (400 MHz, DMSO): 10.46 (1H, bs, NH), 8.60 (1H, s, CH$_{arom}$), 8.50 (1H, 5, CH$_{arom}$), 8.26 (1H, d, NH), 7.78 (1H, d, CH$_{arom}$), 7.08 (1H, t, CH$_{arom}$), 6.86 (2H, d, CH$_{arom}$), 5.86 (1H, dd, CH$_{arom}$), 5.71 (1H, d, CH$_{arom}$), 3.80-3.88 (2H, m, CH), 3.63-3.70 (2H, m, CH), 3.40-3.55 (5H, m, CH), 3.01-3.08 (1H, m, CH), 2.08-2.13 (1H, m, CH), 1.92-1.99 (2H, m, CH$_3$), 1.76-1.82 (1H, m, CH), 1.30-1.41 (2H, m, CH$_{pyranone}$).

Examples of Method F2

Reduction

Example 31

N-(5-(3,5-difluorophenethyl)-1H-pyrazolo[3,4-b]pyridin-3-yl)-4-(4-methylpiperazin-1-yl)-2-(tetrahydro-2H-pyran-4-ylamino)benzamide

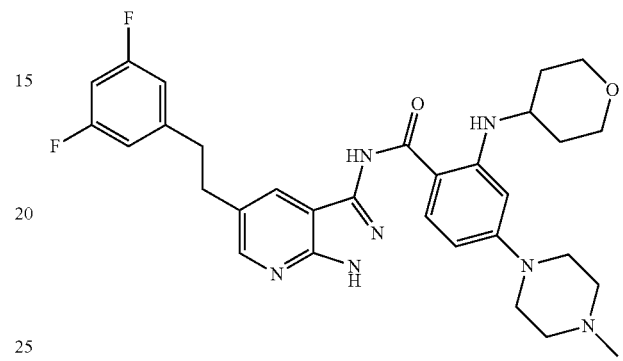

10 mg of 10% Pd/C is added to 100 mg (0.175 mmol) of N-(5-((3,5-difluorophenyl)ethynyl)-1H-pyrazolo[3,4-b]pyridin-3-yl)-4-(4-methylpiperazin-1-yl)-2-(tetrahydro-2H-pyran-4-ylamino)benzamide in solution in a mixture of 10 ml of tetrahydrofuran and 5 ml of methanol before placing the reaction medium under an atmosphere of hydrogen. The reaction mixture is stirred for 12 hours at room temperature and then filtered on Celite and concentrated. 62 mg (yield=60%) of N-(5-(3,5-difluorophenethyl)-1H-pyrazolo[3,4-b]pyridin-3-yl)-4-(4-methylpiperazin-1-yl)-2-(tetrahydro-2H-pyran-4-ylamino)benzamide are isolated in the form of a white solid. LCMS (EI, m/z): (M+1) 576.23.

$^1$H NMR: δH ppm (400 MHz, DMSO): 13.14 (1H, bs, NH), 10.32 (1H, bs, NH), 8.40 (1H, d, CH$_{arom}$), 8.22 (1H, d, NH), 7.96 (1H, d, CH$_{arom}$), 7.80 (1H, d, CH$_{arom}$), 7.03-6.98 (3H, m, CH$_{arom}$), 6.23 (1H, d, CH$_{arom}$), 6.16 (1H, bs, CH$_{arom}$), 3.84-3.81 (2H, dt, CH), 3.70 (1H, m, CH), 3.52-3.46 (2H, m, CH), 3.04-2.93 (4H, m, CH), 2.59-2.69 (4H, m, CH), 2.42-2.46 (4H, m, CH), 2.38 (3H, s, CH$_3$), 1.96-1.93 (2H, m, CH), 1.40-1.33 (2H, m, CH).

The following derivative was obtained according to the same method:

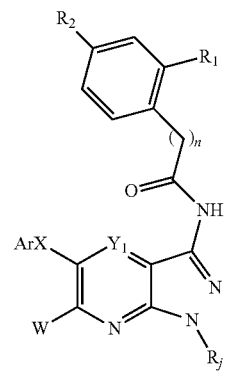

| Ex.** | ArX | R₁ | R₂ | Y₁ | n | W | Rⱼ | Compound names | Yield | Mass |
|---|---|---|---|---|---|---|---|---|---|---|
| 31-1 | 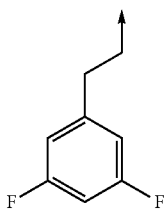 | 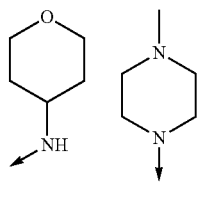 |  | N | 0 | H | H | N-(5-(3,5-difluorophenethyl)-1H-pyrazolo[3,4-b]pyrazin-3-yl)-4-(4-methylpiperazin-1-yl)-2-(tetrahydro-2H-pyran-4-ylamino)benzamide | 47% | 577.07 (M + H) |

**¹H NMR, dmso-d₆, Ex.: 31-1: 13.68 (1H, sl, NH), 10.11 (1H, s, NH), 8.52 (1H, s, CHarom), 8.35 (1H, dl, NH), 7.82 (1H, d, CHarom, J = 9 Hz), 7.05-6.97 (3H, m, CHarom), 6.27 (1H, dd, CHarom), 6.14 (1H, s, CHarom), 3.83-3.76 (2H, m), 3.74-3.64 (1H, m), 3.47 (2H, t), 3.32-3.20 (6H, m), 3.07 (2H, dd), 2.44 (4H, dd), 2.23 (3H, s), 1.91 (2H, d), 1.38-1.27 (2H, m).

Example 32

5-(3,5-difluorophenylthio)-N-(4-(4-methylpiperazin-1-yl)-2-(tetrahydro-2H-pyran-4-ylamino)benzyl)-1H-pyrazolo[3,4-b]pyridin-3-amine

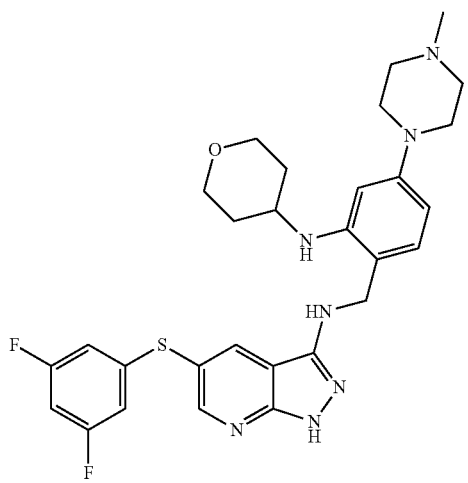 [SMILES: CN1CCN(c2ccc(CNc3n[nH]c4ncc(Sc5cc(F)cc(F)c5)cc34)c(NC3CCOCC3)c2)CC1]

100 mg (0.173 mmol) of N-(5-(3,5-difluorophenylthio)-1H-pyrazolo[3,4-b]pyridine-3-yl)-4-(4-methylpiperazine-1-yl)-2-(tetrahydro-2H-pyran-4-ylamino)benzamide is added, in small fractions, to a solution of 19.64 mg (0.518 mmol) of LiAlH₄ in 3 ml of anhydrous tetrahydrofuran under argon at 0° C. The reaction mixture is heated at 90° C. for 15 hours. An additional portion of 20 mg of LiAlH₄ is then added and the reaction medium stirred at 90° C. for 5 hours. 45 μl of water at 0° C. is then added to the reaction mixture, followed by 45 μl of sodium hydroxide (15% wt) and finally 120 μl of water. The reaction mixture is stirred at 25° C. for 1 hour and then filtered on Dicalite. After evaporation of the solvents, the crude product is purified by chromatography. 16.80 mg (17%) of 5-(3,5-difluorophenylthio)-N-(4-(4-methylpiperazin-1-yl)-2-(tetrahydro-2H-pyran-4-ylamino)benzyl)-1H-pyrazolo[3,4-b]pyridin-3-amine in the form of a yellow solid is obtained.

LCMS (EI, m/z): (M+1) 566.68.

¹H NMR: δH ppm (400 MHz, DMSO): 12.57 (1H, bs, NH), 8.45 (2H, d, CH$_{arom}$), 6.97-7.06 (2H, m, CH$_{arom}$), 6.73-6.75 (2H, m, CH$_{arom}$), 6.65 (1H, t, NH), 6.13-6.19 (2H, m, CH$_{arom}$), 4.98 (1H, d, NH), 4.30 (2H, m, CH₂), 3.73-3.77 (2H, m, CH), 3.60 (1H, m, CH), 3.45-3.50 (2H, m, CH), 3.04 (4H, m, CH), 2.42 (4H, m, CH), 2.18 (3H, s, CH₃), 1.80-1.83 (2H, m, CH), 1.27-1.32 (2H, m, CH).

The following derivatives were obtained according to the same method:

| Ex.** | ArX | R₁ | R₂ | (U)ₙ | V | Y₁, Y₂, Y₃, Y₄ | R₃ | Compound name | Yield | Mass |
|---|---|---|---|---|---|---|---|---|---|---|
| 32-1 | 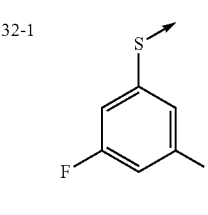 | 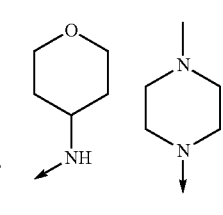 |  | n = 0 | CH₂ | N, ArXC, CH, N | H | 5-(3,5-difluorophenylthio)-N-(4-(4-methylpiperazin-1-yl)-2-(tetrahydro-2H-pyran-4-ylamino)benzyl)-1H-pyrazolo[4,3-b]pyrazin-3-amine | 1% | 567.3 |

Example 33

2-(4-aminophenyl)-N-(5-(3,5-difluorophenylthio)-1H-pyrazolo[3,4-b]pyridin-3-yl)acetamide

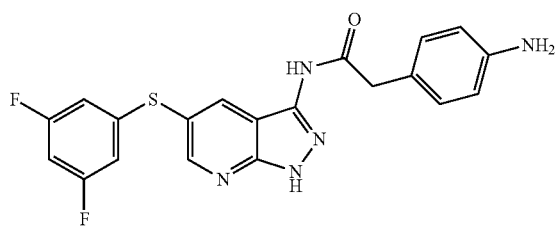 [SMILES: Nc1ccc(CC(=O)Nc2n[nH]c3ncc(Sc4cc(F)cc(F)c4)cc23)cc1]

A solution of 152 mg (2.72 mmol) of iron and 70 mg (1.3 mmol) of ammonium chloride in 100 µl of water is added to a solution of 0.24 g (0.544 mmol) of N-(5-(3,5-difluorophenylthio)-1H-pyrazolo[3,4-b]pyridin-3-yl)-2-(4-nitrophenyl) acetamide in 10 ml of a 2:1 ethanol/water mixture. Several drops of acetic acid are added to this mixture and it is heated at 60° C. for 4 hours. After cooling and concentration of the solvents, the crude reaction product is extracted with ethyl acetate and is washed with saturated sodium bicarbonate solution. The organic phases are combined, dried on magnesium sulfate and then concentrated. The crude product is purified by silica gel chromatography (DCM/MeOH) to yield 11 mg (4%) of 2-(4-aminophenyl)-N-(5-(3,5-difluorophenylthio)-1H-pyrazolo[3,4-b]pyridin-3-yl) acetamide in the form of a brown solid.

LCMS (EI, m/z): (M+1) 412.09.

$^1$H NMR: δH ppm (400 MHz, DMSO): 13.60 (1H, bs, NH), 10.96 (1H, bs, NH), 8.68 (1H, d, CH$_{arom}$), 8.55 (1H, d, CH$_{arom}$), 7.06 (1H, m, CH$_{arom}$), 6.98 (2H, d, CH$_{arom}$), 6.79 (2H, m, CH$_{arom}$), 6.50 (2H, m, CH$_{arom}$), 4.92 (2H, s, NH), 3.51 (2H, m, CH$_2$).

Examples of Method F3

Sulfide Oxidation

Example 34

5-(3,5-difluorophenylsulfonyl)-1H-pyrazolo[3,4-b]pyridin-3-amine

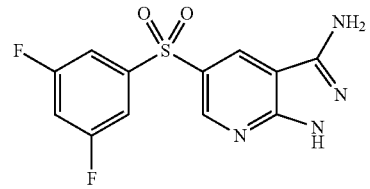 [SMILES: N=C(N)c1cc(S(=O)(=O)c2cc(F)cc(F)c2)cnc1N]

A solution of 663 mg (1.078 mmol) of oxone in 1.1 ml of water is added to a solution of 300 mg (1.078 mmol) of 5-(3,5-difluorophenylthio)-1H-pyrazolo[3,4-b]pyridin-3-amine in 10 ml of a 1:1 mixture of tetrahydrofuran and methanol at 0° C. The reaction mixture is stirred at room temperature for 16 hours. An additional portion of 663 mg of oxone at 0° C. is then added and the reaction medium stirred at room temperature for 24 hours. The solvents are evaporated and the reaction medium is diluted with sodium bicarbonate solution, extracted with ethyl acetate, dried on MgSO$_4$ and then concentrated to yield 340 mg (81%) of 5-(3,5-difluorophenylsulfonyl)-1H-pyrazolo[3,4-b]pyridin-3-amine in the form of a yellow solid.

LCMS (EI, m/z): (M+1) 311.03.

$^1$H NMR: δH ppm (400 MHz, DMSO): 12.72 (1H, bs, NH), 8.92 (1H, d, CH$_{arom}$), 8.84 (1H, d, CH$_{arom}$), 7.89-8.01 (1H, d, CH$_{arom}$), 7.62-7.80 (2H, m, CH$_{arom}$), 6.06 (2H, bs, NH).

The following compounds were also obtained by this method:

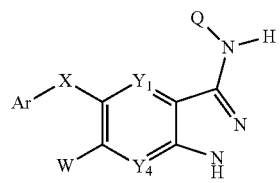

| Ex.** | ArX | Q | Y$_1$, Y$_4$ | W | Compound name | Yield | Mass MH$^+$ |
|---|---|---|---|---|---|---|---|
| 34-2 | ![3,5-difluorobenzylsulfonyl group] | H | CH, N | H | 5-(3,5-difluorobenzylsulfonyl)-1H-pyrazolo[3,4-b]pyridin-3-amine | ND | (M + 1) 325.07 |

| Ex.** | ArX | Q | $Y_1, Y_4$ | W | Compound name | Yield | Mass MH⁺ |
|---|---|---|---|---|---|---|---|
| 34-3 | 3,5-dichlorophenylsulfonyl | tert-butyl carbamate | N, CH | H | tert-butyl 5-(3,5-dichlorophenylsulfonyl)-1H-pyrazolo[4,3-b]pyridin-3-ylcarbamate | ND | ND |

**¹H NMR, DMSO-d₆, Ex.: 33-2: 12.64 (1H, bs, NH), 8.56 (1H, d, $CH_{arom}$), 8.49 (1H, d, $CH_{arom}$), 7.24 (1H, ddd, $CH_{arom}$), 6.94 (2H, bd, $CH_{arom}$), 6.03 (2H, bs, NH), 4.80 (2H, s, CH). (ND: not determined).

Alternatively, a protection step can be carried out before the oxidation reaction, followed by a deprotection step which can lead to the preparation of the corresponding sulfones or sulfoxides.

Example 34-bis 5-(3,5-difluorophenylsulfinyl)-1H-pyrazolo[4,3-b]pyrazin-3-amine

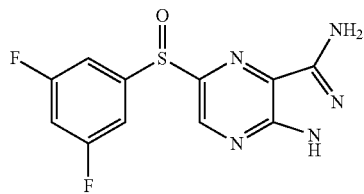 [SMILES: N=C(N)c1nc(S(=O)c2cc(F)cc(F)c2)cnc1N]

0.55 mL of triethylamine and 22 mg of 4-dimethylaminopyridine are added under argon to a solution of 500 mg (1.790 mmol) of 5-(3,5-difluorophenylthio)-1H-pyrazolo[3,4-b]pyrazin-3-amine in 10 mL of tetrahydrofurane. The solution is stirred at 0° C. and 0.915 mL of di-tert-butyl dicarbonate is added and the reaction medium is stirred overnight. An aqueous fraction is added to the reaction medium which is then extracted with ethyl acetate. The organic phases are dried on MgSO₄ and concentrated in vacuum to give a crude product which is used in the oxidation step without further purification. The crude product obtained is dissolved in 10 mL of a 1:1 mixture of tetrahydrofurane and methanol at 0° C. and then a solution of 1.103 g (1.794 mmol) of oxone in 2 mL of water is added. The reaction medium is stirred at room temperature for 16 hours. An additional portion of 550 mg of oxone is then added and the reaction medium is stirred at room temperature for 5 hours. The solvents are evaporated and the reaction medium is diluted with a sodium bicarbonate solution, extracted with ethyl acetate, dried on magnesium sulfate and concentrated to lead to a mixture of the corresponding sulfone and sulfoxide which are used without further purification in the deprotection step.

0.373 mL of TFA in 4 mL of anhydrous THF is added at 0° C. to a solution of 600 mg of the previously obtained mixture in 6 mL of dichloromethane. The mixture is stirred 1 hour at room temperature and an additional portion of 4 equivalents of TFA in 4 mL of THF is added. After 1 hour of stirring, this operation is repeated and the reaction medium is stirred for a total time of 3 h45. The solvents are evaporated and the reaction medium is diluted with a potassium carbonate solution, extracted with ethyl acetate, dried on magnesium sulfate and concentrated to yield a 1:1 mixture of 5-(3,5-difluorophenylsulfonyl)-1H-pyrazolo[3,4-b]pyrazin-3-amine and 5-(3,5-difluorophenyl sulfinyl)-1H-pyrazolo[3,4-b]pyrazin-3-amine. This mixture is used in the following steps without further purification.

The following compounds were also obtained by this method:

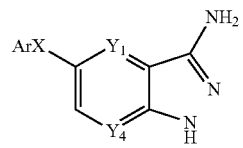

| Ex.** | ArX | $Y_1, Y_4$ | Compound names | Yield | Mass MH⁺ |
|---|---|---|---|---|---|
| 34bis-1 | 2,5-difluorophenylsulfonyl | CH, N | 5-(2,5-difluorophenylsulfonyl)-1H-pyrazolo[4,3-b]pyridin-3-amine | 58% 3 steps | (M + 1) 310.9 |
| 34bis-2 | 3,5-dichlorophenylsulfonyl | CH, N | 5-(3,5-dichlorophenylsulfonyl)-1H-pyrazolo[4,3-b]pyridin-3-amine | 38% 3 steps | (M + 1) 342.8 |

| Ex.** | ArX | $Y_1, Y_4$ | Compound names | Yield | Mass MH+ |
|---|---|---|---|---|---|
| 34bis-3 | 2,5-dichlorophenyl-SO2-Me | CH, N | 5-(2,5-dichlorophenylsulfonyl)-1H-pyrazolo[4,3-b]pyridin-3-amine | 41% 3 steps | (M + 1) 342.9 |
| 34bis-4 | 3,5-difluorobenzyl-SO2-Me | CH, N | 5-(3,5-difluorobenzylsulfonyl)-1H-pyrazolo[4,3-b]pyridin-3-amine | 58% 3 steps | (M + 1) 325.0 |
| 34bis-5 | 2,5-difluorobenzyl-SO2-Me | CH, N | 5-(2,5-difluorobenzylsulfonyl)-1H-pyrazolo[4,3-b]pyridin-3-amine | 45% 3 steps | (M + 1) 325.0 |
| 34bis-6 | 2,5-difluorobenzyl-SO-Me | CH, N | 5-(2,5-difluorobenzylsulfinyl)-1H-pyrazolo[4,3-b]pyridin-3-amine | 5% 3 steps | (M + 1) 308.9 |
| 34bis-7 | 2,5-dichlorobenzyl-SO2-Me | CH, N | 5-(2,5-dichlorobenzylsulfonyl)-1H-pyrazolo[4,3-b]pyridin-3-amine | 3% 3 steps | ND |
| 34bis-8 | 2,5-dichlorobenzyl-SO-Me | CH, N | 5-(2,5-dichlorobenzylsulfinyl)-1H-pyrazolo[4,3-b]pyridin-3-amine | 18% 3 steps | ND |

$^1$H NMR, DMSO-$d_6$, Ex.: 34bis-1: 12.31 (1H, sl, NH), 8.08-8.18 (1H, m, CHarom), 8.05 (1H, d, CHarom, J = 11.6 Hz), 7.97 (1H, d, CHarom, J = 11.6 Hz), 7.87-7.93 (1H, m, CHarom), 7.64-7.76 (1H, m, CHarom), 5.81 (2H, sl, NH$_2$). 34bis-2: 12.32 (1H, sl, NH), 7.94-8.11 (5H, m, CHarom), 5.85 (2H, sl, NH$_2$). 34bis-3: 12.34 (1H, sl, NH), 8.27 (1H, s, CHarom), 8.12 (1H, d, CHarom, J = 11.6 Hz), 8.01 (1H, d, CHarom, J = 11.6 Hz), 7.82-7.89 (1H, m, CHarom), 7.67 (1H, d, CHarom, J = 11.2 Hz), 5.70 (2H, sl, NH$_2$).

34bis-4: 12.28 (1H, sl, NH), 7.89 (1H, d, CHarom, J = 8.8 Hz), 7.68 (1H, d, CHarom, J = 8.8 Hz), 7.21 (1H, m, CHarom), 6.91-6.97 (2H, m, CHarom), 5.87 (2H, s, NH$_2$), 4.94 (2H, s, CH). 34bis-5: 12.28 (1H, sl, NH), 7.89 (1H, d, CHarom, J = 8.8 Hz), 7.68 (1H, d, CHarom, J = 8.8 Hz), 7.20-7.25 (2H, m, CHarom), 7.10-7.15 (1H, m, CHarom), 5.84 (2H, s, NH$_2$), 4.87 (2H, s, CH). 34bis-6: 12.04 (1H, s, NH), 7.87 (1H, d, CHarom, J = 8.8 Hz), 7.40 (1H, d, CHarom, J = 8.8 Hz), 7.10-7.25 (2H, m, CHarom), 6.90-6.97 (1H, m, CHarom), 5.61 (2H, s, NH2), 4.47 (1H, d, CH, J = 13.2 Hz), 4.18 (1H, d, CH, J = 13.2 Hz). 34bis-7: 12.28 (1H, s, NH), 7.89 (1H, d, CHarom, J = 8.8 Hz), 7.64 (1H, d, CHarom, J = 8.8 Hz), 7.40-7.50 (3H, m, CHarom), 5.81 (2H, s, NH$_2$), 4.96 (2H, s, CH).

Example of Method F4: Demethylation

Example 35

N-(5-(3,5-difluorophenylthio)-6-hydroxy-1H-pyrazolo[3,4-b]pyridin-3-yl)-4-(4-methylpiperazin-1-yl)-2-(tetrahydro-2H-pyran-4-ylamino)benzamide

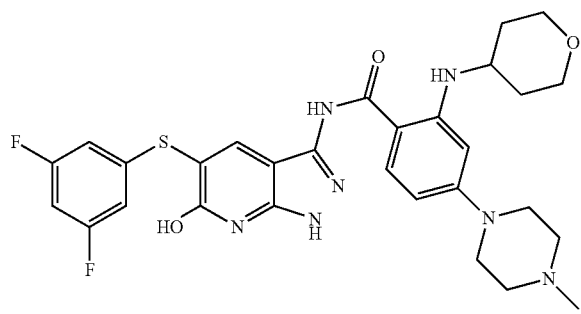 [SMILES: CN1CCN(c2ccc(C(=O)NC(=N)c3cc(Sc4cc(F)cc(F)c4)c(O)nc3N)c(NC3CCOCC3)c2)CC1]

443 µl (3 eq) of a solution of 1 M boron tribromide in dichloromethane is added to a solution of 90 mg (0.148 mmol) of N-(5-(3,5-difluorophenylthio)-6-methoxy-1H-pyrazolo[3,4-b]pyridin-3-yl)-4-(4-methylpiperazin-1-yl)-2-(tetrahydro-2H-pyran-4-ylamino)benzamide (example 18) in 4 ml of 1,2-dichloroethane at 0° C. The reaction medium is stirred at 60° C. for 3 hours and then cooled in an ice bath before adding methanol. The solvents are evaporated and the residue is redissolved in a mixture of methanol and ethyl acetate. The solid formed is filtered, redissolved in 3 ml of tetrahydrofuran and is added to 1 N soda solution. The reaction medium is stirred for 18 hours at room temperature. The pH of the solution is adjusted to 8-9 and the aqueous phase is extracted with ethyl acetate. The organic phase is dried on magnesium sulfate and the crude product is purified on a silica gel column (dichloromethane/methanol as eluent) to yield 21 mg (24%) of N-(5-(3,5-difluorophenylthio)-6-hydroxy-1H-pyrazolo[3,4-b]pyridin-3-yl)-4-(4-methylpiperazin-1-yl)-2-(tetrahydro-2H-pyran-4-ylamino)benzamide in the form of a yellow powder.

LCMS (EI, m/z): (M+1) 596.13.

$^1$H NMR: δH ppm (400 MHz, DMSO): 12.96 (1H, broad flat singlet), 12.02 (1H, broad flat singlet), 10.64 (1H, bs, NH), 8.46 (1H, bs), 8.09 (1H, bs), 7.72 (1H, d, $CH_{arom}$), 6.97-7.10 (1H, m, $CH_{arom}$), 6.60-6.74 (2H, m, $CH_{arom}$), 6.28 (1H, dd, $CH_{arom}$), 6.13 (1H, d, $CH_{arom}$), 3.80-3.90 (2H, m, $CH_{pyranone}$), 3.65-3.77 (1H, m, $CH_{pyranone}$), 3.50 (2H, t, $CH_{pyranone}$)$_5$ 3.25-3.32 (4H, m, 2*$CH_2$), 2.37-2.45 (4H, m, 2*$CH_2$), 2.22 (3H, 5, $CH_3$), 1.91-2.00 (2H, m, $CH_{pyranone}$), 1.28-1.43 (2H, m, $CH_{pyranone}$).

II. Biological Tests of the Compounds According to the Invention

Test for Measuring Inhibition of TrkA, TrkB or TrkC Kinase

These kinases are produced by Millipore or Kinome Scan (DiscoverX) and are screened according to the manufacturer's protocols.

The results are presented in the table below:

| | Enzymatic inhibition at 10 nM (%) | | | | |
|---|---|---|---|---|---|
| | 30 | 30-9 | 27-1 | 14-11 | 30-8 |
| TrkA | 93.8 | 55 | 97.8 | 97.4 | 99 |
| TrkB | 84 | 98 | 93 | 88 | 96.6 |
| TrkC | 64 | | 96.8 | 93.4 | 97.3 |

In Vivo Analgesic Activity Against NGF-Induced Hyperalgesia

Compounds of general formula (I), and particularly compound 30 have been tested in vivo in the mouse receiving an intraplantar injection of NGF. This treatment elicits thermal hyperalgesia (Schuligoi et al., 1998, *Neuroscience Letters* 252:147-149). Briefly, male mice received a 10 µl subcutaneous injection of NGFβ (1 µg; SIGMA) into the plantar surface of the right hind paw. Following the injection, mice were returned to their cages. Four hours after NGF injection, mice were placed on the centre of the hot plate analgesimeter (BIO-HC2.00, Bioseb, France), and the latency time to the first brisk lift or lick of a hind paw or jumping will be recorded. A maximum cut-off time of 60 sec is used to prevent tissue damage. Results are given as the mean±s.e.m. of the latency time. Test compounds were given 30 min before NGF injection.

Figure 1B:
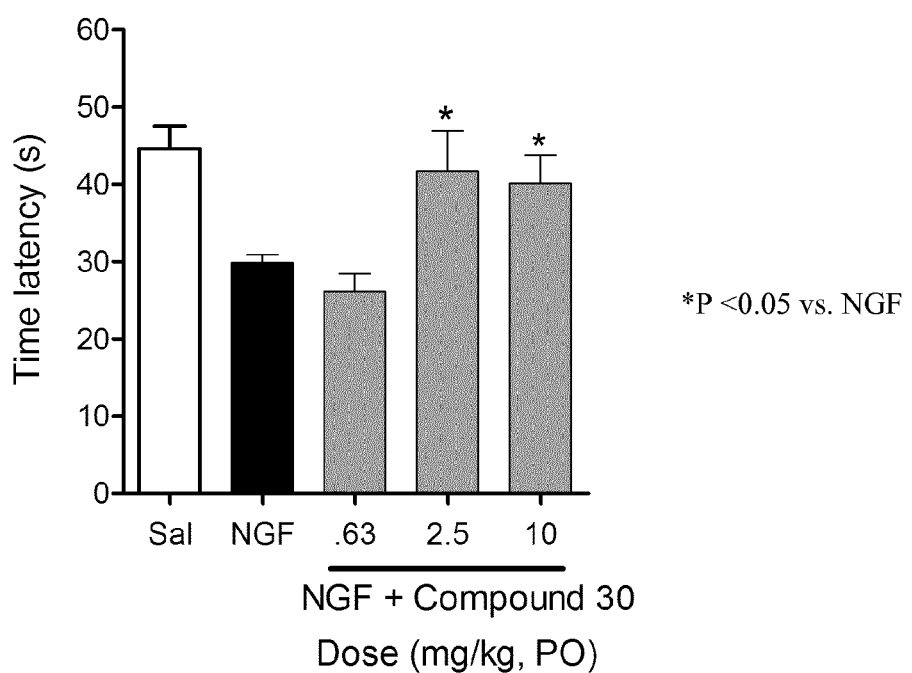
FIG. 1B represents a histogram of the inhibition effect on NGF-induced hyperalgesia (time latency) of Compound 30 administered to a mouse at various doses by oral route.

FIG. 1 shows that Compound 30 dose-dependently inhibited NGF-induced hyperalgesia, either when administered by intraperitoneal route (FIG. 1A) or oral route (FIG. 1B). Complete or nearly complete reversion of NGF-induced hyperalgesia occurred at doses of 10 mg/kg and lower (* P<0.05 vs NGF alone by ANOVA).

In Vivo Analgesic Activity in the Formalin Test in Rats

The method was adapted from Wheeler-Aceto et al. (Pain, 1990, 40:229-38) and Bardin et al. (2003, *Pharmacology* 67: 182-194). In the second phase of the test, Compound 30 inhibited paw licking by 44% vs. vehicle-treated animals (P<0.05 by ANOVA).

In Vivo Analgesic Activity Against Acute and Chronic Inflammatory Pain Induced by Complete Freund Adjuvant (CFA)

Male Sprague-Dawley rats [Crl:OFA(SD) Charles River Lyon, France] weighing 160-180 g upon arrival were used. Rats were first daily habituated to handling and to the test apparatus used for the von-Frey and hot-plate models one week before the induction of inflammation. On the following Monday, they were subjected to nociceptive tests for determination of basal scores. Then, rats will be given a 100 µl subcutaneous injection of CFA (1 mg/1 ml; Sigma) into the plantar surface of the right hind paw (day 0: D0). Saline was injected by the same route in the placebo group.

Figure 2A:
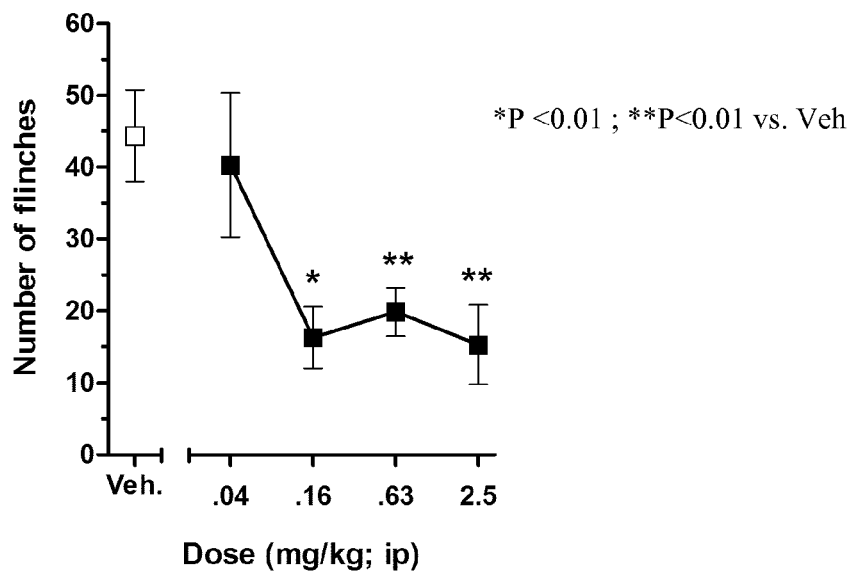
FIG. 2A represents a graph relative to the number of spontaneous flinches after administration to a rat by intraperitoneal route of Compound 30 at various doses.
Figure 2B:
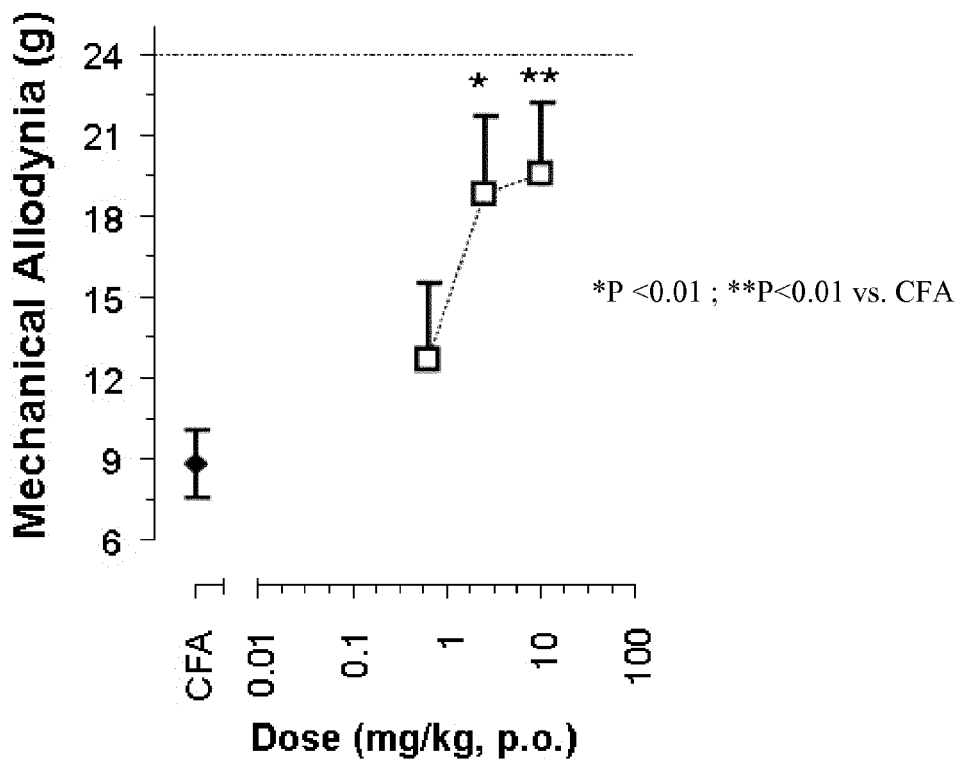
FIG. 2B represents a graph relative to the measure of mechanical allodynia after oral administration to a rat of Compound 30 at various doses.

Then each rat was placed on an elevated plastic mesh in a clear plastic cage and the number of spontaneous flinches (measurement of spontaneous pain) was recorded during 10 min. Mechanical allodynia was assessed using the von Frey Hair test. Each rat was placed on an elevated plastic mesh in a clear plastic cage and allowed to adapt to the testing environment for at least 5 min. The von Frey Hairs (Semmes-Weinstein monofilaments, Stoelting Ill., USA; 0.6, 1.4, 2, 4, 6, 8, 10, and 15 g) was applied to the plantar surface of the injected paw from below the mesh floor for is in the ascending order. The threshold was determined as the lowest force that evoked a withdrawal response. The test was repeated three times with an interval of 5 min between each test. The paw withdrawal score to the tactile stimulus was determined as the average of the 3 measurements. Animals received intraperitoneal or oral injections of test compounds. Compounds of general formula (I) displayed analgesic activity in this test at doses of 0.5 to 20 mg/kg, both against acute inflammatory pain (flinches) and mechanical allodynia. For instance, Compound 30 dose-dependently inhibited flinches after intraperitoneal injection (FIG. 2A) and mechanical allodynia after oral administration (FIG. 2B). Compound completely or nearly completely reversed spontaneous pain from 0.16 mg/kg and mechanical allodynia from 2.5 mg/kg.

In Vivo Analgesic Activity Against Chronic Pain in a Model of Bone Cancer Pain

Bone cancer produces one of the most painful conditions that affect humans and animals. It is also the most common pain in human patients with advanced cancer and it remains difficult to treat and contributes significantly to increased morbidity and reduced quality of life. Several models of murine osteosarcoma-induced pain have been developed (Pacharinsak and Beitz, Animal models of cancer pain. Comp Med. 2008 June; 58:220-33.).

We induced bone cancer pain by implanting 10 µl of PBS containing $2 \times 10^5$ NCTC 2472 osteolytic fibrosarcoma cells into the tibia of 5-6 week-old C3H/HeNCrl mice under isoflurane anesthesia. The presence of these cells induces osteolytic lesions in bone due to both an increase in the number of osteoclasts and to their activation, which leads to the destruction of bone tissue and the invasion of the adjacent soft tissue and pain related behaviours. Pain-related behaviours were evaluated both prior to and at 3, 7, 10, 14 and 17 days following tumor cell injection. The following behaviors were evaluated:

Limb use during spontaneous ambulation on a scale of 0-4 where 0=normal use and 4=no use of the injected hind paw;

Light touch-evoked pain. Light touch induced flinching were measured after the 1 min period of non noxious stimulation of the tumor injected paw with a small paint brush. The numbers of flinches were recorded over 5 min.

Figure 3A:
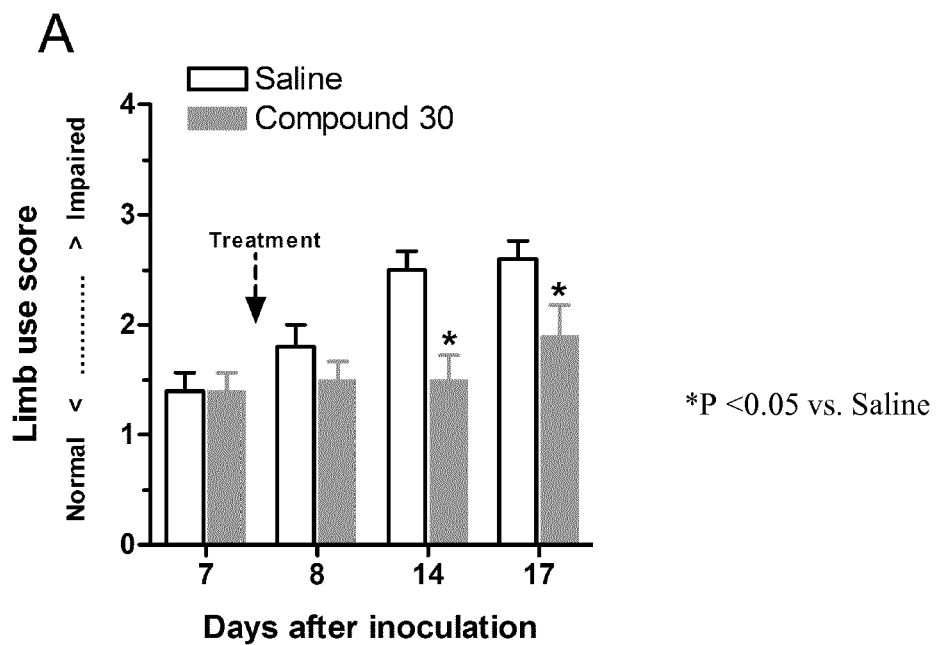
FIG. 3A represents a histogram of the limb use score as a function of time after administration of a saline solution or of Compound 30 at the dose of 2.5 mg/kg.
Figure 3B:
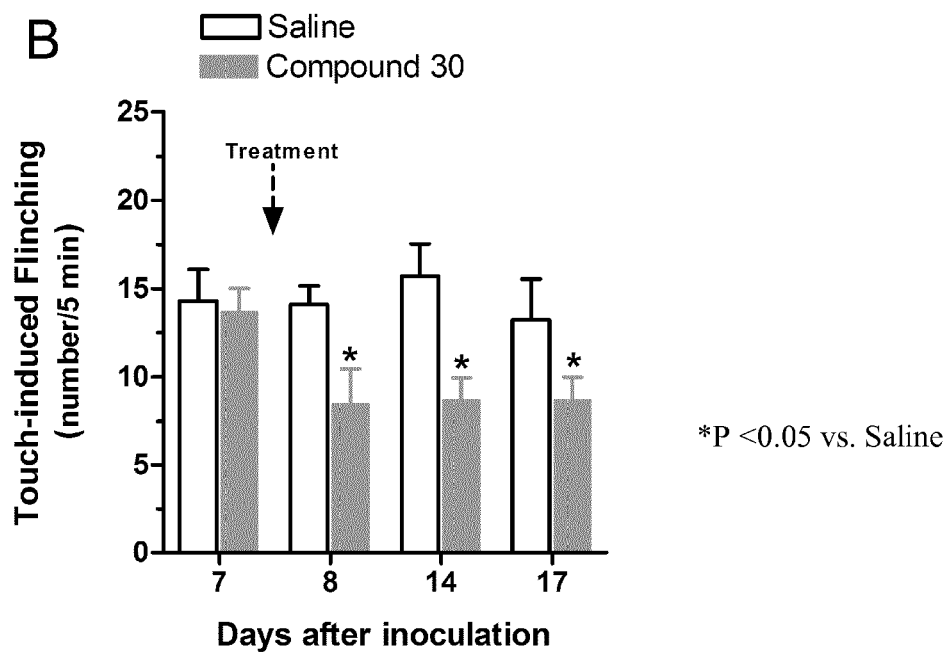
FIG. 3B represents a histogram of the light touch-evoked flinching as a function of time after administration of a saline solution or of Compound 30 at the dose of 2.5 mg/kg.

For drug treatment, animals were treated chronically with the test compound or saline, administered 30 min before testing by i.p. route, starting on day 7 following injection of tumor cells, when pain-related behaviors were clearly present. As an example, compound 30 at the dose of 2.5 mg/kg, significantly reduced limb use score from day 10 (FIG. 3A) and light touch-evoked flinching from day 8 (FIG. 3B).

Comparative Experiments:

An in vitro kinase glo plus-based kinase assay (Promega) was developed in a 96 wells assay plate format to assess the inhibiting properties of compounds on tropomyosin related kinases (Trk) receptors, using the soluble intracellular segment of theses receptors, containing the kinase activity (TrkA (or NTRK1; 400 ng/well; Millipore) and TrkB (or NTRK2; 200 ng/well; Invitrogen)). The assay was performed in a final volume 50 µl containing 8 mM MOPS (pH 7.0), 0.2 mM EDTA, 40 mM Mg Acetate, 25 mM 2-glycerophosphate, 1 mM DTT, 2 mM Na Vanadate, 0.01% Triton X-100, either 1 (TrkA) or 2.5 (TrkB) mg/ml poly EY (poly Glu-Tyr 4:1; substrate) and 30 (Trk A) or 40 (Trk B) µM ATP. Test compounds were dissolved (10 mM), and diluted in 100% DMSO through serial dilution, with tested half log concentrations generally ranging from 1 to 30 000 nM final concentration (5% DMSO final), but these concentrations could be adapted according to compound's potency. The reaction was started by addition of ATP, and the plates were incubated for 2 hours at 30° C. Plates were removed from incubator, and 50 µl of kinase-glo plus was added to each well, followed by a 10 minute incubation at room temperature. The luciferase-induced luminescence, which is proportional to the ATP remaining in the well, was measured on a luminometer. Controls on each plates included wells with the kinase alone (maximal ATP consumption, or 0% inhibition), wells without the kinase (maximal ATP signal or 100% inhibition), and wells with 20 µM staurosporine (positive control of inhibition). A full concentration-response inhibition curve with K252a (half log concentrations from 1 to 10 000 nM) was also included on each plate. $pIC_{50}$ values were derived from fitting the inhibition curve of ATP consumption, using the 0-100% luminescence range defined by the controls, with a sigmoidal dose-response equation: % Inhibition=$100-(100/(1+10^{(X+ pIC 50)*nH}))$, where X is the logarithm of the tested compound concentrations. Under these conditions, K252a had a $pIC_{50}$ of 7.46±0.07 on TrkA (mean±SD; N=42; $IC_{50}$=30 nM), and 7.16±0.18 on TrkB (N=36; $IC_{50}$=74 nM), these values being consistent with in vitro literature data (Tapley et al (1992) Oncogene 7: 371-381, Tan et al (2007) Mob Pharmacol 72: 1440-1446).

The results obtained are presented below:

| Structure | Compound | IC$_{50}$ (µM) | |
|---|---|---|---|
| | | TrkA | TrkB |
| 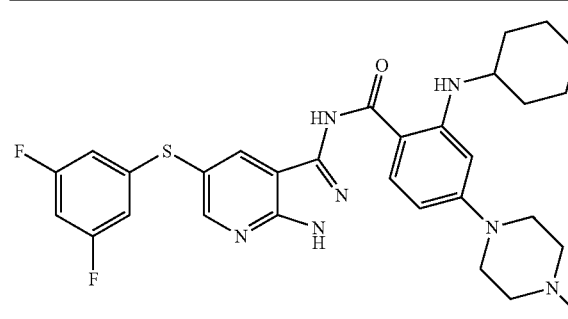 | 30 | 0.045 | 0.031 |

$C_{29}H_{31}F_2N_7O_2S$

-continued

| Structure | Compound | IC$_{50}$ (μM) | |
| --- | --- | --- | --- |
| | | TrkA | TrkB |
| C$_{28}$H$_{31}$F$_2$N$_9$O$_2$ | A | about 10 | >100 |
| C$_{28}$H$_{31}$F$_2$N$_9$O$_2$ | B | 3.3 | 18 |
| C$_{29}$H$_{32}$F$_2$N$_8$O$_2$ | C | 2.1 | 5.8 |
| C$_{12}$H$_8$F$_2$N$_4$S | D | 22 | 35 |

-continued

| Structure | Compound | IC$_{50}$ (μM) TrkA | TrkB |
|---|---|---|---|
| 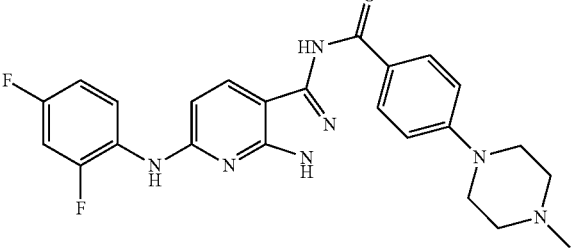 C$_{24}$H$_{22}$F$_2$N$_6$OS | E | 0.04 | 0.048 |
| 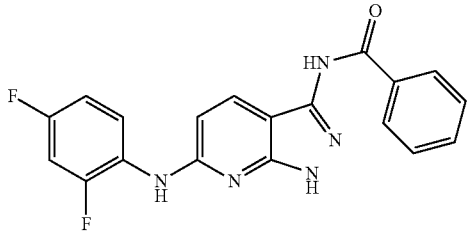 C$_{19}$H$_{12}$F$_2$N$_4$OS | F | 0.31 | 0.31 |

The invention claimed is:

1. A method for the treatment of pain comprising the administration to a person in need thereof of an effective dose of a compound of following general formula (I):

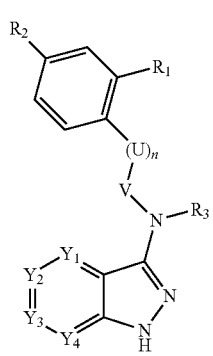

or a pharmaceutically acceptable salt of same, a tautomer of same, or a stereoisomer or mixture of stereoisomers of same in any proportions,
wherein:
  $Y_1$ and $Y_4$ each represent, independently of each other, a CH group or a nitrogen atom on the condition that at least one of $Y_1$ and $Y_4$ represent a nitrogen atom,
  $Y_2$ represents a C—X—Ar group,
  $Y_3$ represents a C—W group,
  Ar represents an aryl or heteroaryl group optionally substituted by one or more groups selected from a halogen atom, (C$_1$-C$_6$)alkyl, (C$_1$-C$_6$)haloalkyl, (C$_1$-C$_6$)haloalkoxy, (C$_1$-C$_6$)halothioalkoxy, CN, NO$_2$, OR$_{11}$, SR$_{12}$, NR$_{13}$R$_{14}$, CO$_2$R$_{15}$, CONR$_{16}$R$_{17}$, SO$_2$R$_{18}$, SO$_2$NR$_{19}$R$_{20}$, COR$_{21}$, NR$_{22}$COR$_{23}$, NR$_{24}$SO$_2$R$_{25}$, and R$_{26}$NR$_{27}$R$_{28}$ and/or optionally fused to a heterocycle, X represents a divalent group selected from O, S, S(O), S(O)$_2$, NR$_4$, S(NR$_4$), S(O)(NR$_4$), S(O)$_2$(NR$_4$), NR$_4$S, NR$_4$S(O), NR$_4$S(O)$_2$, CH$_2$, CH$_2$S, CH$_2$S(O), CH$_2$S(O)$_2$, SCH$_2$, S(O)CH$_2$, S(O)$_2$CH$_2$, CH$_2$CH$_2$, CH=CH, C≡C, CH$_2$O, OCH$_2$, NR$_4$CH$_2$, and CH$_2$NR$_4$,
W represents an R$_5$, SR$_5$, OR$_5$ or NR$_5$R$_6$ group,
U represents a CH$_2$ or NH group, one or more hydrogen atoms which may be replaced by a (C$_1$-C$_6$)alkyl group,
V represents C(O), C(S) or CH$_2$,
n represents 0 or 1,
R$_1$ represents a hydrogen atom, or an OR$_7$ or NR$_7$R$_8$ group,
R$_2$ represents a hydrogen atom, an optionally substituted heterocycle, NO$_2$, OR$_9$ or NR$_9$R$_{10}$,
R$_3$, R$_4$, R$_{11}$ to R$_{25}$ and R$_{27}$ to R$_{28}$ each represent, independently of each other, a hydrogen atom or a (C$_1$-C$_6$)alkyl group,
R$_5$ and R$_6$ each represent, independently of each other, a hydrogen atom or a (C$_1$-C$_6$)alkyl, optionally substituted aryl or optionally substituted benzyl group,
R$_7$, R$_8$, R$_9$ and R$_{10}$ each represent, independently of each other, a hydrogen atom or an optionally substituted (C$_1$-C$_6$)alkyl or (C$_3$-C$_{12}$)cycloalkyl group or an optionally substituted heterocycle, and
R$_{26}$ represents a (C$_1$-C$_6$)alkyl group.

2. The method according to claim 1, wherein the pain is a nociceptive pain, an inflammatory pain, a neuropathic pain, an idiopathic pain or a psychogenic pain.

3. The method according to claim 2, wherein the pain is an inflammatory pain or neuropathic pain.

4. The method according to claim 1, wherein the pain is due to cancer, to a nerve injury or to rheumatic diseases.

5. The method according to claim 1, wherein:
  $Y_1$=CH or N, and
  $Y_4$=N.

6. The method according to claim 1, wherein:

$Y_1$ represents a CH group, and $Y_4$ represents a nitrogen atom.

7. The method according to claim 1, wherein X represents a divalent group selected from S, S(O), S(O)$_2$, NR$_4$, CH$_2$, CH$_2$S, CH$_2$S(O), CH$_2$S(O)$_2$, CH$_2$O, CH$_2$NR$_4$, NHS(O)$_2$, SCH$_2$, S(O)CH$_2$, S(O)$_2$CH$_2$, S(O)$_2$NH, OCH$_2$, NR$_4$CH$_2$, CH$_2$CH$_2$, CH=CH, and C≡C, wherein the first atom of these groups is bound to atom C̲ of chain C̲—X—Ar.

8. The method according to claim 7, wherein X represents a divalent group selected from S, S(O), S(O)$_2$, NR$_4$, CH$_2$, SCH$_2$, S(O)CH$_2$, S(O)$_2$CH$_2$, S(O)$_2$NH, CH$_2$CH$_2$, C≡C, OCH$_2$, and NR$_4$CH$_2$, wherein the first atom of these groups is bound to atom C̲ of chain C̲—X—Ar.

9. The method according to claim 8, wherein X represents a divalent group selected from S, S(O)$_2$, CH$_2$, SCH$_2$, S(O)$_2$CH$_2$, S(O)$_2$NH, CH$_2$CH$_2$, and C≡C, wherein the first atom of these groups is bound to atom C̲ of chain C̲—X—Ar.

10. The method according to claim 1, wherein Ar represents an aryl group optionally substituted by one or more groups selected from a halogen atom, (C$_1$-C$_6$)alkyl, (C$_1$-C$_6$)haloalkyl, (C$_1$-C$_6$)haloalkoxy, (C$_1$-C$_6$)halothioalkoxy, CN, NO$_2$, OR$_{11}$, SR$_{12}$, NR$_{13}$R$_{14}$, CO$_2$R$_{15}$, CONR$_{16}$R$_{17}$, SO$_2$R$_{18}$, SO$_2$NR$_{19}$R$_{20}$, COR$_{21}$, NR$_{22}$COR$_{23}$ and NR$_{24}$SO$_2$R$_{25}$; or a pyridine group.

11. The method according to claim 10, wherein Ar represents a phenyl group optionally substituted by one or more groups selected from a halogen atom, (C$_1$-C$_6$)alkyl, (C$_1$-C$_6$)haloalkyl, (C$_1$-C$_6$)haloalkoxy, (C$_1$-C$_6$)halothioalkoxy, CN, NO$_2$, OR$_{11}$, SR$_{12}$, NR$_{13}$R$_{14}$, CO$_2$R$_{15}$, CONR$_{16}$R$_{17}$, SO$_2$R$_{18}$, SO$_2$NR$_{19}$R$_{20}$, COR$_{21}$, NR$_{22}$COR$_{23}$ and NR$_{24}$SO$_2$R$_{25}$; or a pyridine group.

12. The method according to claim 11, characterized in that Ar represents a group selected from the following groups:

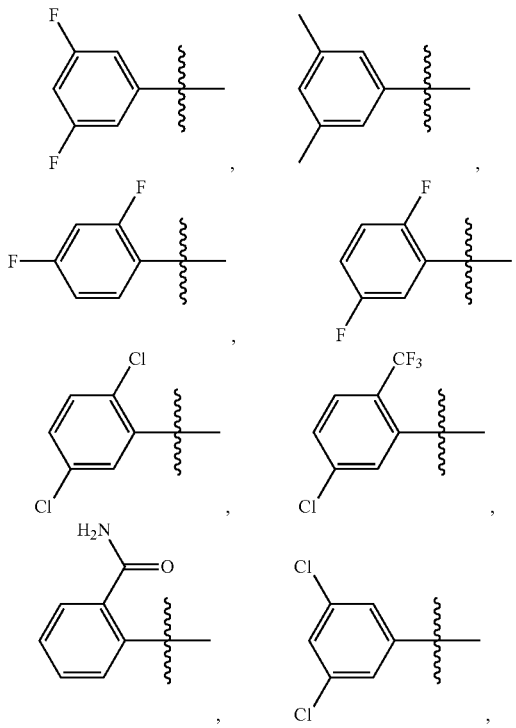

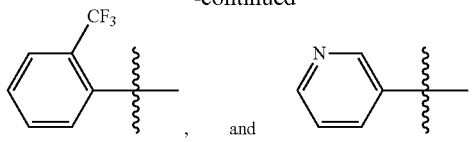

and

13. The method according to claim 1, wherein W represents an R$_5$, SR$_5$, OR$_5$ or NR$_5$R$_6$ group, with R$_5$ and R$_6$ representing, independently of each other, a hydrogen atom or a (C$_1$-C$_6$)alkyl group.

14. The method according to claim 1, wherein:

$R_3$=H,

U=CH$_2$ or NH,

V=C(O) or C(S), and n=0 or 1.

15. The method according to claim 14, wherein:

V=C(O), and n=0.

16. The method according to claim 1, wherein R$_1$ represents a hydrogen atom or an NR$_7$R$_8$ group, with R$_7$ representing a hydrogen atom and R$_8$ representing an optionally substituted (C$_3$-C$_{12}$)cycloalkyl group or an optionally substituted heterocycle.

17. The method according to claim 16, wherein R$_1$ represents one of the following groups:

H,

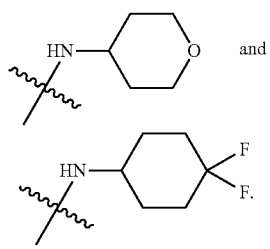

18. The method according claim 1, wherein R$_2$ represents NO$_2$, NR$_9$R$_{10}$ or a heterocycle optionally substituted by (C$_1$-C$_6$)alkyl or NH$_2$.

19. The method according to claim 18, wherein R$_2$ represents one of the following groups:

NH$_2$, NH(CH$_2$)$_3$NMe$_2$, NMe(CH$_2$)$_3$NMe$_2$, NO$_2$,

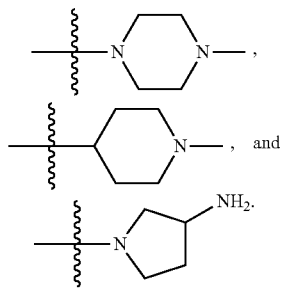

20. The method according to claim 1, wherein the compound of formula (I) is selected from the following compounds:

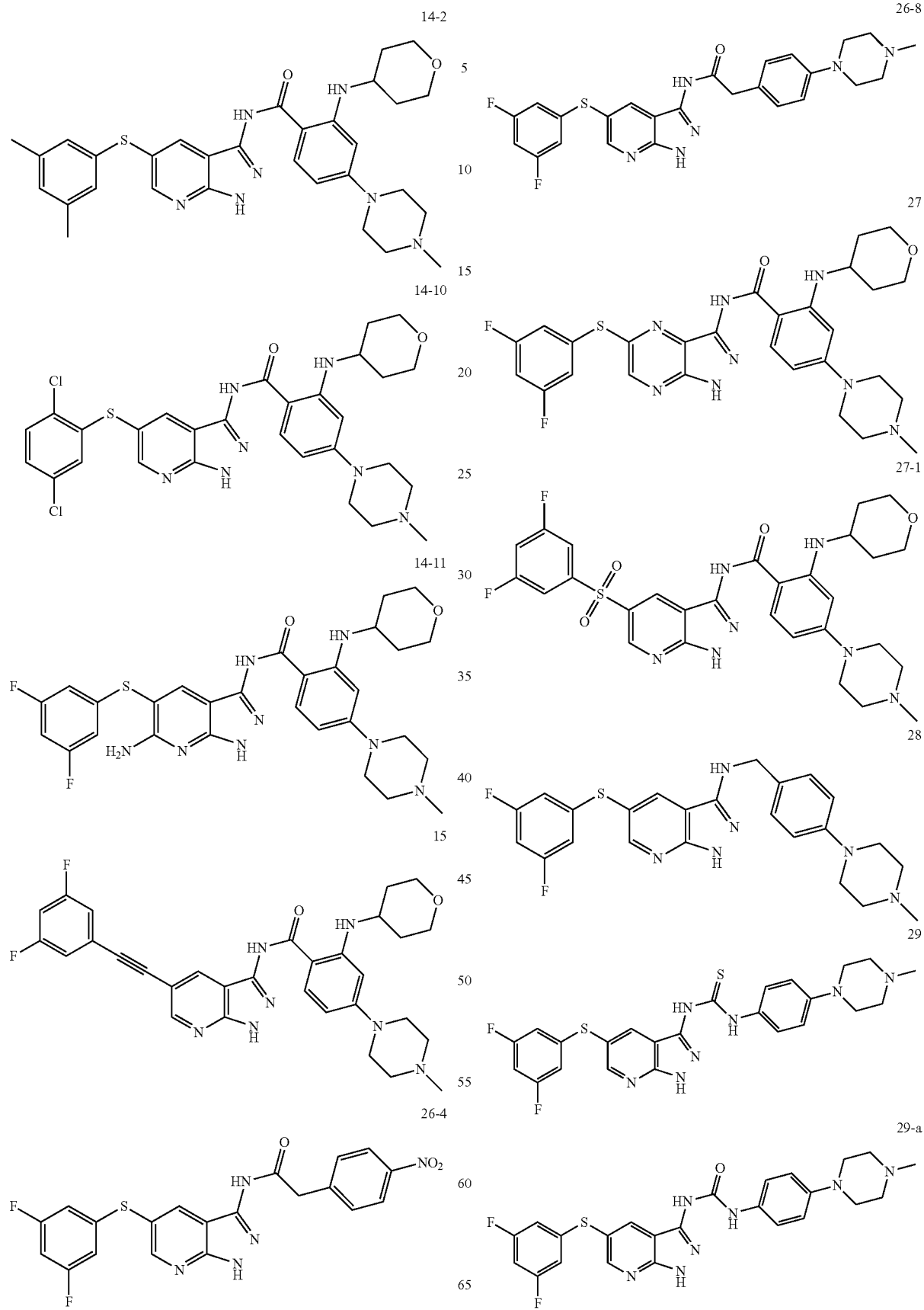

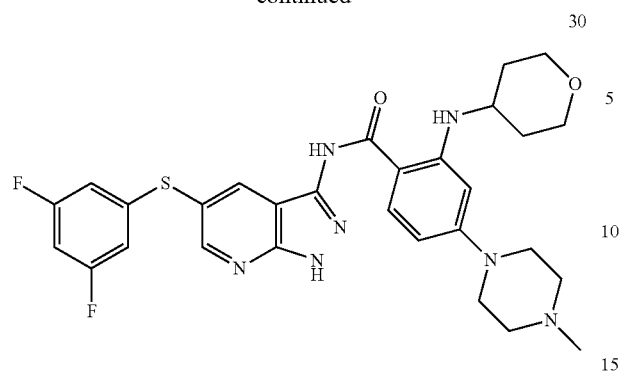
30
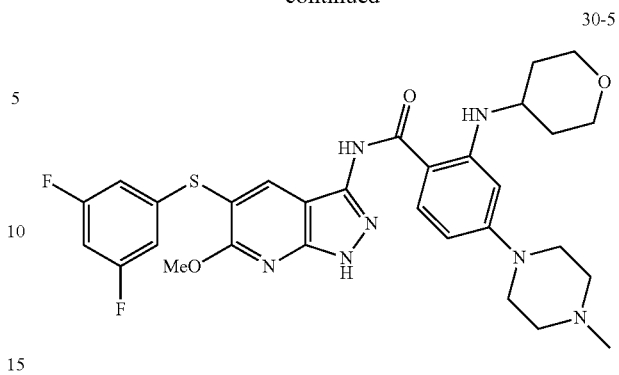
30-5
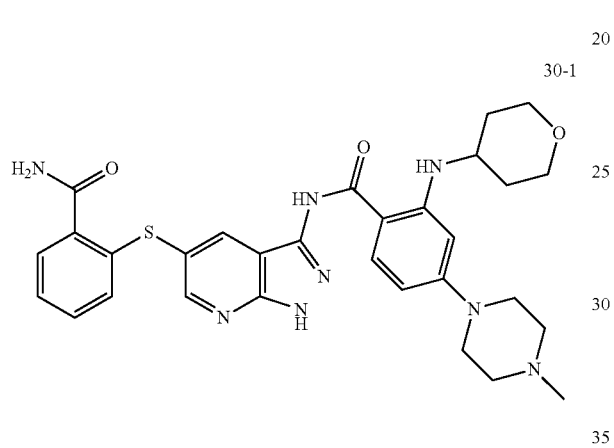
30-1
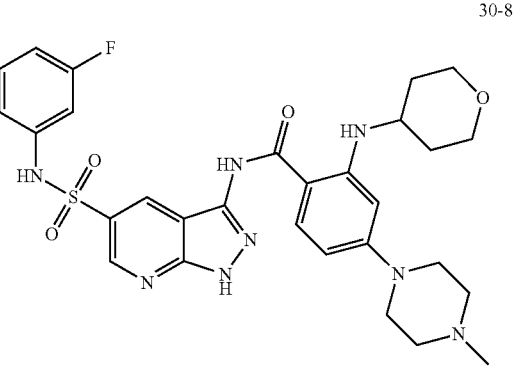
30-8
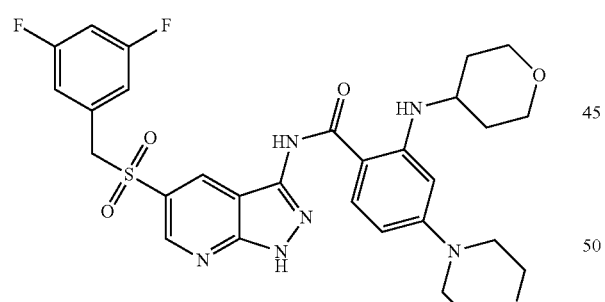
30-3
30-9
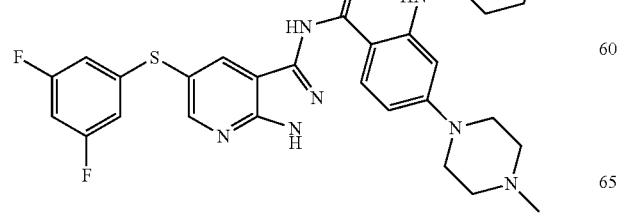
30-4
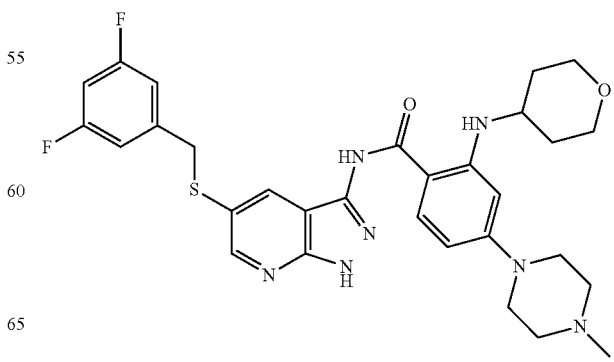
30-10

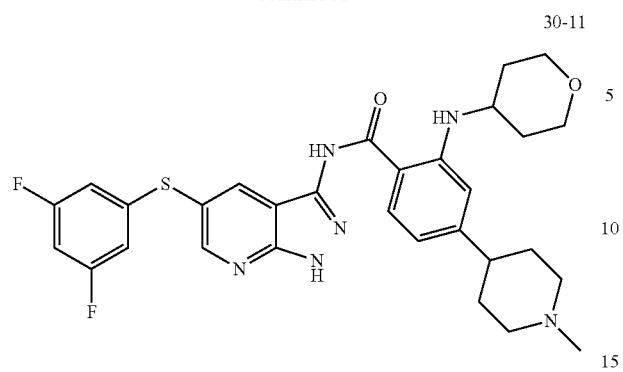
30-11
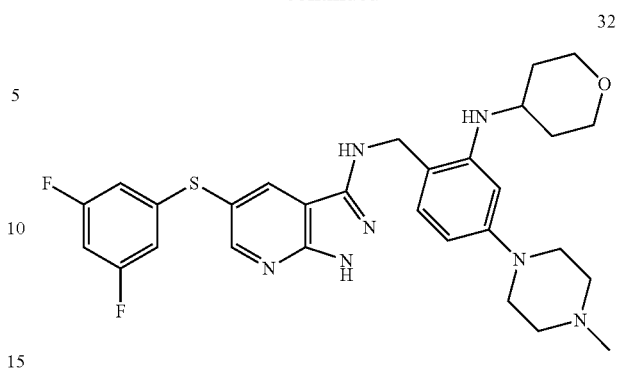
32
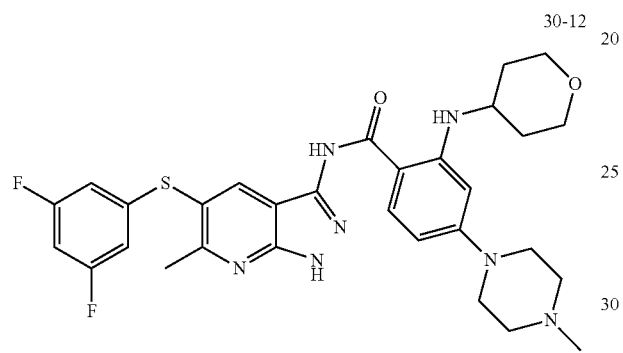
30-12
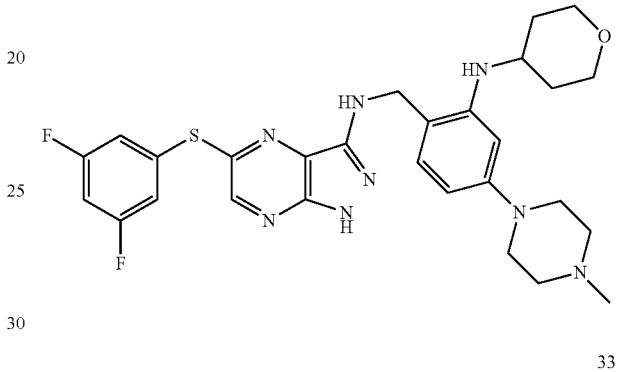
32-1
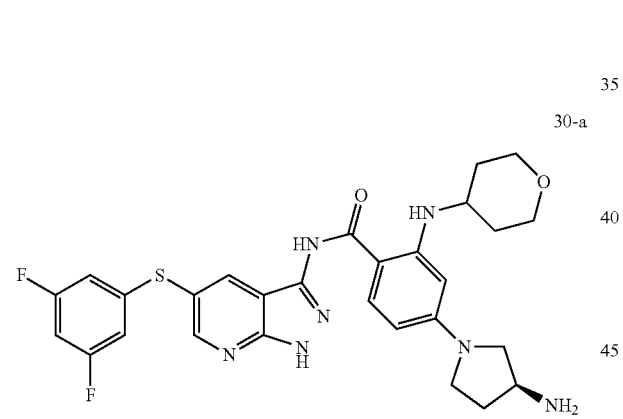
30-a
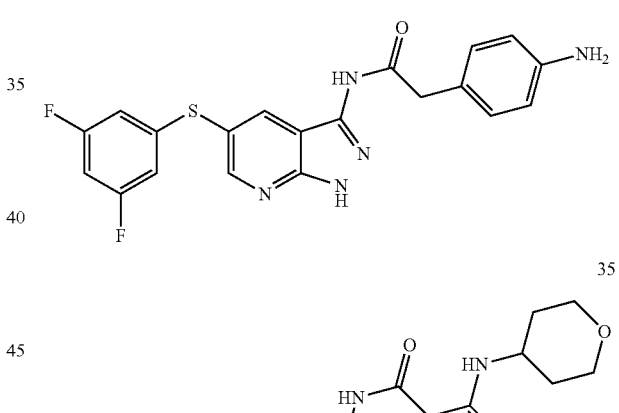
33
35
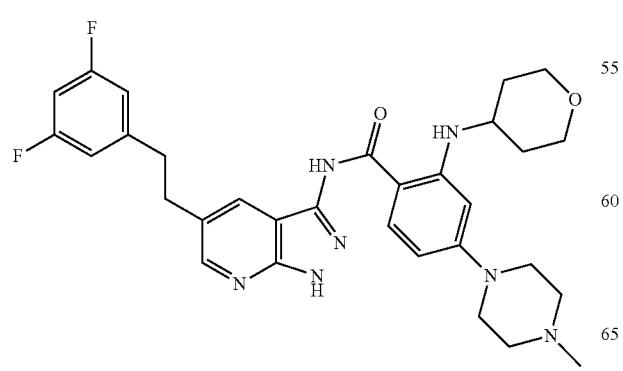
31
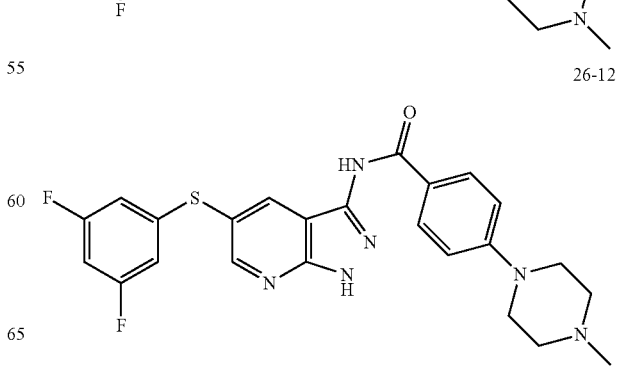
26-12

30-69
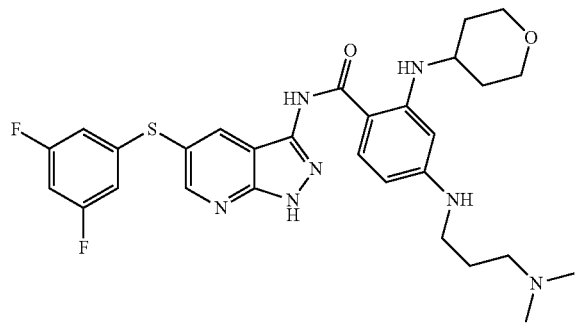
27-2
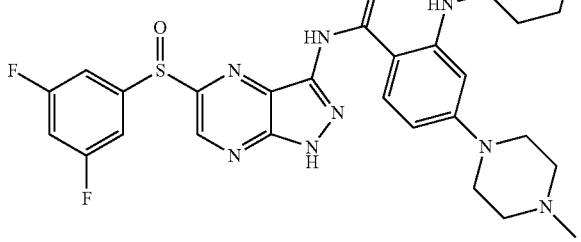
27-3
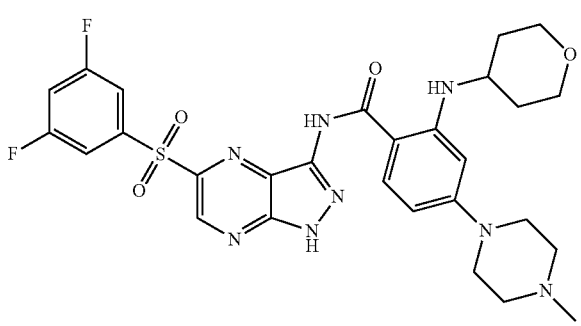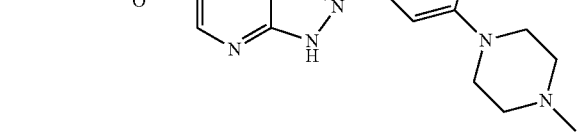
14bis
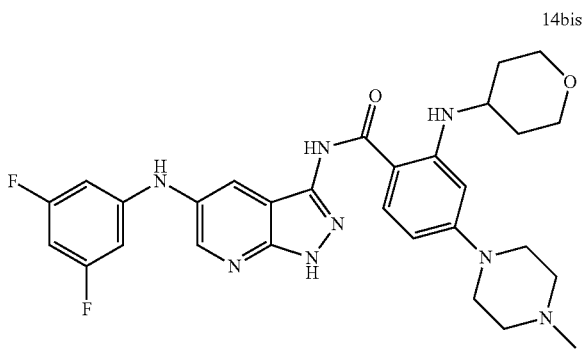
30-72
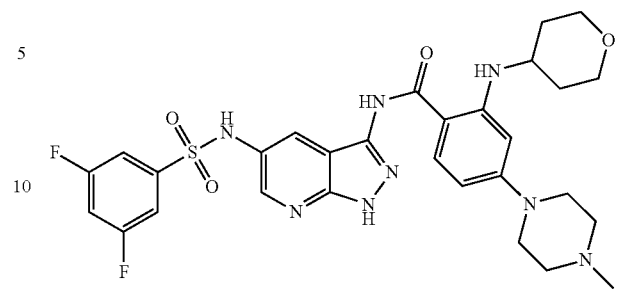
31-1
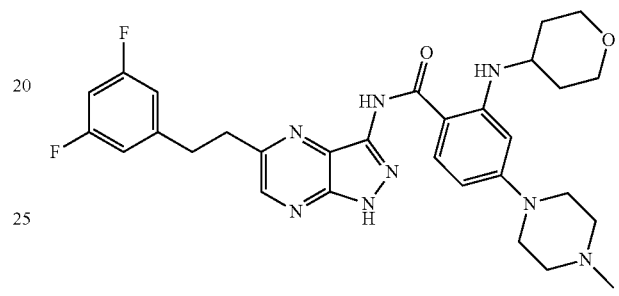
30-13
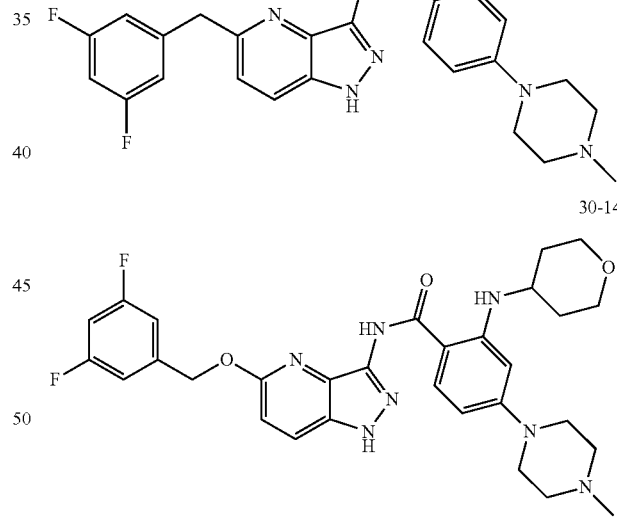
30-14
30-15
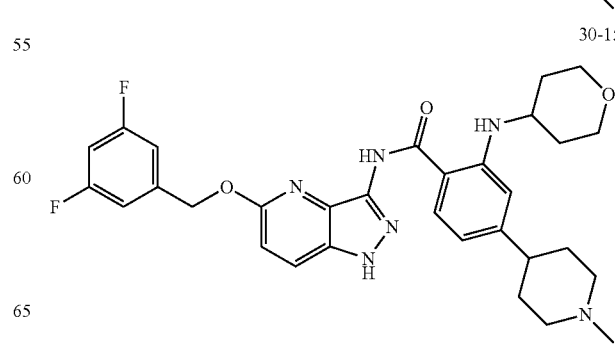

30-16
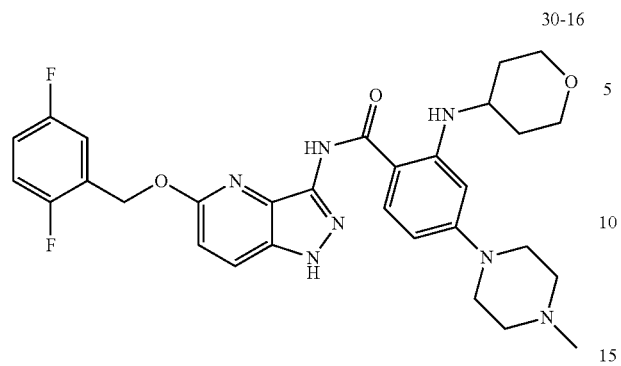
30-17
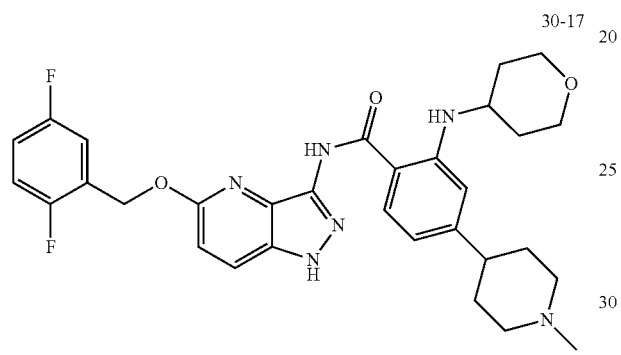
30-18
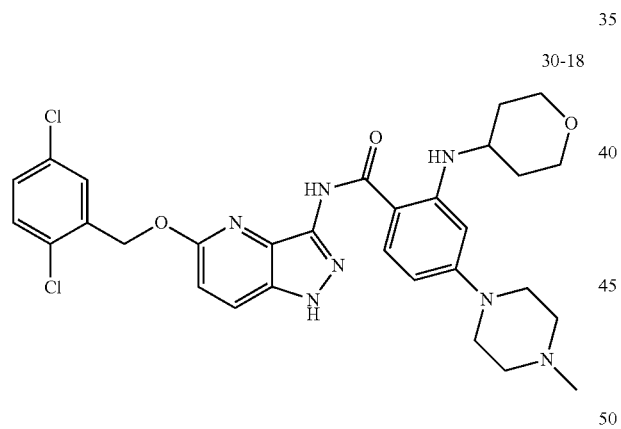
30-19
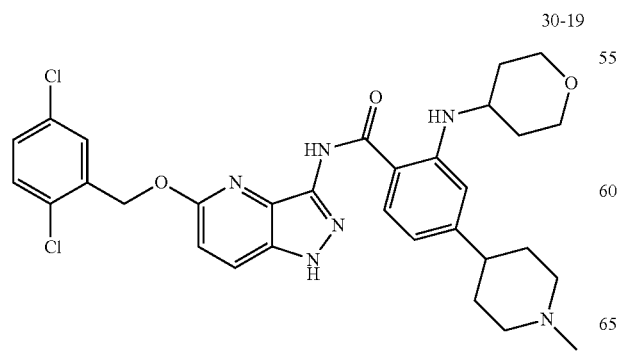
30-20
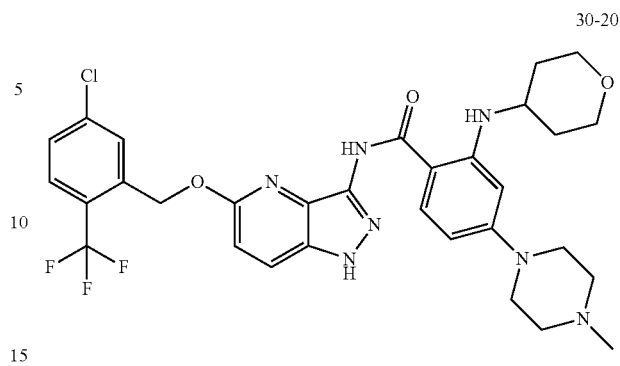
30-21
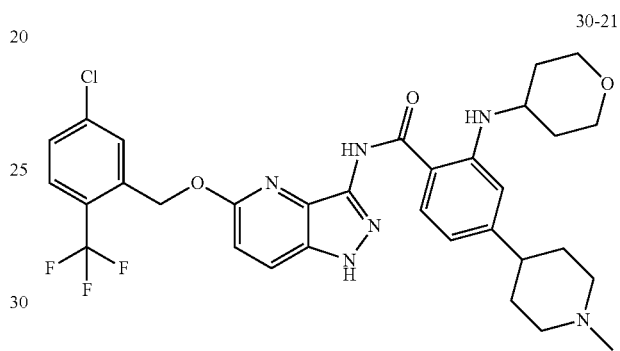
30-22
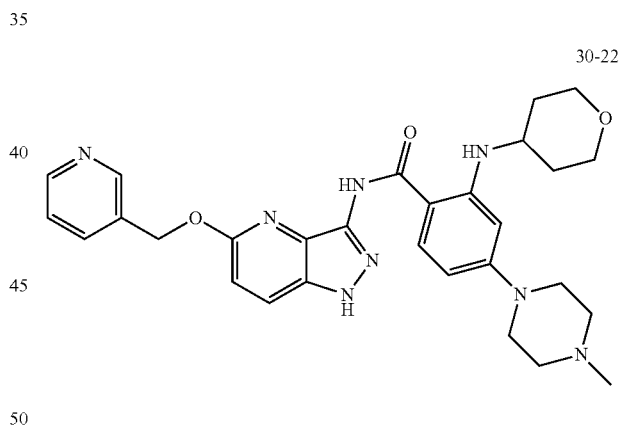
30-23
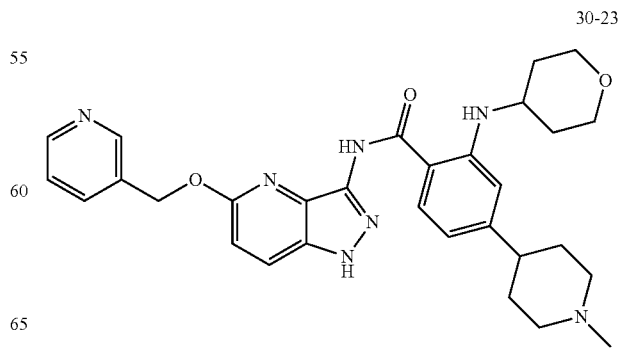

30-24
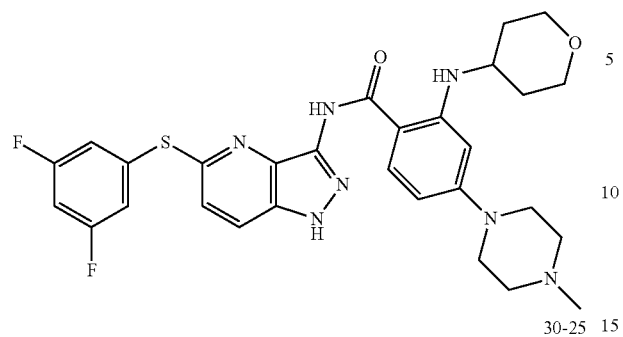
30-29
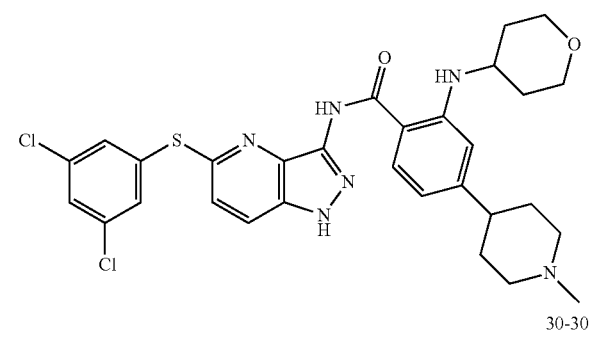
30-25
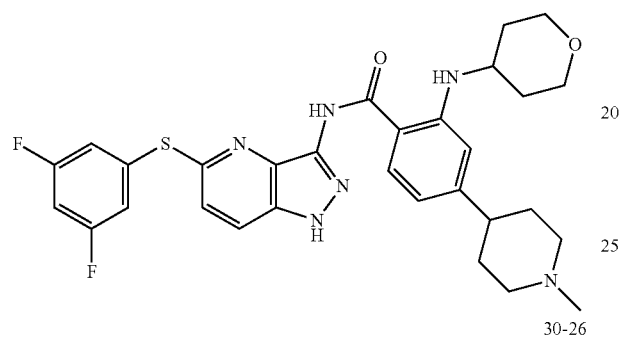
30-30
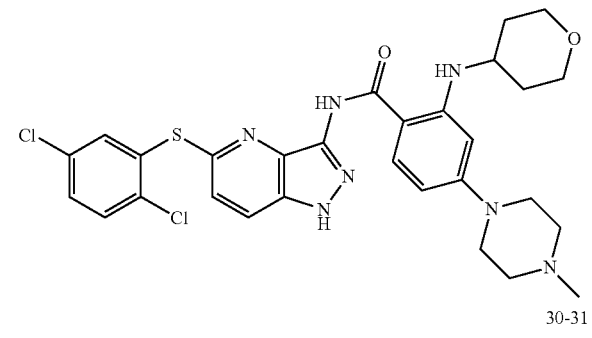
30-26
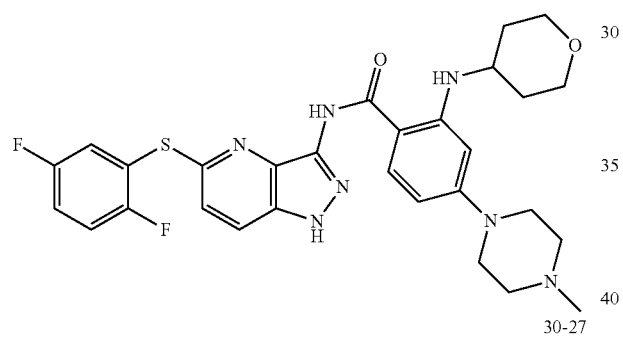
30-31
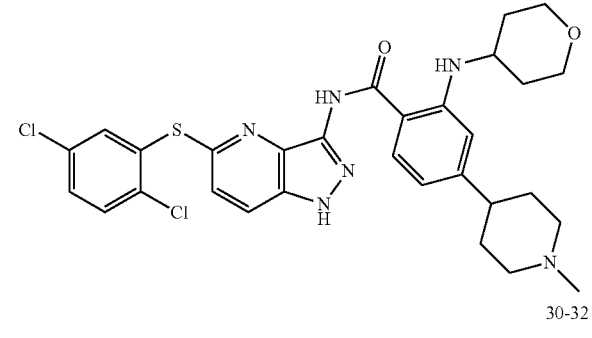
30-27
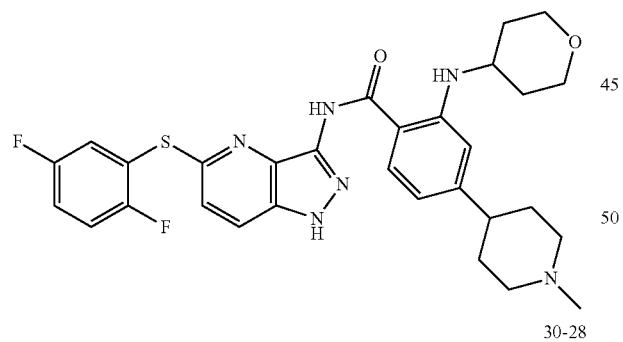
30-32
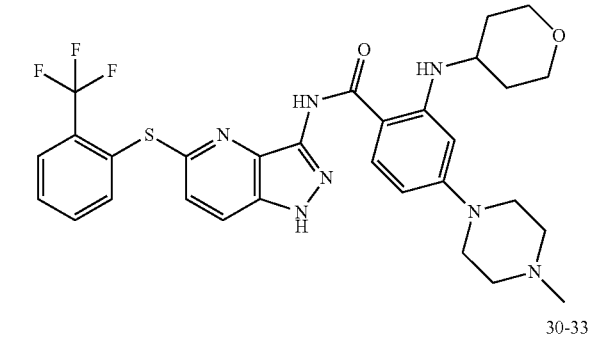
30-28
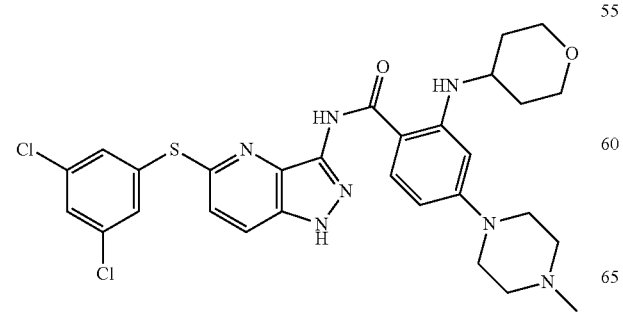
30-33
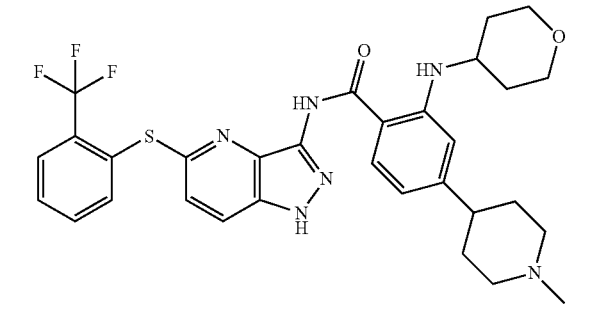

30-34
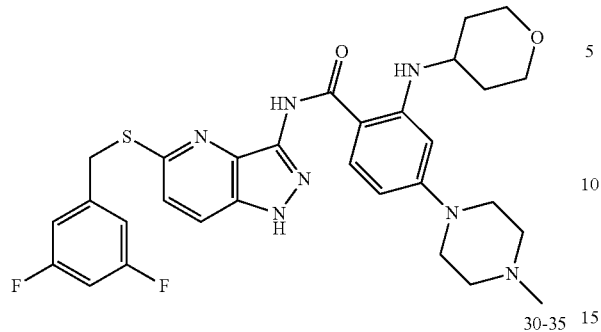
30-35
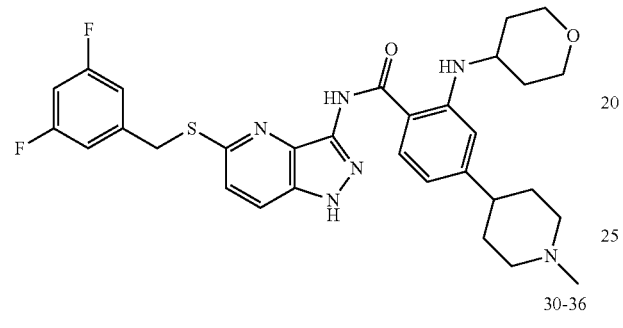
30-36
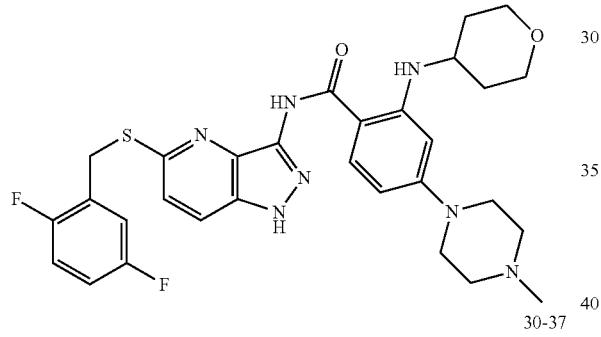
30-37
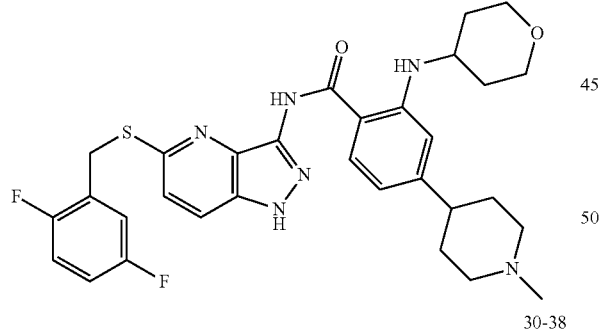
30-38
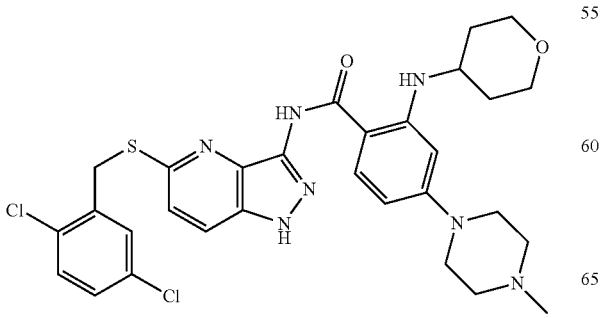
30-39
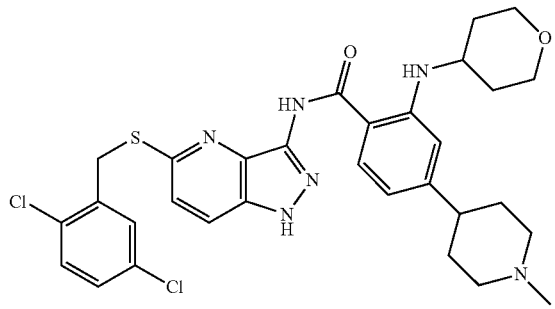
30-40
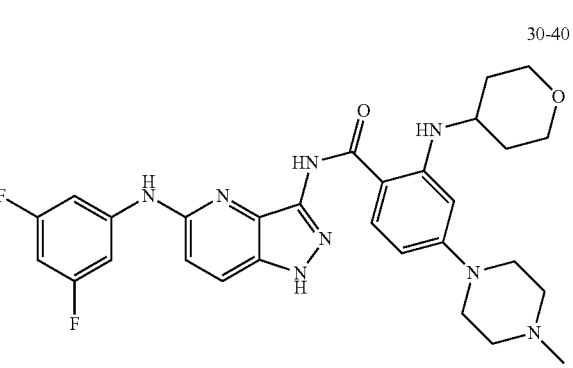
30-41
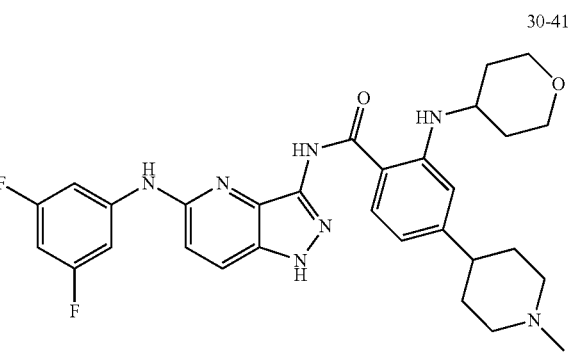
30-42
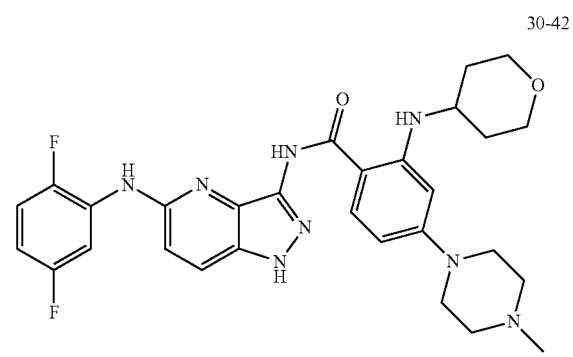

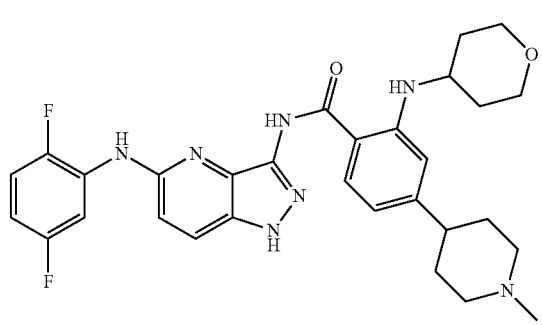
30-43
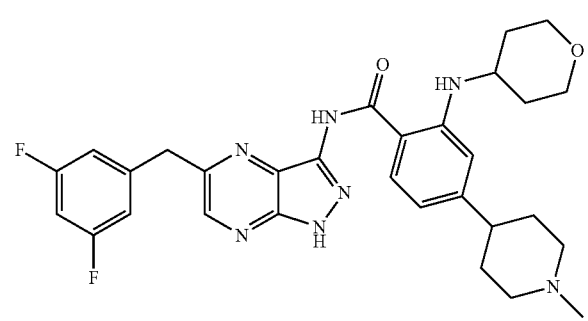
30-47
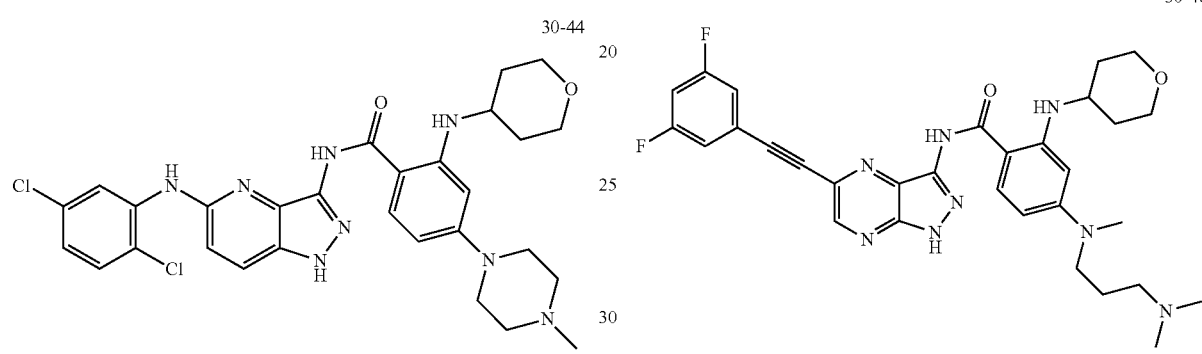
30-44
30-48
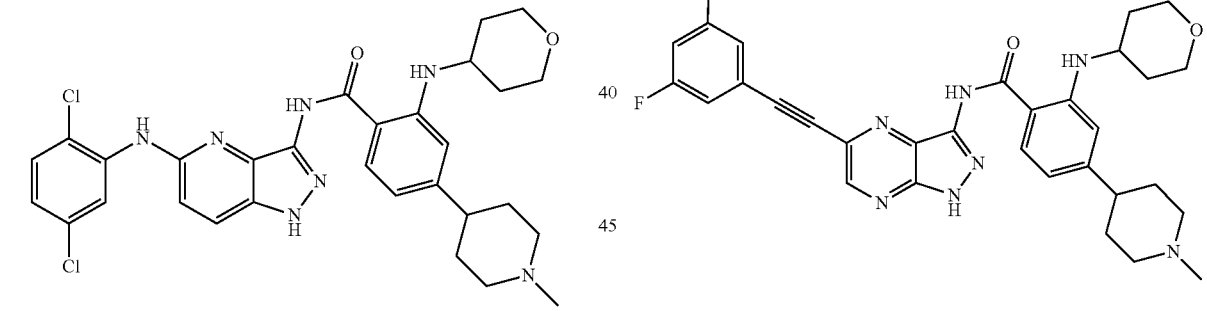
30-45
30-49
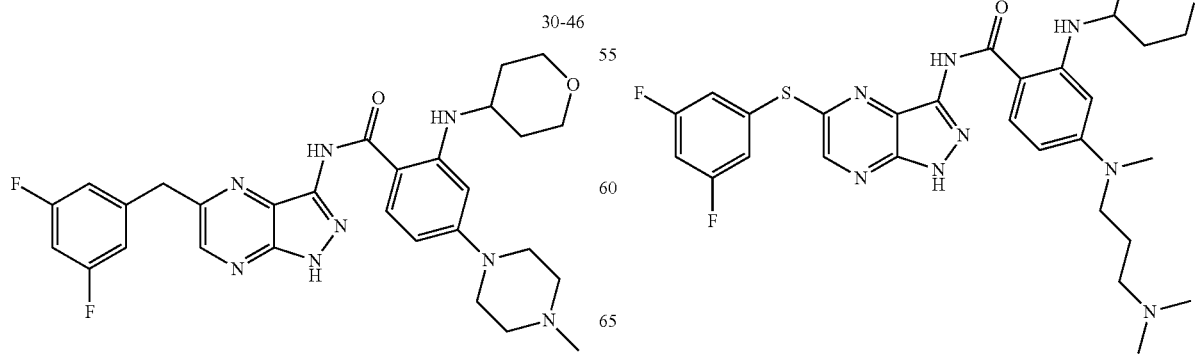
30-46
30-50

225
-continued
30-51
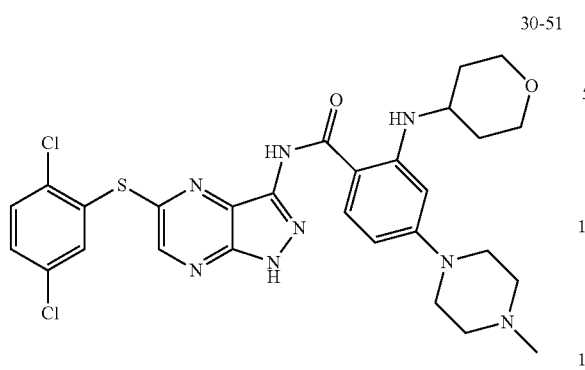
30-52
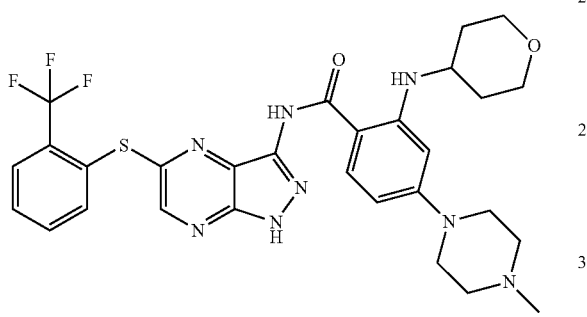
30-53
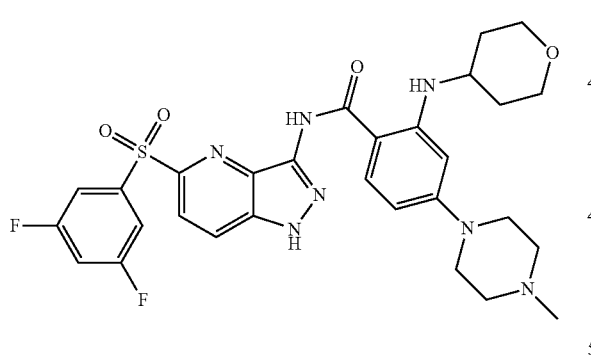
30-54
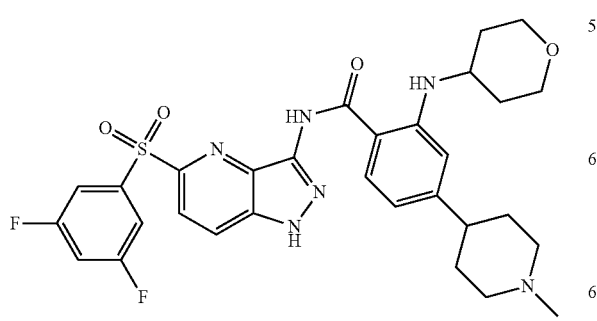
226
-continued
30-55
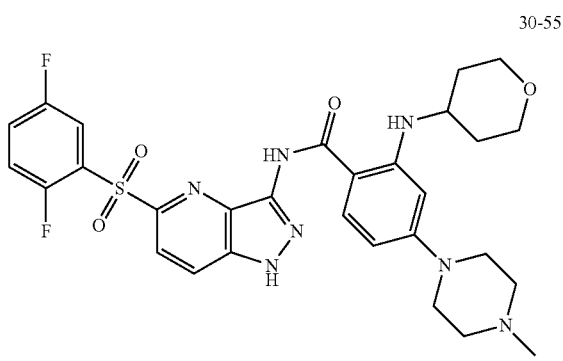
30-56
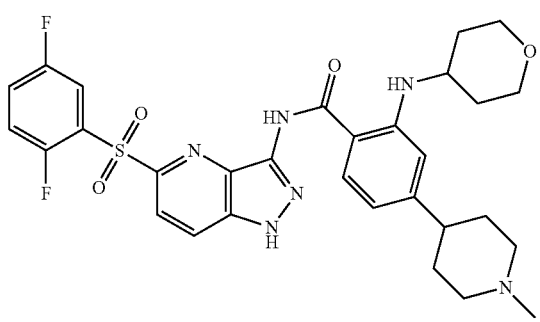
30-57
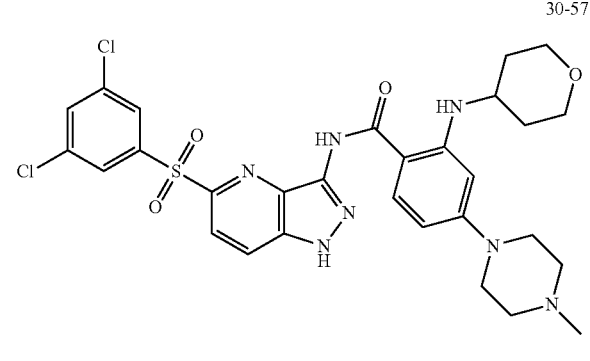
30-58
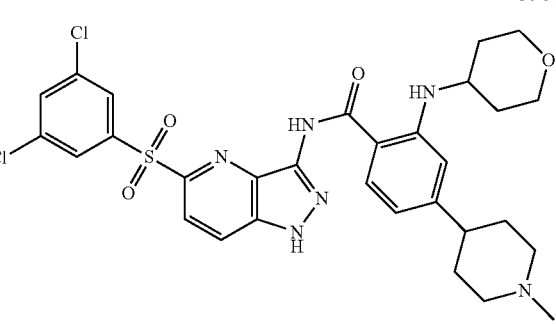

30-59
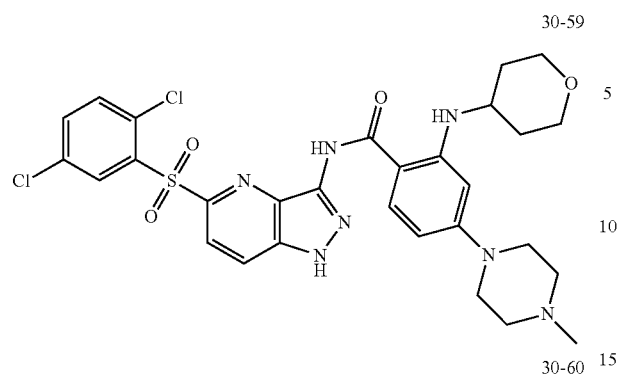
30-60
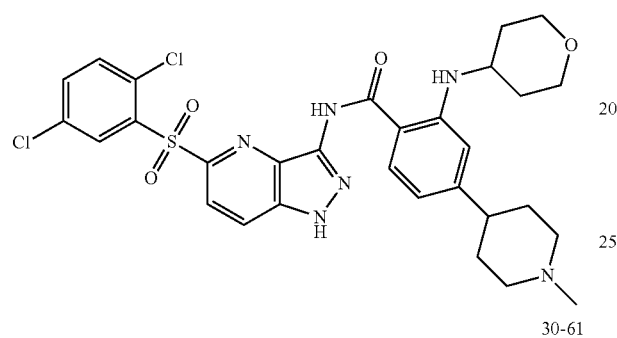
30-61
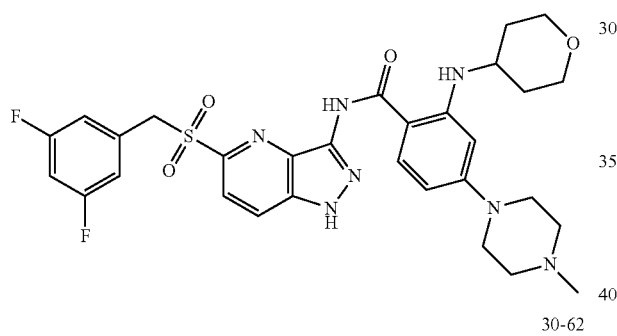
30-62
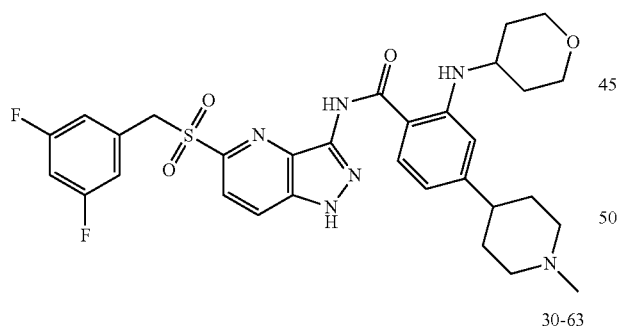
30-63
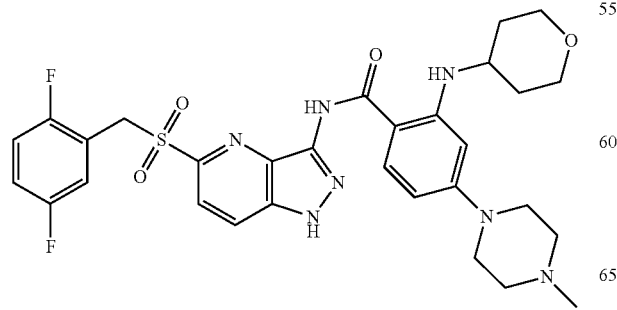
30-64
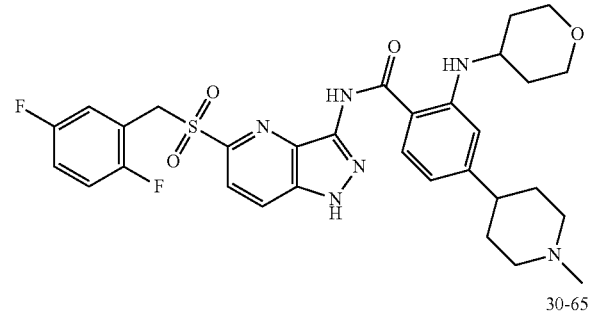
30-65
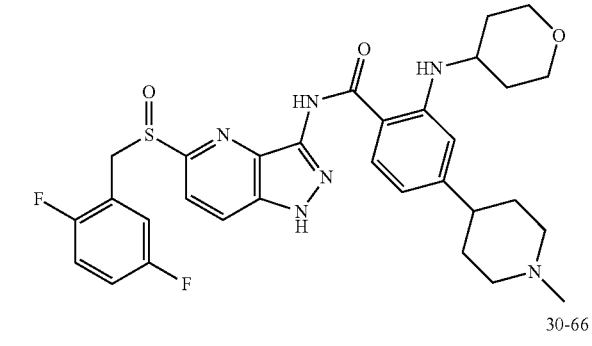
30-66
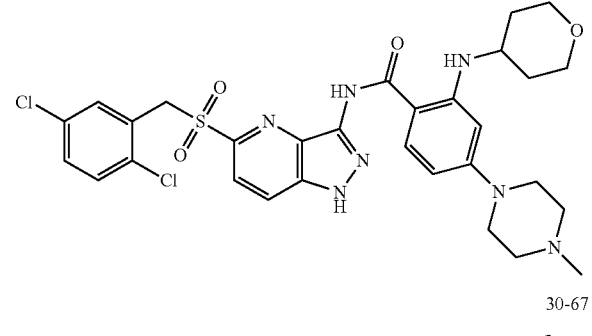
30-67
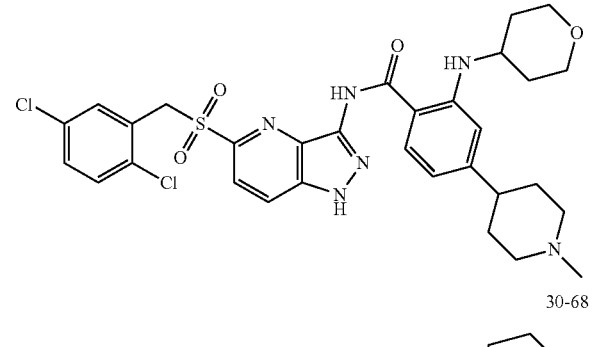
30-68
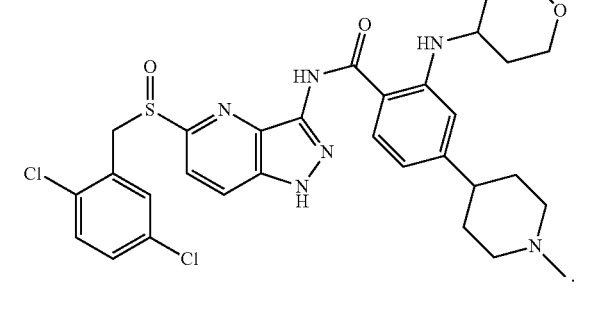

21. A method for the treatment of pain comprising the administration to a person in need thereof of an effective dose of a pharmaceutical composition containing at least one pharmaceutical acceptable excipient and one compound according to claim 1 or a pharmaceutically acceptable salt of same, a tautomer of same, or a stereoisomer or mixture of stereoisomers of same in any proportions.

\* \* \* \* \*